(12) United States Patent
Johns et al.

(10) Patent No.: US 8,129,385 B2
(45) Date of Patent: Mar. 6, 2012

(54) SUBSTITUTED 5-HYDROXY-3,4,6,9,9A, 10-HEXANHYDRO-2H-1-OXA04A,8A-DIAZA-ANTHRACENE-6,10-DIONESS

(75) Inventors: Brian Alvin Johns, Research Triangle Park, NC (US); Takashi Kawasuji, Osaka (JP); Teruhiko Taishi, Osaka (JP); Yoshiyuki Taoda, Osaka (JP)

(73) Assignees: Shionogi & Co., Ltd., Osaka (JP); GlaxoSmithKline LLC, Philadelphia, PA (US)

( * ) Notice: Subject to any disclaimer, the term of this patent is extended or adjusted under 35 U.S.C. 154(b) by 525 days.

(21) Appl. No.: 11/919,386

(22) PCT Filed: Apr. 28, 2006

(86) PCT No.: PCT/US2006/016604
§ 371 (c)(1),
(2), (4) Date: Jul. 28, 2009

(87) PCT Pub. No.: WO2006/116764
PCT Pub. Date: Nov. 2, 2006

(65) Prior Publication Data
US 2009/0318421 A1    Dec. 24, 2009

(30) Foreign Application Priority Data

Apr. 28, 2005  (JP) .................................. 2005-131161
Oct. 27, 2005  (JP) .................................. 2005-312076

(51) Int. Cl.
A61K 31/495    (2006.01)
(52) U.S. Cl. ....................................... 514/250; 544/346
(58) Field of Classification Search .................. 514/250; 544/346
See application file for complete search history.

(56) References Cited

U.S. PATENT DOCUMENTS

| 7,981,879 B2 | 7/2011 | Summa et al. |
| 2005/0054645 A1 | 3/2005 | Miyazaki et al. |
| 2008/0161271 A1 | 7/2008 | Yoshida et al. |
| 2009/0143356 A1 | 6/2009 | Yoshida et al. |

FOREIGN PATENT DOCUMENTS

| EP | 1 422 218 | 5/2004 |
| EP | 1 852 434 | 11/2007 |
| EP | 1 541 558 | 8/2008 |
| JP | 2-96506 | 4/1990 |
| JP | 2-108668 | 4/1990 |
| JP | 2-108683 | 4/1990 |
| JP | 2004-244320 | 9/2004 |
| WO | 03/016275 | 2/2003 |
| WO | 03/035076 | 5/2003 |
| WO | 03/035077 | 5/2003 |
| WO | 2004/004657 | 1/2004 |
| WO | 2004/024693 | 3/2004 |
| WO | 2004/101512 | 11/2004 |
| WO | 2005/016927 | 2/2005 |
| WO | 2005/077050 | 8/2005 |
| WO | 2005/087766 | 9/2005 |
| WO | 2006/066414 | 6/2006 |
| WO | 2006/088173 | 8/2006 |
| WO | 2006/103399 | 10/2006 |
| WO | 2007/019098 | 2/2007 |
| WO | 2007/049675 | 5/2007 |

OTHER PUBLICATIONS

Supplementary European Search Report dated Nov. 27, 2009 in European Application No. EP 06 75 8843.
International Search Report issued Sep. 18, 2006 in the International (PCT) Application of which the present application is the U.S. National Stage.

*Primary Examiner* — James O Wilson
*Assistant Examiner* — Douglas M Willis
(74) *Attorney, Agent, or Firm* — Wenderoth, Lind & Ponack, L.L.P.

(57) ABSTRACT

The present invention is directed to a class of substituted 5-hydroxy-3,4,6,9,9a,10-hexahydro-2H-1-oxa-4a,8a-diaza-anthracene-6,10-diones useful as anti-HIV agents. The compounds have the formula:

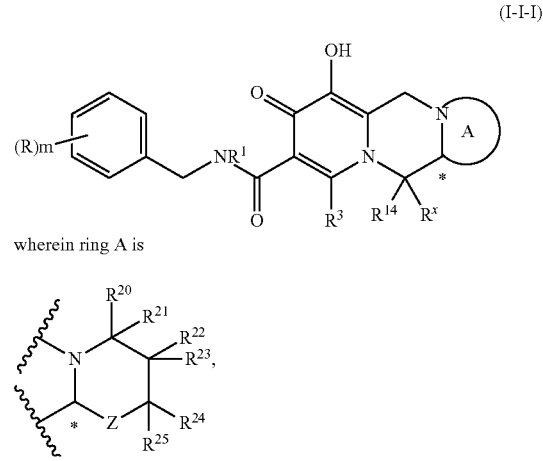

wherein ring A is $Z=O$; $R^{20}$, $R^{21}$, $R^{22}$, $R^{23}$, $R^{24}$ and $R^{25}$ independently are hydrogen, $C_1$-$C_8$ alkyl, $(C_6$-$C_{14})$aryl-$(C_1$-$C_8)$alkyl, $C_6$-$C_{14}$ aryl, or alkoxy; the stereochemistry of an asymmetric carbon represented by * shows R- or S-configuration, or a mixture thereof; $R^X$ is hydrogen; $R^{14}$ is hydrogen or optionally substituted lower alkyl; $R^3$ is hydrogen; $R^1$ is hydrogen or lower alkyl; R is halogen; and m is 1, 2 or 3; or a pharmaceutically acceptable salt thereof.

11 Claims, No Drawings

SUBSTITUTED 5-HYDROXY-3,4,6,9,9A, 10-HEXANHYDRO-2H-1-OXAO4A,8A-DIAZA-ANTHRACENE-6,10-DIONESS

CROSS-REFERENCE TO RELATED APPLICATIONS

This application is a U.S. national stage of International Application No. PCT/US2006/016604 filed Apr. 28, 2006.

BACKGROUND OF THE INVENTION

1. Field of the Invention

The present invention relates to novel compounds possessing an antiviral activity, in detail polycyclic carbamoylpyridone derivatives possessing an inhibitory activity against HIV integrase and a pharmaceutical composition containing the same, especially an anti-HIV agent.

2. Description of Related Art

Among viruses, human immunodeficiency virus (HIV), a kind of retrovirus, is known to cause acquired immunodeficiency syndrome (AIDS). The therapeutic agent for AIDS is mainly selected from a group of reverse transcriptase inhibitors (e.g., AZT, 3TC) and protease inhibitors (e.g., Indinavir), but they are proved to be accompanied by side effects such as nephropathy and the emergence of resistant viruses. Thus, the development of anti-HIV agents having the other mechanism of action has been desired.

On the other hand, a combination therapy is reported to be efficient in treatment for AIDS because of the frequent emergence of the resistant mutant. Reverse transcriptase inhibitors and protease inhibitors are clinically used as an anti-HIV agent, however agents having the same mechanism of action often exhibit cross-resistance or only an additional activity. Therefore, anti-HIV agents having the other mechanism of action are desired.

Under the circumstances above, an HIV integrase inhibitor has been focused on as an anti-HIV agent having a novel mechanism of action (Ref: Patent Documents 1 and 2). As an anti-HIV agent having such a mechanism of action, known are carbamoyl-substituted hydroxypyrimidinone derivative (Ref: Patent Documents 3 and 4) and carbamoyl-substituted hydroxypyrrolidione derivative (Ref: Patent Document 5). Further, a patent application concerning carbamoyl-substituted hydroxypyridone derivative has been filed (Ref: Patent Document 6, Example 8).

Other known carbamoylpyridone derivatives include 5-alkoxypyridine-3-carboxamide derivatives and γ-pyrone-3-carboxamide derivatives, which are a plant growth inhibitor or herbicide (Ref: Patent Documents 7-9).

Other HIV integrase inhibitors include N-containing condensed cyclic compounds (Ref: Patent Document 10).

[Patent Document 1] WO03/0166275
[Patent Document 2] WO2004/024693
[Patent Document 3] WO03/035076
[Patent Document 4] WO03/035076
[Patent Document 5] WO2004/004657
[Patent Document 6] JP Patent Application 2003-32772
[Patent Document 7] JP Patent Publication 1990-108668
[Patent Document 8] JP Patent Publication 1990-108683
[Patent Document 9] JP Patent Publication 1990-96506
[Patent Document 10] WO2005/016927

BRIEF SUMMARY OF THE INVENTION

The development of a novel integrase inhibitor has been desired.

Means to Solve the Problem

The present inventors have intensively studied to find that a novel polycyclic carbamoylpyridone derivative possesses a potent HIV integrase inhibitory activity.

Moreover, the present inventors have discovered that a compound of the present invention and a pharmaceutical composition containing the same are useful as an antiviral agent, an antiretroviral agent, an anti-HIV agent, an anti-HTLV-1 (Human T cell leukemia virus type 1) agent, an anti-FIV (Feline immunodeficiency virus) agent or an anti-SIV (Simian immunodeficiency virus) agent, especially an anti-HIV agent or anti-AIDS agent, to accomplish the present invention shown below.

(1) A compound of the formula:

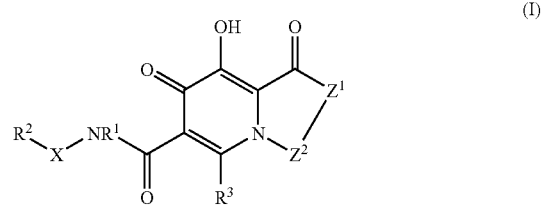

(wherein, $Z^1$ is $NR^4$;

$R^4$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclic group, optionally substituted heterocycle lower alkyl, optionally substituted heterocycleoxy, hydroxy, optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from CO, O, S, SO, $SO_2$, $NR^a$ ($R^a$ is hydrogen or lower alkyl), —N= and =N—)), O or $CH_2$;

$Z^2$ is optionally substituted lower alkylene or optionally substituted lower alkenylene, each may be intervened by a heteroatom group selected from O, S, SO, $SO_2$, $NR^5$ ($R^5$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclic group, optionally substituted heterocycle lower alkyl, optionally substituted heterocycleoxy, hydroxy or optionally substituted amino, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from CO, O, S, SO, $SO_2$, $NR^5$ ($R^5$ is selected independently from the same substituent group as $R^4$), —N= and =N—)), —N= or =N—

$R^1$ is hydrogen or lower alkyl;

X is a single bond, a heteroatom group selected from O, S, SO, $SO_2$ and NH, or lower alkylene or lower alkenylene each may be intervened by the heteroatom;

$R^2$ is optionally substituted aryl;

$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino;

$R^4$ and $Z^2$ part taken together forms a ring, where the compound (I) is represented by the following formula (I-1), or (I-11):

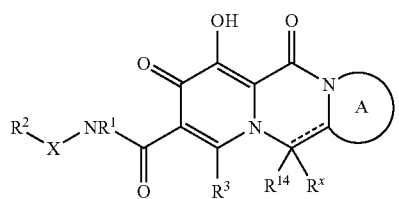

(I-1)

(wherein,

A ring is optionally substituted heterocycle;

$R^{14}$ and $R^X$ are independently hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl dower alkyl, optionally substituted aryloxy, optionally substituted heterocyclic group, optionally substituted heterocycle lower alkyl, optionally substituted heterocycleoxy, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from O, S, SO, $SO_2$, $NR^5$ ($R^6$ is selected independently from the same substituent group as $R^4$), —N= and =N—), hydroxy, optionally substituted amino, optionally substituted lower alkyl carbonyl, optionally substituted cycloalkylcarbonyl, optionally substituted cycloalkyl lower alkyl carbonyl, optionally substituted lower alkoxy carbonyl, optionally substituted arylcarbonyl, optionally substituted aryl lower alkyl carbonyl, optionally substituted aryloxycarbonyl, optionally substituted heterocyclecarbonyl, optionally substituted heterocycle lower alkyl carbonyl, optionally substituted heterocycleoxy carbonyl or optionally substituted aminocarbonyl;

a broken line represents the presence or absence of a bond, provided that when the broken line represents the presence of a bond, $R^X$ is not present;

$R^1$ is hydrogen or lower alkyl;

X is a single bond, a heteroatom group selected from O, S, SO, $SO_2$ and NH, or lower alkylene or lower alkenylene each may be intervened by the heteroatom group;

$R^2$ is optionally substituted aryl;

$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino)

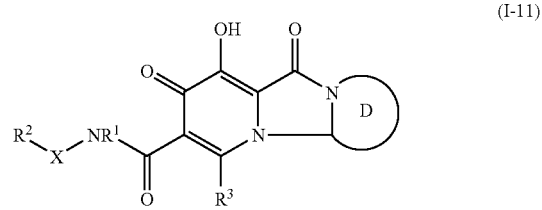

(I-11)

(wherein,

D ring is optionally substituted heterocycle;

$R^1$ is hydrogen or lower alkyl;

X is a single bond, a heteroatom group selected from O, S, SO, $SO_2$ and NH, or lower alkylene or lower alkenylene each may be intervened by the heteroatom group;

$R^2$ is optionally substituted aryl;

$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino)), its pharmaceutically acceptable salt, or solvate thereof.

(2) A compound according to the above (1), pharmaceutically acceptable salt, or solvate thereof, wherein $R^1$ is hydrogen.

(3) A compound according to the above (1), pharmaceutically acceptable salt, or solvate thereof, wherein X is lower alkylene; $R^2$ is phenyl or phenyl substituted with at least halogen.

(4) A compound according to the above (1), pharmaceutically acceptable salt, or solvate thereof, wherein $R^3$ is hydrogen, halogen, hydroxy, lower alkyl, lower alkenyl, lower alkoxy, lower alkenyloxy or optionally substituted amino.

(5) A compound according to the above (1), pharmaceutically acceptable salt, or solvate thereof, wherein $R^3$ is hydrogen.

(6) A compound according to the above (1), pharmaceutically acceptable salt, or solvate thereof, wherein $R^1$ is hydrogen or lower alkyl; X is lower alkylene; $R^2$ is phenyl or phenyl substituted with at least halogen; $R^3$ is hydrogen, halogen, hydroxy, lower alkyl, lower alkenyl, lower alkoxy, lower alkenyloxy or optionally substituted amino.

(7) A compound of the formula:

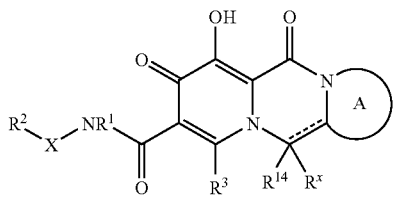

(wherein,
A ring is optionally substituted heterocycle;
$R^{14}$ and $R^X$ are independently hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocycle lower alkyl, optionally substituted heterocycleoxy, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from O, S, SO, $SO_2$, $NR^5$ ($R^5$ is selected independently from the same substituent group as $R^4$), —N═ and ═N—), hydroxy, optionally substituted amino, optionally substituted lower alkyl carbonyl, optionally substituted cycloalkylcarbonyl, optionally substituted cycloalkyl lower alkyl carbonyl, optionally substituted lower alkoxy carbonyl, optionally substituted arylcarbonyl, optionally substituted aryl lower alkyl carbonyl, optionally substituted aryloxycarbonyl, optionally substituted heterocyclecarbonyl, optionally substituted heterocycle lower alkyl carbonyl, optionally substituted heterocycleoxy carbonyl or optionally substituted aminocarbonyl;
a broken line represents the presence or absence of a bond, provided that when the broken line represents the presence of a bond, $R^X$ is not present;
$R^1$ is hydrogen or lower alkyl;
X is a single bond, a heteroatom group selected from O, S, SO, $SO_2$ and NH, or lower alkylene or lower alkenylene each may be intervened by the heteroatom group;
$R^2$ is optionally substituted aryl;
$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino), its pharmaceutically acceptable salt, or solvate thereof
(8) A compound according to the above (7), pharmaceutically acceptable salt, or solvate thereof, wherein $R^1$ is hydrogen or lower alkyl; X is lower alkylene; $R^2$ is phenyl or phenyl substituted with at least halogen; $R^3$ is hydrogen, halogen, hydroxy, lower alkyl, lower alkenyl, lower alkoxy, lower alkenyloxy or optionally substituted amino.
(9) A compound according to the above (7), pharmaceutically acceptable salt, or solvate thereof, wherein a broken line represents the absence of a bond.

(10) A compound according to the above (7), pharmaceutically acceptable salt, or solvate thereof, wherein $R^X$ is hydrogen; $R^{14}$ is hydrogen or optionally substituted lower alkyl.
(11) A compound according to the above (7), pharmaceutically acceptable salt, or solvate thereof, wherein A ring is an optionally substituted and optionally condensed 5- to 7-membered heterocycle containing 1 to 2 hetero atom(s).
(12) A compound of the formula:

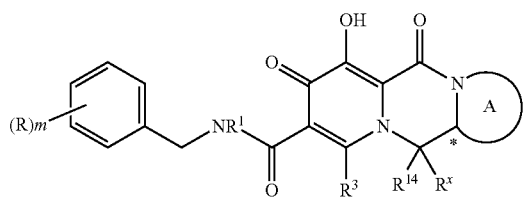

(wherein,
A ring is an optionally substituted and optionally condensed 5- to 7-membered heterocycle containing 1 to 2 hetero atom(s);
the stereochemistry of an asymmetric carbon represented by * shows R- or S-configuration, or a mixture thereof;
$R^{14}$ and $R^X$ are independently hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocycle lower alkyl, optionally substituted heterocycleoxy, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue or lower alkyl substituted with optionally substituted phosphoric acid residue (the lower alkyl may be intervened by a heteroatom group selected from O, S, SO, $SO_2$, $NR^5$ ($R^5$ is selected independently from the same substituent group as $R^4$), —N═ and ═N—), hydroxy, optionally substituted amino, optionally substituted lower alkyl carbonyl, optionally substituted cycloalkylcarbonyl, optionally substituted cycloalkyl lower alkyl carbonyl, optionally substituted lower alkoxy carbonyl, optionally substituted arylcarbonyl, optionally substituted aryl lower alkyl carbonyl, optionally substituted aryloxycarbonyl, optionally substituted heterocyclecarbonyl, optionally substituted heterocycle lower alkyl carbonyl, optionally substituted heterocycleoxy carbonyl or optionally substituted aminocarbonyl;
$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino), its pharmaceutically acceptable salt, or
$R^1$ is hydrogen or lower alkyl;
R is independently selected from halogen and Substituent group S1;

Substituent group S1(: optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (wherein the lower alkyl may be intervened with a heteroatom group(s) selected from CO, O, O, S, SO, $SO_2$, $NR^a$ ($R^a$ is hydrogen or lower alkyl), —N= =N—), lower alkoxy lower alkyl, amino lower alkyl optionally substituted with mono- or di-lower alkyl, halogenated lower alkyl, lower alkoxy, carbamoyl optionally substituted with mono- or di-lower alkyl, optionally substituted lower alkyl sulfonyl amino, halogenated lower alkoxy, hydroxy lower alkyl)

m is an integer of 0 to 3, its pharmaceutically acceptable salt, or solvate thereof.

(13) A compound according to the above (12), pharmaceutically acceptable salt, or solvate thereof, wherein $R^X$ and $R^{14}$ are independently hydrogen or optionally substituted lower alkyl.

(14) A compound according to the above (12), pharmaceutically acceptable salt, or solvate thereof, wherein $R^X$ and $R^{14}$ are hydrogens.

(15) A compound according to the above (12), pharmaceutically acceptable salt, or solvate thereof, wherein $R^3$ is hydrogen.

(16) A compound according to the above (12), pharmaceutically acceptable salt, or solvate thereof, wherein m is 0, or 1 to 3 and at least one of R is halogen.

(17) A compound according to the above (7) or (12), pharmaceutically acceptable salt, or solvate thereof, wherein A ring is any one of the following:

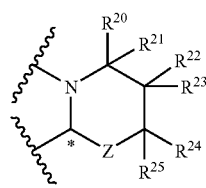

(A-1)

Z = O or $NR^{26}$

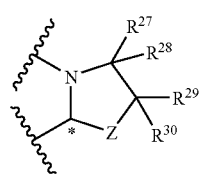

(A-2)

Z = O or $NR^{31}$

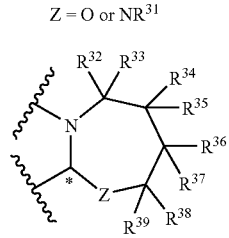

(A-3)

Z = O or $NR^{40}$ (wherein, $R^{20}$ to $R^{40}$ are each independently a group selected from Substituent group S2, or any two groups of $R^{20}$ to $R^{40}$, which bonds to the same carbon atom, taken together with the carbon atom, may form an optionally substituted carbocycle or optionally substituted heterocycle, or each combination of ($R^{20}$ and $R^{22}$), ($R^{23}$ and $R^{24}$), ($R^{25}$ and $R^{26}$), ($R^{27}$ and $R^{29}$), ($R^{30}$ and $R^{31}$), ($R^{32}$ and $R^{34}$), ($R^{35}$ and $R^{36}$), ($R^{37}$ and $R^{38}$), and ($R^{39}$ and $R^{40}$) taken together with the neighboring atom, may form an optionally substituted carbocycle or optionally substituted heterocycle.

Substituent group S2: hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocycle, optionally substituted heterocycle lower alkyl, optionally substituted heterocycleoxy, hydroxy, optionally substituted amino, optionally substituted lower alkylcarbonyl, optionally substituted cycloalkylcarbonyl, optionally substituted cycloalkyl lower alkylcarbonyl, optionally substituted lower alkoxycarbonyl, optionally substituted arylcarbonyl, optionally substituted aryl lower alkylcarbonyl, optionally substituted aryl oxycarbonyl, optionally substituted heterocyclecarbonyl, optionally substituted heterocycle lower alkylcarbonyl, optionally substituted heterocycleoxycarbonyl, optionally substituted aminocarbonyl, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (the lower alkyl may be intervened with a heteroatom group(s) selected from CO, O, S, SO, $SO_2$, $NR^5$ ($R^5$ is independently selected from the same Substituent group as $R^4$), —N= and =N—)

the stereochemistry of an asymmetric carbon represented by * shows R- or S-configuration, or a mixture thereof)

(18) A compound according to the above (17), pharmaceutically acceptable salt, or solvate thereof, wherein $R^{20}$ to $R^{40}$ are each independently hydrogen or substituted lower alkyl, or any two groups of $R^{20}$ to $R^{40}$, which bonds to the same carbon atom, taken together with the carbon atom, may form an optionally substituted 3- to 7-membered carbocycle or optionally substituted 3- to 7-membered heterocycle, or each combination of ($R^{20}$ and $R^{22}$), ($R^{23}$ and $R^{24}$), ($R^{25}$ and $R^{26}$), ($R^{27}$ and $R^{29}$), ($R^{30}$ and $R^{31}$), ($R^{32}$ and $R^{34}$), ($R^{35}$ and $R^{36}$), ($R^{37}$ and $R^{38}$), and ($R^{39}$ and $R^{40}$), taken together with the neighboring atom, may form an optionally substituted 5- to 7-membered carbocycle or optionally substituted 5- to 7-membered heterocycle.

(19) A compound according to the above (17), pharmaceutically acceptable salt, or solvate thereof, wherein A ring is a ring represented by (A-1); one of $R^{20}$ to $R^{25}$ is optionally substituted lower alkyl and the others are hydrogens.

(20) A compound according to the above (17), pharmaceutically acceptable salt, or solvate thereof, wherein A ring is a ring represented by (A-1); one of ($R^{20}$ and $R^{22}$), ($R^{23}$ and $R^{24}$), and ($R^{25}$ and $R^{26}$), taken together with the neighboring atom, may form an optionally substituted 5- to 7-membered carbocycle or optionally substituted 5- to 7-membered heterocycle.

(21) A compound according to the above (17), pharmaceutically acceptable salt, or solvate thereof, wherein A ring is a ring represented by (A-1); Z=$NR^{26}$, and $R^{25}$ and $R^{26}$ taken together with the neighboring atom may form an optionally substituted 5- to 7-membered heterocycle.

(22) A compound according to the above (17), pharmaceutically acceptable salt, or solvate thereof, wherein A ring is a ring represented by (A-2); one of $R^{27}$ to $R^{30}$ is optionally substituted lower alkyl and the others are hydrogens.

(23) A compound according to the above (17), pharmaceutically acceptable salt, or solvate thereof, wherein A ring is a ring represented by (A-2); one of ($R^{27}$ and $R^{29}$) and ($R^{30}$ and $R^{31}$), taken together with the neighboring atom, may form an optionally substituted 5- to 7-membered carbocycle or optionally substituted 5- to 7-membered heterocycle.

(24) A compound according to the above (17), pharmaceutically acceptable salt, or solvate thereof, wherein A ring is a ring represented by (A-2); $Z=NR^{31}$, and $R^{30}$ and $R^{31}$ taken together with the neighboring atom may form an optionally substituted 5- to 7-membered heterocycle.

(25) A compound according to the above (17), pharmaceutically acceptable salt, or solvate thereof, wherein A ring is a ring represented by (A-3); one of $R^{32}$ to $R^{39}$ is optionally substituted lower alkyl and the others are hydrogens.

(26) A compound according to the above (17), pharmaceutically acceptable salt, or solvate thereof, wherein A ring is a ring represented by (A-3); one of ($R^{32}$ and $R^{34}$), ($R^{35}$ and $R^{36}$), ($R^{37}$ and $R^{38}$), and ($R^{39}$ and $R^{40}$), taken together with the neighboring atom, may form an optionally substituted 5- to 7-membered carbocycle or optionally substituted 5- to 7-membered heterocycle.

(27) A compound according to the above (17), pharmaceutically acceptable salt, or solvate thereof, wherein A ring is a ring represented by (A-3); $Z=NR^{40}$, and $R^{39}$ and $R^{40}$ taken together with the neighboring atom may form an optionally substituted 5- to 7-membered heterocycle.

(28) A compound according to the above (12), pharmaceutically acceptable salt, or solvate thereof, wherein $R^X$ is hydrogen; $R^{14}$ is hydrogen or optionally substituted lower alkyl; $R^3$ is hydrogen; m is 1 to 3 and at least one of $R^5$ is halogen; A ring is a ring described in the above (17).

(29) A compound according to the above (12), pharmaceutically acceptable salt, or solvate thereof, wherein $R^X$ is hydrogen; $R^{14}$ is hydrogen; $R^3$ is hydrogen; m is 0, or 1 to 3 and at least one of Rs is halogen; A ring is a ring described in the above (17); $R^{20}$ to $R^{40}$ are each independently hydrogen or substituted lower alkyl, or any two groups of $R^{20}$ to $R^{40}$, which bonds to the same carbon atom, taken together with the carbon atom, may form an optionally substituted 3- to 7-membered carbocycle or optionally substituted 3- to 7-membered heterocycle, or each combination of ($R^{20}$ and $R^{22}$), ($R^{23}$ and $R^{24}$), ($R^{25}$ and $R^{26}$), ($R^{27}$ and $R^{29}$), ($R^{30}$ and $R^{31}$), ($R^{32}$ and $R^{34}$), ($R^{35}$ and $R^{36}$), ($R^{37}$ and $R^{38}$), and ($R^{39}$ and $R^{40}$), taken together with the neighboring carbon atom, may form an optionally substituted 5- to 7-membered carbocycle or optionally substituted 5- to 7-membered heterocycle.

(30) A compound of the formula:

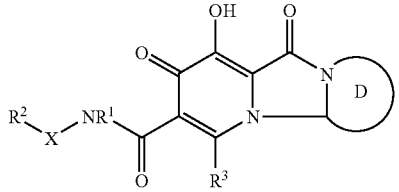

(I-11)

(wherein,
D ring is optionally substituted heterocycle;
$R^1$ is hydrogen or lower alkyl;
X is a single bond, a heteroatom group selected from O, S, SO, $SO_2$ and NH, or lower alkylene or lower alkenylene each may be intervened by the heteroatom group;
$R^2$ is optionally substituted aryl;
$R^3$ is hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy or optionally substituted amino), pharmaceutically acceptable salt, or solvate thereof

(31) A compound selected from the group consisting of:

(3R,11aS)—N-[(2,4-Difluorophenyl)methyl]-6-hydroxy-3-methyl-5,7-dioxo-2,3,5,7,11,11a-hexahydro[1,3]oxazolo[3,2-a]pyrido[1,2-d]pyrazine-8-carboxamide;

(4aR,13aS)—N-[(2,4-Difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide;

(3aS,13aS)—N-[(2,4-Difluorophenyl)methyl]-8-hydroxy-7,9-dioxo-1,2,3,3a,4,5,7,9,13,13a-decahydropyrido[1',2':4,5]pyrazino[1,2-a]pyrrolo[1,2-c]pyrimidine-10-carboxamide;

(4aS,13aR)—N-[(2,4-Difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide;

(4aS,13aR)—N-[(4-Fluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide;

(3S,11aR)—N-[(2,4-Difluorophenyl)methyl]-6-hydroxy-5,7-dioxo-3-(phenylmethyl)-2,3,5,7,11,11a-hexahydro[1,3]oxazolo[3,2-a]pyrido[1,2-d]pyrazine-8-carboxamide;

(3aS,13aS)—N-[(4-Fluorophenyl)methyl]-8-hydroxy-7,9-dioxo-1,2,3,3a,4,5,7,9,13,13a-decahydropyrido[1',2':4,5]pyrazino[1,2-a]pyrrolo[1,2-c]pyrimidine-10-carboxamide;

(3S,11aR)—N-[(2,4-Difluorophenyl)methyl]-6-hydroxy-3-[(1S)-1-methylpropyl]-5,7-dioxo-2,3,5,7,11,11a-hexahydro[1,3]oxazolo[3,2-a]pyrido[1,2-d]pyrazine-8-carboxamide;

(3S,11aR)—N-[(2,4-Difluorophenyl)methyl]-6-hydroxy-3-methyl-5,7-dioxo-2,3,5,7,11,11a-hexahydro[1,3]oxazolo[3,2-a]pyrido[1,2-d]pyrazine-8-carboxamide;

(3S,11aR)—N-[(4-Fluorophenyl)methyl]-6-hydroxy-3-methyl-5,7-dioxo-2,3,5,7,11,11a-hexahydro[1,3]oxazolo[3,2-a]pyrido[1,2-d]pyrazine-8-carboxamide;

(3S,11aR)—N-[(2,4-Difluorophenyl)methyl]-3-(1,1-dimethylethyl)-6-hydroxy-5,7-dioxo-2,3,5,7,11,11a-hexahydro[1,3]oxazolo[3,2-a]pyrido[1,2-d]pyrazine-8-carboxamide;

(3S,11aR)-3-(1,1-Dimethylethyl)-N-[(4-fluorophenyl)methyl]-6-hydroxy-5,7-dioxo-2,3,5,7,11,11a-hexahydro[1,3]oxazolo[3,2-a]pyrido[1,2-d]pyrazine-8-carboxamide;

(3S,11aR)—N-[(2,4-Difluorophenyl)methyl]-6-hydroxy-5,7-dioxo-3-phenyl-2,3,5,7,11,11a-hexahydro[1,3]oxazolo[3,2-a]pyrido[1,2-d]pyrazine-8-carboxamide;

(3S,11aR)—N-[(2,4-Difluorophenyl)methyl]-6-hydroxy-3-(hydroxymethyl)-5,7-dioxo-2,3,5,7,11,11a-hexahydro[1,3]oxazolo[3,2-a]pyrido[1,2-d]pyrazine-8-carboxamide;

(2S,3R)—N-[(2,4-Difluorophenyl)methyl]-6-hydroxy-3-methyl-5,7-dioxo-2-phenyl-2,3,5,7,11,11a-hexahydro[1,3]oxazolo[3,2-a]pyrido[1,2-d]pyrazine-8-carboxamide;

(3R,11aS)—N-[(2,4-Difluorophenyl)methyl]-6-hydroxy-5,7-dioxo-3-(phenylmethyl)-2,3,5,7,11,11a-hexahydro[1,3]oxazolo[3,2-a]pyrido[1,2-d]pyrazine-8-carboxamide;

(3R,11aS)—N-[(2,4-Difluorophenyl)methyl]-6-hydroxy-3-(2-methylpropyl)-5,7-dioxo-2,3,5,7,11,11a-hexahydro[1,3]oxazolo[3,2-a]pyrido[1,2-d]pyrazine-8-carboxamide;

(5aR,14aR)—N-[(2,4-Difluorophenyl)methyl]-11-hydroxy-10,12-dioxo-1,2,3,4,5a,6,10,12,14,14a-decahydropyrido[1,2-d]pyrido[1',2':3,4]imidazo[1,2-d]pyrazine-9-carboxamide;

(2S,3S)—N-[(2,4-Difluorophenyl)methyl]-6-hydroxy-3-[(methyloxy)methyl]-5,7-dioxo-2-phenyl-2,3,5,7,11,11a-hexahydro[1,3]oxazolo[3,2-a]pyrido[1,2-d]pyrazine-8-carboxamide;

(3S,11aR)-3-(Cyclohexylmethyl)-N-[(2,4-difluorophenyl)methyl]-6-hydroxy-5,7-dioxo-2,3,5,7,11,11a-hexahydro[1,3]oxazolo[3,2-a]pyrido[1,2-d]pyrazine-8-carboxamide;

(3S,11aR)—N-[(2,4-Difluorophenyl)methyl]-6-hydroxy-3-(1-methylethyl)-5,7-dioxo-2,3,5,7,11,11a-hexahydro[1,3]oxazolo[3,2-a]pyrido[1,2-d]pyrazine-8-carboxamide;

(5aR,14aS)—N-[(2,4-Difluorophenyl)methyl]-12-hydroxy-11,13-dioxo-5a,6a,7,11,13,14a-hexahydro-5H-indeno[1',2':4,5][1,3]oxazolo[3,2-a]pyrido[1,2-a]pyrazine-10-carboxamide;

(2S,3R,11aS)—N-[(2,4-Difluorophenyl)methyl]-6-hydroxy-5,7-dioxo-2,3-diphenyl-2,3,5,7,11,11a-hexahydro[1,3]oxazolo[3,2-a]pyrido[1,2-d]pyrazine-8-carboxamide;

(2S,3R,11aR)—N-[(2,4-difluorophenyl)methyl]-6-hydroxy-5,7-dioxo-2,3-diphenyl-2,3,5,7,11,11a-hexahydro[1,3]oxazolo[3,2-a]pyrido[1,2-d]pyrazine-8-carboxamide;

(3R,11aS)—N-[(2,4-Difluorophenyl)methyl]-6-hydroxy-3-(1-methylethyl)-5,7-dioxo-2,3,5,7,11,11a-hexahydro[1,3]oxazolo[3,2-a]pyrido[1,2-d]pyrazine-8-carboxamide;

(3S,11aR)—N-[(2,4-Difluorophenyl)methyl]-6-hydroxy-3-[2-(methylthio)ethyl]-5,7-dioxo-2,3,5,7,11,11a-hexahydro[1,3]oxazolo[3,2-a]pyrido[1,2-d]pyrazine-8-carboxamide;

(3S,11aR)—N-[(2,4-Difluorophenyl)methyl]-6-hydroxy-3-[2-(methylsulfonyl)ethyl]-5,7-dioxo-2,3,5,7,11,11a-hexahydro[1,3]oxazolo[3,2-a]pyrido[1,2-d]pyrazine-8-carboxamide;

(3S,11aR)—N-[(2,4-Difluorophenyl)methyl]-6-hydroxy-3-(1H-indol-3-ylmethyl)-5,7-dioxo-2,3,5,7,11,11a-hexahydro[1,3]oxazolo[3,2-a]pyrido[1,2-d]pyrazine-8-carboxamide;

(4R,12aR)—N-[(4-fluorophenyl)methyl]-7-hydroxy-4-methyl-1-(2-methylpropyl)-6,8-dioxo-1,2,3,4,6,8,12,12a-octahydropyrido[1',2':4,5]pyrazino[1,2-a]pyrimidine-9-carboxamide;

(4R,12aR)—N-[(4-Fluorophenyl)methyl]-7-hydroxy-4-methyl-1-(1-methylpropyl)-6,8-dioxo-1,2,3,4,6,8,12,12a-octahydropyrido[1',2':4,5]pyrazino[1,2-a]pyrimidine-9-carboxamide;

(4S,12aS)—N-[(2,4-Difluorophenyl)methyl]-7-hydroxy-4-methyl-1-(2-methylpropyl)-6,8-dioxo-1,2,3,4,6,8,12,12a-octahydropyrido[1',2':4,5]pyrazino[1,2-a]pyrimidine-9-carboxamide;

(4S,12aS)-1-(Cyclopropylmethyl)-N-[(2,4-difluorophenyl)methyl]-7-hydroxy-4-methyl-6,8-dioxo-1,2,3,4,6,8,12,12a-octahydropyrido[1',2':4,5]pyrazino[1,2-a]pyrimidine-9-carboxamide;

(4S,12aS)—N-[(2,4-Difluorophenyl)methyl]-1-(2-furanylmethyl)-7-hydroxy-4-methyl-6,8-dioxo-1,2,3,4,6,8,12,12a-octahydropyrido[1',2':4,5]pyrazino[1,2-a]pyrimidine-9-carboxamide;

(4S,12aS)—N-[(2,4-Difluorophenyl)methyl]-7-hydroxy-4-methyl-6,8-dioxo-1-(1,3-thiazol-2-ylmethyl)-1,2,3,4,6,8,12,12a-octahydropyrido[1',2':4,5]pyrazino[1,2-a]pyrimidine-9-carboxamide;

(4aR,6aR,14aS)—N-[(2,4-Difluorophenyl)methyl]-12-hydroxy-11,13-dioxo-1,3,4,4a,5,6a,7,11,13,14a-decahydro-2H-pyrido[1',2':4,5]pyrazino[1,2-a][3,1]benzoxazine-10-carboxamide;

(4aR,6aR,14aS)—N-[(4-Fluorophenyl)methyl]-12-hydroxy-11,13-dioxo-1,3,4,4a,5,6a,7,11,13,14a-decahydro-2H-pyrido[1',2':4,5]pyrazino[1,2-a][3,1]benzoxazine-10-carboxamide;

(3S,4aR,6aR,14aS)—N-[(2,4-Difluorophenyl)methyl]-12-hydroxy-11,13-dioxo-3-phenyl-1,3,4,4a,5,6a,7,11,13,14a-decahydro-2H-pyrido[1',2':4,5]pyrazino[1,2-a][3,1]benzoxazine-10-carboxamide;

(4aS,6aS,14aS)—N-[(2,4-Difluorophenyl)methyl]-12-hydroxy-6-(2-methylpropyl)-11,13-dioxo-1,2,3,4,4a,5,6,6a,7,11,13,14a-dodecahydropyrido[1',2':4,5]pyrazino[1,2-a]quinazoline-10-carboxamide;

(6aR,7aS,11aS)—N-[(2,4-Difluorophenyl)methyl]-1-hydroxy-2,13-dioxo-2,6a,7,7a,8,9,10,11,11a,13-decahydro-6H-pyrido[1',2':4,5]pyrazino[1,2-a]benzimidazole-3-carboxamide;

(6aS,7aS,11aS)—N-[(2,4-Difluorophenyl)methyl]-1-hydroxy-2,13-dioxo-2,6a,7,7a,8,9,10,11,11a,13-decahydro-6H-pyrido[1',2':4,5]pyrazino[1,2-a]benzimidazole-3-carboxamide;

(5aS,14aS)—N-[(2,4-Difluorophenyl)methyl]-11-hydroxy-10,12-dioxo-1,2,3,4,5a,6,10,12,14,14a-decahydropyrido[1,2-a]pyrido[1',2':3,4]imidazo[1,2-d]pyrazine-9-carboxamide;

(4aR,14aR)—N-[(2,4-Difluorophenyl)methyl]-9-hydroxy-8,10-dioxo-2,3,4,4a,5,6,8,10,14,14a-decahydro-1H-pyrido[1,2-c]pyrido[1',2':4,5]pyrazino[1,2-a]pyrimidine-11-carboxamide;

(4R,12aR)—N-[(2,4-Difluorophenyl)methyl]-7-hydroxy-4-methyl-1-(3-methylbutyl)-6,8-dioxo-1,2,3,4,6,8,12,12a-octahydropyrido[1',2':4,5]pyrazino[1,2-a]pyrimidine-9-carboxamide;

(4S,12aS)—N-[(2,4-Difluorophenyl)methyl]-7-hydroxy-4-methyl-1-(1-methylethyl)-6,8-dioxo-1,2,3,4,6,8,12,12a-octahydropyrido[1',2':4,5]pyrazino[1,2-a]pyrimidine-9-carboxamide;

(4S,12aS)—N-[(2,4-Difluorophenyl)methyl]-7-hydroxy-4-methyl-1-(3-methylbutyl)-6,8-dioxo-1,2,3,4,6,8,12,12a-octahydropyrido[1',2':4,5]pyrazino[1,2-a]pyrimidine-9-carboxamide;

(4S,12aS)—N-[(2,4-Difluorophenyl)methyl]-7-hydroxy-4-methyl-6,8-dioxo-1-(3-pyridinylmethyl)-1,2,3,4,6,8,12,12a-octahydropyrido[1',2':4,5]pyrazino[1,2-a]pyrimidine-9-carboxamide;

(4S,12aS)-1-Cyclopropyl-N-[(2,4-difluorophenyl)methyl]-7-hydroxy-4-methyl-6,8-dioxo-1,2,3,4,6,8,12,12a-octahydropyrido[1',2':4,5]pyrazino[1,2-a]pyrimidine-9-carboxamide;

(4S,12aS)—N-[(2,4-Difluorophenyl)methyl]-7-hydroxy-4-methyl-1-[2-(methyloxy)ethyl]-6,8-dioxo-1,2,3,4,6,8,12,12a-octahydropyrido[1',2':4,5]pyrazino[1,2-a]pyrimidine-9-carboxamide;

(3aS,5aS,13aS)—N-[(2,4-Difluorophenyl)methyl]-11-hydroxy-5-(2-methylpropyl)-10,12-dioxo-2,3,3a,4,5,5a,6,10,12,13a-decahydro-1H-cyclopenta[e]pyrido[1',2':4,5]pyrazino[1,2-a]pyrimidine-9-carboxamide;

(3R,11aS)—N-[(2,4-Difluorophenyl)methyl]-3-ethyl-6-hydroxy-5,7-dioxo-2,3,5,7,11,11a-hexahydro[1,3]oxazolo[3,2-a]pyrido[1,2-d]pyrazine-8-carboxamide;

(4aS,6aS,14aS)—N-[(2,4-Difluorophenyl)methyl]-12-hydroxy-6-[2-(4-morpholinyl)ethyl]-11,13-dioxo-1,2,3,4,4a,5,6,6a,7,11,13,14a-dodecahydropyrido[1',2':4,5]pyrazino[1,2-a]quinazoline-10-carboxamide;

(3aR,5aR,13aS)—N-[(2,4-Difluorophenyl)methyl]-11-hydroxy-10,12-dioxo-1,2,3,3a,4,5a,6,10,12,13a-decahydrocyclopenta[d]pyrido[1',2':4,5]pyrazino[2,1-b][1,3]oxazine-9-carboxamide;

(4aS,6aS,14aS)—N-[(2,4-Difluorophenyl)methyl]-12-hydroxy-6-methyl-11,13-dioxo-1,2,3,4,4a,5,6,6a,7,11,13,14a-dodecahydropyrido[1',2':4,5]pyrazino[1,2-a]quinazoline-10-carboxamide;

(4aS,6aS,14aS)—N-[(2,4-Difluorophenyl)methyl]-12-hydroxy-6-[2-(methyloxy)ethyl]-11,13-dioxo-1,2,3,4,4a,5,6,6a7,11,13,14a-dodecahydropyrido[1',2':4,5]pyrazino[1,2-a]quinazoline-10-carboxamide;

(4aS,6aS,14aS)-6-[2-(Acetylamino)ethyl]-N-[(2,4-difluorophenyl)methyl]-12-hydroxy-11,13-dioxo-1,2,3,4,4a,5,6,6a,7,11,13,14a-dodecahydropyrido[1',2':4,5]pyrazino[1,2-a]quinazoline-10-carboxamide;

(3S,11aR)—N-[(2,4-Difluorophenyl)methyl]-3-ethyl-6-hydroxy-5,7-dioxo-2,3,5,7,11,11a-hexahydro[1,3]oxazolo[3,2-a]pyrido[1,2-d]pyrazine-8-carboxamide;

(3S,11aR)-3-Butyl-N-[2,4-difluorophenyl)methyl]-6-hydroxy-5,7-dioxo-2,3,5,7,11,11a-hexahydro[1,3]oxazolo[3,2-a]pyrido[1,2-d]pyrazine-8-carboxamide;

(3S,11aR)—N-[(2,4-Difluorophenyl)methyl]-6-hydroxy-3-[(4-hydroxyphenyl)methyl]-5,7-dioxo-2,3,5,7,11,11a-hexahydro[1,3]oxazolo[3,2-a]pyrido[1,2-d]pyrazine-8-carboxamide (4S,12aS)-1-Cyclobutyl-N-[(2,4-difluorophenyl)methyl]-7-hydroxy-4-methyl-6,8-dioxo-1,2,3,4,6,8,12,12a-octahydropyrido[1',2':4,5]pyrazino[1,2-a]pyrimidine-9-carboxamide;

(4S,12aS)—N-[(2,4-Difluorophenyl)methyl]-7-hydroxy-4-methyl-6,8-dioxo-1-(tetrahydro-2H-thiopyran-4-yl)-1,2,3,4,6,8,12,12a-octahydropyrido[1',2':4,5]pyrazino[1,2-a]pyrimidine-9-carboxamide;

(4S,12aS)—N-[(2,4-Difluorophenyl)methyl]-7-hydroxy-1,4-bis(2-methylpropyl)-6,8-dioxo-1,2,3,4,6,8,12,12a-octahydropyrido[1',2':4,5]pyrazino[1,2-a]pyrimidine-9-carboxamide;

(4aS,6aS,14aS)—N-[(2,4-Difluorophenyl)methyl]-12-hydroxy-6-(2-hydroxyethyl)-11,13-dioxo-1,2,3,4,4a,5,6,6a,7,11,13,14a-dodecahydropyrido[1',2':4,5]pyrazino[1,2-a]quinazoline-10-carboxamide;

(4aS,6aS,14aS)-6-Cyclopropyl-N-[(2,4-difluorophenyl)methyl]-12-hydroxy-11,13-dioxo-1,2,3,4,4a,5,6,6a,7,11,13,14a-dodecahydropyrido[1',2':4,5]pyrazino[1,2-a]quinazoline-10-carboxamide;

(4aS,6aS,14aS)—N-[(2,4-Difluorophenyl)methyl]-12-hydroxy-11,13-dioxo-6-[2-(1-pyrrolidinyl)ethyl]-1,2,3,4,4a,5,6,6a,7,11,13,14a-dodecahydropyrido[1',2':4,5]pyrazino[1,2-a]quinazoline-10-carboxamide;

(4aS,14aS)—N-[(2,4-Difluorophenyl)methyl]-9-hydroxy-8,10-dioxo-2,3,4,4a,5,6,8,10,14,14a-decahydro-1H-pyrido[1,2-c]pyrido[1',2':4,5]pyrazino[1,2-a]pyrimidine-11-carboxamide;

(4S,12aS)—N-[(4-Fluorophenyl)methyl]-7-hydroxy-4-methyl-1-[2-(methyloxy)ethyl]-6,8-dioxo-1,2,3,4,6,8,12,12a-octahydropyrido[1',2':4,5]pyrazino[1,2-a]pyrimidine-9-carboxamide;

(4S,12aS)-1-Cyclobutyl-N-[(4-fluorophenyl)methyl]-7-hydroxy-4-methyl-6,8-dioxo-1,2,3,4,6,8,12,12a-octahydropyrido[1',2':3,4]pyrazino[1,2-a]pyrimidine-9-carboxamide;

(4S,12aS)—N-[(4-Fluorophenyl)methyl]-7-hydroxy-4-methyl-1-(2-methylpropyl)-6,8-dioxo-1,2,3,4,6,8,12,12a-octahydropyrido[1',2':4,5]pyrazino[1,2-a]pyrimidine-9-carboxamide;

(4S,12aS)—N-[(4-Fluorophenyl)methyl]-7-hydroxy-1,4-dimethyl-6,8-dioxo-1,2,3,4,6,8,12,12a-octahydropyrido[1',2':4,5]pyrazino[1,2-a]pyrimidine-9-carboxamide;

(4S,12aS)—N-[(4-Fluorophenyl)methyl]-7-hydroxy-4-methyl-6,8-dioxo-1-(tetrahydro-2H-thiopyran-4-yl)-1,2,3,4,6,8,12,12a-octahydropyrido[1',2':4,5]pyrazino[1,2-a]pyrimidine-9-carboxamide;

(4S,12aS)—N-[(2,4-Difluorophenyl)methyl]-7-hydroxy-1,4-dimethyl-6,8-dioxo-1,2,3,4,6,8,12,12a-octahydropyrido[1',2':4,5]pyrazino[1,2-a]pyrimidine-9-carboxamide;

(4S,12aS)—N-[(4-Fluorophenyl)methyl]-7-hydroxy-4-methyl-1-(1-methylethyl)-6,8-dioxo-1,2,3,4,6,8,12,12a-octahydropyrido[1',2':4,5]pyrazino[1,2-a]pyrimidine-9-carboxamide;

(4S,12aS)—N-[(4-Fluorophenyl)methyl]-7-hydroxy-1,4-bis(2-methylpropyl)-6,8-dioxo-1,2,3,4,6,8,12,12a-octahydropyrido[1',2':4,5]pyrazino[1,2-a]pyrimidine-9-carboxamide;

enantiomers thereof; diastereomers thereof; mixtures of enantiomers thereof; mixtures of diastereomers thereof; mixtures of enantiomers and diastereomers thereof; and pharmaceutically acceptable salts thereof.

(32) A compound selected from the group consisting of:

(4aS,13aR)—N-[(2,4-Difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide;

(4aS,13aR)—N-[(4-Fluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide;

(3S,11aR)—N-[(2,4-Difluorophenyl)methyl]-6-hydroxy-3-[(1S)-1-methylpropyl]-5,7-dioxo-2,3,5,7,11,11a-hexahydro[1,3]oxazolo[3,2-a]pyrido[1,2-d]pyrazine-8-carboxamide;

(3S,11aR)—N-[(2,4-Difluorophenyl)methyl]-6-hydroxy-3-methyl-5,7-dioxo-2,3,5,7,11,11a-hexahydro[1,3]oxazolo[3,2-a]pyrido[1,2-d]pyrazine-8-carboxamide;

(3S,11aR)—N-[(4-Fluorophenyl)methyl]-6-hydroxy-3-methyl-5,7-dioxo-2,3,5,7,11,11a-hexahydro[1,3]oxazolo[3,2-a]pyrido[1,2-d]pyrazine-8-carboxamide;

(4S,12aS)—N-[(2,4-Difluorophenyl)methyl]-7-hydroxy-4-methyl-1-(2-methylpropyl)-6,8-dioxo-1,2,3,4,6,8,12,12a-octahydropyrido[1',2':4,5]pyrazino[1,2-a]pyrimidine-9-carboxamide;

(4S,12aS)-1-(Cyclopropylmethyl)-N-[(2,4-difluorophenyl)methyl]-7-hydroxy-4-methyl-6,8-dioxo-1,2,3,4,6,8,12,12a-octahydropyrido[1',2':4,5]pyrazino[1,2-a]pyrimidine-9-carboxamide;

(4aR,6aR,14aS)—N-[(2,4-Difluorophenyl)methyl]-12-hydroxy-11,13-dioxo-1,3,4,4a,5,6a,7,11,13,14a-decahydro-2H-pyrido[1',2':4,5]pyrazino[1,2-a][3,1]benzoxazine-10-carboxamide;

(4aR,6aR,14aS)—N-[(4-Fluorophenyl)methyl]-12-hydroxy-11,13-dioxo-1,3,4,4a,5,6a,7,11,13,14a-decahydro-2H-pyrido[1',2':4,5]pyrazino[1,2-a][3,1]benzoxazine-10-carboxamide (4S,9aR)-5-Hydroxy-4-methyl-6,10-dioxo-3,4,6,9,9a,10-hexahydro-2H-1-oxa-4a,8a-diaza-anthracene-7-carboxylic acid 2,4-difluorobenzylamide;

(4R,9aS)-5-Hydroxy-4-methyl-6,10-dioxo-3,4,6,9,9a,10-hexahydro-2H-1-oxa-4a,8a-diaza-anthracene-7-carboxylic acid 2,4-difluorobenzylamide;

(2R,9aS)-5-Hydroxy-2-methyl-6,10-dioxo-3,4,6,9,9a,10-hexahydro-2H-1-oxa-4a,8a-diaza-anthracene-7-carboxylic acid 4 fluoro-benzylamide;

enantiomers thereof; diastereomers thereof, mixtures of enantiomers thereof; mixtures of diastereomers thereof; mixtures of enantiomers and diastereomers thereof; and pharmaceutically acceptable salts thereof.

(33) A compound according to the above (31) or (32) wherein the pharmaceutically acceptable salt is a sodium salt.

(34) A pharmaceutical composition comprising a compound according to any one of the above (1) to (33), or a pharmaceutically acceptable salt, or solvate thereof.

(35) A pharmaceutical composition according to the above (34), which is an anti-HIV agent.

(36) A process for the preparation of a compound of formula (I-20a)

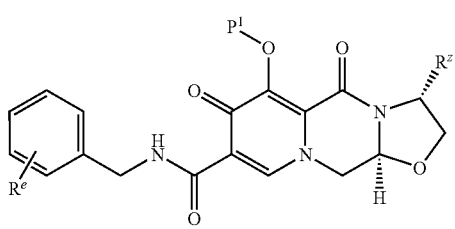

wherein $R^e$ is one or two halogen; $R^z$ is $C_{1-8}$alkyl, $C_{6-14}$aryl$C_{1-8}$alkyl, $C_{6-14}$aryl, or alkoxy; and $P^1$ is $C_{6-14}$aryl$C_{1-8}$alkyl;

comprising condensing a compound of the formula

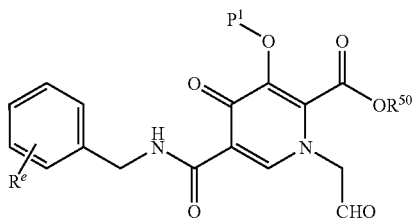

wherein $R^e$ is one or two halogen; $R^{50}$ is $C_{1-8}$alkyl; and $P^1$ is $C_{6-14}$aryl$C_{1-8}$alkyl;

with a compound of the formula

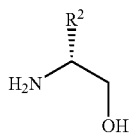

wherein $R^z$ is $C_{1-8}$alkyl, $C_{6-14}$aryl$C_{1-8}$alkyl, $C_{6-14}$aryl, or alkoxy;

to form a compound of formula (I-20a).

(37) A process for the preparation of a compound of formula (I-20b)

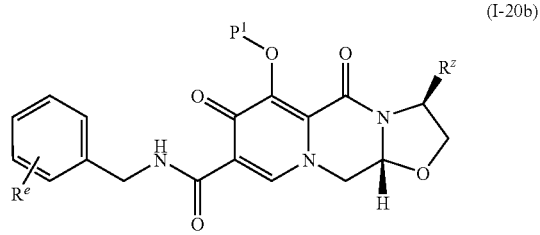

wherein $R^e$ is one or two halogen; $R^z$ is $C_{1-8}$alkyl, $C_{6-14}$aryl$C_{1-8}$alkyl, $C_{6-14}$aryl, or alkoxy; and $P^1$ is $C_{6-14}$aryl$C_{1-8}$alkyl;

comprising condensing a compound of the formula

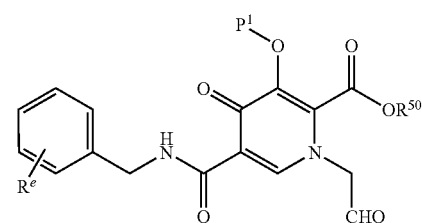

wherein $R^e$ is one or two halogen; $R^{50}$ is $C_{1-8}$alkyl; and $P^1$ is $C_{6-14}$aryl$C_{1-8}$alkyl;

with a compound of the formula

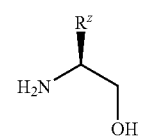

wherein $R^z$ is $C_{1-8}$alkyl, $C_{6-14}$aryl$C_{1-8}$alkyl, $C_{6-14}$aryl, or alkoxy;

to form a compound of formula (I-20b).

(38) A process for the preparation of a compound of formula (I-21a)

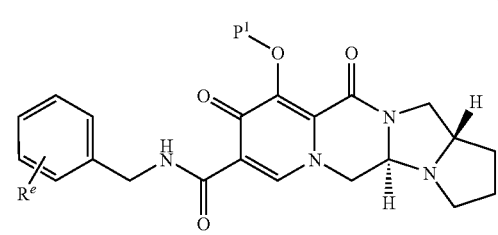

wherein $R^e$ is one or two halogen; and $P^1$ is $C_{6-14}$aryl $C_{1-8}$alkyl;

comprising condensing a compound of the formula

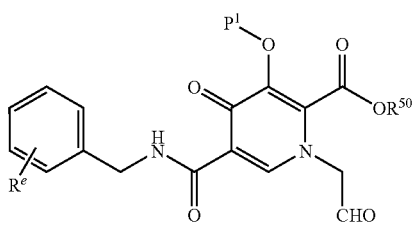

wherein $R^e$ is one or two halogen; $R^{50}$ is $C_{1-8}$alkyl; and $P^1$ is $C_{6-14}$aryl$C_{1-8}$alkyl;
with a compound of the formula

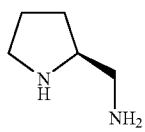

to form a compound of formula (I-21a).

(39) A process for the preparation of a compound of formula (I-21b)

(I-21b)

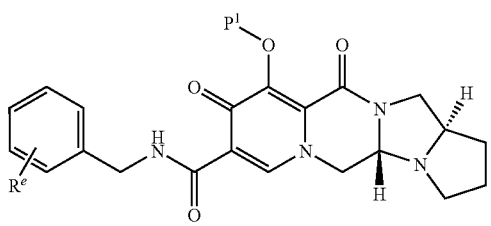

wherein $R^e$ is one or two halogen; and $P^1$ is $C_{6-14}$aryl $C_{1-8}$alkyl;
comprising condensing a compound of the formula

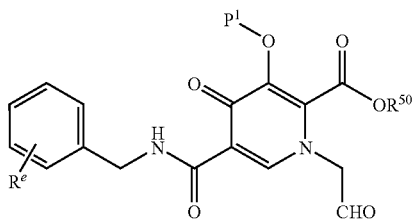

wherein $R^e$ is one or two halogen; $R^{50}$ is $C_{1-8}$alkyl; and $P^1$ is $C_{6-14}$aryl$C_{1-8}$alkyl;
with a compound of the formula

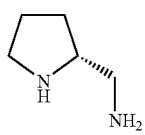

to form a compound of formula (I-21b).

(40) A process for the preparation of a compound of formula (I-22a)

(I-22a)

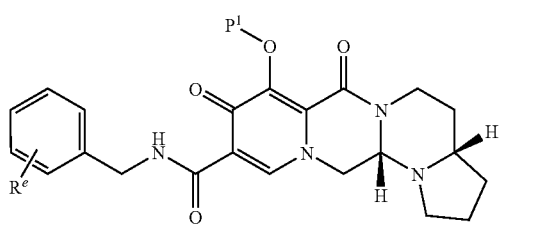

wherein $R^e$ is one or two halogen; and $P^1$ is $C_{6-14}$aryl $C_{1-8}$alkyl;
comprising condensing a compound of the formula

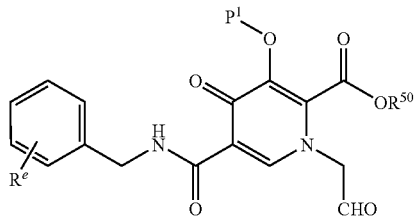

wherein $R^e$ is one or two halogen; $R^{50}$ is $C_{1-8}$alkyl; and $P^1$ is $C_{6-14}$aryl$C_{1-8}$alkyl;
with a compound of the formula

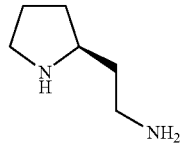

to form a compound of formula (I-22a).

(41) A process for the preparation of a compound of formula (I-22b)

(I-22b)

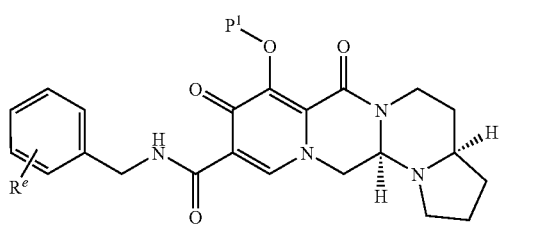

wherein $R^e$ is one or two halogen; and $P^1$ is $C_{6-14}$aryl $C_{1-8}$alkyl;

comprising condensing a compound of the formula

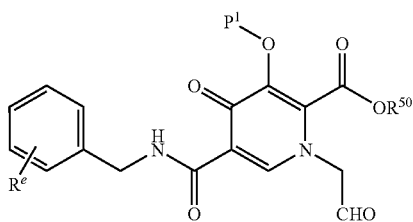

wherein $R^e$ is one or two halogen; $R^{50}$ is $C_{1-8}$alkyl; and $P^1$ is $C_{6-14}$aryl$C_{1-8}$alkyl;
with a compound of the formula

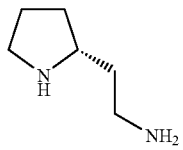

to form a compound of formula (I-22b).

(42) A process for the preparation of a compound of formula (I-23a)

(I-23a)

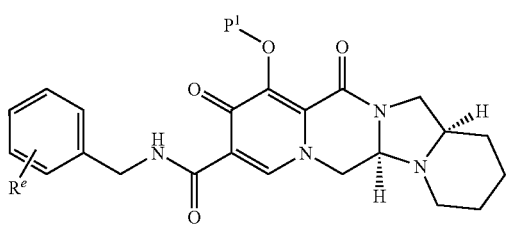

wherein $R^e$ is one or two halogen; and $P^1$ is $C_{6-14}$aryl $C_{1-8}$alkyl;
comprising condensing a compound of the formula

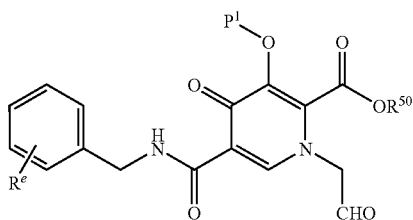

wherein $R^e$ is one or two halogen; $R^{50}$ is $C_{1-8}$alkyl; and $P^1$ is $C_{6-14}$aryl$C_{1-8}$alkyl;
with a compound of the formula

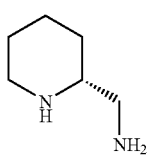

to form a compound of formula (I-23a).

(43) A process for the preparation of a compound of formula (I-23b)

(I-23b)

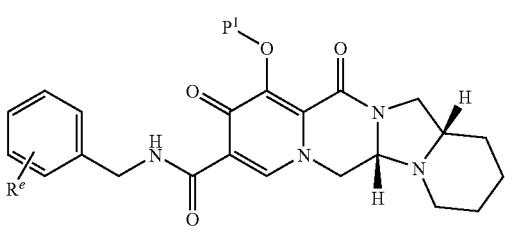

wherein $R^e$ is one or two halogen; and $P^1$ is $C_{6-14}$aryl $C_{1-8}$alkyl;
comprising condensing a compound of the formula

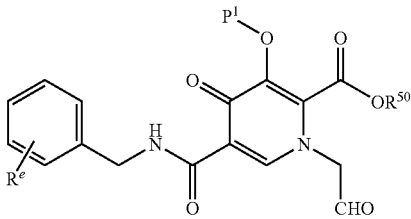

wherein $R^e$ is one or two halogen; $R^{50}$ is $C_{1-8}$alkyl;
with a compound of the formula

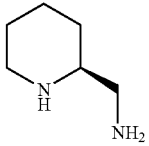

to form a compound of formula (I-23b).

(44) A process for the preparation of a compound of formula (I-24a)

(I-24a)

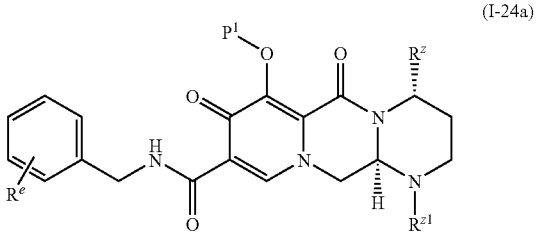

wherein $R^e$ is one or two halogen; $R^z$ is $C_{1-8}$alkyl; $R^{z1}$ is hydrogen, $C_{3-6}$cycloalkyl, heterocycle, or $C_{1-8}$alkyl optionally substituted with hydroxy, $C_{3-6}$cycloalkyl, alkoxy, heterocycle, heteroaryl, $C_{6-14}$aryl, or amino, wherein said amino may be optionally substituted with —C(O)$C_{1-8}$alkyl or $C_{1-8}$alkyl; and $P^1$ is $C_{6-14}$aryl$C_{1-8}$alkyl;

comprising condensing a compound of the formula

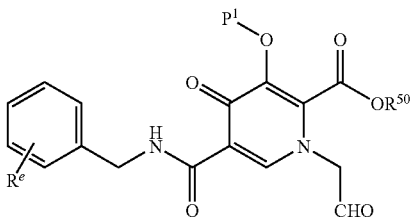

wherein $R^e$ is one or two halogen; and $R^{50}$ is $C_{1-8}$alkyl; and $P^1$ is $C_{6-14}$aryl$C_{1-8}$alkyl;
with a compound of the formula

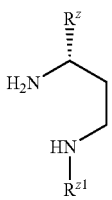

wherein $R^z$ is $C_{1-8}$alkyl; $R^{z1}$ is hydrogen, $C_{3-6}$cycloalkyl, heterocycle, or $C_{1-8}$alkyl optionally substituted with hydroxy, $C_{3-6}$cycloalkyl, alkoxy, heterocycle, heteroaryl, $C_{6-14}$aryl, or amino, wherein said amino may be optionally substituted with —C(O)$C_{1-8}$alkyl or $C_{1-8}$alkyl;
to form a compound of the formula (I-24a).

(45) A process for the preparation of a compound of formula (I-24b)

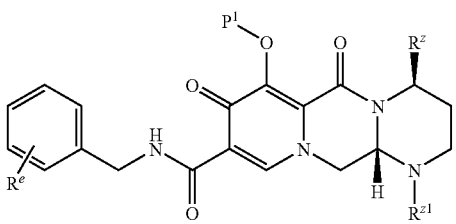

(I-24b)

wherein $R^e$ is one or two halogen; $R^z$ is $C_{1-8}$alkyl; $R^{z1}$ is hydrogen, $C_{3-6}$cycloalkyl, heterocycle, or $C_{1-8}$alkyl optionally substituted with hydroxy, $C_{3-6}$cycloalkyl, alkoxy, heterocycle, heteroaryl, $C_{6-14}$aryl, or amino, wherein said amino may be optionally substituted with —C(O)$C_{1-8}$alkyl or $C_{1-8}$alkyl; and $P^1$ is $C_{6-14}$aryl$C_{1-8}$alkyl;
comprising condensing a compound of the formula

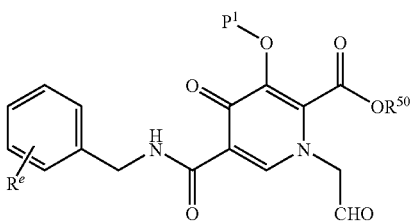

wherein $R^e$ is one or two halogen; $R^{50}$ is $C_{1-8}$alkyl; and $P^1$ is $C_{6-14}$aryl$C_{1-8}$alkyl;

with a compound of the formula

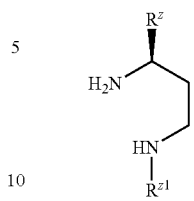

wherein $R^z$ is $C_{1-8}$alkyl; and $R^{z1}$ is hydrogen, $C_{3-6}$cycloalkyl, heterocycle, or $C_{1-8}$alkyl optionally substituted with hydroxy, $C_{3-6}$cycloalkyl, alkoxy, heterocycle, heteroaryl, $C_{6-14}$aryl, or amino, wherein said amino may be optionally substituted with —C(O)$C_{1-8}$alkyl or $C_{1-8}$alkyl;
to form a compound of the formula (I-24b).

(46) A process for the preparation of a racemic compound of formula (I-25)

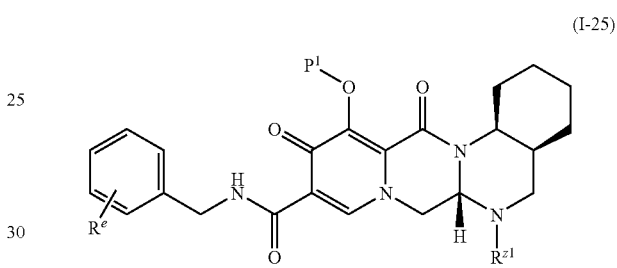

(I-25)

wherein $R^e$ is one or two halogen; $R^{z1}$ is hydrogen, $C_{3-6}$cycloalkyl, heterocycle, or $C_{1-8}$alkyl optionally substituted with hydroxy, $C_{3-6}$cycloalkyl, alkoxy, heterocycle, heteroaryl, $C_{6-14}$aryl, or amino, wherein said amino may be optionally substituted with —C(O)$C_{1-8}$alkyl or $C_{1-8}$alkyl; and $P^1$ is $C_{6-14}$aryl$C_{1-8}$alkyl;
comprising condensing a compound of the formula

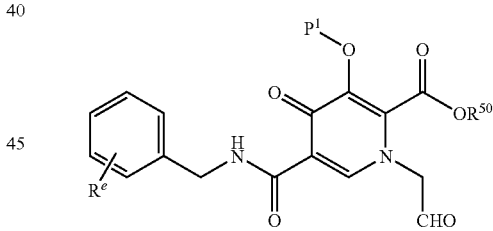

wherein $R^e$ is one or two halogen; and $R^{50}$ is $C_{1-8}$alkyl; and $P^1$ is $C_{6-14}$aryl$C_{1-8}$alkyl;
with a racemic compound of the formula

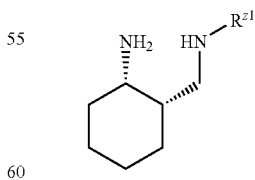

wherein $R^{z1}$ is hydrogen, $C_{3-6}$cycloalkyl, heterocycle, or $C_{1-8}$alkyl optionally substituted with hydroxy, $C_{3-6}$cycloalkyl, alkoxy, heterocycle, heteroaryl, $C_{6-14}$aryl, or amino, wherein said amino may be optionally substituted with —C(O)$C_{1-8}$alkyl or $C_{1-8}$alkyl;
to form a racemic compound of the formula (I-25).

(47) A process for the preparation of a racemic compound of formula (I-26)

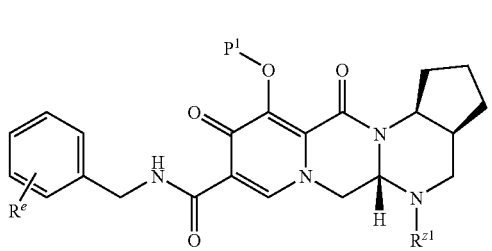

(I-26)

wherein $R^e$ is one or two halogen; $R^{z1}$ is hydrogen, $C_{3-6}$cycloalkyl, heterocycle, or $C_{1-8}$alkyl optionally substituted with hydroxy, $C_{3-6}$cycloalkyl, alkoxy, heterocycle, heteroaryl, $C_{6-14}$aryl, or amino, wherein said amino may be optionally substituted with —C(O)$C_{1-8}$alkyl or $C_{1-8}$alkyl; and $P^1$ is $C_{6-14}$aryl$C_{1-8}$alkyl;
comprising condensing a compound of the formula

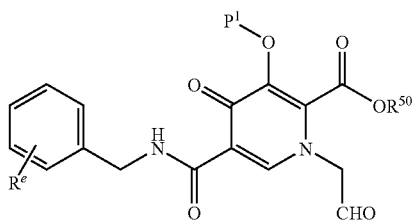

wherein $R^e$ is one or two halogen; $R^{50}$ is $C_{1-8}$alkyl; and $P^1$ is $C_{6-14}$aryl$C_{1-8}$alkyl;
with a racemic compound of the formula

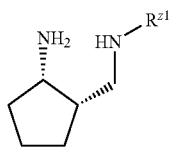

wherein $R^{z1}$ is hydrogen, $C_{3-6}$cycloalkyl, heterocycle, or $C_{1-8}$alkyl optionally substituted with hydroxy, $C_{3-6}$cycloalkyl, alkoxy, heterocycle, heteroaryl, $C_{6-14}$aryl, or amino, wherein said amino may be optionally substituted with —C(O)$C_{1-8}$alkyl or $C_{1-8}$alkyl;
to form a racemic compound of formula (I-26).

(48) A process for the preparation of a racemic compound of formula (I-27)

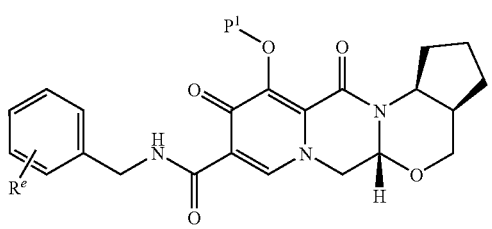

(I-27)

wherein $R^e$ is halogen; and $P^1$ is $C_{6-14}$aryl$C_{1-8}$alkyl;
comprising condensing a compound of the formula

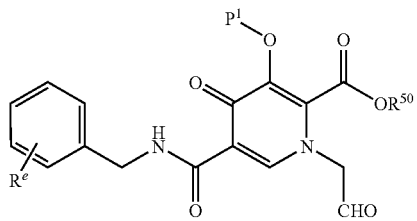

wherein $R^e$ is one or two halogen: $R^{50}$ is $C_{1-8}$alkyl; and $P^1$ is $C_{6-14}$aryl$C_{1-8}$alkyl;
with a racemic compound of the formula

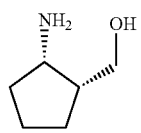

to form a racemic compound of formula (I-27).

(49). A compound of formula (I-20a) described in above (36), formula (I-20b) described in above (37), formula (I-21a) described in above (38), formula (I-21b) described in above (39), formula (I-22a) described in above (40), formula (I-22b) described in above (41), formula (I-23a) described in above (42), formula (I-23b) described in above (43), formula (I-24a) described in above (44), formula (I-24b) described in above (45), formula (I-25) described in above (46), formula (I-26) described in above (47), or formula (I-27) described in above (48), or a pharmaceutically acceptable salt thereof.

(50) A compound of formula (I-20a) described in above (36), formula (I-20b) described in above (37), formula (I-21a) described in above (38), formula (I-21b) described in above (39), formula (I-22a) described in above (40), formula (I-22b) described in above (41), formula (I-23a) described in above (42), formula (I-23b) described in above (43), formula (I-24a) described in above (44), formula (I-24b) described in above (45), formula (I-25) described in above (46), formula (I-26) described in above (47), or formula (I-27) described in above (48), or a pharmaceutically acceptable salt thereof, wherein each $P^1$ is hydrogen.

The present invention further provides a pharmaceutical composition containing any of the compounds shown above, a pharmaceutically acceptable salt or a solvate thereof, especially an anti-HIV agent.

DETAILED DESCRIPTION OF THE INVENTION

The present invention compounds possess an integrase inhibitory activity and/or a cell-growth inhibitory activity against virus, especially HIV. Accordingly, they are useful for the prevention or treatment of various diseases mediated by integrase or virus infection diseases (e.g., AIDS). The present invention further provides a process for preparing a diastereomer, a mixture thereof, or racemate.

PREFERRED EMBODIMENT OF THE INVENTION

The terms used herein are explained below. Each term, alone or in combination with another term, means as follows.

"Lower alkyl" means a straight or branched C1 to C10 alkyl such as methyl, ethyl, n-propyl, i-propyl, t-butyl, isobutyl, sec-butyl, n-pentyl, and n-hexyl, and preferred is C1 to C3 alkyl, more preferred is methyl, ethyl or n-propyl, n-pentyl, isopentyl, neopentyl, tert-pentyl, n-hexyl, isohexyl, n-heptyl, n-octyl, n-nonyl, and n-decyl, preferably C1 to C6 lower alkyl, more preferably C1 to C4 lower alkyl such as methyl, ethyl, n-propyl, isopropyl, n-butyl, isobutyl, sec-butyl, tert-butyl, n-pentyl, isopentyl, neopentyl, tert-pentyl, n-hexyl, and isohexyl.

"Lower alkenylene" means a straight or branched C2 to C6 alkenylene, which consists of the above "Lower alkylene" having one or more double bonds, such as vinylene, propylene, or butenylene, preferably a straight C2 to C3 alkenylene such as vinylene or propylene.

"Lower alkyl" means a straight or branched C1 to C10 alkyl such as methyl, ethyl, n-propyl, i-propyl, t-butyl, isobutyl, sec-butyl, n-pentyl, and n-hexyl, and preferred is C1 to C3 alkyl, more preferred is methyl, ethyl or n-propyl, n-pentyl, isopentyl, neopentyl, tert-pentyl, n-hexyl, isohexyl, n-heptyl, n-octyl, n-nonyl, and n-desyl, preferably C1 to C6 lower alkyl, more preferably C1 to C4 lower alkyl such as methyl, ethyl, n-propyl, isopropyl, n-butyl, isobutyl, sec-butyl, tert-butyl, n-pentyl, isopentyl, neopentyl, tert-pentyl, n-hexyl, and isohexyl.

When lower alkyl is intervened with "—N=" or "=N—", the lower alkyl may have a double bond to form —CH$_2$—N=CH$_2$, —CH=N—CH$_3$ etc.

"Alkenyl" means a straight or branched C2 to C8 alkenyl, which consists of the above "alkyl" having one or more double bonds, such as vinyl, 1-propenyl, 2-propenyl, 1-butenyl, 2-butenyl, 3-butenyl, 1,3-butadienyl, and 3-methyl-2-butenyl, preferably C2 to C6 alkenyl, and more preferably C2 to C4 alkenyl.

"Lower alkenyloxy" means oxy attached to the above lower alkenyl, such as vinyloxy, 1-propenyloxy, 2-propenyloxy, 1-butenyloxy, 2-butenyloxy, 3-butenyloxy, 1,3-butadienyloxy, and 3-methyl-2-butenyloxy.

"Cycloalkyl" means C3 to C8 cyclic saturated hydrocarbon, such as cyclopropyl, cyclobutyl, cyclopentyl, cyclohexyl, cyclopentyl, and cyclooctyl, preferably C3 to C6 cycloalkyl.

"Cycloalkyl lower alkyl" means lower alkyl substituted with the above cycloalkyl, such as cyclopropylmethyl, cyclopropylethyl, cyclobutylmethyl, cyclopentylmethyl, cyclohexylmethyl, and cyclohexylethyl, and preferably C3 to C6 cycloalkyl lower alkyl.

"Aryl" means monocyclic aromatic hydrocarbon (e.g., phenyl) and polycyclic hydrocarbon (e.g., 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl), preferably phenyl or naphthyl (e.g., 1-napthyl, 2-naphthyl).

"Aralkyl" or "aryl lower alkyl" means the above lower alkyl substituted with 1 to 3 of the above aryl, such as benzyl, diphenylmethyl, triphenylmethyl, phenethyl, 1-napthylmethyl, 2-napthylmethyl, preferably benzyl.

"Aryloxy" means oxy attached to the above aryl, such as 1-naphthyloxy, 2-naphthyloxy, 1-anthryloxy, 2-anthryloxy, 9-anthryloxy, 1-phenanthryloxy, 2-phenanthryloxy, 3-phenanthryloxy, 4-phenanthryloxy, and 9-phenanthryloxy, preferably phenyloxy or naphthyloxy (e.g., 1-napthyloxy, 2-naphthyloxy).

"Heterocyclic group" means "heteroring" or "heteroaryl".

"Heteroring" means a non-aromatic ring which has at least one of N, O and/or S in the ring and may be bonded at any substitutable position, preferably 5- to 7-membered ring, such as 1-pyrrolyl, 2-pyrrolyl, 3-pyrrolyl, 1-pyrrolidinyl, 2-pyrrolidinyl, 3-pyrrolidinyl, 1-imidazolyl, 2-imidazolyl, 4-imidazolyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, 1-piperadinyl, 2-piperadinyl, 2-morpholinyl, 3-morpholinyl, morpholino, and tetrahydropyranyl. The non-aromatic ring is a saturated or unsaturated ring.

"Heteroaryl" means monocyclic aromatic hetero-type ring or condensed aromatic hetero-type ring.

"Monocyclic aromatic hetero-type ring" means a 5- to 8-membered aromatic ring, which contains 1 to 4 of O, S, P and/or N and may be bonded at any substitutable position.

"Condensed aromatic hetero-type ring" means a group wherein an aromatic ring containing 1 to 4 of O, S, P and/or N is condensed with 1 to 4 of 5- to 8-membered aromatic ring(s) or the other 5- to 8-membered aromatic heteroring(s).

Examples of "heteroaryl" include furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazole-1-yl, 1,2,4-triazole-3-yl, 1,2,4-triazole-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridil (e.g., 2-pyridil, 3-pyridil, 4-pyridil), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazole-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzoimidazolyl (e.g., 1-benzoimidazolyl, 2-benzoimidazolyl, 4-benzoimidazolyl, 5-benzoimidazolyl), dibenzofuryl, benzooxazolyl, quinoxalinyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolinyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), purinyl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl) or phenothiadinyl (e.g., 1-phenothiadinyl, 2-phenothiadinyl, 3-phenothiadinyl, 4-phenothiadinyl).

"Heterocycle" means a cycle which can be lead to the above heterocyclic group.

"Heterocyclic group lower alkyl" or "Heterocycle lower alkyl" means lower alkyl substituted with the above heterocyclic group.

"Heterocyclic group oxy" or "Heterocycle oxy" means an oxy attached to the above heterocyclic group.

"Heterocyclic group carbonyl" or "Heterocyclecarbonyl" means a carbonyl attached to the above heterocyclic group "Lower alkoxy" or "alkoxy" means an oxy attached to the above lower alkyl, such as methoxy, ethoxy, n-propoxy, isopropoxy, n-butoxy, isobutoxy, tert-butoxy.

"Lower alkylcarbonyl", "cycloalkylcarbonyl", "cycloalkyl lower alkylcarbonyl", "lower alkoxycarbonyl", "arylcarbonyl", "aryl lower alkylcarbonyl", "aryloxycarbonyl", "heterocyclecarbonyl", "heterocycle lower alkylcarbonyl", and "heterocycle oxycarbonyl", each means a carbonyl attached to the above "lower alkyl", "cycloalkyl", "cycloalkyl lower alkyl", "lower alkoxy", "aryl", "aryl lower alkyl", "aryloxy", "heterocycle", "heterocycle lower alkyl", and "heterocycleoxy", respectively.

When a substituent(s) is/are present on "optionally substituted lower alkyl", "optionally substituted cycloalkyl", "optionally substituted cycloalkyl lower alkyl", "optionally substituted lower alkenyl", "optionally substituted lower alkoxy", "optionally substituted aryl", "optionally substituted aryl lower alkyl", "optionally substituted aryloxy", "optionally substituted aryloxy lower alkyl", "optionally substituted heterocyle, "optionally substituted heterocyclic group", "optionally substituted heterocycle lower alkyl", "optionally substituted heterocycleoxy", "optionally substituted lower alkenyloxy", "optionally substituted lower alkylcarbonyl", "optionally substituted cycloalkylcarbonyl", "optionally substituted cycloalkyl lower alkylcarbonyl", "optionally substituted lower alkoxycarbonyl", "optionally substituted arylcarbonyl", "optionally substituted aryl lower alkylcarbonyl", "optionally substituted aryloxycarbonyl", "optionally substituted heterocyclecarbonyl", "optionally substituted heterocycle lower alkylcarbonyl", "optionally substituted heterocycleoxycarbonyl", "optionally substituted lower alkylene", "optionally substituted lower alkenylene", "optionally substituted phosphoric acid residue", "optionally substituted carbocycle" or "optionally substituted heterocycle", each may be substituted with the same or different, 1 to 4 group(s) selected from Substituent group B at any position.

Examples of Substituent group B include hydroxy, carboxy, halogen (F, Cl, Br, I), halo lower alkyl (e.g., $CF_3$, $CH_2CF_3$, $CH_2CCl_3$), halo lower alkoxy (e.g., $OCF_3$, $OCH_2CF_3$, $OCH_2CCl_3$), lower alkyl (e.g., methyl, ethyl, isopropyl, tert-butyl), lower alkenyl (e.g., vinyl), lower alkynyl (e.g., ethynyl), cycloalkyl (e.g., cyclopropyl), cycloalkenyl (e.g., cyclopropenyl), lower alkoxy (e.g., methoxy, ethoxy, propoxy, butoxy), lower alkenyloxy (e.g., vinyloxy, allyloxy), lower alkoxycarbonyl (e.g., methoxycarbonyl, ethoxycarbonyl, tert-butoxycarbonyl), nitro, nitroso, optionally substituted amino (e.g., alkylamino (e.g., methylamino, ethylamino, dimethylamino), acylamino (e.g., acetylamino, benzoylamino), aralkylamino (e.g., benzylamino, tritylamino), hydroxyamino), azido, aryl (e.g., phenyl), aralkyl (e.g., benzyl), cyano, isocyano, isocyanate, thiocyanate, isothiocyanate, mercapt, alkylthio (e.g., methylthio), alkylsulfonyl (e.g., methansulfonyl, ethansulfonyl), optionally substituted alkylsulfonylamino (e.g., methanesulfonylamino, ethansulfonylamino, N-methylsulfonyl-N'-methylamino), optionally substituted carbamoyl (e.g., alkylcarbamoyl (e.g., methylcarbamoyl, ethylcarbamoyl, dimethylcarbamoyl)), sulfamoyl, acyl (e.g., formyl, acetyl), formyloxy, haloformyl, oxal, thioformyl, thiocarboxy, dithiocarboxy, thiocarbamoyl, sulfino, sulfo, sulfoamino, hydrazino, azido, ureido, amizino, quanidino, phthalimide, oxo, phosphoric acid residue, lower alkyl which is substituted with a phosphoric acid residue and may be intervened with a heteroatom group(s), aryl substituted with a phosphoric acid residue, aralkyl substituted with a phosphoric acid residue, hydroxyl lower alkyl, preferably hydroxy, carboxy, halogen (F, Cl, Br, I), halo lower alkyl (e.g., $CF_3$, $CH_2CF_3$, $CH_2CCl_3$), halo lower alkoxy (e.g., $OCF_3$, $OCH_2CF_3$, $OCH_2CCl_3$), lower alkyl (e.g., methyl, ethyl, isopropyl, tert-butyl), lower alkoxy (e.g., methoxy, ethoxy, propoxy, butoxy), optionally substituted amino (e.g., alkylamino (e.g., methylamino, ethylamino, dimethylamino), oxo, or phosphoric acid residue.

Examples of a substituent of "optionally substituted amino" or "optionally substituted carbamoyl" include mono- or di-lower alkyl, lower alkylcarbonyl, lower alkylsulfonyl, optionally substituted lower alkyl (e.g., methyl, ethyl, isopropyl, benzyl, carbamoylalkyl (e.g., carbamoylmethyl), mono- or di-lower alkylcarbamoyl lower alkyl (e.g., dimethylcarbamoylethyl), hydroxyl lower alkyl, heterocycle lower alkyl (e.g., morpholinoethyl, tetrahydropyranylethyl), alkoxycarbonyl lower alkyl (e.g., ethoxycarbonylmethyl, ethoxycarbonylethyl), mono- or di-lower alkylamino lower alkyl (e.g., dimethylaminoethyl)), lower alkoxy lower alkyl (e.g., methoxyethyl, ethoxymethyl, ethoxyethyl, isopropoxyethyl), acyl (e.g., formyl, optionally substituted lower alkylcarbonyl (e.g., acetyl, propionyl, butylyl, isobutylyl, valeryl, isovaleryl, pivaroyl, hexanoyl, octanoyl, methoxyethylcarbonyl, 2,2,2-trifluoroethylcarbonyl, ethoxycarbonylmethylcarbonyl), lower alkoxy lower alkylcarbonyl (e.g., methoxyethylcarbonyl), lower alkylcarbamoyl lower alkylcarbonyl (e.g., methylcarbamoylethylcarbonyl), alkoxycarbonylacetyl), optionally substituted arylcarbonyl (e.g., benzoyl, toloyl), optionally substituted aralkyl (e.g., benzyl, 4-fluorobenzyl), hydroxy, optionally substituted lower alkylsulfonyl (e.g., methanesulfonyl, ethanesulfonyl, isopropylsulfonyl, 2,2,2-trifluoroethanesulfonyl, benzylsulfonyl, methoxyethylsulfonyl), lower alkyl, or arylsulfonyl optionally substituted with halogen (e.g., benzenesulfonyl, toluenesulfonyl, 4-fluorobenzenesulfonyl, fluorobenzenesulfonyl), cycloalkyl (e.g., cyclopropyl), aryl optionally substituted with lower alkyl (e.g., phenyl, trityl), lower alkylaminosulfonyl (e.g., methylaminosulfonyl, dimethylaminosulfonyl), lower alkylaminocarbonyl (e.g., dimethylaminocarbonyl), lower alkoxycarbonyl (e.g., ethoxycarbonyl), cycloalkylcarbonyl (e.g., cyclopropylcarbonyl, cyclohexylcarbonyl), optionally substituted sulfamoyl (e.g., sulfamoyl, methylsulfamoyl, dimethylsulfamoyl), lower alkylcarbonylamino (e.g., methylcarbonylamino), heterocycle (e.g., morpholino, tetrahydropyranyl), optionally substituted amino (e.g., mono- or di-alkylamino (e.g., dimethylamino), formylamino).

As to amino of "optionally substituted amino", "optionally substituted carbamoyl", or "optionally substituted carbamoylcarbonyl", two substituents on the amino together with the neighboring N atom may form an N-containing heterocycle which optionally contains S and/or O in the ring (preferably 5- to 7-membered ring or saturated ring) and is optionally substituted with oxo or hydroxy. The optional S atom in the ring may be substituted with oxo. The N-containing heterocycle is preferably a 5- or 6-membered ring such as piperadinyl, piperidino, morpholino, pyrrolidino, 2-oxopiperidino, 2-oxopyrrolidino, 4-hydroxymorpholino.

"Phosphoric acid residue" means a group shown of the formula: $-PO(OH)_2$. "Optionally substituted phosphoric acid residue" means a phosphoric acid residue wherein the OH part and/or a hydrogen of the OH is optionally substituted with a phosphoric acid residue, preferably shown by the formula:

(P-1)

(wherein, $R^A$ and $R^B$ each is independently $OR^C$ or $NR^D R^E$ (wherein $R^C$, $R^D$ and $R^E$ are each independently hydrogen, optionally substituted lower alkyl, optionally substituted cycloalkyl, optionally substituted aryl, optionally substituted heterocyclic group, or $R^D$ and $R^E$ taken together with the neighboring N atom may form an optionally substituted heterocycle (preferably 5- to 6-membered ring)) or $R^A$ and $R^B$ taken together with the neighboring P atom may form an optionally substituted heterocycle (preferably 5- to 6-membered ring)).

Preferably, $R^A$ and $R^B$ are both $OR^C$, or one of them is $ORG$ and the other is $NR^D R^E$.

$R^C$, $R^D$ and $R^E$ each is preferably, independently, lower alkyl (e.g., methyl, ethyl).

The optionally substituted heterocycle formed by $R^A$ and $R^B$ taken together with the neighboring P atom may be the following structure:

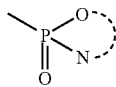

(wherein, the broken line means a part of the ring)

Hydroxy substituted with optionally substituted phosphoric acid residue is preferably hydroxy substituted with a phosphoric acid residue substituted with di lower alkyls, and more preferably a group of the formula:

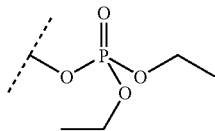

Amino substituted with optionally substituted phosphoric acid residue is preferably amino substituted with a phosphoric acid residue substituted with di lower alkyls, and more preferably a group of the formula:

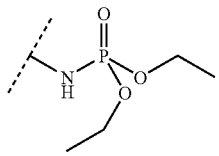

More Preferable Embodiments $R^1$ is hydrogen or lower alkyl, preferably hydrogen.

X is a single bond, a heteroatom group selected from O, S, SO, $SO_2$ and NH (hereafter also referred to as "M"), or lower alkylene or lower alkenylene each may be intervened by the heteroatom. The term of "intervened by" means the following cases:

1) The heteroatom group is present between carbon atoms which constitutes the alkylene or alkenylene.
2) The heteroatom group is attached to the N atom of the carbamoyl group neighboring to X.
3) The heteroatom group is attached to $R^2$ neighboring to X.

The heteroatom group (M) may be the same or different, and one or more atoms. Examples of that lower alkylene is intervened by a heteroatom group include $-M-CH_2-$, $-CH_2-M-CH_2-$, $-CH_2-M-$, and $-CH_2-M-M-CH_2-$.

X is preferably a spacer consisting 1 to 3 joined atoms. X is more preferably lower alkylene or lower alkenylene each may be intervened by a heteroatom group, or O. X is most preferably C1 to C3 alkylene, C2 to C3 alkenylene, or O. Especially preferred is methylene or O.

$R^2$ is optionally substituted aryl, preferably phenyl. A substituent on the aryl is the same or different, 1 to 3, preferably 1 to 2 substituent(s), including preferably halogen, hydroxy, amino, lower alkylamino, cyano, carboxy, formyl, oxo, lower alkyl, lower alkoxy, lower alkylthio, carbamoyl, and lower alkylcarbamoyl, and Substituent group S1(: optionally substituted phosphoric acid residue, aryl substituted with optionally substituted phosphoric acid residue, aralkyl substituted with optionally substituted phosphoric acid residue, hydroxyl substituted with optionally substituted phosphoric acid residue, amino substituted with optionally substituted phosphoric acid residue, lower alkyl substituted with optionally substituted phosphoric acid residue (said lower alkyl may be intervened with a hetero atom group(s) selected from O, S, SO, $SO_2$, $NR^5$ ($R^5$ is independently selected from the same substituent group for $R^4$), $-N=$ and $=N-$), lower alkoxy lower alkyl, amino lower alkyl optionally substituted with mono- or di-lower alkyl, halogenated lower alkyl, lower alkoxy, carbamoyl optionally substituted with mono- or di-lower alkyl, optionally substituted lower alkylsulfonylamino, halogenated lower alkoxy, hydroxyl lower alkyl), more preferably halogen, hydroxy, amino, cyano, lower alkyl, lower alkoxy or Substituent group S1, and most preferred is halogen (e.g., F) and/or a group selected from Substituent group S1. A substituent on the aryl is preferably at the 4-position. $R^2$ is more preferably phenyl or phenyl substituted with at least halogen, and most preferably 4-halogenophenyl (e.g., 4-F-phenyl). In another embodiment, $R^2$ is preferably phenyl optionally substituted with 1 to 3 R(s) mentioned below.

In all compounds of the present invention, the structure of "—X—$R^2$" is preferably shown by the formula below:

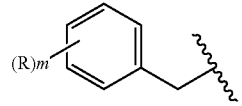

R each is independently a group selected from halogen and Substituent group S1.

Substituent group S1: optionally substituted phosphoric acid residue, aryl substituted with optionally substituted phosphoric acid residue, aralkyl substituted with optionally substituted phosphoric acid residue, hydroxyl substituted with optionally substituted phosphoric acid residue, amino substituted with optionally substituted phosphoric acid residue, lower alkyl substituted with optionally substituted phosphoric acid residue (said lower alkyl may be intervened by a heteroatom group(s) selected from CO, O, S, SO, $SO_2$, $NR^a$ ($R^a$ is hydrogen or lower alkyl), $-N=$ and $=N-$), lower alkoxy lower alkyl, optionally substituted amino lower alkyl (the substituent: mono- or di-lower alkyl, lower alkylcarbonyl, or lower alkylsulfonyl), halogenated lower alkyl, lower alkoxy, optionally substituted carbamoyl (the substituent: mono- or di-lower alkyl, lower alkylcarbonyl, or lower alkylsulfonyl), optionally substituted lower alkylsulfonylamino, halogenated lower alkoxy, and hydroxyl lower alkyl.

m is an integer of 0 to 3, preferably 0 or 1 to 2, when m is 1, R is preferably halogen. When m is 2, R is more preferably the same or different group selected from halogen, lower alkyl, lower alkoxy, lower alkoxy lower alkyl, halogenated lower alkyl, halogenated lower alkoxy, lower alkylsulfonylamino, carbamoyl, and lower alkylcarbamoyl. More preferably, R is two halogens, or halogen and another group. R preferably locates at the 4-position and optional another position of the benzene ring.

R³ can be a various substituent which does not bring a negative effect to the pharmacological activity, including hydrogen, halogen, hydroxy, optionally substituted lower alkyl, optionally substituted cycloalkyl, optionally substituted lower alkenyl, optionally substituted lower alkoxy, optionally substituted lower alkenyloxy, optionally substituted aryl, optionally substituted aryloxy, optionally substituted heterocyclic group, optionally substituted heterocycleoxy, and optionally substituted amino. Examples of substituent of "optionally substituted" include halogen, hydroxy, amino, lower alkylamino, cyano, carboxy, formyl, oxo, lower alkyl, lower alkoxy, lower alkylthio, carbamoyl, lower alkylcarbamoyl, aryl, heterocyclic group, lower alkylcarbonyl, lower alkylcarbonyloxy, lower alkoxycarbonyl, halogenated lower alkyl, halogenated lower alkoxy, and preferably halogen, hydroxy, amino, lower alkylamino, lower alkyl, and lower alkoxy. R³ is more preferably hydrogen, halogen, hydroxy, lower alkyl, lower alkenyl, lower alkoxy, lower alkenyloxy or optionally substituted amino, and most preferably hydrogen or lower alkyl (e.g., methyl), esp. hydrogen.

Z² shows C, CH, optionally substituted lower alkylene, lower alkenylene etc., and Z² and R⁴ of Z¹ taken together form a ring, whereby compound (I) shows a tricyclic compound (I-1) or (I-11) shown below, or its derivative, tetracyclic compound.

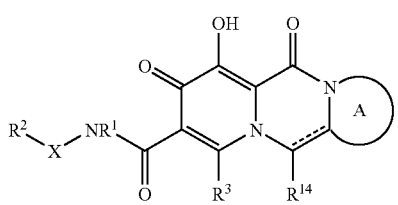
(I-1)

A ring is optionally substituted heterocycle containing at least an N atom. The heterocycle is a 5- to 7-membered ring which contains preferably 1 to 3, more preferably 2 to 3 atoms of O, S and/or N. The heterocycle is preferably selected from the above heterocycle. The arc optionally contains 1 to 2 heteroatom(s) at any possible position. One of preferable embodiments of A ring is an optionally substituted ring shown below.

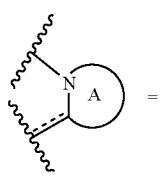 =

-continued

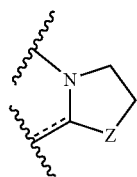 (a)

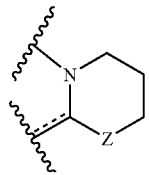 (b)

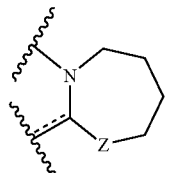 (c)

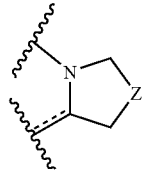 (d)

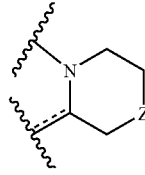 (e)

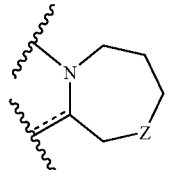 (f)

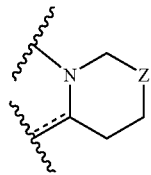 (g)

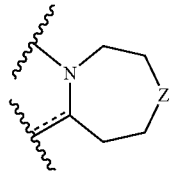 (h)

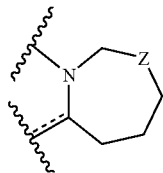

(Z is $CH_2$, O, S, SO, $SO_2$ or $NR^{19}$)

A ring is preferably a ring of (a), (b), or (c).

Z is preferably O or $NR^{19}$.

When Z is $NR^{19}$, examples of $R^{19}$ include 1) hydrogen, 2) optionally substituted lower alkyl (the substituent is e.g., amino optionally substituted with mono- or di-lower alkyl; cycloalkyl; hydroxy; optionally substituted heterocyclic group (preferably 5- to 7-membered ring, e.g., furyl, thienyl, thiazolyl, pyridil, morpholino, imidazole; examples of the substituent include lower alkyl, halogen): optionally substituted heterocyclecarbonyl (the heterocycle is preferably 5- to 7-membered ring, e.g., morpholinocarbonyl); optionally substituted phenyl (the substituent is e.g., lower alkyl, amino, lower alkylamino, hydroxy, halogen, halogenated lower alkyl, lower alkoxy, halogenated lower alkoxy, lower alkylthio, lower alkylsulfonyl), acetylamino, carbamoyl, carbamoyl substituted with mono- or di-lower alkyl, lower alkylsulfonylamino, lower alkoxy, carbonyl, halogen, thiol, lower alkylthio), 3) lower alkenyl, 4) acyl (e.g., lower alkylcarbonyl), 5) lower alkylsulfonyl. $R^{19}$ may be selected from Substituent group S2 shown below.

The other substituent on A ring may be selected from $R^{15}$ to $R^{18}$ or Substituent group S2, preferably lower alkyl. Substituents on A ring may form a condensed ring or a spiro ring as mentioned below, whereby compound (I) includes a tetracyclic compound.

A ring is more preferably any of the following rings:

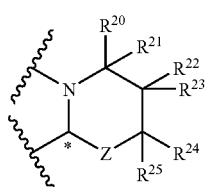

(A-1)

$Z = O$ or $NR^{26}$

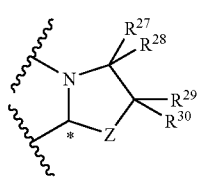

(A-2)

$Z = O$ or $NR^{31}$

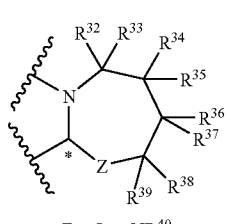

(A-3)

$Z = O$ or $NR^{40}$ (wherein, $R^{20}$ to $R^{40}$ are each independently a group selected from Substituent group S2, or any two groups of $R^{20}$ to $R^{40}$, which bonds to the same carbon atom, taken together with the carbon atom, may form a spiro ring, i.e., an optionally substituted carbocycle or optionally substituted heterocycle, or each combination of ($R^{20}$ and $R^{22}$), ($R^{23}$ and $R^{24}$), ($R^{25}$ and $R^{26}$), ($R^{27}$ and $R^{29}$), ($R^{30}$ and $R^{31}$), ($R^{32}$ and $R^{34}$), ($R^{35}$ and $R^{36}$), ($R^{37}$ and $R^{38}$), and ($R^{39}$ and $R^{40}$), taken together with the neighboring atom, may form an optionally substituted carbocycle or optionally substituted heterocycle.

Substitution group S2: hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy optionally substituted heterocycle, optionally substituted heterocycle lower alkyl, optionally substituted heterocycleoxy, hydroxy, optionally substituted amino, optionally substituted lower alkylcarbonyl, optionally substituted cycloalkylcarbonyl, optionally substituted cycloalkyl lower alkylcarbonyl, optionally substituted lower alkoxycarbonyl, optionally substituted arylcarbonyl, optionally substituted aryl lower alkylcarbonyl, optionally substituted aryl oxycarbonyl, optionally substituted heterocyclecarbonyl, optionally substituted heterocycle lower alkylcarbonyl, optionally substituted heterocycleoxycarbonyl, optionally substituted aminocarbonyl, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue (the lower alkyl may be intervened with a heteroatom group(s) selected from CO, O, S, SO, $SO_2$, $NR^5$ ($R^5$ is independently selected from the same substitution group as $R^4$), —N═ and ═N—)

The stereochemistry of an asymmetric carbon represented by * shows the R- or S-configuration, or a mixture thereof)

In one embodiment, $R^{20}$ to $R^{40}$ each is preferably hydrogen, optionally substituted lower alkyl (examples of the substituent: OH, lower alkoxy, cycloalkyl, lower alkylthio, lower alkylsulfonyl, heterocyclic group, aryl, optionally substituted amino (examples of the substituent: lower alkyl, acyl)), cycloalkyl, optionally substituted aryl (examples of the substituent: OH, lower alkyl), and optionally substituted heterocyclic group.

In one embodiment, $R^{20}$ to $R^{25}$, $R^{27}$ to $R^{30}$, and $R^{32}$ to $R^{39}$, each is preferably hydrogen, C1-C8 alkyl, C6-C14 aryl C1-C8 alkyl, C6-C14 aryl, or alkoxy.

In one embodiment, $R^{26}$, $R^{31}$, and $R^{40}$, each is preferably hydrogen, C3-6 cycloalkyl, heterocycle, or C1-8 alkyl optionally substituted with hydroxy, C3-6 cycloalkyl, alkoxy, heterocycle, heteroaryl, C6-14 aryl, or amino, wherein said amino may be optionally substituted with —C(O)C1-8 alkyl or C1-8 alkyl.

More Preferred embodiments are shown below for example

I) When A ring is A-1, preferred is that 1) Z is $NR^{26}$ and $R^{26}$ and $R^{24}$ taken together form heterocycle, and the others are hydrogens; 2) Z is O or $NR^{26}$, ($R^{20}$ and $R^{22}$) or ($R^{23}$ and $R^{24}$) taken together form cycloalkyl which is substituted with phenyl, the others are hydrogens or optionally substituted lower alkyl.

II) When A ring is A-2, preferred is that 1) Z is O, $R^{27}$ or $R^{28}$ is lower alkyl, and the others are hydrogens; 2) Z is $NR^{31}$ and $R^{30}$ and $R^{31}$ taken together form heterocycle and the others are hydrogens, or $R^{27}$ and $R^{29}$ taken together form cycloalkyl and the others are hydrogens; 3) Z is O, $R^{27}$ and $R^{29}$ taken together form cycloalkyl which may be condensed with phenyl, and the others are hydrogens $R^{14}$ and $R^x$ are each independently hydrogen, optionally substituted lower alkyl, optionally substituted cycloalkyl, optionally substituted cycloalkyl lower alkyl, optionally substituted lower alkenyl, optionally substituted lower alkoxy, optionally substituted lower alkenyloxy, optionally substituted aryl, optionally substituted aryl lower alkyl, optionally substituted aryloxy, optionally substituted heterocyclic group, optionally substituted heterocycle lower alkyl, optionally substituted heterocycleoxy, hydroxy, optionally substituted amino, optionally substituted lower alkylcarbonyl, optionally substituted cycloalkylcarbonyl, optionally substituted cycloalkyl lower alkylcarbonyl, optionally substituted lower alkoxycarbonyl, optionally substituted arylcarbonyl, optionally substituted aryl lower alkylcarbonyl, optionally substituted aryloxycarbonyl, optionally substituted heterocyclecarbonyl, optionally substituted heterocycle lower alkylcarbonyl, optionally substituted heterocycleoxycarbonyl, optionally substituted aminocarbonyl, optionally substituted phosphoric acid residue, aryl substituted with optionally substituted phosphoric acid residue, aralkyl substituted with optionally substituted phosphoric acid residue, hydroxy optionally substituted with optionally substituted phosphoric acid residue, amino substituted with optionally substituted phosphoric acid residue, or lower alkyl substituted with optionally substituted phosphoric acid residue (the lower alkyl may be intervened with a heteroatom group(s) selected from O, S, SO, $SO_2$, $NR^a$ ($R^a$ is hydrogen or lower alkyl), —N= and =N—).

$R^{14}$ and $R^x$ are each independently, preferably, hydrogen, hydroxyl, optionally substituted lower alkyl (the substituent is preferably, e.g., amino, lower alkyl amino, hydroxy, lower alkoxy). $R^{14}$ and $R^x$ are preferably hydrogens.

A broken line in the compound (I-1) represents the presence or absence of a bond, provided that when the broken line represents the presence of a bond, $R^x$ is not present.

The compound (I) includes the following compounds.

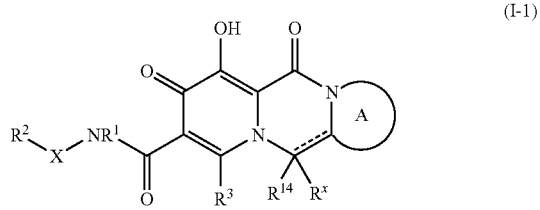
(I-1)

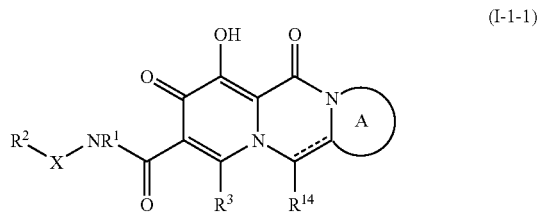
(I-1-1)

(wherein each symbol is as defined above)

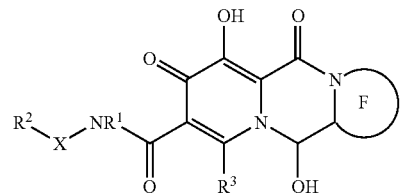
(I-8)

F ring means the same heterocycle as A ring, preferably 5- to 7-membered ring, and the substituents on F ring are the same as those for A ring. The other symbols are as defined above.

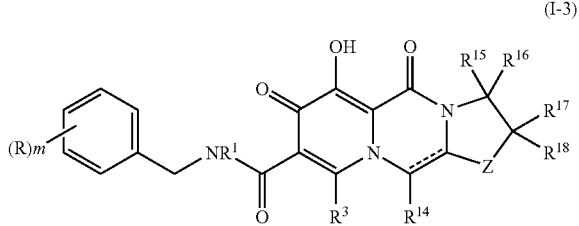
(I-3)

(wherein each symbol is as defined above; Z is O or $NR^{19}$; $R^{15}$ to $R^{19}$ are each independently hydrogen or a group selected from the above Substituent group S2, or each combination of ($R^{15}$ and $R^{16}$), ($R^{17}$ and $R^{18}$), ($R^{16}$ and $R^{18}$), and ($R^{18}$ and $R^{19}$) taken together with the neighboring atom(s), may form an optionally substituted carbocycle (preferably 5- to 6-membered ring) or an optionally substituted heterocyle (preferably 5- to 6-membered ring); or each combination of ($R^{15}$ and $R^{16}$) and ($R^{17}$ and $R^{18}$) taken together may form oxo)

Compound (I-3) is preferably as follows.
(1) $R^1$ is hydrogen; $R^3$ is hydrogen; m is 1 or 2; $R^{14}$ is hydrogen.
(2) m is 1 or 2, R is each independently halogen, halogenated lower alkyl, lower alkoxy, halogenated lower alkoxy, lower alkoxy lower alkyl, hydroxy lower alkyl, optionally substituted amino lower alkyl (the substituent is mono- or di-lower alkyl, lower alkylcarbonyl, or lower alkylsulfonyl), optionally substituted carbamoyl (the substituent is mono- or di-lower alkyl, lower alkylcarbonyl, or lower alkylsulfonyl), phosphoric acid residue, aryl substituted with optionally substituted phosphoric acid residue, aralkyl substituted with optionally substituted phosphoric acid residue or sulfonylamino optionally substituted with lower alkyl; $R^1$ is hydrogen; $R^3$ is hydrogen; $R^{14}$ is hydrogen, hydroxyl or lower alkyl optionally substituted with mono- or di-lower alkylamino; Z is O or $NR^{19}$ ($R^{19}$ is hydrogen or lower alkyl, lower alkoxy lower alkyl, optionally substituted phosphoric acid residue, aryl substituted with optionally substituted phosphoric acid residue, aralkyl substituted with optionally substituted phosphoric acid residue, hydroxy substituted with optionally substituted phosphoric acid residue, amino substituted with optionally substituted phosphoric acid residue, or lower alkyl substituted with optionally substituted phosphoric acid residue).
(3) R is each independently, —F, —$CF_3$, —OMe, —$OCF_3$, —$CH_2$OMe, —$CH_2$OH, —$CH_2$N(Me)$_2$, —CONHMe, —CON(Me)$_2$, —$CH_2$PO(OEt)$_2$, —PO(OEt)$_2$, —NHSO$_2$Me, or —NMeSO$_2$Me; $R^1$ is hydrogen; $R^3$ is hydrogen; m is 1 or 2; $R^{14}$ is hydrogen, hydroxyl or —$CH_3$N(Me)$_2$; Z is O or $NR^{19}$ ($R^{19}$ is hydrogen or CH(Me)$_2$, —(CH$_2$)$_2$OMe, —(CH$_2$)$_2$PO(OEt)$_2$).

(4) $R^{15}$ and $R^{16}$ are hydrogens; $R^{17}$ and $R^{18}$ are hydrogens or taken together with the neighboring atom form a 3- to 7-membered carbocycle; and/or Z is O or NH. This case preferably also satisfies the above (2) or (3).

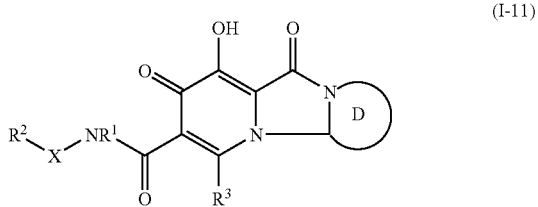

(I-11)

D ring means the same heterocycle as A ring, preferably 5- to 7-membered ring, and the substituents on D ring are the same as those for A ring. The other symbols are as defined above.

The structure of compound (I) has at least the following characteristics.
(1) The main structure, condensed heterocycle, is substituted with oxo (=O), hydroxyl (OH) and oxo.
(2) A substituted carbamoyl group (—CONR$^1$XR$^2$) is attached to the position neighboring to the oxo group on the condensed heterocycle.

The above structure contributes to a remarkably potent integrase inhibitory activity and/or cell-growth inhibitory activity against virus including HIV. In contrast, the structures of the other parts such as $Z^1$, $Z^2$, and $R^3$ each may be of variety, being optionally substituted or optionally condensed, and its condensed ring is also optionally substituted.

The present invention provides a pharmaceutically acceptable salt or a solvate of compound (I). All theoretically possible tautomer, geometrical isomer, optically active compound, and race mate thereof are within the scope of the invention.

Pharmaceutically acceptable salts of a compound of the present invention include, as basic salts, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine or procaine salts; aralkyl amine salts such as N,N-dibenzylethylenediamine salts; heterocyclic aromatic amine salts such as pyridin salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts, and basic amino acid salts such as arginine salts or lysine salts. Acid salts include, for example, mineral acid salts such as hydrochloride, sulfates salts, nitrate salts, phosphates salts, carbonates salts, hydrogencarbonates or perchlorate; organic acid salts such as acetates, propionates, lactates, maleates, fumarates, tararic acid salts, malates, citrates salts, ascorbates, formic acid; sulfonates such as methanesulfonates, isethionates, benzenesulfonates, or p-toluenesulfonates; and acidic amino acid salts such as aspartates or glutamates.

Solvates of a compound of the present invention include alcholates and hydrates.

A general process for producing the present compound will be exemplified below.
(Method of Preparing Raw Material)

[Chemical formula 41]

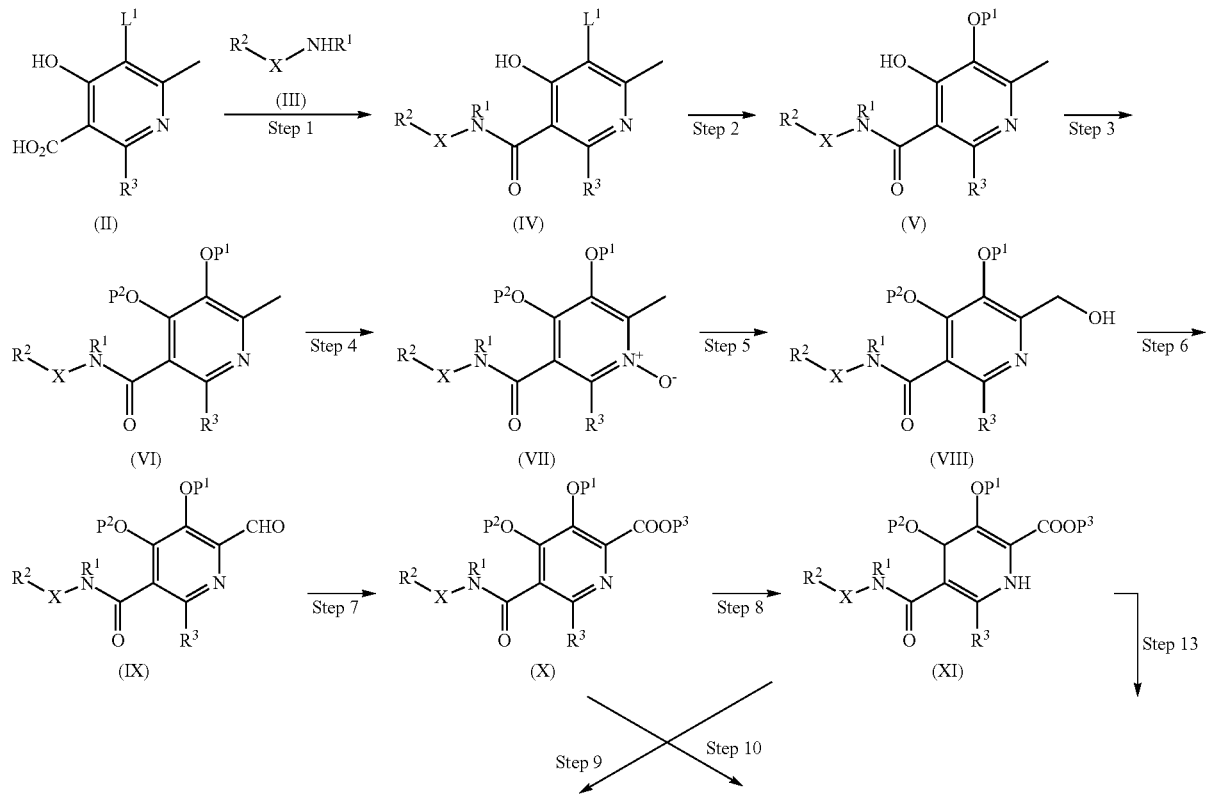

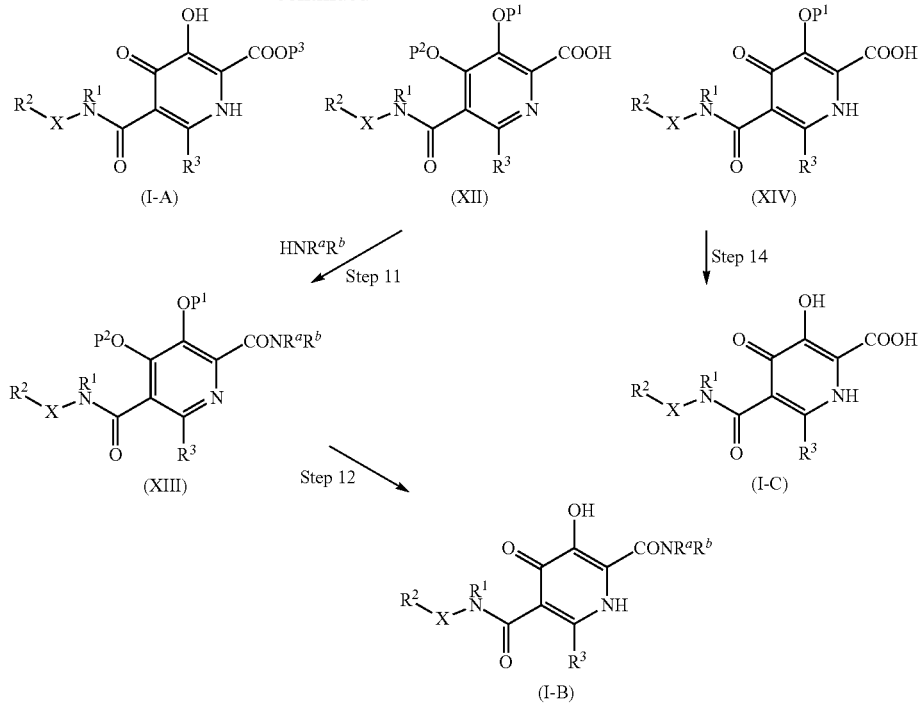

(wherein $L^1$ is a leaving group (e.g.; halogen); $P^1$ and $P^2$ are a hydroxy protecting group; $P^3$ is a carboxy protecting group (e.g.: lower alkyl); $R^a$ and $R^b$ are hydrogen or a substituent on an amino group)

Examples of a hydroxy protecting group ($P^1$, $P^2$) include acyl (e.g.: acetyl, pivaloyl, benzoyl), aralkyl (e.g.: benzyl), lower alkyl (e.g.: methyl), alkoxyalkyl (e.g.: methoxymethyl, methoxyethyl), lower alkylsulfonyl (e.g.: methanesulfonyl), arylsulfonyl (e.g.: benzenesulfonyl, toluenesulfonyl), alkoxycarbonyl (e.g.: methoxycarbonyl) and the like.

As a carboxy protecting group ($P^3$), lower alkyl (e.g.; methyl, ethyl), and aralkyl (e.g.: benzyl) are exemplified.

(First Step)

The present step is a reaction for condensing a compound (II) and a compound (III) to synthesize a compound (IV). The reaction may be performed according to the condition for a reaction of amidating carboxylic acid which is generally performed. A compound (II) may be reacted as it is, or may be reacted after converted into corresponding acid chloride or active ester. Preferably, the reaction is performed in a suitable solvent in the presence of a condensing agent.

As a condensing agent, dicyclohexylcarbodiimide, 1-ethyl-3-(3-dimethylaminopropyl)carbodiimide hydrochloride and the like may be used. If necessary, a reagent such as 1-hydroxybenzotriazole and N-hydroxysuccinimide, or a base such as triethylamine, N-methylmorpholine, and pyridine may be added.

A reaction temperature is 0 to 150° C., preferably room temperature to 70° C.

As a reaction solvent, a non-protonic solvent can be broadly used, and tetrahydrofuran (THF), 1,4-dioxane, dimethylformamide (DMF), methylene chloride, chloroform and the like are preferable.

A reaction time is a few minutes to a few tens hours, preferably 9 to 17 hours.

(Second Step)

The present step is a reaction for introducing a protected hydroxy group ($OP^1$) into a compound (IV) to produce a compound (V). The reaction may be performed according to the condition for an alkoxylating reaction which is generally performed.

For example, a compound (V) in which $P^1$ is methyl can be synthesized by reacting a compound (IV) with metal alkoxide (e.g.: sodium methoxide).

A reaction temperature is 0 to 200° C., preferably 80 to 120° C.

As a reaction solvent, alcohol, dimethylformamide (DMF), and dimethyl sulfoxide (DMSO) are exemplified.

A reaction time is a few minutes to a few tens hours, preferably 5 to 10 hours.

(Third Step)

The present step is a reaction for protecting a hydroxy group of a compound (V) to produce a compound (VI). The reaction may be performed according to the condition for a reaction of protecting a hydroxy group which is generally performed. For example, by using diisopropyl azodicarboxylate or diethyl azodicarboxylate together with an alcohol and various phosphines, a compound (VI) in which $P^2$ is alkyl can be synthesized.

A reaction temperature is 0 to 100° C., preferably 0° C. to room temperature.

As a reaction solvent, THF, toluene, dichloromethane and the like are exemplified.

A reaction time is a few minutes to a few tens hours, preferably 1 to 3 hours.

(Fourth Step)

The present step is a reaction of oxidizing a nitrogen atom of a compound (VI) to produce a compound (VII). The reaction may be performed according to the condition for an oxidation reaction using an oxidizing agent which is generally performed.

A reaction temperature is 0 to 100° C., preferably under ice-cooling to room temperature.

As a reaction solvent, chloroform, methylene chloride, acetic acid and the like are exemplified.

Examples of an oxidizing agent include metachloroperbenzoic acid, hydrogen peroxide and the like.

A reaction time is a few minutes to a few tens hours, preferably 1 to 5 hours.

(Fifth Step)

The present step is a reaction for hydroxylating a methyl group of a compound (VII). Preferably, after acetoxylation by a reaction with acetic anhydride (reaction temperature: 0 to 150° C., preferably 120 to 3.40° C.), this may be hydrolyzed (e.g.: treatment with a base (e.g.: alkali metal hydroxide)).

A reaction time is a few minutes to a few tens hours, preferably 0.5 to 2 hours for acetoxylation, and 0.5 to 1 hour for hydrolysis.

(Sixth Step)

The present step is a reaction for oxidizing a hydroxy group of a compound (VIII) to synthesize a compound (IX).

A reaction temperature is 0 to 150° C., preferably room temperature to 70° C.

As a reaction solvent, chloroform and the like are exemplified.

As an oxidizing agent, dimethyl sulfoxide and the like are exemplified.

A reaction time is a few minutes to a few tens hours, preferably 0.1 to 1 hour.

(Seventh Step)

The present step is a reaction for oxidizing a formyl group of a compound (IX) to synthesize a compound (X).

A reaction temperature is 0 to 150° C., preferably under ice-cooling to room temperature.

As a reaction solvent; an alcohol and the like are exemplified.

As an oxidizing agent, potassium hydroxide and iodine are exemplified.

A reaction time is a few minutes to a few tens hours, preferably 0.5 to 3 hours.

(Eighth Step)

The present step is a reaction for deprotecting an $OP^2$ part of a compound (X) to synthesize a compound (XI). The reaction may be performed according to the condition for a reaction of deprotecting a hydroxy protecting group which is generally performed.

A reaction temperature is 0 to 150° C., preferably under ice-cooling to room temperature.

As a reaction solvent, acetonitrile, methylene chloride, THF and the like are exemplified.

A reaction time is a few minutes to a few tens hours, preferably 1 to 3 hours.

(Ninth Step)

The present step is a reaction for deprotecting an $OP^1$ part of a compound (XI) to synthesize a compound (I-A). The reaction may be treated preferably with a Lewis acid (e.g.; aluminum chloride).

A reaction temperature is 0 to 150° C., preferably 10 to 50° C.

As a reaction solvent, methylene chloride, THF and the like are exemplified.

A reaction time is a few minutes to a few tens hours, preferably 1 to 3 hours.

(Tenth Step)

The present step is a reaction for deprotecting an ester part ($COOP^3$) of a compound (X) to synthesize carboxylic acid (XII). Preferably, hydrolysis with an alkali (e.g.: NaOH) may be performed.

A reaction temperature is 0 to 150° C., preferably 10 to 50° C.

As a reaction solvent, methanol, water and the like are exemplified.

A reaction time is a few minutes to a few tens hours, preferably a few minutes to 2 hours.

Carboxylic acid (XII) can be converted into various derivatives (e.g.; amide).

(Eleventh Step)

The present step is at reaction for reacting a compound (XII) with various amines to synthesize a compound (XIII). The reaction may be performed according to the condition for a reaction of amidating carboxylic acid which is generally performed and, for example, the reaction may be performed as in the first step.

A reaction temperature is 0 to 150° C., preferably room temperature to 70° C.

As a reaction solvent, a non-protonic solvent can be broadly used, and tetrahydrofuran (THF), 1,4-dioxane, dimethylformamide (DMF), methylene chloride, chloroform and the like are preferable.

A reaction time is a few minutes to a few tens hours, preferably a few minutes to 3 hours.

An amide part of the resulting compound (XIII) may be further chemically modified (e.g.: N-alkylation).

(Twelfth Step)

The present step is a reaction for deprotecting $OP^1$ and $OP^2$ parts of a compound (XIII) to synthesize a compound (I-B). The reaction may be performed according to the condition for a reaction of deprotecting a hydroxy protecting group which is generally performed.

For example, when pyridine hydrochloride is used, a reaction temperature is 0 to 200° C., preferably 150 to 180 degree.

A reaction time is a few minutes to a few tens hours, preferably 1 to 5 minutes.

(Thirteenth Step)

The present step is a reaction for deprotecting an ester part ($COOP^3$) of a compound (XI) to synthesize carboxylic acid (XIV). Preferably, hydrolysis with an alkali (e.g.; lithium hydroxide) may be performed.

A reaction temperature is 0 to 150° C., preferably 10 to 50° C.

As a reaction solvent, methanol, water and the like are exemplified.

A reaction time is a few minutes to a few tens hours, preferably a few minutes to 3 hours.

(Fourteenth Step)

The present step is a reaction for deprotecting an $OP^1$ part of a compound (XIV) to synthesize a compound (I-C). The reaction may be treated preferably with a Lewis acid (e.g.: boron tribromide).

A reaction temperature is 0 to 150° C., preferably under ice-cooling to room temperature.

As a reaction solvent, dichloromethane and the like are exemplified.

A reaction time is a few minutes to a few tens hours, preferably a few minutes to 5 hours.

The monocyclic carbamoylpyridone derivative obtained above is derived into a bicyclic compound by the following method.

(Process 1)

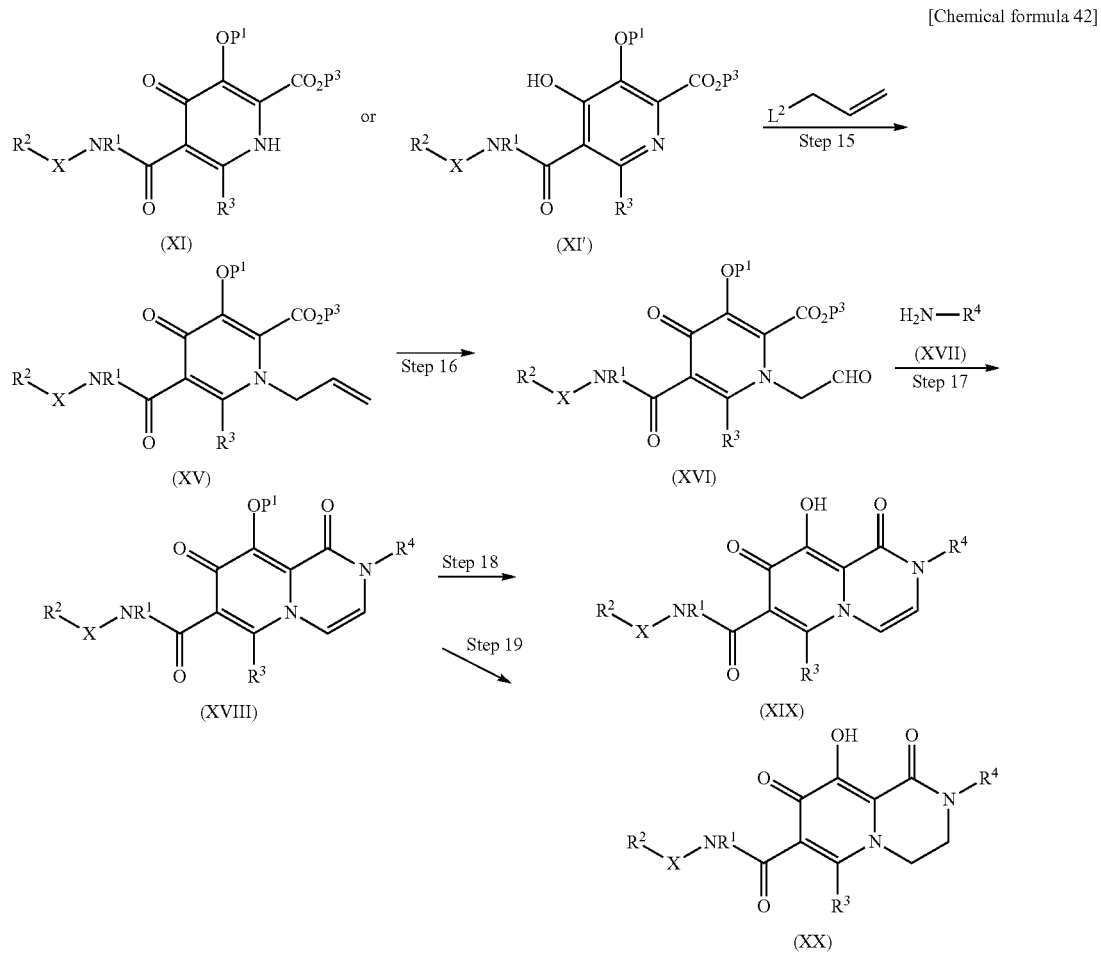

(wherein $R^1$, X, $R^2$, $P^1$, $P^3$ and $R^4$ are as define above, and $L^2$ is a leaving group such as halogen etc.)

(Fifteenth Step)

The present step is a reaction for reacting the compound (XI) or a compound (XI') which is a tautomer thereof with an allyl compound to synthesize a compound (XV). A compound (XI') can be synthesized, for example, according to the method of Example A-1.

The reaction is performed preferably in the presence of a base (e.g.: cesium carbonate).

A reaction temperature is 0 to 100° C., preferably 10 to 40° C.

As a reaction solvent, dimethylformamide and the like are exemplified.

A reaction time is a few minutes to a few tens hours, preferably 1 to 10 hours.

(Sixteenth Step)

The present step is a reaction for oxidizing a compound (XV) to synthesize a compound (XVI). As an oxidizing agent, osmium tetraoxide and alkali metal osmium tetraoxide (e.g.; $KaOsO_4$) are exemplified.

A reaction temperature is 0 to 100° C., preferably 10 to 40° C.

As a reaction solvent, 1,4-dioxane, tetrahydrofuran and the like are exemplified.

A reaction time is a few minutes to a few tens hours, preferably 1 to 5 hours.

(Seventeenth Step)

The present step is a reaction for reacting a compound (XVI) with amine (XVII) to perforin dehydration condensation to synthesize a compound (XVIII).

A reaction temperature is 0 to 200° C., preferably 140 to 180° C.

As a reaction solvent, methylene chloride, acetonitrile and the like are exemplified.

A reaction timers a few minutes to a few tens hours, preferably 0.5 to 1.5 hours.

(Eighteenth Step)

The present step is a reaction for deprotecting a compound (XVIII) preferably with an acid to synthesize a compound (XIX), and may be performed according to the condition for a conventional reaction of deprotecting a protected hydroxy group.

A reaction temperature is 0 to 200° C.

As an acid, pyridine hydrochloride, trifluoroacetic acid and the like are exemplified.

As a reaction solvent, the acid and trimethylsilyl iodide are exemplified.

A reaction time is a few minutes to a few tens hours, preferably 15 minutes to 1 hour.

(Nineteenth Step)

The present step is a reaction for reducing a compound (XVIII) to synthesize a compound (XX).

As a reducing agent, $H_2/Pd$—C and the like are exemplified.

A reaction temperature is 0 to 100° C., preferably 10 to 30° C.

As a reaction solvent, dimethylformamide, methanol, tetrahydrofuran and the like are exemplified.

A reaction time is a few minutes to a few tens hours, preferably 5 to 20 hours.

(Process 2)

The intermediate (XVIII) may be also synthesized by a method shown below.

[Chemical formula 43]

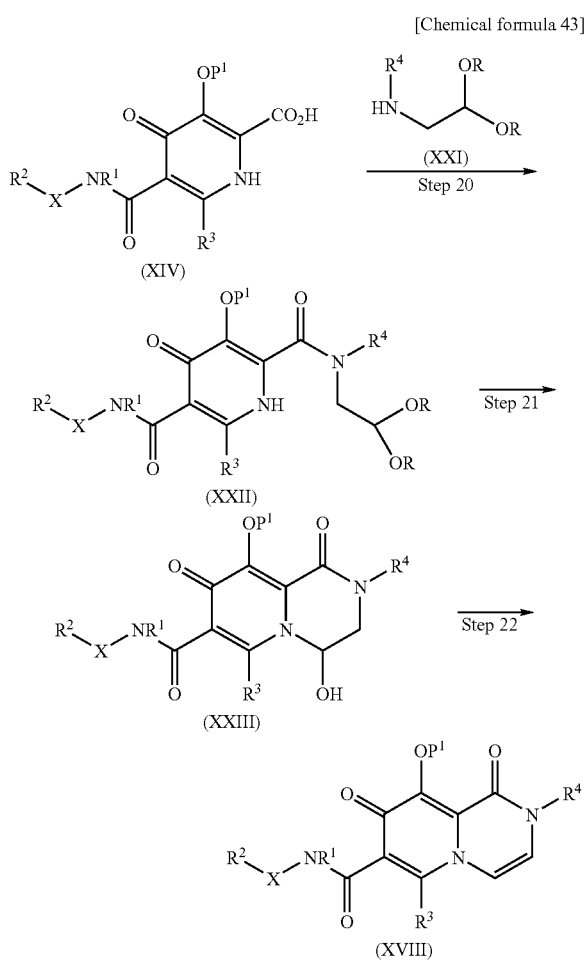

(Twentieth Step)

The present step is a reaction for reacting a compound (XIV) with a compound (XXI) to synthesize a compound (XXII). The present reaction may be performed according to the condition for a conventional amidation reaction.

A reaction temperature is 0 to 100° C., preferably 0 to 50° C.

As a reaction solvent, dimethylformamide, methylene chloride, tetrahydrofuran and the like are exemplified.

A reaction time is a few minutes to a few tens hours, preferably 1 to 10 hours;

(Twenty-First Step)

The present step is a reaction for reacting a compound (XXII) with an acid to perform deprotection and intramolecular ring closure, to synthesize a compound (XXIII). The present reaction may be performed according to the condition for a conventional reaction of deprotecting acetal.

A reaction temperature is 0 to 100° C., preferably room temperature to 80° C.

As a reaction solvent, dioxane, tetrahydrofuran and the like are exemplified.

A reaction time is a few minutes to a few tens hours, preferably 0.5 to 1 hour.

As an acid, hydrochloric acid, and paratoluenesulfonic acid are exemplified.

(Twenty-Second Step)

The present step is a reaction for dehydrating a compound (XXIII) to synthesize a compound (XXIV). The present reaction may be performed according to the condition for a conventional dehydration reaction.

A reaction temperature is 0 to 100° C., preferably room temperature to 80° C.

As a reaction solvent, acetonitrile, methylene chloride and the like are exemplified.

A reaction time is a few minutes to a few tens hours, preferably 1 to 5 hours.

(Process 3)

[Chemical formula 44]

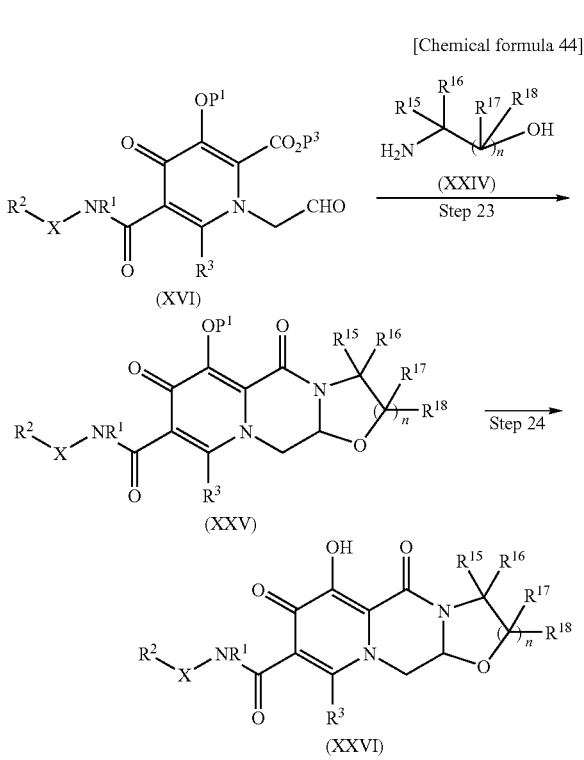

(Twenty-Third Step)

The present step is a reaction for reacting a compound (XVI) with amine (XXIV) to perform dehydration condensation to synthesize a compound (XXV) according to the seventeenth step or a method of synthesizing a compound 17-1. Preferably, as a reaction catalyst, an acid (e.g.: acetic acid) is added, and a microwave reaction apparatus is used.

A reaction temperature is 0 to 200° C., preferably 140 to 180° C.

As a reaction solvent, methylene chloride, acetonitrile and the like are exemplified.

A reaction time is a few minutes to a few tens hours, preferably 0.5 to 1.5 hours.

47

(Twenty-Fourth Step)

The present step is a reaction for deprotecting a compound (XXV) preferably with an acid to synthesize a compound (XXVI) according to the eighteenth step, and may be performed according to the condition for a conventional reaction of deprotecting a protected hydroxy group.

A reaction temperature is 0 to 200° C.

As an acid, pyridine hydrochloride, trifluoroacetic acid and the like are exemplified.

As a reaction solvent, the aforementioned acid and trimethylsilyl iodide are exemplified.

A reaction time is a few minutes to a few tens hours, preferably 15 minutes to 1 hour.

(Process 4)

[Chemical formula 45]

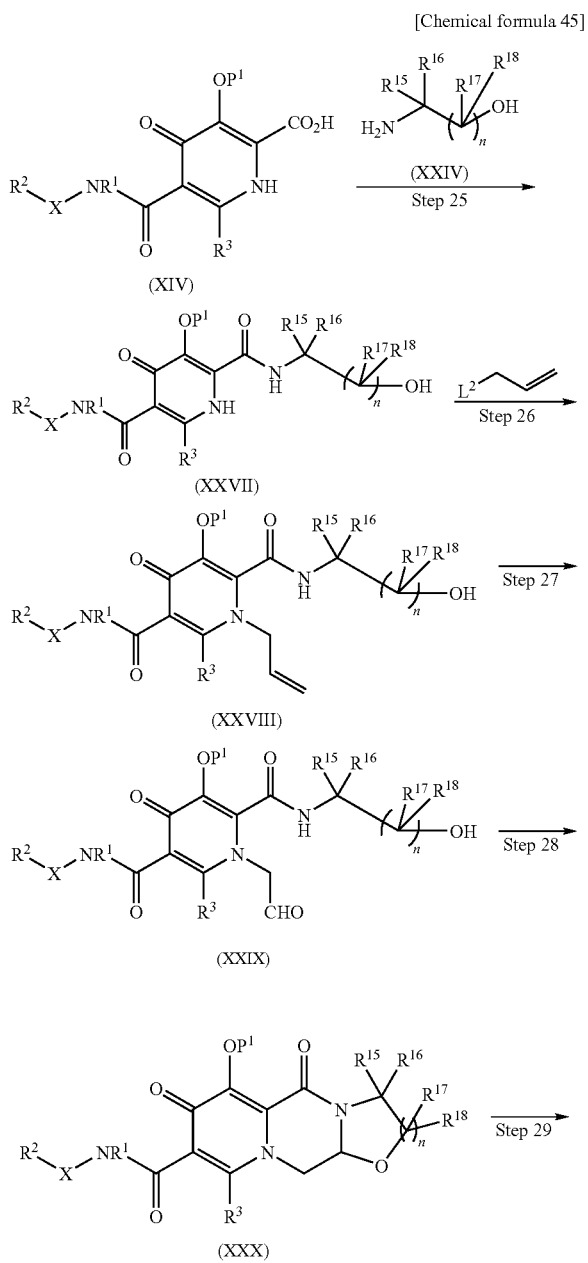

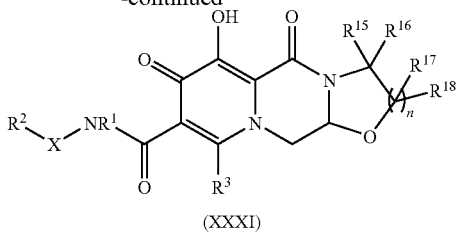

48

(Twenty-Fifth Step)

The present step is a reaction for reacting a compound (XIV) with a compound (XXIV) to synthesize a compound (XXVII) according to the twentieth step. The present reaction may be performed according to the condition for a conventional amidation reaction.

A reaction temperature is 0 to 100° C., preferably 0 to 50° C.

As a reaction solvent, dimethylformamide, methylene chloride, tetrahydrofuran and the like are exemplified.

A reaction time is a few minutes to a few tens hours, preferably 1 to 10 hours.

(Twenty-Sixth Step)

The present step is a reaction for reacting a compound (XXVII) or a tautomer thereof with an allyl compound to synthesize a compound (XXVIII) according to the fifteenth step.

A reaction is performed preferably in the presence of a base (e.g.: cesium carbonate).

A reaction temperature is 0 to 100° C., preferably 10 to 40° C.

As a reaction solvent, dimethylformamide and the like are exemplified.

A reaction time is a few minutes to a few tens hours, preferably 1 to 10 hours.

(Twenty-Seventh Step)

The present step is a reaction for oxidizing a compound (XXVIII) to synthesize a compound (XXIX) according to the sixteenth step.

As an oxidizing agent, osmium tetraoxide and alkali metal osmium tetraoxide (e.g.: $K_2OsO_4$) are exemplified.

A reaction temperature is 0 to 100° C., preferably 10 to 40° C.

As a reaction solvent 1,4-dioxane, tetrahydrofuran and the like are exemplified.

A reaction time is a few minutes to a few tens hours, preferably 1 to 5 hours.

(Twenty-Eighth Step)

The present step is a reaction for dehydration-condensing a compound (XXIX) to synthesize a compound (XXX) according to the seventeenth step or a method of synthesizing a compound 17-1. Preferably, as a reaction catalyst, an acid (e.g.: acetic acid) is added, and a microwave reaction apparatus is used.

A reaction temperature is 0 to 200° C., preferably 140 to 180° C.

As a reaction solvent, methylene chloride, acetonitrile and the like are exemplified.

A reaction time is a few minutes to a few tens hours, preferably 0.5 to 1.5 hours.

(Twenty-Ninth Step)

The present step is a reaction for deprotecting a compound (XXX) preferably with an acid to synthesize a compound (XXXI) according to the eighteenth step, and may be performed according to the condition for a conventional reaction of deprotecting a protected hydroxy group.

A reaction temperature is 0 to 200° C.

As an acid, pyridine hydrochloride, trifluoroacetic acid and the like are exemplified.

As a reaction solvent, the aforementioned acid and trimethylsilyl iodide are exemplified.

A reaction time is a few minutes to a few tens hours, preferably 15 minutes to 1 hour.

(Process 5)

A compound (I-3) in which Z is $NR^{19}$ can be synthesized according to the following reaction scheme, according to Process 4.

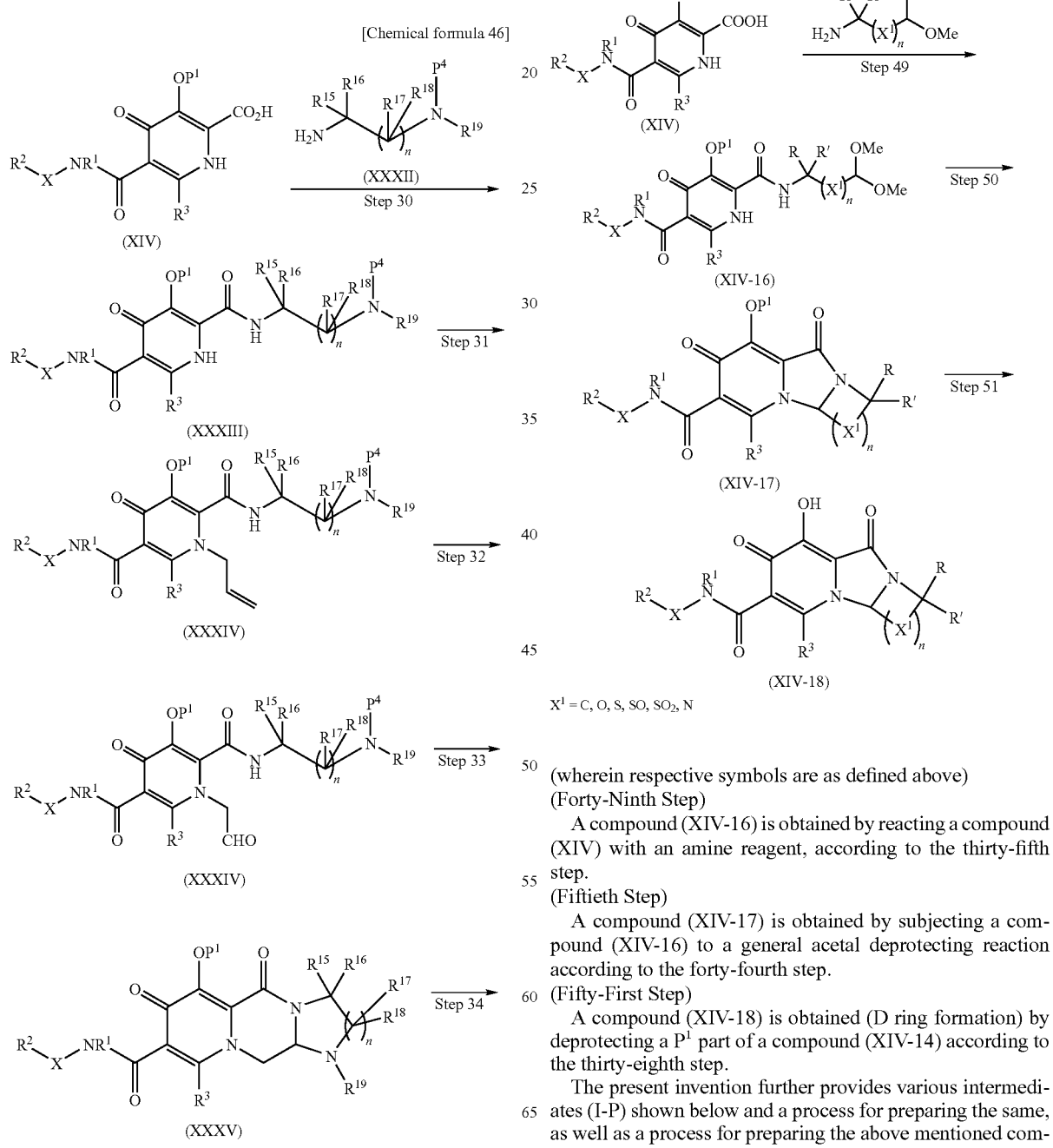

$X^1 = C, O, S, SO, SO_2, N$ (wherein respective symbols are as defined above)

(Forty-Ninth Step)

A compound (XIV-16) is obtained by reacting a compound (XIV) with an amine reagent, according to the thirty-fifth step.

(Fiftieth Step)

A compound (XIV-17) is obtained by subjecting a compound (XIV-16) to a general acetal deprotecting reaction according to the forty-fourth step.

(Fifty-First Step)

A compound (XIV-18) is obtained (D ring formation) by deprotecting a $P^1$ part of a compound (XIV-14) according to the thirty-eighth step.

The present invention further provides various intermediates (I-P) shown below and a process for preparing the same, as well as a process for preparing the above mentioned compound (I) comprising the deprotection of the intermediate.

(Intermediates)

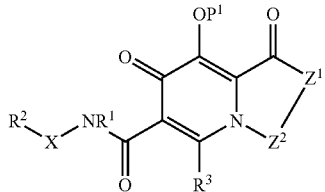
(I-P)

(P¹ is a hydroxyl-protecting group; the other symbols are as defined above)

Preferred Compounds are shown below. Each P¹ is a hydroxyl-protecting group, such as $C_{6-14}arylC_{1-8}alkyl$ (e.g., benzyl (=Bn)).

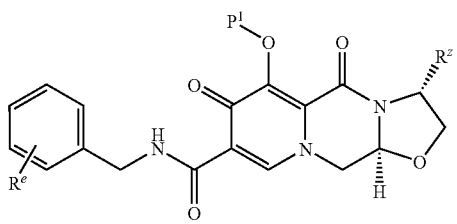
(I-20a)

Preferably, wherein $R^e$ is one or two halogen; $R^z$ is $C_{1-8}alkyl$, $C_{6-14}arylC_{1-8}alkyl$, $C_{6-14}aryl$, or alkoxy; and $P^1$ is $C_{6-14}arylC_{1-8}alkyl$;

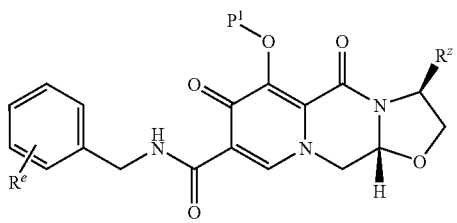
(I-20b)

Preferably, wherein $R^e$ is one or two halogen; $R^z$ is $C_{1-8}alkyl$, $C_{6-14}arylC_{1-8}alkyl$, $C_{6-14}aryl$, or alkoxy; and $P^1$ is $C_{6-14}arylC_{1-8}alkyl$;

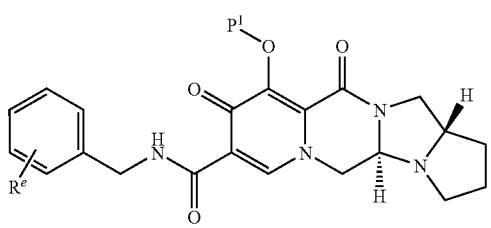
(I-21a)

Preferably, wherein $R^e$ is one or two halogen; and $P^1$ is $C_{6-14}arylC_{1-8}alkyl$;

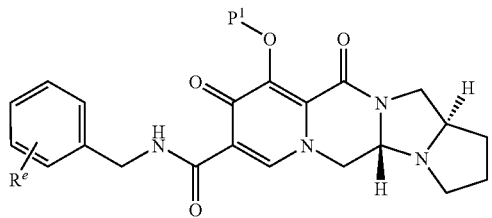
(I-21b)

Preferably, wherein $R^e$ is one or two halogen; and $P^1$ is $C_{6-14}arylC_{1-8}alkyl$;

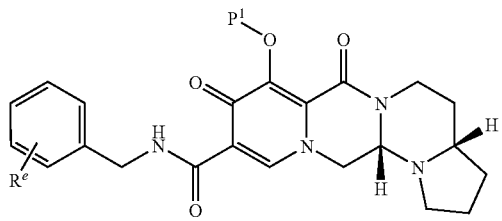
(I-22a)

Preferably, wherein $R^e$ is one or two halogen; and $P^1$ is $C_{6-14}arylC_{1-8}alkyl$;

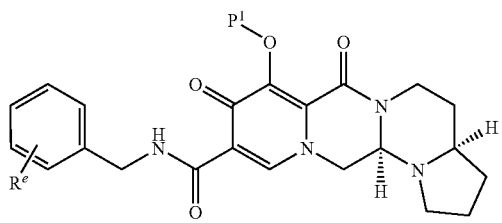
(I-22b)

Preferably, wherein $R^e$ is one or two halogen; and $P^1$ is $C_{6-14}arylC_{1-8}alkyl$;

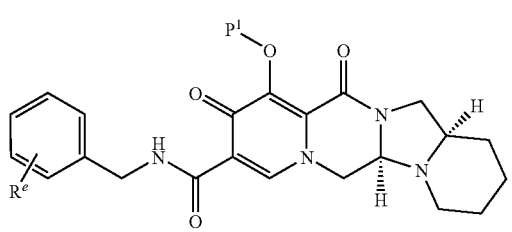
(I-23a)

Preferably, wherein $R^e$ is one or two halogen; and $P^1$ is $C_{6-14}arylC_{1-8}alkyl$;

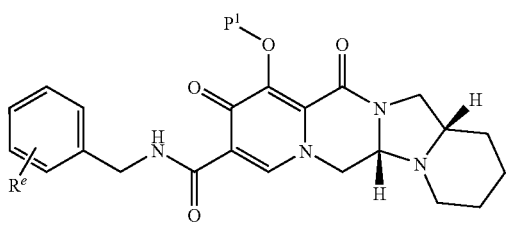
(I-23b)

Preferably, wherein $R^e$ is one or two halogen; and $P^1$ is $C_{6-14}arylC_{1-8}alkyl$;

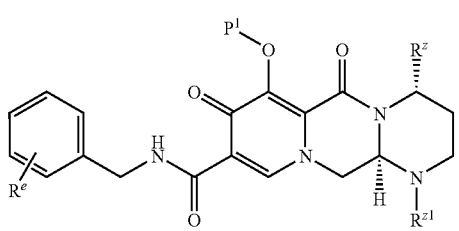
(I-24a)

Preferably, wherein $R^e$ is one or two halogen; $R^z$ is $C_{1-8}alkyl$; $R^{z1}$ is hydrogen, $C_{3-6}cycloalkyl$, heterocycle, or $C_{1-8}alkyl$ optionally substituted with hydroxy, $C_{3-6}cycloalkyl$, alkoxy, heterocycle, heteroaryl, $C_{6-14}aryl$, or amino, wherein said amino may be optionally substituted with $-C(O)C_{1-8}alkyl$ or $C_{1-8}alkyl$;

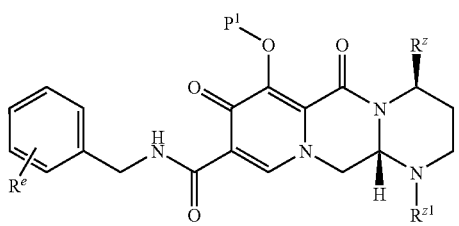
(I-24b)

Preferably, wherein $R^e$ is one or two halogen; $R^z$ is $C_{1-8}alkyl$; $R^{z1}$ is hydrogen, $C_{3-6}cycloalkyl$, heterocycle, or $C_{1-8}alkyl$ optionally substituted with hydroxy, $C_{3-6}cycloalkyl$, alkoxy, heterocycle, heteroaryl, $C_{6-14}aryl$, or amino, wherein said amino may be optionally substituted with $-C(O)C_{1-8}alkyl$ or $C_{1-8}alkyl$; and $P^1$ is $C_{6-14}arylC_{1-8}alkyl$;

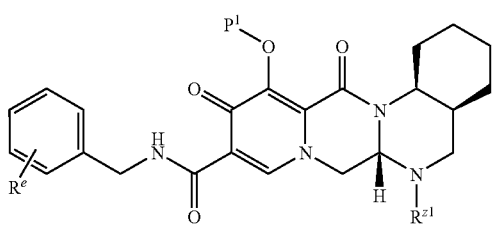
(I-25)

Preferably, wherein $R^e$ is one or two halogen; $R^{z1}$ is hydrogen, $C_{3-6}cycloalkyl$, heterocycle, or $C_{1-8}alkyl$ optionally substituted with hydroxy, $C_{3-6}cycloalkyl$, alkoxy, heterocycle, heteroaryl, $C_{6-14}aryl$, or amino, wherein said amino may be optionally substituted with $-C(O)C_{1-8}alkyl$ or $C_{1-8}alkyl$; and $P^1$ is $C_{6-14}arylC_{1-8}alkyl$;

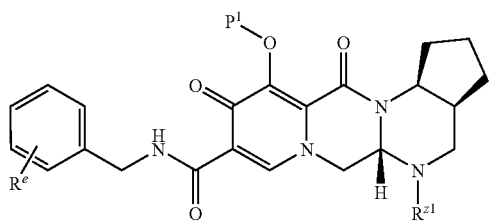
(I-26)

Preferably, wherein $R^e$ is one or two halogen; $R^{z1}$ is hydrogen, $C_{3-6}cycloalkyl$, heterocycle, or $C_{1-8}alkyl$ optionally substituted with hydroxy, $C_{3-6}cycloalkyl$, alkoxy, heterocycle, heteroaryl, $C_{6-14}aryl$, or amino, wherein said amino may be optionally substituted with $-C(O)C_{1-8}alkyl$ or $C_{1-8}alkyl$; and $P^1$ is $C_{6-14}arylC_{1-8}alkyl$;

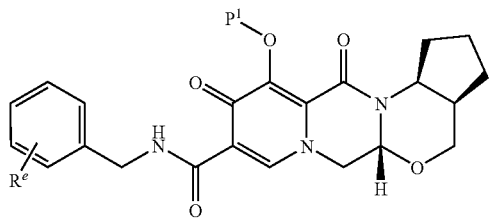
(I-27)

Preferably, wherein $R^e$ is halogen; and $P^1$ is $C_{6-14}aryl$ $C_{1-8}alkyl$;

The above intermediates, compound (I-20a), (I-20b), (I-21a), (I-21b), (I-22a), (I-22b), (I-23a), (I-23b), (I-24a), (I-24b), (I-25), (I-26), or (I-27), can be prepared by condensing a compound of the formula:

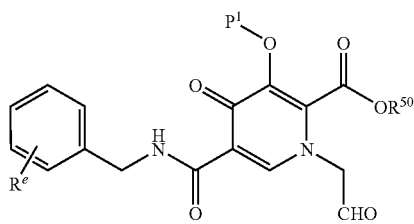

wherein $R^e$ is one or two halogen; and $R^{50}$ is $C_{1-8}alkyl$;
with each amine shown below, respectively:

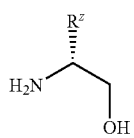

wherein $R^z$ is $C_{1-8}alkyl$, $C_{6-14}arylC_{1-8}alkyl$, $C_{6-14}aryl$, or alkoxy;

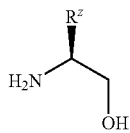

wherein $R^z$ is $C_{1-8}$alkyl, $C_{6-14}$aryl$C_{1-8}$alkyl, $C_{6-14}$aryl, or alkoxy;

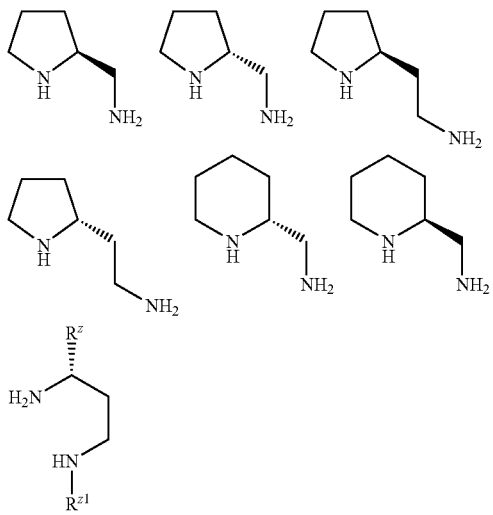

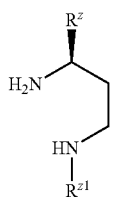

wherein $R^z$ is $C_{1-8}$alkyl; $R^{z1}$ is hydrogen, $C_{3-6}$cycloalkyl, heterocycle, or $C_{1-8}$alkyl optionally substituted with hydroxy, $C_{3-6}$cycloalkyl, alkoxy, heterocycle, heteroaryl, $C_{6-14}$aryl, or amino, wherein said amino may be optionally substituted with —C(O)$C_{1-8}$alkyl or $C_{1-8}$alkyl;

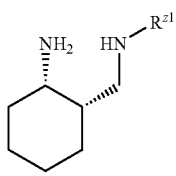

wherein $R^z$ is $C_{1-8}$alkyl; $R^{z1}$ is hydrogen, $C_{3-6}$cycloalkyl, heterocycle, or $C_{1-8}$alkyl optionally substituted with hydroxy, $C_{3-6}$cycloalkyl, alkoxy, heterocycle, heteroaryl, $C_{6-14}$aryl, or amino, wherein said amino may be optionally substituted with —C(O)$C_{1-8}$alkyl or $C_{1-8}$alkyl;

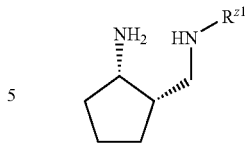

wherein $R^{z1}$ is hydrogen, $C_{3-6}$cycloalkyl, heterocycle, or $C_{1-8}$alkyl optionally substituted with hydroxy, $C_{3-6}$cycloalkyl, alkoxy, heterocycle, heteroaryl, $C_{6-14}$aryl, or amino, wherein said amino may be optionally substituted with —C(O)$C_{1-8}$alkyl or $C_{1-8}$alkyl;

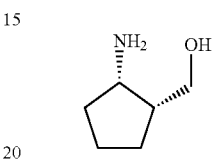

wherein $R^{z1}$ is hydrogen, $C_{3-6}$cycloalkyl, heterocycle, or $C_{1-8}$alkyl optionally substituted with hydroxy, $C_{3-6}$cycloalkyl, alkoxy, heterocycle, heteroaryl, $C_{6-14}$aryl, or amino, wherein said amino may be optionally substituted with —C(O)$C_{1-8}$alkyl or $C_{1-8}$alkyl;

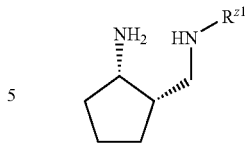

The condition for the above condensation is illustrated below for example.

Examples of the solvent include halocarbons such as dichloromethane, dichloroethane, and acetic acid.

The reaction temperature is preferably, 0 to 200° C., more preferably, 50 to 170° C.

The reaction time is usually several minutes to several hours.

The above intermediates, compound (I-20a), (I-20b), (I-21a), (I-21b), (I-22a), (I-22b), (I-23a), (I-23b), (I-24a), (I-24b), (I-25), (I-26), or (I-27), can be deprotected to give each corresponding deprotected compound wherein $P^1$ is hydrogen, or its pharmaceutically acceptable salt, which are encompassed within the scope of compound (I) of the present invention.

In addition, the present compound obtained above may be further chemically modified to synthesize another compound. In addition, when there is a reactive functional group (e.g.: OH, COOH, $NH_2$) on a side chain part etc. in the above reaction, the group may be protected before the reaction and may be deprotected after the reaction, if desired.

The present compound is useful, for example, as a drug such as an anti-virus drug. The present compound has the remarkable inhibitory action on integrase of a virus. Therefore, the present compound can be expected to have the preventive or therapeutic effect for various diseases derived from a virus which produces at least integrase, and is grown at infection in an animal cell, and is useful as an integrase inhibiting agent for retrovirus (e.g. HIV-1, HIV-2, HTLV-1, SIV, FIV etc.), and is useful as an anti-HIV drug etc.

In addition, the present compound may be used in joint use therapy by combining an anti-HIV drug having the different action mechanism such as a reverse trascriptase inhibitor and/or a protease inhibiting agent. Particularly, currently, an integrase inhibitor is not marketed, and it is useful to use in joint use therapy by combining the present compound with a reverse transcriptase inhibitor and/or a protease inhibitor.

Further, the above use includes not only use as a medical mixture for anti-HIV, but also use as a joint use agent for increasing the anti-HIV activity of other anti-HIV drug such as cocktail therapy.

In addition, the present compound can be used in order to prevent infection with a retrovirus vector from spreading into a tissue other than an objective tissue, upon use of a retrovirus vector based on HIV or MLV in the field of gene therapy. Particularly, when a cell is infected with a vector in vitro, and the cell is returned into a body, if the present compound is administered in advance, extra infection can be prevented in a body.

The present compound can be administered orally or parenterally. In the case of oral administration, the present compound can be also used as a conventional preparation, for example, as any dosage form of a solid agent such as tablets, powders, granules, capsules and the like; an aqueous agent; an oily suspension; or a liquid agent such as syrup and elixir. In the case of parenteral administration, the present compound can be used as an aqueous or oily suspension injectable, or a nasal drop. Upon preparation of it, conventional excipients, binders, lubricants, aqueous solvents, oily solvents, emulsifiers, suspending agents, preservatives, stabilizers and the like may be arbitrarily used. As an anti-HIV-drug, particularly, an oral agent is preferable. A preparation of the present invention is prepared by combining (e.g. mixing) a therapeutically effective amount of the present compound with a pharmaceutically acceptable carrier or diluent.

A dose of the present invention is different depending on an administration method, an age, a weight and condition of a patient, and a kind of a disease and, usually, in the case of oral administration, about 0.05 mg to 3000 mg, preferably about 0.1 mg to 1000 mg may be administered per adult a day, if necessary, by dividing the dose. In addition, in the case of parenteral administration, about 0.01 mg to 1000 mg, preferably about 0.05 mg to 500 mg is administered per adult a day.

Examples are shown below.

Example A-1

9-Hydroxy-2-(2-methoxy-ethyl)-1,8-dioxo-1,8-dihydro-2H-pyrid[1,2-a]pyrazine-7-carboxylic acid 4-fluoro-benzylamide Example B-1

9-Hydroxy-2-(2-methoxy-ethyl)-1,8-dioxo-1,3,4,8-tetrahydro-2H-pyrid[1,2-a]pyrazine-7-carboxylic acid 4-fluoro-benzylamide

[Chemical formula 52]

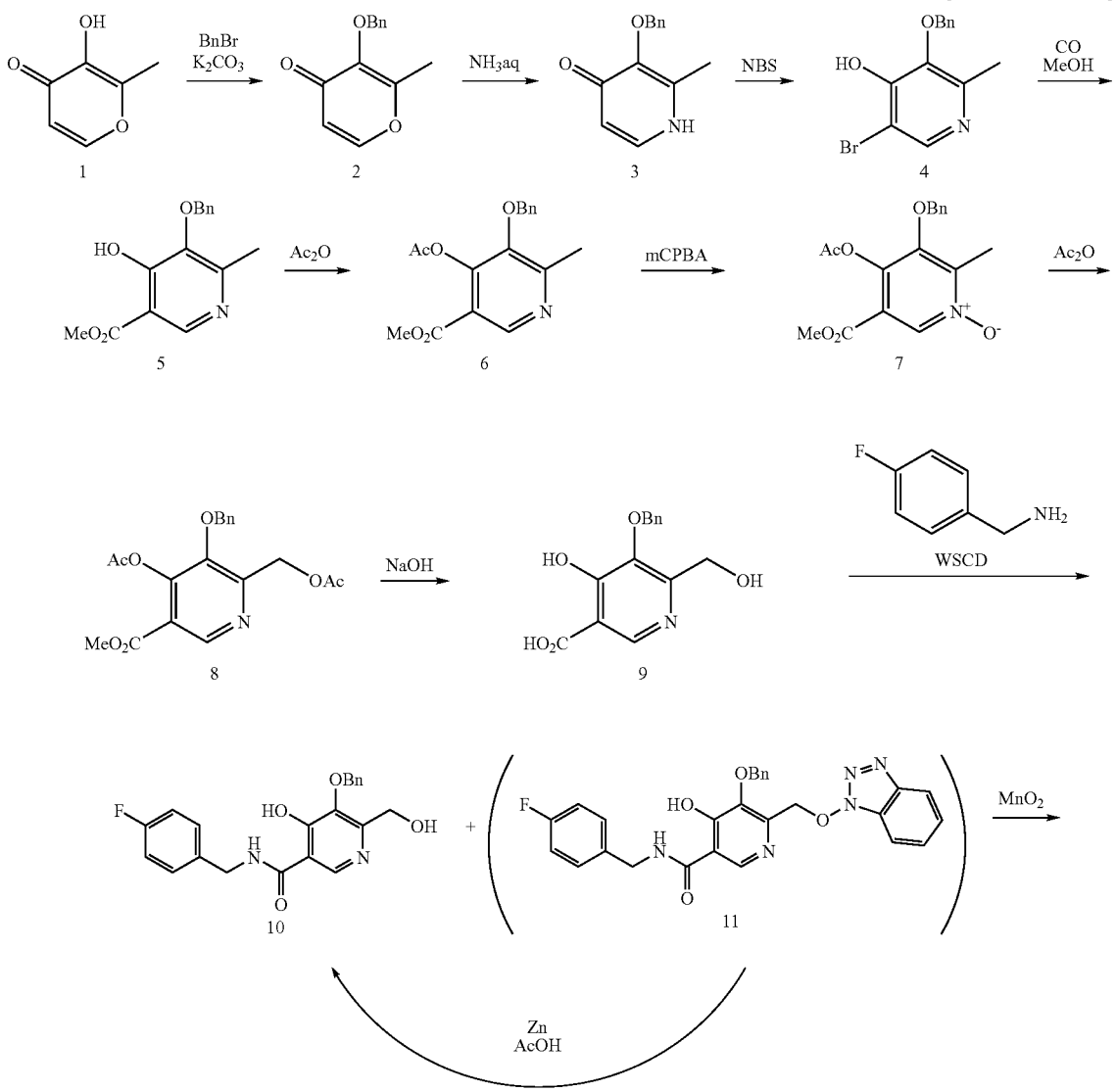

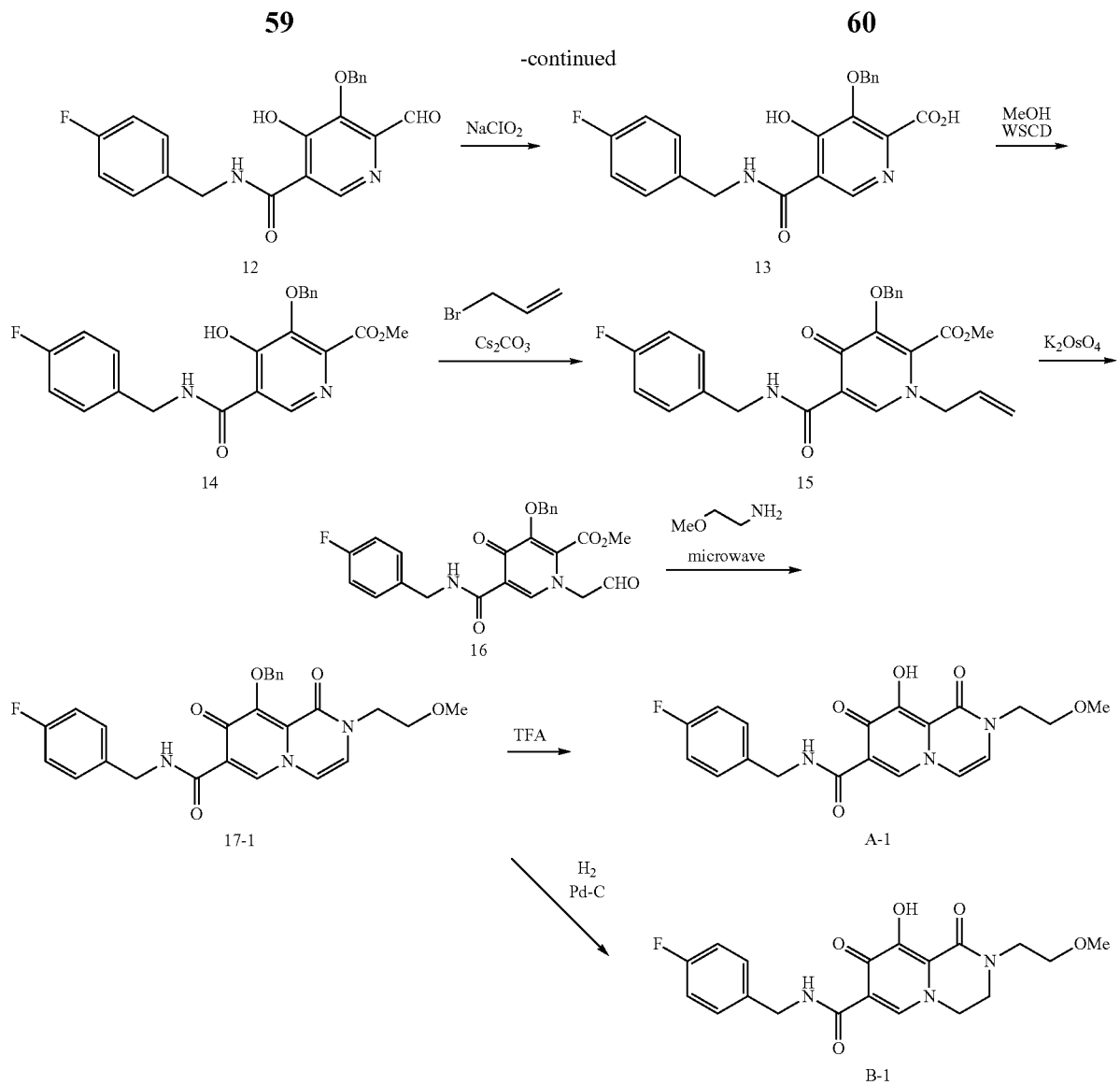

1) Maltol 1 (189 g, 1.5 mol) was dissolved in dimethylformamide (1890 ml), and benzyl bromide (184 ml, 1.5 mol) was added. After the solution was stirred at 80° C. for 15 minutes, potassium carbonate (228 g, 1.65 mol) was added, and the mixture was stirred for 1 hour. After the reaction solution was cooled to room temperature, an inorganic salt was filtered, and the filtrate was distilled off under reduced pressure. To the again precipitated inorganic salt was added tetrahydrofuran (1000 ml), this was filtered, and the filtrate was distilled off under reduced pressure to obtain the crude product (329 g, >100%) of 3-benzyloxy-2-methyl-pyran-4-one 2 as a brown oil.

NMR (CDCl$_3$) δ: 2.09 (3H, s), 5.15 (2H, s), 6.36 (1H, d, J=5.6 Hz), 7.29-7.41 (5H, m), 7.60 (1H, d, J=5.6 Hz).

2) The compound 2 (162.2 g, 750 mmol) was dissolved in ethanol (487 ml), and aqueous ammonia (28%, 974 ml) and a 6N aqueous sodium hydroxide solution (150 ml, 900 mmol) were added. After the reaction solution was stirred at 90° C. for 1 hour, this was cooled to under ice-cooling, and ammonium chloride (58 g, 1080 mmol) was added. To the reaction solution was added chloroform, this was extracted, and the organic layer was washed with an aqueous saturated sodium bicarbonate solution, and dried with anhydrous sodium sulfate. The solvent was distilled off under reduced pressure, isopropyl alcohol and diethyl ether were added to the residue, and precipitated crystals were filtered to obtain 3-benzyloxy-2-methyl-1H-pyridine-4-one 3 (69.1 g, 43%) as a pale yellow crystal.

NMR (DMSO-d$_6$) δ: 2.05 (3H, s), 5.04 (2H, s), 6.14 (1H, d, J=7.0 Hz), 7.31-7.42 (5H, m), 7.46 (1H, d, J=7.2 Hz), 11.29 (1H, brs).

3) The above compound 3 (129 g, 699 mmol) was suspended in acetonitrile (1300 ml), and N-bromosuccinic acid imide (117 g, 659 mmol) was added, followed by stirring at room temperature for 90 minutes. Precipitated crystals were filtered, and washed with acetonitrile and diethyl ether to obtain 3-benzyloxy-5-bromo-2-methyl-pyridine-4-ol 4 (154 g, 88%) as a colorless crystal.

NMR (DMSO-d$_6$) δ: 2.06 (3H, s), 5.04 (2H, s), 7.32-7.42 (5H, m), 8.03 (1H, d, J=5.5 Hz), 11.82 (1H, brs).

4) To a solution of the compound 4 (88 g, 300 mmol), palladium acetate (13.4 g, 60 mmol) and 1,3-bis(diphenylphosphino)propane (30.8 g, 516 mmol) in dimethylformamide (660 ml) were added methanol (264 ml) and triethylamine (210 ml, 1.5 mol) at room temperature. The interior of a reaction vessel was replaced with carbon monoxide, and the material was stirred at room temperature for 30 minutes, and stirred at 80 degree for 18 hours. A vessel to which ethyl acetate (1500 ml), an aqueous saturated ammonium chloride solution (1500 ml) and water (1500 ml) had been added was stirred under ice-cooling, and the reaction solution was added thereto. Precipitates were filtered, and washed with water (300 ml), ethyl acetate (300 ml) and diethyl ether (300 ml) to obtain 5-benzyloxy-4-hydroxy-6-methyl-nicotinic acid methyl ester 5 (44.9 g, 55%) as a colorless crystal.

NMR (DMSO-$d_6$) δ: 2.06 (3H, s), 3.72 (3H, s), 5.02 (2H, s), 7.33-7.42 (5H, m), 8.07 (1H, s).

5) After a solution of the compound 5 (19.1 g, 70 mmol) in acetic anhydride (134 ml) was stirred at 130° C. for 40 minutes, the solvent was distilled off under reduced pressure to obtain 4-acetoxy-5-benzyloxy-6-methyl-nicotinic acid methyl ester 6 (19.9 g, 90%) as a flesh colored crystal.

NMR (CDCl$_3$) δ: 2.29 (3H, s), 2.52 (3H, s), 3.89 (3H, s), 4.98 (2H, s), 7.36-7.41 (5H, m), 8.85 (1H, s).

6) To a solution of the compound 6 (46.2 g, 147 mmol) in chloroform (370 ml) was added metachloroperbenzoic acid (65%) (42.8 g, 161 mmol) in portions under ice-cooling, and this was stirred at room temperature for 90 minutes. To the reaction solution was added a 10% aqueous potassium carbonate solution, and this was stirred for 10 minutes, followed by extraction with chloroform. The organic layer was washed with successively with a 10% aqueous potassium carbonate solution, an aqueous saturated ammonium chloride solution, and an aqueous saturated sodium chloride solution, and dried with anhydrous sodium sulfate. The solvent was distilled off under induced pressure, and the residue was washed with diisopropyl ether to obtain 4-acetoxy-5-benzyloxy-6-methyl-1-oxy-nicotinic acid methyl ester 7 (42.6 g, 87%) as a colorless crystal.

NMR (CDCl$_3$) δ: 2.30 (3H, s), 2.41 (3H, s), 3.90 (3H, s), 5.02 (2H, s), 7.37-7.39 (5H, m), 8.70 (1H, s).

7) To acetic anhydride (500 ml) which had been heated to stir at 130° C. was added the compound 7 (42.6 g, 129 mmol) over 2 minutes, and this was stirred for 20 minutes. The solvent was distilled off under reduced pressure to obtain 4-acetoxy-6-acetoxymethyl-5-benzyloxy-nicotinic acid methyl ester 8 (49.6 g, >100%) as a black oil.

NMR (CDCl$_3$) δ: 2.10 (3H, s), 2.28 (3H, s), 3.91 (3H, s), 5.07 (2H, s), 5.20 (2H, s), 7.35-7.41 (5H, m), 8.94 (1H, s).

8) To a solution of the compound 8 (46.8 g, 125 mmol) in methanol (140 ml) was added a 2N aqueous sodium hydroxide solution (376 ml) under ice-cooling, and this was stirred at 50° C. for 40 minutes. To the reaction solution were added diethyl ether and 2N hydrochloric acid under ice-cooling, and precipitated crystals were filtered. Resulting crystals were washed with water and diethyl ether to obtain 5-benzyloxy-4-hydroxy-6-hydroxymethyl-nicotinic acid 9 (23.3 g, 68%) as a colorless crystal.

NMR (DMSO-$d_6$) δ: 4.49 (2H, s), 5.19 (2H, s), 5.85 (1H, brs), 7.14-7.20 (2H, m), 7.33-7.43 (7H, m), 8.30 (1H, s), 10.73 (1H, t, J=5.8 Hz), 11.96 (1H, brs).

9) To a solution of the compound 9 (131 g, 475 mmol), 1-(3-dimethylaminopropyl)-3-ethylcarbodiimide hydrochloride (219 g, 1140 mmol) and 1-hydroxybenzotriazole (128 g, 950 mmol) in dimethylformamide (1300 ml) was added 4-fluorobenzylamine (109 ml, 950 mmol), and this was stirred at 80° C. for 1.5 hours. After the reaction solution was cooled to room temperature, hydrochloric acid was added, followed by extraction with ethyl acetate. The extract was washed with a 5% aqueous potassium carbonate solution, an aqueous saturated ammonium chloride solution, and an aqueous saturated sodium chloride solution, and dried with anhydrous sodium sulfate. The solvent was distilled off under reduced pressure to obtain a mixture (175 g) of 10 and 11. the resulting mixture was dissolved in acetic acid (1050 ml) and water (1050 ml), and zinc (31.1 g, 475 mmol) was added, followed by heating to reflux for 1 hour. After the reaction solution was cooled to room temperature, a 10% aqueous potassium carbonate solution was added, followed by extraction with ethyl acetate. The extract was washed with an aqueous saturated ammonium chloride solution, and an aqueous saturated sodium chloride solution, and dried with anhydrous sodium sulfate. After the solvent was distilled off under reduced pressure, this was washed with diethyl ether to obtain 5-benzyloxy-N-(4-fluoro-benzyl)-4-hydroxy-6-hydroxymethyl-nicotinic acid amide 10 (107 g, 59%) as a colorless crystal.

NMR (DMSO-$d_6$) δ: 4.45 (2H, d, J=4.3 Hz), 4.52 (2H, d, J=5.8 Hz), 5.09 (2H, s), 6.01 (1H, brs), 7.36-7.43 (5H, m), 8.31 (1H, s), 12.63 (1H, brs).

10) After manganese dioxide (49 g) was added to a suspension of the compound 10 (9.8 g, 25.6 mmol) in chloroform (490 ml), the mixture was stirred at room temperature for 1 hour. After the reaction solution was stirred at 60° C. for 20 minutes, Celite filtration was performed, and this was washed with chloroform heated at 50° C. The filtrate was distilled off under reduced pressure to obtain 5-benzyloxy-N-(4-fluorobenzyl)-6-formyl-4-hydroxy-nicotinic acid amide 12 (8.2 g, 84%) as a pale yellow crystal.

NMR (DMSO-$d_6$) δ: 4.53 (2H, d, J=5.8 Hz), 5.38 (2H, s), 7.15-7.21 (2H, m), 7.35-7.46 (7H, m), 8.33 (1H, s), 9.90 (1H, s), 10.35 (1H, t, J=5.8 Hz), 12.49 (1H, brs).

11) To an aqueous solution (105 ml) of sodium chlorite (7.13 g, 78.8 mmol), and sulfamic acid (7.65 g, 78.8 mmol) was added a solution of the compound 12 (15.0 g, 39.4 mmol) in tetrahydrofuran (630 ml) under ice-cooling, and the mixture was stirred at room temperature for 1 hour. After water (2500 ml) was added to the reaction solution, precipitated crystals were filtered. Washing with diethyl ether afforded 3-benzyloxy-5-(4-fluoro-benzylcarbamoyl)-4-hydroxy-pyridine-2-carboxylic acid 13 (14.0 g, 90%) as a colorless crystal.

NMR (DMSO-$d_6$) δ: 4.52 (2H, d, J=5.8 Hz), 5.13 (2H, s), 7.14-7.19 (2H, m), 7.31-7.40 (5H, m), 7.47-7.49 (2H, m), 8.31 (1H, d, J=4.5 Hz), 10.44 (1H, t, J=5.9 Hz), 12.47 (1H, brs).

12) A solution of the compound 13 (198 mg, 0.500 mmol), 1-(3-dimethylaminopropyl)-3-ethylcarbodiimide hydrochloride (115 mg, 0.600 mmol) and 1-hydroxybenzotriazole (81 mg, 0.600 mmol) in dimethylformamide (3 ml) was stirred at room temperature for 1.5 hours. Then, methanol (3 ml) and triethylamine (153 ul, 1.10 mmol) were added, and the mixture was heated to reflux for 1.5 hours. The reaction solution was diluted with ethyl acetate, washed with an aqueous saturated sodium bicarbonate solution, a 10% aqueous citric acid solution, and an aqueous saturated sodium chloride solution, and dried with anhydrous sodium sulfate. The solvent was distilled off under reduced pressure, and the residue was washed with diethyl ether to obtain 3-benzyloxy-5-(4-fluoro-benzylcarbamoyl)-4-hydroxy-pyridine-2-carboxylic acid methyl ester 14 (141 mg, 69%) as a colorless crystal.

NMR (DMSO-$d_6$) δ: 3.85 (3H, s), 4.52 (2H, d, J=6.0 Hz), 5.15 (2H, s), 7.13-7.21 (2H, m), 7.31-7.47 (7H, m), 8.33 (1H, s), 10.41 (1H, t, J=6.0 Hz), 12.59 (1H, brs).

13) After 3-bromopropene (2.15 ml, 24.8 mmol) was added to a solution of the compound 6 (6.79 g, 16.5 mmol), and cesium carbonate (8.09 g, 24.8 mmol) in dimethylformamide (54 ml), the mixture was stirred at room temperature for 4.5 hours. To the reaction solution was added an aqueous ammonium chloride solution, and this was extracted with ethyl acetate, washed with water and an aqueous saturated sodium chloride solution, and dried with anhydrous sodium sulfate. The solvent was distilled off under reduced pressure, and the residue was washed with diethyl ether to obtain 1-allyl-3-benzyloxy-5-(4-fluoro-benzylcarbamoyl)-4-oxo-1,4-dihydro-pyridine-2-carboxylic acid methyl ester 15 (6.15 g, 83%) as a colorless crystal.

NMR (CDCl$_3$) δ: 3.76 (3H, s), 4.54 (2H, d, J=6.0 Hz), 4.60 (2H, d, J=6.0 Hz), 5.20-5.37 (2H, m), 5.25 (2H, s) 5.80-5.93 (1H, m), 6.98-7.04 (2H, m), 7.31-7.35 (7H, m), 8.45 (1H, s), 10.41 (1H, m).

14) To a solution of the compound 15 (7.6 g, 16.9 mmol) in 1,4-dioxane (228 ml) was added an aqueous solution (38 ml) of potassium osmate dihydrate (372 mg, 1.01 mmol), and sodium metaperiodate (14.5 g, 67.6 mmol) was further added, followed by stirring at room temperature for 2 hours. The reaction solution was added to a vessel to which ethyl acetate (300 ml) and water (300 ml) had been added, while stirring. The organic layer was washed with water, a 5% aqueous sodium hydrogen sulfite solution and an aqueous saturated sodium chloride solution, and dried with anhydrous sodium sulfate. The solvent was distilled off under reduced pressure, and the residue was washed with diethyl ether to obtain 3-benzyloxy-5-(4-fluoro-benzylcarbamoyl)-4-oxo-1-(2-oxo-ethyl)-1,4-dihydro-pyridine-2-carboxylic acid methyl ester 16 (5.39 g, 71%) as a colorless crystal.

NMR (CDCl$_3$) δ: 3.74 (3H, s), 4.60 (2H, d, J=5.9 Hz), 4.87 (2H, s), 5.27 (2H, s), 6.98-7.04 (2H, m), 7.30-7.40 (7H, m), 8.39 (1H, s), 9.58 (1H, s), 10.38 (1H, s).

15) To a solution of the compound 16 (400 mg, 0.884 mmol) in methylene chloride (12 ml) were added 2-methoxyethylamine (77 ul, 0.884 mmol) and acetic acid (18 ul), and the mixture was stirred at room temperature for 5 minutes. Thereafter, the reaction was performed at 140° C. for 30 minutes in a microwave reaction apparatus. The solvent was distilled off under reduced pressure, the residue was subjected to silica gel column chromatography, and fractions eluting with toluene-acetone were concentrated under reduced pressure to obtain 9-benzyloxy-2-(2-methy-ethyl)-1,8-dioxo-1,8-dihydro-2H-pyrid[1,2-a]pyrazine-7-carboxylic acid 4-fluoro-benzylamide 17-1 (226 mg, 54%) as a yellow solid.

NMR (CDCl$_3$) δ: 3.35 (3H, s), 3.65 (2H, t, J=5.1 Hz), 3.97 (2H, t, J=4.5 Hz), 4.63 (2H, d, J=5.7 Hz), 5.28 (2H, s), 6.56 (2H, m), 7.01 (2H, t, J=8.7 Hz), 7.38-7.30 (5H, m), 7.65 (2H, d, J=6.6 Hz), 10.63 (1H, s).

16) To the compound 17-1 (140 mg, 0.293 mmol) was added trifluoroacetic acid (1.4 ml) under ice-cooling, and the mixture was stirred at 0° C. for 5 minutes and, then, at room temperature for 1.5 hours. The solvent was distilled off under reduced pressure, and this was diluted with chloroform, and added to ice water. This was washed with an aqueous saturated sodium bicarbonate solution, a 10% aqueous citric acid solution and water, and dried with anhydrous sodium sulfate. The solvent was distilled off under reduced pressure, and the residue was recrystallized with methylene chloride-ethanol to obtain Example A-1 (89 mg, 79%) as a yellow crystal.

melting point: 223-224° C.

NMR (DMSO-d$_6$) δ: 3.25 (3H, s), 3.58 (2H, t, J=5.4 Hz), 3.92 (2H, t, J=5.1 Hz), 4.53 (2H, d, J=5.7 Hz), 6.87 (1H, d, 6.3 Hz), 7.14 (2H, t, J=9.0 Hz), 7.33-7.38 (2H, m), 7.47 (1H, d, J=6.0 Hz), 8.77 (1H, s), 10.56 (1H, t, J=6.0 Hz), 12.00 (1H, brs).

17) The compound 17-1 (157 mg, 0.329 mmol) was dissolved in dimethylformamide (18 ml) and methanol (1 ml), 10% palladium-carbon powder (31 mg) was added, and the mixture was stirred at room temperature for 20 hours under the hydrogen atmosphere. The reaction solution was filtered with Celite, and the filtrate was concentrated under reduced pressure. The residue was dissolved in chloroform, this was filtered with Celite again, and the filtrate was concentrated under reduced pressure. The residue was recrystallized with methylene chloride-methanol to obtain Example B-1 (66 mg, 52%) as a brown crystal.

melting point: 197-199° C.

NMR (DMSO-d$_6$) δ: 3.27 (3H, s), 3.55 (2H, t, J=5.1 Hz), 3.68 (2H, t, J=5.1 Hz), 3.79 (2H, s), 4.36 (2H, s), 4.51 (2H, d, J=5.7 Hz), 7.15 (2H, t, J=8.7 Hz), 7.32-7.37 (2H, m), 8.38 (1H, s), 10.46 (1H, t, J=5.4 Hz), 12.41 (1H, s).

Example C-1

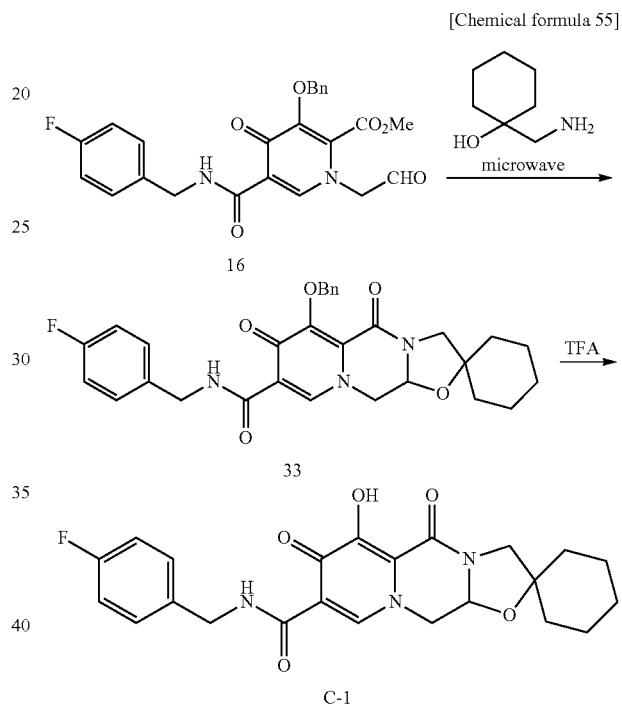

1) A compound 33 was synthesized using 1-aminomethylcyclopentanol hydroxyethylamine according to the method of synthesizing a compound 17-1.

1H-NMR (CDCl$_3$) δ: 1.30-1.80 (10H, m), 3.47 (1H, d, J=11.4 Hz), 3.61 (1H, d, J=11.4 Hz), 3.80-3.95 (1H, m), 4.30 (1H, dd, J=14.7, 3.0 Hz), 4.60 (2H, d, J=5.7 Hz), 5.17-5.23 (2H, m), 5.39 (1H, d, J=9.9 Hz), 6.95-7.10 (2H, m), 7.20-7.40 (5H, m), 7.58 (2H, d, J=7.2 Hz), 8.41 (1H, s), 10.40 (1H, s).

2) A compound 33-2 was synthesized using hydroxyethylamine according to the similar method.

Compound 33-2

5-Benzyloxy-4,6-dioxo-2,3,4,6,9,9a-hexahydro-1-oxa-3a,8a-diaza-cyclopenta[b]naphthalene-7-carboxylic acid 4-fluorobenzylamide 1H-NMR (DMSO-d$_6$) δ: 3.48-3.58 (1H, m), 3.73-3.86 (1H, m), 3.97-4.10 (2H, m), 4.20-4.30 (1H, m), 4.46-4.60 (2H, m), 4.85 (1H, dd, J=12.3, 3.5 Hz), 5.40 (1H, d, J=10.2 Hz), 5.18 (1H, d, J=10.2 Hz), 5.28 (1H, dd, J=10.2, 3.2 Hz), 7.10-7.20 (2H, m), 7.23-7.40 (5H, m), 7.50-7.73 (2H, m), 8.60 (1H, s), 10.22 (1H, m).

3) Example C-1 was synthesized using a compound 33, according to the method of synthesizing Example A-1.

Melting point: >300° C.

1H-NMR (DMSO-d$_6$) δ: 1.10-1.60 (10H, m), 3.25 (1H, d, J=11.4 Hz), 3.37 (1H, d, J=11.4 Hz), 3.76 (1H, t, J=10.5 Hz), 4.30 (2H, d, J=5.8 Hz), 4.66 (1H, dd, J=12.2, 3.8 Hz), 5.22 (1H, dd, J=3.8, 10.4 Hz), 6.90-6.96 (2H, m), 7.10-7.15 (2H, m), 8.25 (1H, s), 10.10 (1H, brs), 11.32 (1H, brs).

The following compounds were synthesized using the similar method.

Example C-2

5-Hydroxy-4,6-dioxo-2,3,4,6,9,9a-hexahydro-1-oxa-3a,8a-diaza-cyclopenta[b]naphthalene-7-carboxylic acid 4-fluorobenzylamide Melting point-272-274° C.

1H-NMR (DMSO-d$_6$) δ: 3.59-3.67 (1H, m), 3.72-3.81 (1H, m), 3.98-4.10 (2H, m), 4.27-4.35 (1H, m), 4.52 (2H, d, J=7.2 Hz), 4.92 (1H, dd, J=12.3, 12.3 Hz), 5.27 (1H, dd, J=3.6, 9.9 Hz), 7.11-7.20 (2H, m), 7.30-7.40 (2H, m), 8.49 (1H, s), 10.32 (1H, t, J=5.6 Hz), 11.53 (1H, s).

Example C-3

5-Hydroxy-6,10-dioxo-3,4,6,9,9a,10-hexahydro-2H-1-oxa-4a,8a-diazaanthracene-7-carboxylic acid 4-fluorobenzylamide melting point: 259° C.

1H-NMR (DMSO-d$_6$) δ: 1.60-1.67 (1H, m), 1.72-1.85 (1H, m), 3.25 (1H, td, J=12.8, 3.5 Hz), 3.86-3.93 (1H, m), 4.06 (1H, dd, J=11.4, 4.2 Hz), 4.44-4.57 (5H, m), 5.28 (1H, t, J=3.8 Hz), 7.13-7.18 (2H, m), 7.33-7.37 (2H, m), 8.51 (1H, s), 10.36 (1H, t, J=6.0 Hz), 12.47 (1H, s).

Example C-4

5-Hydroxy-1-isopropyl-4,6-dioxo-2,3,4,6,9,9a-hexahydro-1H-1,3a,8a-triaza-cyclopenta[b]naphthalene-7-carboxylic acid 4-fluoro-benzylamide melting point: 232-234° C.

NMR (DMSO-d$_6$) δ: 1.03 (3H, d, 6.6 Hz), 1.14 (3H, d, 6.6 Hz), 2.79-3.66 (5H, m), 3.82 (1H, t, 10.8 Hz), 4.51 (3H, m), 4.90 (1H, m), 7.15 (2H, t, 9.0 Hz), 7.34 (2H, m), 8.45 (1H, s), 10.39 (1H, t, 5.4 Hz), 11.60 (1H, s).

Example C-5

5-Hydroxy-4,6-dioxo-2,3,4,6,9,9a-hexahydro-1H-1,3a,8a-triaza-cyclopenta[b]naphthalene-7-carboxylic acid 4-fluoro-benzylamide melting point: 256-258° C.

NMR (DMSO-d$_6$) δ: 3.00-3.55 (5H, m), 3.96 (1H, t, 11.4 Hz), 4.52 (2H, d, 11.7 Hz), 4.76 (2H, m), 7.16 (2H, t, 8.7 Hz), 7.35 (2H, m), 8.48 (1H, s), 10.42 (1H, t, 5.4 Hz), 11.91 (1H, s).

Example C-6

5-Hydroxy-6,10-dioxo-1,2,3,4,6,9,9a,10-octahydro-1,4a,8a-triaza-anthracene-7-carboxylic acid 4-fluoro-benzylamide melting point: 255° C.

NMR (DMSO-d$_6$) δ: 1.60 (1H, s), 2.75-3.16 (4H, m), 4.52 (2H, d, 6.0 Hz), 4.13-4.68 (4H, m), 7.16 (2H, 9.0 Hz, t), 7.34 (2H, m), 10.42 (1H, s), 10.44 (1H, 6.0 Hz, t), 12.81 (1H, s).

Example C-7

1-(2-Diethylamino-ethyl)-5-hydroxy-4,6-dioxo-2,3,4,6,9,9a-hexahydro-1H-1,3a,8a-triaza-cyclopenta[b]naphthalene-7-carboxylic acid 4-fluoro-benzylamide melting point: 186-187° C.

NMR (DMSO-d$_6$) δ: 0.97 (6H, t, 7.2 Hz), 2.42-2.91 (10H, m), 3.44-3.87 (5H, m), 4.23 (1H, m), 4.51 (2H, d, 5.7 Hz), 5.00 (1H, m), 7.16 (2H, t, 9.0 Hz), 7.33-7.37 (2H, m), 8.43 (1H, s), 10.39 (1H, t, 5.7 Hz), 11.81 (1H, s).

Example C-8

1-Hydroxy-2,11-dioxo-2,5,5a,7,8,9,10,11-octahydro-6-oxa-4a,10a-diaza-cyclohepta[b]naphthalene-3-carboxylic acid 4-fluoro-benzylamide melting point: 242-244° C.

NMR (DMSO-d$_6$) δ: 1.40-2.00 (4H, m), 3.20-3.30 (1H, m), 3.66-3.77 (2H, m), 4.14-4.23 (1H, m), 4.38-4.41 (1H, m), 4.52 (2H, d, 6.3 Hz), 4.58-4.63 (1H, m), 5.34 (1H, brs), 7.15 (2H, t, 9.0 Hz), 7.33-7.37 (2H, m), 8.50 (1H, s), 10.39 (1H, brs), 12.14 (1H, s).

Example C-9

5-Hydroxy-1-(2-hydroxy-ethyl)-6,10-dioxo-1,2,3,4,6,9,9a,10-octahydro-1,4a,8a-triaza-anthracene-7-carboxylic acid 4-fluoro-benzylamide NMR (DMSO-d$_6$) δ: 1.58-1.80 (1H, m), 2.70-3.60 (7H, m), 4.40-4.54 (6H, m), 4.77-4.82 (1H, m), 7.15 (2H, t, 9.0 Hz), 7.33-7.38 (2H, m), 8.52 (1H, s), 10.43 (1H, brs), 12.57 (1H, s).

Example C-10

1-Hydroxy-2,11-dioxo-2,5a,6,7,8,9,10,11-octahydro-5H-4a,6,10a-triaza-cyclohepta[b]naphthalene-3-carboxylic acid 4-fluoro-benzylamide melting point: 256° C.

NMR (DMSO-d$_6$) δ: 1.47-1.77 (4H, m), 2.69-2.81 (2H, m), 3.34-3.41 (1H, m), 4.08-4.12 (1H, m), 4.26-4.40 (2H, m), 4.52 (2H, d, J=6.0 Hz), 7.15 (2H, t, 8.8 Hz), 7.33-7.36 (2H, m), 8.43 (1H, s), 10.46 (1H, t, J=6.0 Hz), 12.68 (1H, s).

Example C-11

5-Hydroxy-1-(2-methoxy-ethyl)-6,10-dioxo-1,2,3,4,6,9,9a,10-octahydro-1,4a,8a-triaza-anthracene-7-carboxylic acid 4-fluoro-benzylamide melting point: 147° C.

NMR (DMSO-d$_6$) δ: 1.56-1.74 (2H, m), 2.53-2.58 (1H, m), 2.66-3.10 (4H, m), 3.18 (3H, s), 3.41-3.39 (2H, m), 4.37-

4.52 (5H, m), 4.73-4.80 (1H, m), 7.15 (2H, t, 8.8 Hz), 7.33-7.37 (2H, m), 8.56 (1H, s), 10.40 (1H, t, J=6.0 Hz), 12.62 (1H, s).

Example C-12

5-Hydroxy-1-(2-isopropoxy-ethyl)-6,10-dioxo-1,2,3,4,6,9,9a,10-octahydro-1,4a,8a-triaza-anthracene-7-carboxylic acid 4-fluoro-benzylamide melting point: 151° C.

NMR (DMSO-$d_6$) δ: 1.02 (6H, dd, J=4.0, 6.0 Hz), 1.56-1.67 (2H, m), 2.53-2.58 (1H, m), 2.74-3.04 (4H, m), 3.18 (3H, s), 3.41-3.52 (3H, m), 4.41-4.59 (5H, m), 4.79-4.83 (1H, m), 7.15 (2H, t, 8.8 Hz), 7.34-7.36 (2H, m), 8.58 (1H, s), 10.40 (1H, t, J=6.0 Hz), 12.56 (1H, s).

Example C-13

5-Hydroxy-3,3-dimethyl-6,10-dioxo-3,4,6,9,9a,10-hexahydro-2H-1-oxa-4a,8a-diaza-anthracene-7-carboxylic acid 4-fluoro-benzylamide melting point: 275-277° C.

NMR (DMSO-$d_6$) δ: 2.97 (3H, s), 3.01 (3H, s), 3.00-3.18 (3H, m), 4.45-4.56 (5H, m), 5.16 (1H, s), 7.15 (2H, t, J=9 Hz), 7.35 (2H, dd, J=5.4 Hz, 8.7 Hz), 8.5 (1H, s), 10.36 (1H, t, J=5.7 Hz), 12.4 (1H, s).

Example C-14

1-Cyclohexyl-5-hydroxy-6,10-dioxo-1,2,3,4,6,9,9a,10-octahydro-1,4a,8a-triaza-anthracene-7-carboxylic acid-4-fluoro-benzylamide melting point: 275-277° C.

NMR (DMSO-$d_6$) δ: 1.22-1.70 (2H, m), 2.50-3.02 (3H, m), 4.45 (4H, m), 4.52 (2H, s), 4.78 (1H, d, J=13.2 Hz), 7.16 (2H, t, J=8.7 Hz), 7.35 (2H, dd, J=5.7 Hz, 8.4 Hz), 8.62 (1H, s), 10.52 (1H, s), 12.55 (1H, s).

Example C-15)

5-Hydroxy-1-isopropyl-6,10-dioxo-1,2,3,4,6,9,9a,10-octahydro-1,4a,8a-triaza-anthracene-7-carboxylic acid-4-fluoro-benzylamide melting point: 220° C.

NMR (DMSO-$d_6$) δ: 0.94 (6H, d, J=9.6 Hz), 1.53-1.67 (2H, m), 2.92-3.30 (3H, m), 4.32-4.40 (4H, m), 4.52 (2H, d, J=5.7 Hz), 4.89 (1H, d, J=14.1 Hz), 7.16 (2H, t, J=9.0 Hz), 7.35 (2H, dd, J=6.3 Hz, 9.0 Hz), 8.61 (1H, s), 10.46 (1H, s), 12.55 (1H, s).

Example C-16

5-Hydroxy-3,3-dimethyl-6,10-dioxo-1,2,3,4,6,9,9a,10-octahydro-1,4a,8a-triaza-anthracene-7-carboxylic acid 4-fluoro-benzylamide melting point: 280° C.

NMR (DMSO-$d_6$) δ: 0.87 (3H, s), 0.93 (3H, s), 2.59-3.15 (6H, m), 4.09-4.57 (6H, m), 7.14 (2H, d, J=9.0 Hz), 7.34 (2H, dd, J=5.4 Hz, 8.4 Hz), 8.42 (1H, s), 10.46 (1H, s), 12.77 (1H, s).

Example C-17

5-Hydroxy-1-(2-morpholin-4-yl-2-oxoethyl)-6,10-dioxo-1,2,3,4,6,9,9a,10-octahydro-1,4a,8a-triaza-anthracene-7-carboxylic acid 4-fluoro-benzylamide melting point: 140° C.

NMR (DMSO-$d_6$) δ: 1.60 (2H, m), 2.91-3.62 (13H, m), 4.41 (2H, m), 4.51 (2H, d, J=4.8 Hz), 4.80 (2H, m), 7.15 (2H, t, J=8.7 Hz), 7.34 (2H, m), 8.44 (1H, s), 10.43 (1H, s), 12.54 (1H, s).

Example C-18

1-(3-Acetylamino-propyl)-5-hydroxy-6,10-dioxo-1,2,3,4,6,9,9a,10-octahydro-1,4a,8a-triaza-anthracene-7-carboxylic acid 4-fluoro-benzylamide melting point: 177-178° C.

NMR (DMSO-$d_6$) δ: 1.74 (3H, s), 1.49-2.98 (9H, m), 3.60 (1H, s), 4.25-4.65 (7H, m), 7.14 (2H, t, J=8.4 Hz), 7.34 (2H, m), 7.71 (1H, s), 8.26 (1H, s), 10.60 (1H, s).

Example C-19

1-Dimethycarbamoylmethyl-5-hydroxy-6,10-dioxo-1,2,3,4,6,9,9a,10-octahydro-1,4a,8a-triaza-anthracene-7-carboxylic acid 4-fluoro-benzylamide melting point: 190° C.

NMR (DMSO-$d_6$) δ: 1.60 (2H, m), 2.76 (3H, s), 2.83 (3H, s), 2.90-3.59 (5H, s), 4.40 (2H, m), 4.51 (2H, d, 5.7 Hz), 4.80 (1H, d, d=14.4 Hz), 4.98 (1H, s), 7.16 (2H, t, J=8.4 Hz), 7.34 (2H, m), 8.54 (1H, s), 10.42 (1H, s).

Example C-20

5-Hydroxy-1-(3-methanesulfonylamino-propyl)-6,10-dioxo-1,2,3,4,6,9,9a,10-octahydro-1.4a,8a-triaza-anthracene-7-carboxylic acid 4-fluoro-benzylamide melting point: 176° C.

NMR (DMSO-$d_6$) δ: 1.54-1.75 (4H, m), 2.80 (3H, s), 2.30-3.04 (8H, m), 4.45 (2H, m), 4.52 (2H, d, J=5.6 Hz), 4.75 (1H, d, J=13.2 Hz), 6.91 (1H, t, J=5.6 Hz), 7.16 (2H, t, J=8.8 Hz), 7.36 (2H, m), 8.61 (1H, s), 10.41 (1H, t, J=5.6 Hz), 12.58 (1H, s).

Example C-21

5-Hydroxy-2-methyl-6,10-dioxo-3,4,6,9,9a,10-hexahydro-2H-1-oxa-4a,8a-diazaanthracene-7-carboxylic acid 4-fluorobenzylamide NMR (CDCl3) δ: 1.27 (3H, d, J=6.0 Hz), 1.55-1.78 (2H, m), 3.11 (1H, td, J=12.9, 3.7 Hz), 3.89-4.00 (1H, m), 4.16 (1H, dd, J=13.8, 3.9 Hz), 4.34 (1H, dd, J=13.8, 3.9 Hz), 4.60 (2H, d, J=6.0 Hz), 4.71 (1H, ddd, J=13.5, 4.8, 1.8 Hz), 5.08

(1H, t, J=3.9 Hz), 6.96-7.04 (2H, m), 7.26-7.35 (2H, m), 8.32 (1H, s), 10.41 (1H, br s), 12.41 (1H, brs).

Example F-1

5-Hydroxy-1-isobutyl-4,6-dioxo-2,3,4,6,9,9a-hexahydro-1H-1,3a,8a-triazacyclopenta[b]naphthalene-7-carboxylic acid-4 fluorobenzylamide

[Chemical formula 59]

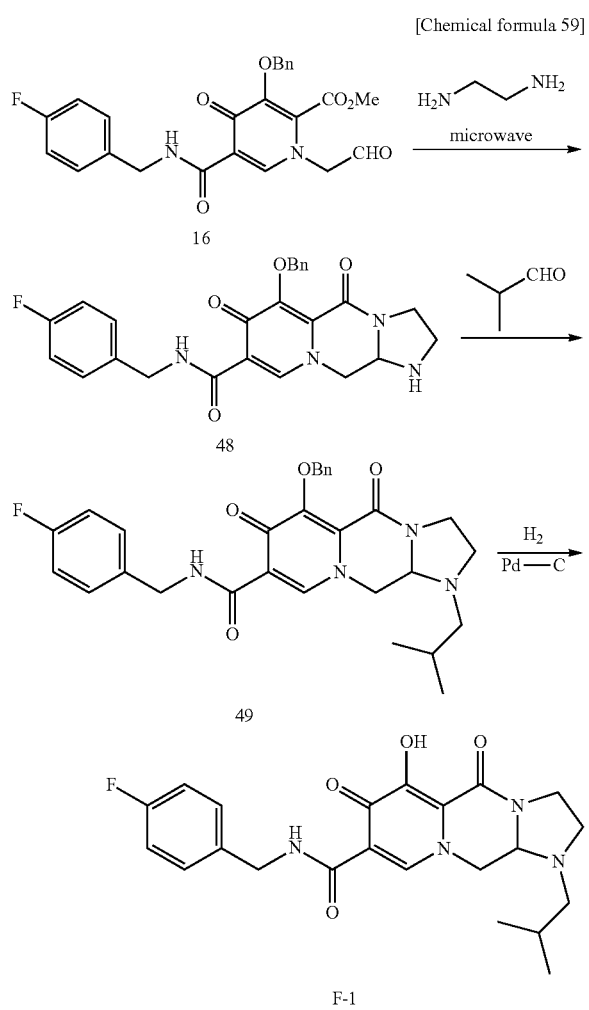

1) According to the method of synthesizing a compound 17-1, the crude purified product (503 mg) of a compound 48 was obtained at a yield of 82% from a compound 16 (600 mg).
2) To a solution of a compound 48 (100 mg, 0.22 mmol), isobutylaldehyde (39 μl, 0.432 mmol) and acetic acid (25 μl, 0.432 mmol) in dichloromethane (4 ml) was added sodium triacetoxyborohydride (92 mg, 0.432 mmol) under ice-cooling, and the mixture was stirred at room temperature for 2 hours. Further, isobutylaldehyde (20 μl) and sodium triacetoxyborohydride (46 mg) were added, and the mixture was stirred for 30 minutes. To the reaction solution was added water, this was extracted with chloroform, and the organic layer was washed with an aqueous saturated sodium bicarbonate solution. After drying, the solvent was distilled off under reduced pressure, and this was purified by silica gel column chromatography. A compound 49 (87 mg) was obtained as a colorless crystal at a yield of 78%.

1H-NMR (CDCl$_3$) δ: 0.96 (3H, d, J=6.6 Hz), 0.97 (3H, d, J=6.3 Hz), 1.72-1.86 (1H, m), 2.25-2.41 (2H, m), 2.47-2.58 (1H, m), 3.39-3.46 (1H, m), 3.69-3.76 (2H, m), 3.85-3.93 (1H, m), 4.06 (1H, dd, J=9.9, 2.7 Hz), 4.16-4.22 (1H, m), 4.57 (1H, dd, J=15.3, 5.1 Hz), 4.64 (1H, dd, J=14.7, 5.1 Hz), 5.20 (1H, d, J=9.9 Hz), 5.38 (1H, d, J=9.9 Hz), 6.96-7.05 (2H, m), 7.28-7.36 (5H, m), 7.58-7.62 (2H, m), 8.40 (1H, s), 10.44 (1H, br s).
3) According to the method of a step 17) of Example B-1, a compound F-1 (43 mg) was obtained at a yield of 64% from a compound 49 (81 mg).

1H-NMR (DMSO-d$_6$) δ: 0.90 (3H, d, J=6.4 Hz), 0.91 (3H, d, J=6.0 Hz), 1.75-1.84 (1H, m), 2.24-2.39 (1H, m), 2.39-2.54 (2H, m), 3.36-3.43 (1H, m), 3.52-3.60 (1H, m), 3.67-3.73 (1H, m), 3.81-3.88 (1H, m), 4.19-4.23 (1H, m), 4.52 (2H, d, J=6.0 Hz), 4.94-4.99 (1H, m), 7.12-7.20 (2H, m), 7.32-7.38 (2H, m), 8.45 (1H, s), 10.37 (1H, t, J=2.0 Hz), 11.74 (1H, s).

According to the same manner as that of Example F-1, the following Example compounds F-2 to F-63 were synthesized.

Example F-2

5-Hydroxy-1-isobutyl-6,10-dioxo-1,2,3,4,6,9,9a,10-octahydro-1,4a,8a-triazaanthracene-7-carboxylic acid 4-fluorobenzylamide melting-point: 146-148° C.
1H-NMR (DMSO-d$_6$) δ: 0.63 (3H, d, J=6.6 Hz), 0.79 (3H, d, J=6.6 Hz), 1.56-1.66 (2H, m), 1.67-1.75 (1H, m), 1.94-1.99 (1H, m), 2.41-2.54 (2H, m), 2.96-3.06 (2H, m), 4.41-4.59 (5H, m), 4.76-4.8 (1H, m), 7.14-7.21 (2H, m), 7.33-7.38 (2H, m), 8.61 (1H, s), 10.40 (1H, d, J=5.8 Hz), 12.56 (1H, s).

Example F-3

1-Cyclopropylmethyl-5-hydroxy-6,10-dioxo-1,2,3,4,6,9,9a,10-octahydro-1,4a,8a-triaza-anthracene-7-carboxylic acid 4-fluoro-benzylamide melting point: 182-184° C.
NMR (DMSO-d$_6$) δ: 0.06 (2H, m), 0.43 (2H, d, 8.4 Hz), 0.80 (1H, m), 1.66 (2H, m), 2.28-3.30 (4H, m), 4.40-4.50 (4H, m), 4.52 (2H, d, 6.0 Hz), 4.78 (2H, m), 7.15 (2H, t, 8.7 Hz), 7.34 (2H, m), 8.55 (1H, s), 10.47 (1H, s), 12.55 (1H, s).

Example F-4

1-Cyclopentylmethyl-5-hydroxy-6,1-dioxo-1,2,3,4,6,9,9a,10-octahydro-1,4a,8a-triaza-anthracene-7-carboxylic acid 4-fluoro-benzylamide melting point: 184-185° C.° C.
NMR (DMSO-d$_6$) δ: 0.88-2.10 (1H, m), 2.60 (2H, m), 2.95-3.28 (2H, m), 4.38-4.53 (6H, m), 4.82 (1H, m), 7.15 (2H, t, 9.0 Hz), 7.34 (2H, m), 8.57 (1H, s), 10.42 (1H, s), 12.45 (1H, s).

Example F-5

5-Hydroxy-1-(4-methylsulfanylbenzyl)-6,10-dioxo-1,2,3,4,6,9,9a,10-octahydro-1,4a,8a-triazaanthracene-7-carboxylic acid 4-fluorobenzylamide (DMSO-d$_6$) δ: 1.51-1.56 (1H, m), 1.69-1.74 (1H, m), 2.42 (3H, s), 2.55-2.62 (1H, m), 2.80-2.84 (1H, m), 3.00-3.08 (1H, m), 3.32-3.36 (1H, m), 3.93 (1H, d, J=13.6 Hz), 4.45-4.53

(4H, m), 4.58 (1H, s), 4.83 (1H, d, J=15.2 Hz), 7.11-7.19 (6H, m), 7.33-7.40 (2H, m), 8.34 (1H, s), 10.38 (1H, t, J=6.0 Hz), 12.58 (1H, s).

Example F-6

1-(5-Chloro-1,3-dimethyl-1H-pyrazol-4-ylmethyl)-5-hydroxy-6,10-dioxo-1,2,3,4,6,9,9a,10-octahydro-1,4a,8a-triazaanthracene-7-carboxylic acid 4-fluorobenzylamide (DMSO-$d_6$) δ: 1.56-1.59 (2H, m), 1.88 (3H, s), 2.37-2.45 (1H, m), 2.76-2.80 (1H, m), 3.00-3.06 (2H, m), 3.64 (3H, s), 3.87 (1H, d, J=13.2 Hz), 4.40-4.55 (5H, m), 4.97 (1H, d, J=14.4 Hz), 7.13-7.19 (2H, m), 7.33-7.38 (2H, m), 8.56 (1H, s), 10.39 (1H, t, J=6.0 Hz), 12.46 (1H, s).

Example F-7

5-Hydroxy-1-(3-methoxybenzyl)-6,10-dioxo-1,2,3,4,6,9,9a,10-octahydro-1,4a,8a-triazaanthracene-7-carboxylic acid 4-fluorobenzylamide (DMSO-$d_6$) δ: 1.52-1.57 (1H, m), 1.70-1.80 (1H, m), 2.60-2.68 (1H, m), 2.84-2.90 (1H, m), 3.01-3.09 (1H, m), 3.36 (1H, d, J=14.0 Hz), 3.61 (3H, s), 3.91 (1H, d, J=14.0 Hz), 4.45-4.52 (4H, m), 4.58 (1H, s), 4.76 (1H, d, J=14.8 Hz), 6.68-6.73 (2H, m), 6.77 (1H, d, J=7.6 Hz), 7.13-7.19 (3H, m), 7.33-7.38 (2H, m), 8.17 (1H, s), 10.38 (1H, t, J=6.0 Hz), 12.57 (1H, s).

Example F-8

5-Hydroxy 1-(4-methanesulfonylbenzyl)-6,10-dioxo-1,2,3,4,6,9,9a,10-octahydro-1,4a,8a-triazaanthracene-7-carboxylic acid 4-fluorobenzylamide (DMSO-$d_6$) δ: 1.54-1.58 (1H, m), 1.74-1.80 (1H, m), 2.67-1.74 (1H, m), 2.83-2.87 (1H, m), 3.05-3.12 (1H, m), 3.18 (3H, s), 3.52 (1H, d, J=14.8 Hz), 4.09 (1H, d, J=14.8 Hz), 4.46-4.52 (4H, m), 4.67 (1H, s), 4.73 (1H, d, J=14.8 Hz), 7.12-7.18 (2H, m), 7.32-7.36 (2H, m), 7.46 (2H, m), 7.80 (2H, d, J=8.0 Hz), 8.17 (1H, s), 10.37 (1H, t, J=5.8 Hz), 12.59 (1H, s).

Example F-9

5-Hydroxy-1-(6-methoxypyridin-3-ylmethyl)-6,10-dioxo-1,2,3,4,6,9,9a,10-octahydro-1,4a,8a-triazaanthracene-7-carboxylic acid 4-fluorobenzylamide (DMSO-$d_6$) δ: 1.51-1.56 (1H, m), 1.71-1.77 (1H, m), 2.58-2.66 (1H, m), 2.80-2.86 (1H, m), 3.01-3.09 (1H, m), 3.38 (1H, d, J=13.6 Hz), 3.78 (3H, s), 3.87 (1H, d, J=13.6 Hz), 4.45-4.52 (4H, m), 4.60 (1H, s), 4.82 (1H, d, J=13.6 Hz), 6.71 (1H, d, J=8.6 Hz), 7.12-7.19 (2H, m), 7.33-7.38 (2H, m), 7.49 (1H, d, J=8.6 Hz), 7.98 (1H, s), 8.30 (1H, s), 10.37 (1H, t, J=6.0 Hz), 12.58 (1H, s).

Example F-10

5-Hydroxyl-1-isobutyl-3,3-dimethyl-6,10-dioxo-1,2,3,4,6,9,9a,10-octahydro-1,4a,8a-triazaanthracene-7-carboxylic acid 4-fluorobenzylamide (DMSO-$d_6$) δ: 0.64 (3H, d, J=6.4 Hz), 0.82 (3H, d, J=6.8 Hz), 0.90 (3H, s), 0.91 (3H, s), 1.59-1.67 (1H, m), 1.92-1.97 (1H, m), 2.11-2.15 (1H, m), 2.51-2.57 (1H, m), 2.67 (1H, d, J=12.0 Hz), 2.77 (1H, d, J=12.8 Hz), 4.13 (1H, s), 4.21 (1H, d, J=12.8 Hz), 4.47-4.59 (3H, s), 4.80 (1H, dd, J=14.4, 2.8 Hz), 7.14-7.19 (2H, m), 7.34-7.38 (2H, m), 8.66 (1H, s), 10.41 (1H, t, J=6.0 Hz), 12.44 (1H, s).

Example F-11

5-Hydroxy-1,3,3-trimethyl-6,10-dioxo-1,2,3,4,6,9,9a,10-octahydro-1,4a,8a-triazaanthracene-7-carboxylic acid 4-fluorobenzylamide (DMSO-$d_6$) δ: 0.89 (6H, s), 2.14-2.18 (1H, m), 2.24 (3H, s), 2.54-2.58 (1H, m), 2.74-2.78 (1H, s), 3.88 (1H, s), 4.21 (1H, d, J=13.2 Hz), 4.45-4.53 (3H, m), 4.72-4.76 (1H, m), 7.13-7.19 (2H, m), 7.33-7.38 (2H, m), 8.64 (1H, s), 10.40 (1H, t, J=6.0 Hz), 12.46 (1H, s).

Example F-12

4-[7-(4-Fluorobenzylcarbamoyl)-5-hydroxy-6,10-dioxy-3,4,6,9,9a,10-hexahydro-2H-1,4a,8a-triazaanthracene-1-yl]butanoic acid ethyl ester (CDCl$_3$) δ: 1.23 (3H, t, J=7.1 Hz), 1.70-1.79 (1H, m), 1.86-2.00 (1H, m), 2.17-2.34 (2H, m), 2.46-2.57 (1H, m), 2.61-2.77 (2H, m), 2.85-2.92 (1H, m), 3.13-3.18 (1H, m), 4.13 (2H, q, J=7.1 Hz), 4.27-4.34 (2H, m), 4.57-4.63 (3H, m), 4.66-4.73 (1H, m), 6.95-7.03 (2H, m), 7.29-7.36 (2H, m), 8.36 (1H, s), 10.48 (1H, t, J=4.8 Hz), 12.50 (1H, s).

Example F-13

1-(3-Dimethylcarbamoylpropyl)-5-hydroxy-6,10-dioxo-1,2,3,4,6,9,9a,10-octahydro-1,4a, 8a-triazaanthracene-7-carboxylic acid 4-fluorobenzylamide (CDCl$_3$) δ: 1.62-1.82 (3H, m), 1.83-2.00 (1H, m), 2.10-2.35 (2H, m), 2.57-2.65 (2H, m), 2.75-2.95 (2H, m), 2.92 (3H, s), 2.96 (3H, s), 3.07-3.14 (1H, m), 4.23-4.30 (2H, m), 4.60 (2H, d, J=6.0 Hz), 4.68 (1H, dd, J=13.2, 4.5 Hz), 5.12 (1H, d, J=12.6 Hz), 6.95-7.02 (2H, m), 7.28-7.35 (2H, m), 8.42 (1H, s), 1054 (1H, t, J=5.4 Hz), 12.51 (1H, s).

Example F-14

5-Hydroxy-1-(4-morpholin-4-yl-4-oxobutyl)-6,10-dioxo-1,2,3,4,6,9,9a,10-octahydro-1,4a,8a-triazaanthracene-7-carboxylic acid 4-fluorobenzylamide (CDCl$_3$) δ: 1.61-1.83 (3H, m), 1.84-2.00 (1H, m), 2.12-2.23 (1H, m), 2.25-2.36 (1H, m), 2.56-2.64 (2H, m), 2.75-2.95 (2H, m), 3.09-3.15 (1H, m), 3.37 (2H, t, J=4.8 Hz), 3.61-3.66 (6H, m), 4.26-4.32 (2H, m), 4.59 (2H, d, J=5.7 Hz), 4.68 (1H, dd, J=13.2, 4.5 Hz), 4.95-5.01 (1H, m), 6.95-7.03 (2H, m), 7.28-7.35 (2H, m), 8.40 (1H, s), 10.52 (1H, t, J=5.7 Hz), 12.51 (1H, s).

Example F-15

5-Hydroxy-1-methyl-6,10-dioxo-1,2,3,4,6,9,9a,10-octahydro-1,4a,8a-triazaanthracene-7-carboxylic acid 4-fluorobenzylamide melting point: 252-253° C.
(DMSO-$d_6$) δ: 1.56-1.75 (2H, m), 2.22 (3H, s), 2.50-2.55 (1H, m), 2.90-3.10 (2H, m), 4.17 (1H, brs), 4.39-4.42 (2H, m), 4.52 (2H, d, J=6.0 Hz), 4.74-4.78 (1H, m), 7.13-7.17 (2H, m), 7.33-7.37 (2H, m), 8.61 (1H, s), 10.40 (1H, t, J=6.0 Hz), 12.54 (1H, s).

Example F-16

5-Hydroxy-6,10-dioxo-1-thiophen-3-ylmethyl-1,2,3,4,6,9,9a,10-octahydro-1,4a,8a-triazaanthracene-7-carboxylic acid 4-fluorobenzylamide melting point: 242-243° C.
(DMSO-$d_6$) δ: 1.52-1.73 (2H, m), 2.59-2.62 (1H, m), 2.87-3.03 (2H, m), 3.52 (1H, d, J=13.6 Hz), 3.90 (1H, d, J=14.4 Hz), 4.40-4.56 (5H, m), 4.83-4.90 (1H, m), 6.92 (1H, d, J=5.2 Hz), 7.13-7.17 (2H, m), 7.28-7.37 (3H, m), 7.42-7.44 (1H, m), 8.46 (1H, s), 10.39 (1H, t, J=6.0 Hz), 12.58 (1H, s).

Example F-17

5-Hydroxy-6,10-dioxo-1-thiazol-2-ylmethyl-1,2,3,4,6,9,9a,10-octahydro-1,4a,8a-triazaanthracene-7-carboxylic acid 4-fluorobenzylamide melting point 214-215° C.
(DMSO-$d_6$) δ: 1.54-1.72 (2H, m), 2.75-2.81 (1H, m), 2.95-3.07 (2H, m), 3.80 (1H, d, J=16.0 Hz), 4.37 (1H, d, J=16.4 Hz), 4.44-4.51 (4H, m), 4.69 (1H, brs), 4.89-4.93 (1H, m), 7.13-7.17 (2H, m), 7.32-7.35 (2H, m), 7.55 (1H, d, J=3.2 Hz), 7.69 (1H, d, J=3.2 Hz), 8.37 (1H, s), 10.36 (1H, t, J=6.0 Hz), 12.50 (1H, s).

Example F-18

5-Hydroxy-(3-methylsulfanyl-propyl)-6,10-dioxo-1,2,3,4,6,9,9a,10-octahydro-1,4a,8a-triazaanthracene-7-carboxylic acid 4-fluorobenzylamide melting point: 162-164° C.
(DMSO-$d_6$) δ: 1.50-1.82 (4H, m), 2.27 (3H, s), 2.32-2.44 (3H, m), 2.60-2.82 (2H, m), 3.00-3.14 (2H, m), 4.37-4.59 (5H, m), 4.75-4.79 (1H, m), 7.13-7.17 (2H, m), 7.33-7.35 (2H, m), 8.60 (1H, s) 10.40 (1H, t, J=6.0 Hz), 12.57 (1H, s).

Example F-19

5-Hydroxy-6,10-dioxo-1-pyridin-4-ylmethyl-1,2,3,4,6,9,9a,10-octahydro-1,4a,8a-triazaanthracene-7-carboxylic acid 4-fluorobenzylamide melting point: 180-183° C.
(DMSO-$d_6$) δ: 1.52-1.76 (2H, m), 2.62-2.80 (2H, m), 3.01-3.07 (1H, m), 3.42 (1H, d, J=15.2 Hz), 4.05 (1H, d, J=15.2 Hz), 4.49-4.50 (4H, m), 4.64 (1H, brs), 4.78-4.81 (1H, m), 7.12-7.21 (4H, m), 7.32-7.36 (2H, m), 8.33 (1H, s), 8.42 (2H, d, J=4.4 Hz), 10.39 (1H, t, J=6.0 Hz), 12.55 (1H, s).

Example F-20

1-Cyclohexylmethyl-5 hydroxy-6,10-dioxo-1,2,3,4,6,9,9a,10-octahydro-1,4a,8a-triazaanthracene-7-carboxylic acid 4-fluorobenzylamide melting point: 201-202° C.
(DMSO-$d_6$) δ: 0.56-0.59 (1H, m), 0.87-0.84 (1H, m), 1.02-1.13 (3H, m), 1.23-1.29 (1H, m), 1.49-1.70 (6H, m), 1.92-1.97 (1H, m), 2.52-2.55 (1H, m), 2.96-3.03 (2H, m), 4.40-4.43 (3H, m), 4.52 (2H, d, J=6.0 Hz), 4.73-4.77 (1H, m), 7.12-7.16 (2H, m), 7.32-7.36 (2H, m), 8.59 (1H, s), 10.40 (1H, t, J=5.2 Hz), 12.58 (1H, s).

Example F-21

5-Hydroxy-6,10-dioxo-1-pyridin-2-ylmethyl-1,2,3,4,6,9,9a,10-octahydro-1,4a,8a-triazaanthracene-7-carboxylic acid 4-fluorobenzylamide melting point: 216-219° C.
(DMSO-$d_6$) δ: 1.52-1.76 (2H, m), 2.66-2.80 (1H, m), 2.90-3.07 (2H, m), 3.67 (1H, d, J=15.2 Hz), 4.01 (1H, d, J=13.2 Hz), 4.37-4.97 (4H, m), 4.62 (1H, brs), 4.85-4.88 (1H, m), 7.07-7.25 (4H, m), 7.33-7.36 (2H, m), 7.64-7.68 (1H, m), 8.26 (1H, s), 8.45 (1H, s), 10.36 (1H, t, J=6.0 Hz), 12.57 (1H, s).

Example F-22

1-(2-Ethylbutyl)-5-hydroxy-6,10-dioxo-1,2,3,4,6,9,9a,10-octahydro-1,4a,8a-triazaanthracene-7-carboxylic acid 4-fluorobenzylamide melting point: 137-140° C.
(DMSO-$d_6$) δ: 0.62 (3H, t, J=7.2 Hz), 0.77 (3H, t, J=7.2 Hz), 0.99-1.30 (5H, m), 1.57-1.71 (2H, m), 1.97-2.02 (1H, m), 2.44-2.58 (2H, m), 3.02-3.32 (2H, m), 4.34-4.57 (5H, m), 4.78-4.82 (1H, m), 7.13-7.17 (2H, m), 7.32-7.36 (2H, m), 8.60 (1H, s), 10.39 (1H, t, J=5.2 Hz), 12.54 (1H, s).

Example F-23

5-Hydroxy-1-(2-morpholin-4-ylethyl)-6,10-dioxo-1,2,3,4,6,9,9a,10-octahydro-1,4a,8a-triazaanthracene-7-carboxylic acid 4-fluorobenzylamide melting point: 254-256° C.
(DMSO-$d_6$) δ: 1.55-1.68 (2H, m), 2.28-2.39 (8H, m), 2.59-2.65 (1H, m), 2.82-3.09 (3H, m), 3.33-3.58 (5H, m), 4.34-4.50 (3H, m), 4.52 (2H, d, J=5.2 Hz), 4.79-4.84 (1H, m), 7.12-7.17 (2H, m), 7.32-7.36 (2H, m), 8.52 (1H, s), 10.45 (1H, t, J=5.2 Hz), 12.55 (1H, s).

Example F-24

1-Hydroxy-6-methyl-2,11-dioxo-2,5a,6,7,8,9,10,11-octahydro-5H-4a,6,10a-triaza-cyclohepta[b]naphthalene-3-carboxylic acid 4-fluorobenzylamide melting point: 255° C.
(DMSO-$d_6$) δ: 1.48-1.55 (1H, m), 1.67-1.80 (3H, m), 2.29 (3H, s), 2.75-2.80 (2H, m), 3.23-3.31 (1H, m), 4.07-4.09 (1H, m), 4.36-4.40 (1H, m), 4.45-4.59 (3H, m), 4.68-4.69 (1H, m), 7.13-7.17 (2H, m), 7.30-7.37 (2H, m), 8.50 (1H, s), 10.42 (1H, t, J=6.0 Hz), 12.42 (1H, s).

Example F-25

1-Hydroxy-6-isobutyl-2,11-dioxo-2,5a,6,7,8,9,10,11-octahydro-5H-4a,6,10a-triaza-cyclohepta[b]naphthalene-3-carboxylic acid 4-fluorobenzylamide melting point: 221-223° C.
DMSO-$d_6$) δ: 0.81 (3H, d, J=6.8 Hz), 0.84 (3H, d, J=6.4 Hz), 1.45-1.78 (5H, m), 2.36-2.54 (2H, m), 2.27-2.93 (2H, m), 3.17-3.23 (1H, m), 4.03-4.06 (1H, m), 4.32-4.56 (4H, m), 4.82-4.85 (1H, m), 7.13-7.17 (2H, m), 7.30-7.37 (2H, m), 8.48 (1H, s), 10.42 (1H, t, J=6.0 Hz), 12.53 (1H, s).

Example F-26

6-Cyclopropylmethyl-1-hydroxy-2,11-dioxo-2,5a,6,7,8,9,10,11-octahydro-5H-4a,6,10a-triaza-cyclohepta[b]naphthalene-3-carboxylic acid 4-fluorobenzylamide melting point: 213° C.
DMSO-$d_6$) δ: 0.15-0.26 (2H, m), 0.46-0.48 (2H, m), 0.86-1.06 (1H, m), 1.45-1.75 (4H, m), 2.45-2.65 (1H, m), 2.68-2.83 (1H, m), 2.91-2.98 (2H, m), 3.17-3.26 (1H, m), 4.08-4.14 (1H, m), 4.43-4.45 (2H, m), 4.54 (2H, d, J=5.6 Hz), 4.89-4.91 (1H, m), 7.15-7.19 (2H, m), 7.35-7.39 (2H, m), 8.50 (1H, s), 10.47 (1H, t, J=6.0 Hz), 12.52 (1H, s).

Example F-27

1-Furan-2-ylmethyl-5-hydroxy-6,10-dioxo-1,2,3,4,6,9,9a,10-octahydro-1,4a,8a-triaza-anthracene-7-carboxylic acid 4-fluorobenzylamide melting point: 193-197° C.
DMSO-$d_6$) δ: 1.67 (2H, m), 2.61 (1H, s), 2.93 (2H, m), 3.75 (1H, d, J=14.8 Hz), 3.84 (1H, d, J=14.8 Hz), 4.34-4.47 (3H, m), 4.52 (2H, d, J=6.0 Hz), 4.96 (1H, d, J=14.8 Hz), 6.36 (2H, s), 7.16 (2H, t, J=8.8 Hz), 7.35 (2H, m), 7.59 (1H, s), 8.97 (1H, s), 10.43 (1H, s), 12.51 (1H, s).

Example F-28

1-(4-Dimethylamino-benzyl)-5-hydroxy-6,10-dioxo-1,2,3,4,6,9,9a,10-octahydro-1,4a,8a-triaza-anthracene-7-carboxylic acid 4 fluorobenzylamide melting point: 221-223° C.
DMSO-$d_6$) δ: 1.55-1.99 (2H, m), 2.87 (6H, s), 2.87-3.06 (4H, m), 3.80 (1H, d, J=14.0 Hz), 4.50 (5H, m), 4.83 (1H, d, J=14.0 Hz), 6.58 (2H, d, J=9.6 Hz), 6.98 (2H, d, J=8.8 Hz), 7.15 (2H, t, J=8.8 Hz), 7.35 (2H, m), 8.31 (1H, s), 10.39 (1H, s), 12.58 (1H, s).

Example F-29

5-Hydroxy-6,10-dioxo-1-(4-trifluoromethyl-benzyl)-1,2,3,4,6,9,9a,10-octahydro-1,4a,8a-triaza-anthracene-7-carboxylic acid 4-fluorobenzylamide melting point: 273-277° C.
DMSO-$d_6$) δ: 1.52-1.70 (2H, m), 2.63-3.04 (3H, m), 3.50 (1H, d, J=14.8 Hz), 4.10 (1H, d, J=14.8 Hz), 4.54 (5H, m), 4.79 (1H, d, J=14.8 Hz), 7.14 (2H, t, J=8.8 Hz), 7.33 (2H, m), 7.55 (2H, d, J=6.8 Hz), 7.61 (2H, d, J=8.0 Hz), 8.22 (1H, s), 10.40 (1H, s), 12.56 (1H, s).

Example F-30

5-Hydroxy-6,10-dioxo-1-pyridin-3-ylmethyl-1,2,3,4,6,9,9a,10-octahydro-1,4a,8a-triaza-anthracene-7-carboxylic acid 4-fluorobenzylamide melting point: 210-212° C.
DMSO-$d_6$) δ: 1.51-1.76 (2H, m), 2.63 (1H, t, J=12.8 Hz), 2.80 (1H, d, J=12.0 Hz), 3.07 (1H, t, J=12.8 Hz), 3.44 (1H, d, J=13.2 Hz), 4.00 (1H, d, 14.0 Hz), 4.47 (4H, m), 4.62 (1H, s), 4.84 (1H, d, J=14.0 Hz), 7.16 (2H, t, J=8.8 Hz), 7.33 (2H, m), 7.58 (1H, d, J=7.6 Hz), 8.30 (1H, s), 8.45 (2H, s), 10.41 (1H, s), 12.57 (1H, s).

Example F-31

1-(2-Chloro-6-fluoro-benzyl)-5-hydroxy-6,10-dioxo-1,2,3,4,6,9,9a,10-octahydro-1,4a,8a-triaza-anthracene-7-carboxylic acid 4-fluorobenzylamide melting point: 213-215° C.
DMSO-$d_6$) δ: 1.58 (2H, 2H), 2.55-3.09 (3H, m), 3.45 (1H, d, J=12.4 Hz), 4.16 (1H, d, J=12.4 Hz), 4.40-4.58 (4H, m), 5.12 (1H, d, J=14.4 Hz), 7.15-7.38 (7H, m), 8.66 (1H, s), 10.41 (1H, t, J=6.4 Hz), 12.46 (1H, s).

Example F-32

5-Hydroxy-1-(4-methoxy-benzyl)-6,10-dioxo-1,2,3,4,6,9,9a,10-octahydro-1,4a,8a-triaza-anthracene-7-carboxylic acid 4-fluorobenzylamide melting point-191-193° C.
NMR (DMSO-$d_6$) δ: 1.50-1.77 (2H, m), 2.58-3.06 (3H, m), 3.68 (3H, s), 3.88 (1H, d, J=13.6 Hz), 4.41-4.55 (4H, m), 4.80 (2H, d, J=14.4 Hz), 6.80 (2H, d, J=8.8 Hz), 7.09 (2H, d, J=8.4 Hz), 7.15 (2H, t, J=8.8 Hz), 7.35 (2H, m), 8.28 (1H, s), 10.48 (1H, s), 12.58 (1H, s).

Example F-33

1-(3,5-Bis-trifluoromethyl-benzyl)-5-hydroxy-6,10-dioxo-1,2,3,4,6,9,9a,10-octahydro-1,4a,8a-octahydro-1,4a,8a-triaza-anthracene-7-carboxylic acid 4-fluorobenzylamide melting point: 275-277° C.
NMR (DMSO-$d_6$) δ: 1.58-1.88 (2H, m), 2.51-3.14 (3H, m), 3.33-4.10 (3H, m), 4.51 (2H, m), 4.73 (1H, m), 7.15 (2H, m), 7.34 (2H, m), 7.82-7.93 (4H, m), 10.31 (1H, s), 12.57 (1H, s).

Example F-34

1-(4-Diethylaminobenzyl)-5-hydroxy-6,10-dioxo-1,2,3,4,6,9,9a,10-octahydro-1,4a,8a-triaza-anthracene-7-carboxylic acid 4-fluorobenzylamide melting point: 182° C.
NMR (DMSO-$d_6$) δ: 1.04 (6H, t, J=6.8 Hz), 1.50-1.69 (2H, m), 2.55-3.05 (3H, m), 3.26 (4H, q, J=7.2 Hz), 3.80 (1H, d, J=13.6 Hz), 4.44-4.57 (4H, m), 4.91 (1H, d, J=12.4 Hz), 6.52 (2H, d, J=8.8 Hz), 6.94 (2H, d, J=8.4 Hz), 7.15 (2H, t, J=8.4 Hz), 7.35 (2H, m), 8.46 (1H, s), 10.41 (1H, s), 12.60 (1H, s).

Example F-35

5-Hydroxy-1-((E)-2-methyl-but-2-enyl)-6,10-dioxo-1,2,3,4,6,9,9a,10-octahydro-1,4a,8a-triaza-anthracene-7-carboxylic acid 4-fluoro-benzylamide melting point: 175-177° C.
NMR (DMSO-$d_6$) δ: 1.35 (3H, s), 1.51 (3H, d, J=6.0 Hz), 1.52-1.69 (3H, m), 2.60-3.15 (3H, m), 4.31-4.52 (5H, m), 4.67-4.76 (1H, m), 5.30-5.40 (1H, m), 7.15 (2H, t, J=8.4 Hz), 7.28-43 (2H, m), 8.46 (1H, s), 10.39 (1H, brs), 12.60 (1H, s).

Example F-36

1-(3-Dimethylamino-2-methyl-propyl)-5-hydroxy-6,10-dioxo-1,2,3,4,6,9,9a,10-octahydro-1,4a,8a-triaz-aanthracene-7-carboxylic acid 4-fluoro-benzylamide NMR (DMSO-$d_6$) δ: 0.63-0.68 (2H, m), 1.57-1.82 (3H, m), 2.11-2.49 (10H, m), 2.98-3.11 (2H, m), 4.41-4.54 (5H, m), 4.73-4.80 (1H, m), 7.14-7.18 (2H, m), 7.31-7.38 (2H, m), 8.58 (1H, s), 10.40 (1H, s), 12.57 (1H, s).

Example F-37

1-(3,3-Dimethyl-butyl)-5-hydroxy-6,10-dioxo-1,2,3,4,6,9,9a,10-octahydro-1,4a,8a-triaza-anthracene-7-carboxylic acid 4-fluoro-benzylamide melting point: 175-177° C.
NMR (DMSO-$d_6$) δ: 1.19-1.36 (2H, m), 1.57-1.70 (2H, m), 2.23-2.30 (1H, m), 2.51-2.69 (2H, m), 2.97-3.04 (2H, m), 4.42-4.54 (5H, m), 4.78 (1H, d, J=14.0 Hz), 7.13-7.17 (2H, m), 7.33-7.36 (2H, m), 8.63 (1H, s), 10.39 (1H, t, J=6.0 Hz), 12.56 (1H, s).

Example F-38

1-Ethyl-5-hydroxy-6,10-dioxo-1,2,3,4,6,9,9a,10-octahydro-1,4a,8a-triaza-anthracene-7-carboxylic acid 4-fluoro-benzylamide melting point: 221° C.
NMR (DMSO-$d_6$) δ: 0.94 (3H, t, J=6.8 Hz), 1.56-1.71 (2H, m), 2.45-2.50 (1H, m), 2.59-2.76 (2H, m), 2.96-3.03 (2H, m), 4.40-4.44 (3H, m), 4.52 (2H, d, J=6.0 Hz), 4.77-4.82 (1H, m), 7.14-7.18 (2H, m), 7.34-7.38 (2H, m), 8.62 (1H, s), 10.41 (1H, t, J=6.0 Hz), 12.59 (1H, s).

Example F-39

5-Hydroxy-6,10-dioxo-1-(2-oxo-propyl)-1,2,3,4,6,9,9a,10-octahydro-1,4a,8a-triaza-anthracene-7-carboxylic acid 4-fluoro-benzylamide melting point: 244-246° C.
NMR (DMSO-$d_6$) δ: 1.54-1.61 (1H, m), 1.67-1.76 (1H, m), 2.22 (3H, s), 2.50-2.56 (1H, m), 2.91-3.02 (2H, m), 4.18 (1H, s), 4.38-4.45 (2H, m), 4.52 (2H, d, J=6.0 Hz), 4.76 (1H, d, J=14.4 Hz), 7.13-7.18 (2H, m), 7.34-7.37 (2H, m), 8.6 (1H, s), 10.40 (1H, t, J=6.0 Hz), 12.54 (1H, s).

Example F-40

5-Hydroxy-6,10-dioxo-1-(4,4,4-trifluorobutyl)-1,2,3,4,6,9,9a,10-octahydro-1,4a,8a-triaza-anthracene-7-carboxylic acid 4-fluoro-benzylamide melting point: 220° C.
NMR (DMSO-$d_6$) δ: 1.53-1.62 (2H, m), 1.67-1.75 (1H, m), 2.07-2.18 (2H, m), 2.40-2.47 (1H, m), 2.64-2.78 (2H, m), 2.96-3.04 (2H, m), 4.42-4.49 (2H, m), 4.53 (2H, d, J=5.2 Hz), 4.74 (1H, d, J=12.8 Hz), 7.13-7.17 (2H, m), 7.33-7.37 (2H, m), 8.61 (1H, s), 10.40 (1H, t, J=6.0 Hz), 12.57 (1H, s).

Example F-41

5-Hydroxy-1-(3-methyl-butyl)-6,10-dioxo-1,2,3,4,6,9,9a,10-octahydro-1,4a,8a-triaza-anthracene-7-carboxylic acid 4-fluoro-benzylamide melting point: 151° C.
NMR (DMSO-$d_6$) δ: 0.78 (6H, dd, J=7.6, 16.2 Hz), 1.21-1.28 (2H, m), 1.41-1.48 (1H, m), 1.56-1.71 (2H, m), 2.22-2.31 (1H, m), 2.51-2.59 (1H, m), 2.66-2.73 (1H, m), 2.96-3.05 (2H, m), 4.41-4.55 (5H, m), 4.80 (1H, d, J=13.2 Hz), 7.13-7.18 (2H, m), 7.33-7.37 (2H, m), 8.64 (1H, s), 10.40 (1H, t, J=6.0 Hz), 12.57 (1H, s).

Example F-42

5-Hydroxy-1-isobutyl-6,10-dioxo-1,2,3,4,6,9,9a,10-octahydro-1,4a,8a-triaza-anthracene-7-carboxylic acid 3-chloro-2-fluoro-benzylamide melting point: 180-182° C.
NMR (DMSO-$d_6$) δ: 0.62 (3H, d, J=6.0 Hz), 0.78 (3H, d, J=6.4 Hz), 1.55-1.69 (3H, m), 1.93-1.99 (1H, m), 2.97-3.08 (2H, m), 4.39-4.46 (3H, m), 4.59-4.64 (2H, m), 4.75-4.81 (1H, m), 7.16-7.23 (1H, m), 7.27-7.34 (1H, m), 7.47-7.53 (1H, m), 8.59 (1H, s), 10.44 (1H, s), 12.57 (1H, s).

Example F-43

1-Cyclopropylmethyl-5-hydroxy-6,10-dioxo-1,2,3,4,6,9,9a,10-octahydro-1,4a,8a-triaza-anthracene 1-carboxylic acid 3-chloro-2-fluorobenzylamide melting point: 189-192° C.
NMR (DMSO-$d_6$) δ: 0.00-0.10 (2H, m), 0.35-0.41 (2H, m), 0.70-0.77 (1H, m), 1.57-1.69 (2H, m), 2.52-2.65 (1H, m), 2.67-2.85 (1H, m), 2.91-2.99 (1H, m), 4.30-4.41 (2H, m), 4.48-4.52 (2H, m), 4.71-4.80 (1H, m), 7.06-7.10 (1H, m), 7.18-7.22 (1H, m), 7.36-7.40 (1H, m), 8.52 (1H, s), 10.30 (1H, s), 12.26 (1H, s).

Example F-44

1-Furan-2-ylmethyl-5-hydroxy-6,10-dioxo-1,2,3,4,6,9,9a,10-octahydro-1,4a,8a-triazaanthracene-7-carboxylic acid 3-chloro-2-fluoro-benzylamide melting point: 190-192° C.
NMR (DMSO-$d_6$) δ: 1.56-1.68 (2H, m), 2.54-2.63 (1H, m), 2.89-2.99 (2H, m), 3.80 (2H, dd, J=18.4, 33.2 Hz), 4.37-4.51 (3H, m), 4.62 (2H, d, J=6.0 Hz), 4.97 (1H, d, J=15.2 Hz), 6.39 (2H, s), 7.18-7.22 (1H, m), 7.31-7.34 (1H, m), 7.48-7.51 (1H, m), 7.58 (1H, s), 8.64 (1H, s), 10.45 (1H, t, J=6.0 Hz), 12.55 (1H, s).

Example F-45

5-Hydroxy-6,10-dioxo-1-thiazol-2-ylmethyl-1,2,3,4,6,9,9a,10-octahydro-1,4a,8a-triaza-anthracene-7-carboxylic acid 3-chloro-2-fluoro-benzylamide melting point: 217-219° C.
NMR (DMSO-$d_6$) δ: 1.59-1.74 (2H, m), 2.76-2.83 (1H, m), 2.97-3.08 (2H, m), 3.90 (1H, d, J=16.0 Hz), 4.36 (1H, d, J=16.0 Hz), 4.45-4.69 (5H, m), 4.89 (1H, d, J=14.8 Hz), 7.18-7.22 (1H, m), 7.28-7.31 (1H, m), 7.47-7.53 (1H, m), 7.54 (1H, d, J=3.2 Hz), 7.68 (1H, d, J=3.2 Hz), 8.34 (1H, s), 10.40 (1H, d, J=6.0 Hz), 12.52 (1H, s).

Example F-46

5-Hydroxy-6,10-dioxo-1-pyridin-2-ylmethyl-1,2,3,4,6,9,9a,10-octahydro-1,4a,8a-triaza-anthracene-7-carboxylic acid 3-chloro-2-fluoro-benzylamide melting point: 190-193° C.
NMR (DMSO-$d_6$) δ: 1.54-1.61 (1H, m), 1.69-1.75 (1H, m), 2.66-2.74 (1H, m), 2.91-3.08 (2H, m), 3.68 (1H, d, J=14.4

Hz), 4.02 (1H, d, J=14.8 Hz), 4.40-4.67 (5H, m), 4.85 (1H, d, J=12.4 Hz), 7.16-7.35 (3H, m), 7.46-7.52 (1H, m), 7.61-7.69 (1H, m), 8.20 (1H, s), 8.43-8.47 (1H, m), 10.41 (1H, d, J=6.0 Hz), 12.58 (1H, s).

Example F-47

5-Hydroxy-1-isobutyl-6,10-dioxo-1,2,3,4,6,9,9a,10-octahydro-1,4a,8a-triaza-anthracene-7-carboxylic acid 2,4-difluoro-benzylamide melting point: 194° C.
NMR (DMSO-$d_6$) δ: 0.62 (3H, d, J=6.4 Hz), 0.78 (3H, d, J=6.4 Hz), 1.55-1.69 (3H, m), 1.93-1.99 (1H, m), 2.97-3.08 (2H, m), 4.39-4.46 (3H, m), 4.50-4.59 (2H, m), 4.77 (1H, d, J=14.4 Hz), 7.03-7.09 (1H, m), 7.20-7.28 (1H, m), 7.36-7.43 (1H, m), 8.59 (1H, s), 10.39 (1H, s), 12.56 (1H, s).

Example F-48

1-Cyclopropylmethyl-5-hydroxy-6,10-dioxo-1,2,3,4,6,9,9a,10-octahydro-1,4a,8a-triaza-anthracene-7-carboxylic acid 2,4-difluoro-benzylamide melting point: 169-171° C.
NMR (DMSO-$d_6$) δ: 0.00-0.10 (2H, m), 0.42-0.44 (2H, m), 0.77-0.81 (1H, m), 1.59-1.74 (2H, m), 2.27-2.32 (1H, m), 2.62-2.72 (1H, m), 3.05-3.12 (1H, m), 4.30-4.58 (5H, m), 4.69 (1H, d, J=14.8 Hz), 7.03-7.11 (1H, m), 7.22-7.26 (1H, m), 7.37-7.40 (1H, m), 8.62 (1H, s), 10.40 (1H, t, J=6.0 Hz), 12.57 (1H, s).

Example F-49

1-Furan-2-ylmethyl-5-hydroxy-6,10-dioxo-1,2,3,4,6,9,9a,10-octahydro-1,4a,8a-triaza-anthracene-7-carboxylic acid 2,4-difluoro-benzylamide melting point: 186-188° C.
NMR (DMSO-$d_6$) δ: 1.55-1.68 (2H, m), 2.55-2.64 (1H, m), 2.88-2.99 (2H, m), 3.80 (2H, dd, J=15.6, 34.8 Hz), 4.36-4.56 (5H, m), 4.97 (1H, d, J=16.0 Hz), 6.39 (2H, s), 7.05-7.08 (1H, m), 7.21-7.26 (1H, m), 7.37-7.44 (1H, m), 7.58 (1H, s), 8.64 (1H, s), 10.38 (1H, t, J=5.6 Hz), 12.53 (1H, s).

Example F-50

5-Hydroxy-6,10-dioxo-1-thiazol-2-ylmethyl-1,2,3,4,6,9,9a,10-octahydro-1,4a,8a-triaza-anthracene-7-carboxylic acid 2,4-difluoro-benzylamide melting point: 168-170° C.
NMR (DMSO-$d_6$) δ: 1.59-1.74 (2H, m), 2.76-2.83 (1H, m), 2.97-3.08 (2H, m), 3.89 (1H, d, J=16.4 Hz), 4.36 (1H, d, J=16.0 Hz), 4.44-4.55 (4H, m), 4.69 (1H, s), 4.89 (1H, d, J=14.8 Hz), 7.03-7.09 (1H, m), 7.20-7.27 (1H, m), 7.34-7.41 (1H, m), 7.54 (1H, d, J=3.2 Hz), 7.68 (1H, d, J=3.2 Hz), 8.34 (1H, s), 10.35 (1H, d, J=6.0 Hz), 12.50 (1H, s).

Example F-51

5-Hydroxy-6,10-dioxo-1-pyridin-2-ylmethyl-1,2,3,4,6,9,9a,10-octahydro-1,4a,8a-triaza-anthracene-7-carboxylic acid 2,4-difluoro-benzylamide melting point: 200-203° C.
NMR (DMSO-du) δ: 1.54-1.61 (1H, m), 1.69-1.78 (1H, m), 2.71-2.79 (1H, m), 2.91-3.09 (2H, m), 3.72 (1H, d, J=14.4 Hz), 4.07 (1H, d, J=14.4 Hz), 4.44-4.54 (4H, m), 4.70 (1H, s), 4.82 (1H, d, J=14.4 Hz), 7.04-7.10 (1H, m), 7.21-7.42 (4H, m), 7.74-7.80 (1H, m), 8.17 (1H, s), 8.47-8.49 (1H, m), 10.35 (1H, d, J=6.0 Hz), 12.57 (1H, s).

Example F-52

1-Hydroxy-6-methyl-2,11-dioxo-2,5a,6,7,8,9,10,11-octahydro-5H-4a,6,10a-triaza-cyclohepta[b]naphthalene-3-carboxylic acid 3-chloro-2-fluoro-benzylamide melting-point: 230-231° C.
NMR (DMSO-$d_6$) δ: 1.47-1.53 (1H, m), 1.62-1.78 (3H, m), 2.29 (3H, s), 2.77-2.81 (2H, m), 4.05-4.10 (1H, m), 4.35-4.40 (1H, m), 4.54-4.64 (3H, m), 4.70 (1H, s), 7.18-7.22 (1H, m), 7.30-7.34 (1H, m), 7.47-7.52 (1H, m), 8.49 (1H, s), 10.47 (1H, d, J=6.0 Hz), 12.44 (1H, s).

Example F-53

1-Hydroxy-6-isobutyl-2,11-dioxo-2,5a,6,7,8,9,10,11-octahydro-5H-4a,6,10a-triaza-cyclohepta[b]naphthalene-3-carboxylic acid 3-chloro-2-fluoro-benzylamide melting point: 215-216° C.
NMR (DMSO-$d_6$) δ: 0.83 (6H, dd, J=6.8, 13.6 Hz), 1.45-1.80 (5H, m), 2.36-2.41 (1H, m), 2.77-2.93 (2H, m), 3.17-3.24 (1H, m), 4.02-4.09 (1H, m), 4.32-4.40 (2H, m), 4.61 (2H, d, J=5.6 Hz), 4.82-4.84 (1H, m), 7.18-7.22 (1H, m), 7.30-7.33 (1H, m), 7.48-7.51 (1H, m), 8.47 (1H, s), 10.48 (1H, t, J=6.0 Hz), 12.55 (1H, s).

Example F-54

6-Cyclopropylmethyl-1-hydroxy-2,11-dioxo-2,5a,6,7,8,9,10,11-octahydro-5H-4a,6,10a-triaza-cyclohepta[b]naphthalene-3-carboxylic acid 3-chloro-2-fluoro-benzylamide melting point: 212° C.
NMR (DMSO-$d_6$) δ: 0.00-0.10 (2H, m), 0.40-45 (2H, m), 0.80-0.87 (1H, m), 1.45-1.77 (3H, m), 2.64-2.69 (1H, m), 2.85-2.95 (2H, m), 3.13-3.20 (1H, m), 4.03-4.09 (1H, m), 4.36-4.40 (2H, m), 4.59 (2H, d, J=5.6 Hz), 4.84-4.86 (1H, m), 7.16-7.20 (1H, m), 7.28-7.32 (1H, m), 7.46-7.50 (1H, m), 8.45 (1H, s), 10.46 (1H, t, J=6.0 Hz), 12.50 (1H, s).

Example F-55

6-Furan-2-ylmethyl-1-hydroxy-2,11-dioxo-2,5a,6,7,8,9,10,11-octahydro-5H-4a,6,10a-triaza-cyclohepta[b]naphthalene-3-carboxylic acid 3-chloro-2-fluoro-benzylamide Melting point: 189-190° C.
NMR (DMSO-$d_6$) δ: 1.48-1.63 (3H, m), 1.70-1.77 (1H, m), 2.79-2.83 (2H, m), 3.90 (2H, dd, J=14.8, 39.6 Hz), 4.05-4.11 (1H, m), 4.40-4.51 (2H, m), 4.61 (2H, d, J=5.6 Hz), 4.89-4.91 (1H, m), 6.30-6.33 (1H, m), 6.38-6.40 (1H, m), 7.18-7.22 (1H, m), 7.30-7.34 (1H, m), 7.48-7.53 (1H, m), 7.57 (1H, s), 8.45 (1H, s), 10.45 (1H, t, J=6.0 Hz), 12.44 (1H, s).

Example F-56

1-Hydroxy-6-methyl-2,11-dioxo-2,5a,6,7,8,9,10,11-octahydro-5H-4a,6,10a-triaza-cyclohepta[b]naphthalene-3-carboxylic acid 2,4-difluoro-benzylamide melting point: 241° C.
NMR (DMSO-$d_6$) δ: 1.47-1.53 (1H, m), 1.62-1.78 (3H, m), 2.29 (3H, s), 2.77-2.81 (2H, m), 4.05-4.10 (1H, m), 4.35-4.40 (1H, m), 4.53-4.61 (3H, m); 4.69 (1H, s), 7.03-7.08 (1H, m), 7.20-7.27 (1H, m), 7.37-7.43 (1H, m), 8.49 (1H, s), 10.42 (1H, d, J=6.0 Hz), 12.43 (1H, s).

Example F-57

1-Hydroxy-6-isobutyl-2,11-dioxo-2,5a,6,7,8,9,10,11-octahydro-5H-4a,6,10a-triaza-cyclohepta[b]naphthalene-3-carboxylic acid 2,4-difluoro-benzylamide melting point: 203° C.
NMR (DMSO-$d_6$) δ: 0.82 (6H, dd, J=6.4, 13.2 Hz), 1.45-1.80 (5H, m), 2.36-2.42 (1H, m), 2.77-2.93 (2H, m), 3.15-3.23 (1H, m), 4.02-4.08 (1H, m), 4.32-4.41 (2H, m), 4.54 (2H, d, J=5.6 Hz), 4.82-4.84 (1H, m), 7.02-7.09 (1H, m), 7.20-7.27 (1H, m), 7.36-7.43 (1H, m), 8.47 (1H, s), 10.41 (1H, t, J=6.0 Hz), 12.54 (1H, s).

Example F-58

6-Cyclopropylmethyl-1-hydroxy-2,11-dioxo-2,5a,6,7,8,9,10,11-octahydro-5H-4a,6,10a-triaza-cyclohepta[b]naphthalene-3-carboxylic acid 2,4-difluoro-benzylamide melting point: 182-183° C.
NMR (DMSO-$d_6$) δ: 0.00-0.10 (2H, m), 0.40-46 (2H, m), 0.80-0.87 (1H, m), 1.43-1.77 (3H, m), 2.60-2.69 (1H, m), 2.85-2.95 (2H, m), 3.11-3.19 (1H, m), 4.00-4.06 (1H, m), 4.36-4.40 (2H, m), 4.51 (2H, d, J=5.6 Hz), 4.83-4.87 (1H, m), 7.00-7.07 (1H, m), 7.16-7.23 (1H, m), 7.34-7.38 (1H, m), 8.44 (1H, s), 10.39 (1H, t, J=6.0 Hz), 12.47 (1H, s).

Example F-59

6-Furan-2-ylmethyl-1-hydroxy-2,11-dioxo-2,5a,6,7,8,9,10,11-octahydro-5H-4a,6,10a-triaza-cyclohepta[b]naphthalene-3-carboxylic acid 2,4-difluoro-benzylamide melting-point: 171-173° C.
NMR (DMSO-$d_6$) δ: 1.47-1.64 (3H, m), 1.70-1.77 (1H, m), 2.79-2.83 (2H, m), 3.90 (2H, dd, J=15.6, 39.6 Hz), 4.05-4.11 (1H, m), 4.41-4.57 (4H, m), 4.90-4.92 (1H, m), 6.30-6.33 (1H, m), 6.38-6.40 (1H, m), 7.03-7.09 (1H, m), 7.20-7.27 (1H, m); 7.37-7.45 (1H, m), 7.57 (1H, s), 8.44 (1H, s) 10.41 (1H, t, J=6.0 Hz), 12.43 (1H, s).

Example F-60

5-Hydroxy-6,10-dioxo-3,4,6,9,9a,10-hexahydro-2H-1-oxa-4a,8a-diaza-anthracene-7-carboxylic acid 3-chloro-2-fluorobenzylamide melting point: 276° C.
NMR (DMSO-$d_6$) δ: 1.60-1.68 (1H, m), 1.77-1.84 (1H, m), 3.85-3.93 (1H, m), 4.03-4.07 (1H, m), 4.43-4.62 (5H, m), 5.28 (1H, s), 7.17-7.22 (1H, m), 7.29-7.34 (1H, m), 7.47-7.52 (1H, m), 8.49 (1H, s), 10.41 (1H, d, J=6.0 Hz), 12.48 (1H, s).

Example F-61

5-Hydroxy-6,10-dioxo-3,4,6,9,9a,10-hexahydro-2H-1-oxa-4a,8a-diaza-anthracene-7-carboxylic acid 2,4-difluoro-benzylamide melting point: 258° C.
NMR (DMSO-$d_6$) δ: 1.60-1.69 (1H, m), 1.77-1.85 (1H, m), 3.86-3.92 (1H, m), 4.04-4.08 (1H, m), 4.43-4.55 (5H, m), 5.28 (1H, s), 7.03-7.09 (1H, m), 7.21-7.27 (1H, m), 7.36-7.43 (1H, m), 8.50 (1H, s), 10.35 (1H, d, J=6.0 Hz), 12.47 (1H, s).

Example F-62

5-Hydroxy-1-(2-methoxy-ethyl)-6,10-dioxo-1,2,3,4,6,9,9a,10-octahydro-1,4a,8a-triaza-anthracene-7-carboxylic acid 3-chloro-2-fluoro-benzylamide melting point: 193° C.
NMR (DMSO-$d_6$) δ: 1.53-1.73 (2H, m), 2.51-2.58 (1H, m), 2.71-2.78 (1H, m), 2.81-2.87 (1H, m), 2.95-3.08 (2H, m), 3.17 (3H, s), 4.40-4.52 (3H, m), 4.62 (1H, d, J=5.6 Hz), 4.78 (1H, d, J=14.4 Hz), 7.18-7.22 (1H, m), 7.30-7.34 (1H, m), 7.47-7.52 (1H, m), 8.55 (1H, s), 10.45 (1H, d, J=6.0 Hz), 12.59 (1H, s).

Example F-63

5-Hydroxy-1-(2-methoxy-ethyl)-6,10-dioxo-1,2,3,4,6,9,9a,10-octahydro-1,4a,8a-triaza-anthracene-7-carboxylic acid 2,4-difluoro-benzylamide melting-point: 166-168° C.
NMR (DMSO-$d_6$) δ: 1.55-1.72 (2H, m), 2.51-2.58 (1H, m), 2.70-2.77 (1H, m), 2.80-2.87 (1H, m), 2.97-3.07 (2H, m), 3.18 (3H, s), 4.39-4.52 (3H, m), 4.54 (1H, d, J=5.2 Hz), 4.78 (1H, d, J=13.6 Hz), 7.03-7.09 (1H, m), 7.20-7.27 (1H, m), 7.37-7.43 (1H, m), 8.55 (1H, s), 10.40 (1H, d, J=6.0 Hz), 12.58 (1H, s).

Example F-64

5-Hydroxy-1-(1H-imidazol-4-ylmethyl)-6,10-dioxo-1,2,3,4,6,9,9a,10-octahydro-1,4a,8a-triazaanthracene-7-carboxylic acid 4-fluorobenzylamide (DMSO-$d_6$) δ: 1.55-1.59 (1H, m), 1.64-1.70 (1H, m), 2.58-2.66 (1H, m), 2.87-2.95 (2H, m), 3.67 (1H, d, J=15.2 Hz), 3.73 (1H, d, J=15.2 Hz), 4.34 (1H, s), 4.38-4.43 (1H, m), 4.47-4.54 (3H, m), 5.05 (1H, d, J=14.0 Hz), 7.00 (1H, s), 7.13-7.19 (2H, m), 7.33-7.38 (1H, m), 7.59 (1H, s), 8.55 (1H, s), 10.41 (1H, t, J=5.6 Hz), 11.95 (1H, br s), 12.59 (1H, s).

Example H-1

1-Acetyl-5-hydroxy-4,6-dioxo-2,3,4,6,9,9a-hexahydro-1H-1,3a,8a-triaza-cyclopenta[b]naphthalene-7-carboxylic acid 4-fluoro-benzylamide

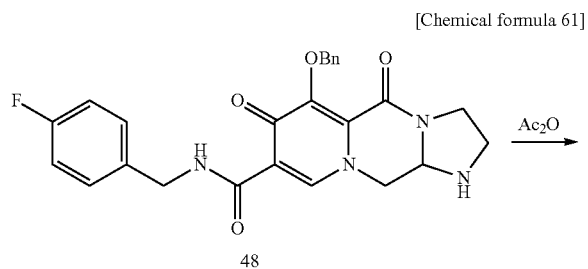

1) To a solution of a compound 48 (120 mg, 0.26 mmol) in methylene chloride (1.2 ml) were added triethylamine (43 μl, 0.31 mmol), acetic anhydride (29 μl, 0.31 mmol), and 4-dimethylaminopyridine (cat.) at room temperature, and the mixture was stirred for 30 minutes. Further, triethylamine (18 μl, 0.13 mmol) and acetic anhydride (12 μl, 0.13 mmol) were added, and the mixture was stirred for 4 hours. 2N hydrochloric acid was added, this was extracted with chloroform, and the organic layer was washed with water, dried with sodium sulfate, and concentrated under reduced pressure. Diisopropyl ether was added to crystallize the material, which was filtered to obtain 53 (112 mg) as a pale orange crystal at a yield of 86%.

2) An Example compound H-1 (71 mg) was obtained at a yield of 82% from a compound 53 (106 mg), according to the method of Example B-1 17).

melting point 290° C.

NMR (DMSO-$d_6$) δ: 2.08 (3H, s), 3.44-4.21 (5H, m), 4.51 (2H, d, 5.7 Hz), 4.93 (1H, m), 5.46-5.62 (1H, m), 7.15 (2H, t, 9.0 Hz), 7.34 (2H, m), 8.49 (1H, s), 10.40 (1H, t, 5.7 Hz), 11.48 (1H, s).

An Example compound H-2 was synthesized according to the same manner as that of Example H-1.

Example H-2

1-Acetyl-5-hydroxy-6,10-dioxo-1,2,3,4,6,9,9a,10-octahydro-1,4a,8a-triaza-anthracene-carboxylic acid 4-fluorobenzylamide melting point: 290° C.

NMR (DMSO-$d_6$) δ: 1.95 (2H, m), 2.14 (3H, s), 2.85 (2H, m), 4.45 (4H, m), 4.51 (2H, d, 5.7 Hz), 5.99 (1H, s), 7.15 (2H, t, 9.0 Hz), 7.34 (2H, m), 8.37 (1H, s), 10.46 (1H, s), 12.28 (1H, s).

Example I-1

5-Hydroxy-1-methanesulfonyl-4,6-dioxo-2,3,4,6,9,9a-hexahydro-1H-1,3a,8a-triaza-cyclopenta[b]naphthalene-7-carboxylic acid 4-fluoro-benzylamide

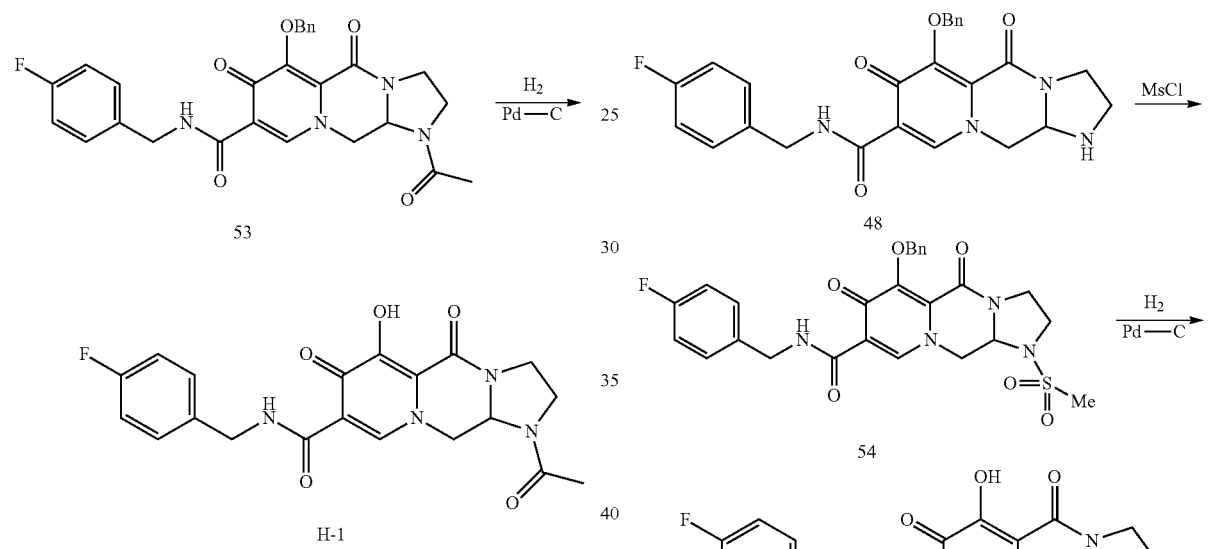

1) To a solution of a compound 48 (140 mg, 0.30 mmol) in pyridine (1.4 ml) were added methanesulfonyl chloride (28 μl, 0.36 mmol), and 4-dimethylaminopyridine (cat.) at room temperature, and the mixture was stirred for 3 hours. After 2N hydrochloric acid was added, this was extracted with ethyl acetate, and the organic layer was washed with water, dried with sodium sulfate, and concentrated under reduced pressure. Diisopropylether was added to crystallize the material, which was filtered to obtain 54 (127 mg) as a pale orange crystal at a yield of 78%.

2) According to the method of Example B-1 17), an Example compound I-1 (21 mg) was obtained at a yield of 21% from a compound 54 (123 mg).

melting point: 260° C.

NMR (DMSO-$d_6$) δ: 3.16 (3H, s), 3.30-4.15 (5H, m), 4.45 (2H, d, 5.7 Hz), 4.27 (2H, m), 5.36 (1H, m), 7.14 (2H, t, 8.7 Hz), 7.33 (2H, m), 8.22 (1H, s), 10.53 (1H, s).

According to the same manner as that of Example I-1, an Example compound I-2 was synthesized.

Example I-2

5-Hydroxy-1-methanesulfonyl-6,10-dioxo-1,2,3,4,6,9,9a,10-octahydro-1,4a,8a-triaza-anthracene-7-carboxylic acid 4-fluoro-benzylamide melting point: 257-259° C.

NMR (DMSO-d$_6$) δ: 1.80-1.96 (2H, m), 3.02-3.58 (2H, m), 3.16 (3H, s), 4.76 (2H, m), 5.56 (1H, s) 7.16 (2H, t, 9.0 Hz), 7.35 (2H, m), 8.36 (1H, s), 10.39 (1H, s).

Example L-1

5,9-Dihydroxy-6,10-dioxo-3,4,6,9,9a,10-hexahydro-1H-2-oxa-4a,8a-diaza-anthracene-7-carboxylic acid 4-fluoro-benzylamide

[Chemical formula 65]

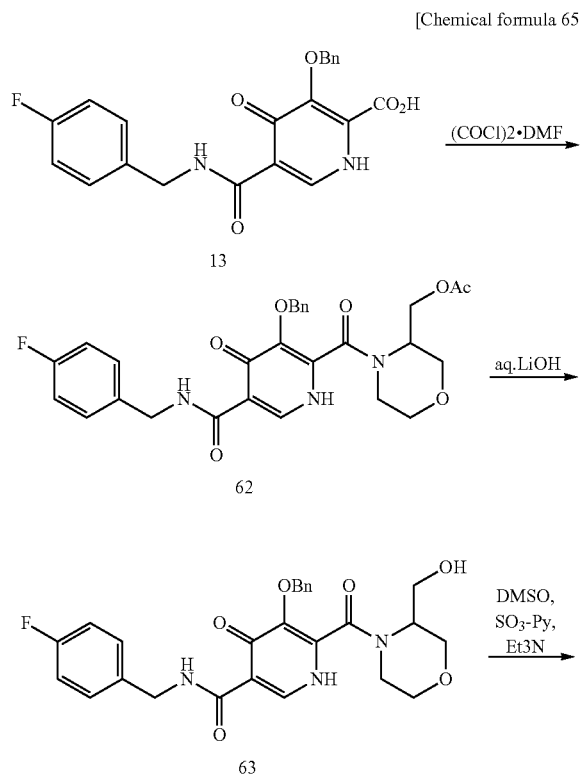

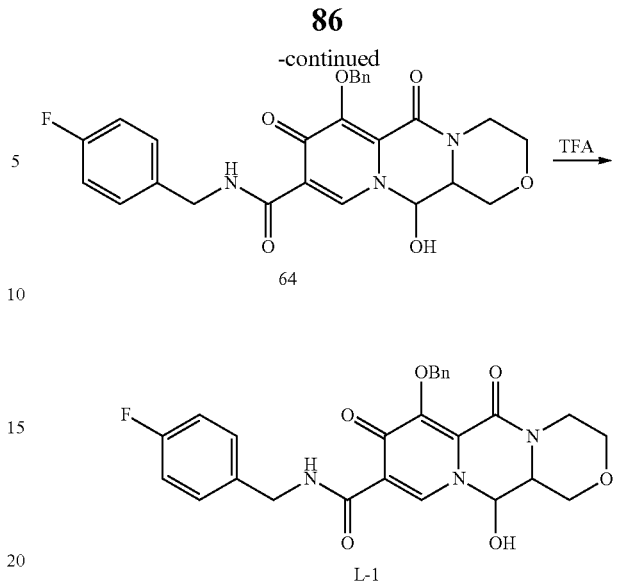

1) According to the method of synthesizing a compound 66, a compound 62 (278 mg, 57%) was obtained from a compound 13 (357 mg).

2) According to the method of synthesizing a compound 57, a compound 63 (202 mg, 79%) was obtained from a compound 62 (278 mg).

3) To a solution of a compound 63 (200 mg, 0.403 mmol) in chloroform (2 ml) were added dimethyl sulfoxide (286 μl, 4.03 mmol), and triethylamine (337 μl, 2.42 mmol), the mixture was stirred for 10 minutes under ice-cooling, a sulfur trioxide-pyridine complex (321 mg, 2.02 mmol) was added, and the mixture was stirred at room temperature for 2 hours. To the reaction solution was added water (3 ml), and chloroform was distilled off under reduced pressure, followed by extraction with ethyl acetate. The organic layer was washed with water, dried with anhydrous sodium sulfate, and the solvent was distilled off under reduced pressure. The crystalline residue was washed with ethyl acetate to obtain a compound 64 (60 mg) at a yield of 30%.

4) Using a compound 64, and according to the method of synthesizing Example A-1, an Example compound L-1 was synthesized.

NMR (DMSO-d$_6$) δ: 2.98-3.10 (1H, m), 3.38-3.60 (2H, m), 3.80-4.20 (5H, m), 4.40-4.55 (2H, m), 5.48 (1H, brs), 5.85 (1H, s), 7.15 (2H, t, J=8.4 Hz), 7.33-7.37 (2H, m), 8.45 (1H, s), 8.60 (1H, s), 10.27-10.42 (1H, m), 12.61 (1H, brs).

Example M-1

1-Hydroxy-2,10-dioxo-2,4b,5,6,7,8,9,10-octahydro-4a,9a-diaza-benzo[a]azulene-3-carboxylic acid 4-fluoro-benzylamide

[Chemical formula 66]

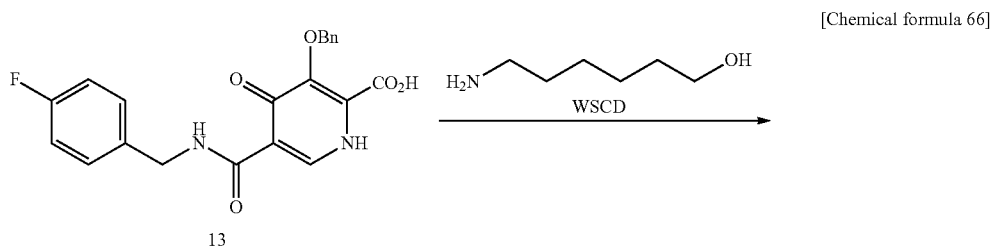

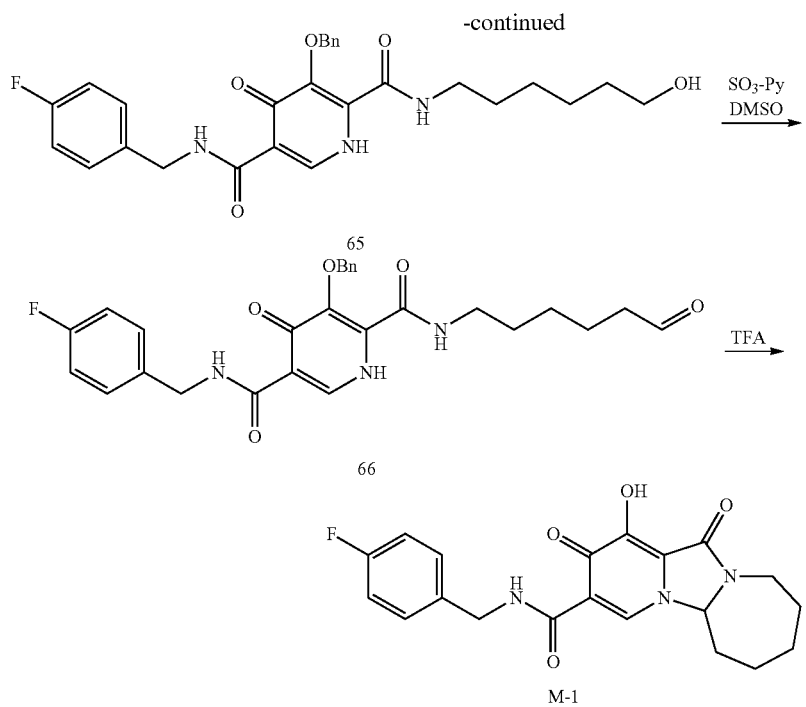

1) According to the method of synthesizing a compound 21, a compound 65 (207 mg) was obtained at a yield of 24% from a compound 13 (250 mg).
2) According to the method of synthesizing a compound 64, a compound 66 (313 mg, 67%) was obtained from a compound 65 (470 mg).
3) After trifluoroacetic acid (10 ml) was added to a compound 66 (100 mg, 0.020 mmol), the mixture was stirred at 75° C. for 4 hours. The solvent was distilled off under reduced pressure, and this was diluted with chloroform, and added to ice water. This was washed with an aqueous saturated sodium bicarbonate solution, a 10% aqueous citric acid solution, and water, and dried with anhydrous sodium sulfate, and the solvent was distilled off under reduced pressure. The residue was subjected to silica gel column chromatography, and fractions eluted with chloroform-methanol were concentrated under reduced pressure, and recrystallized with ethyl acetate-diisopropyl ether to obtain an Example compound M-1 (23 mg, 16%).

melting point 281-283° C.

NMR (DMSO-$d_6$) δ: 1.43-1.52 (2H, m), 1.62-1.83 (3H, m), 2.04-2.18 (1H, m), 2.23-2.35 (1H, m), 4.08-4.16 (1H, m), 4.48-4.53 (2H, m), 5.58-5.61 (1H, m), 7.11-7.20 (2H, m), 7.30-7.38 (2H, m), 8.29 (1H, s), 10.30-10.36 (1H, m), 12.78 (1H, brs).

Example X-1

(R)-6-Hydroxy-5,7-dioxo-2,3,5,7,11,11a-hexahydro-1H-pyrido[1,2-a]pyrrolo[1,2-d]pyrazine-8-carboxylic acid 4-fluoro-benzylamide

[Chemical formula 67]

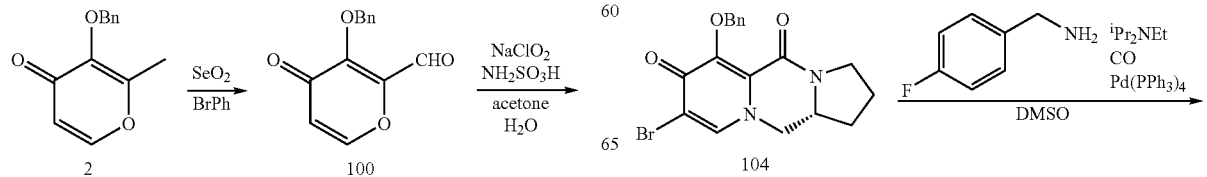

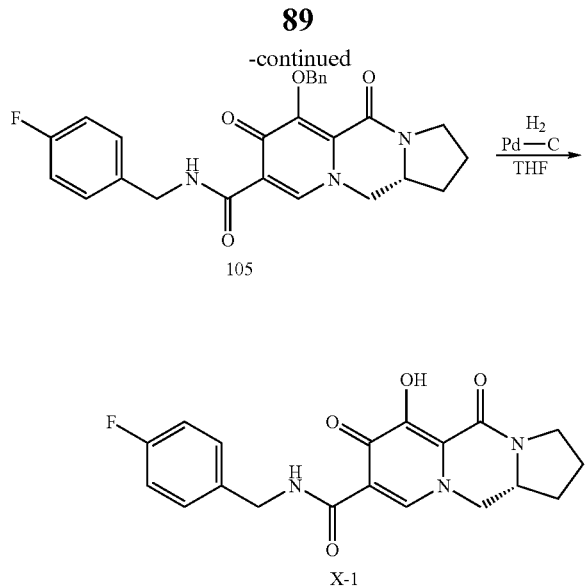

1) Selenium dioxide (666 mg, 6.0 mmol) was added to the solution of compound 2 (216 mg, 1.0 mmol) in bromobenzene (2 ml). Then the mixture was heated up to 160° C., and stirred for 16 h. After celite filtration the solvent was evaporate. The precipitate was purified by silica gel column chromatography, and fractions eluting with n-hexan/EtOAc were concentrated under reduced pressure to obtain compound 100 (164 mg, 71%) as a yellow oil.

1H-NMR (CDCl$_3$) δ: 5.52 (1H, s), 6.50 (1H, d, J=6.0 Hz), 7.36 (5H, m), 7.74 (1H, d, J=6.3 Hz), 9.88 (1H, s).

2) Sulfamic acid (1.50 g, 15.4 mmol) and NaClO$_2$ (1.05 g, 11.6 mmol) was added to the solution of compound 100 (2.54 g, 11.0 mmol) in acetone (20 ml) and water (30 ml). Then the mixture was stirred for 3 h. The solvent was evaporated under reduced pressure to obtain compound 101 (2.18 mg, 80%) as a white solid.

1H-NMR (DMSO-d$_6$) δ: 5.11 (2H, s), 6.55 (1H, d, J=5.4 Hz), 7.32-7.46 (5H, m), 8.21 (1H, d, J=5.7 Hz).

3) (R)-2-N-BOC-aminomethyl pyrrolidine (391 mg, 1.95 mmol) was added to the solution of compound 101 (400 mg, 1.62 mmol), 1-(3-dimethylaminopropyl)-3-ethylcarbodiimide hydrochloride (373 mg, 1.95 mmol), and 1-hydroxybenzotriazole (219 mg, 1.62 mmol) in THF (6 ml). After stirring for 16 h NaHCO$_3$ aqueous solution was added to the mixture. The mixture was extracted with EtOAc, which was washed with NH$_4$Cl aqueous solution and brine. The organic phase was dried over MgSO$_4$. After a filtration the solvent was removed under reduced pressure to obtain compound 102 (694 mg, 100%) as a white solid.

1H-NMR (CDCl$_3$) δ: 1.46 (9H, s), 1.56-2.14 (4H, m), 3.29 (4H, m), 4.18 (1H, m), 5.24 (1H, s), 5.27 (1H, s), 6.46 (1H, d, J=5.7 Hz), 7.35 (5H, m), 7.69 (1H, d, J=5.7 Hz).

4) The solution of compound 102 (694 mg, 1.95 mmol) in HCl/EtOAc (4 mol/l, 8 ml) was stirred for 30 min. The solvent was removed under reduced pressure, diluted with EtOH (16 ml) then. A saturated NaHCO$_3$ aqueous solution was added to the solution to control pH at 9. The mixture was stirred at 50° C. for 2 h, then diluted with water. The mixture was extracted with CHCl$_3$, washed with brine, and dried over MgSO$_4$. The solvent was removed under reduced pressure to obtain compound 103 (413 mg, 68%) as a yellow solid.

$^1$H-NMR (CDCl$_3$) δ: 1.54-2.22 (4H, m), 3.60 (2H, m), 3.80 (1H, t, J=12.0 Hz), 4.18 (1H, d, J=12.0 Hz), 5.15 (1H, d, J=9.9 Hz), 5.35 (1H, d, J=9.9 Hz), 6.71 (1H, d, J=5.4 Hz), 7.33 (3H, m), 7.50 (1H, d, J=5.1 Hz), 7.63 (2H, d, J=7.2 Hz).

5) NaOAc (118 mg, 1.44 mmol) and bromine (0.234 ml, 2.62 mmol) were added to the solution of compound 103 (408 mg, 1.31 mmol) in acetic acid (8 ml), stirred for 30 min then. An aqueous solution of NaOH (2M) was added to the mixture, and extracted with CH$_2$Cl$_2$, washed with brine, and dried over Na$_2$SO$_4$. The solvent was removed under reduced pressure to give compound 104 (390 mg, 77%) as a white solid.

1H-NMR (CDCl$_3$) δ: 1.55-2.19 (4H, m), 3.55-4.02 (5H, m), 5.12 (1H, d, J=9.6 Hz), 5.35 (1H, d, J=9.9 Hz), 7.29-7.38 (3H, m), 7.61 (1H, s), 7.67 (2H, d, J=6.6 Hz).

6) Tetrakis triphenylphosphine palladium (0) (77 mg, 0.067 mmol) and N,N-diisopropylethylamine (0.29 ml, 1.67 mmol) were added to the solution of compound 104 (130 mg, 0.334 mmol) in DMSO (2.6 ml). The mixture was stirred under CO atmosphere for 2 h at 80° C. The reaction mixture was diluted with a saturated NH$_4$Cl aqueous solution, extracted with EtOAc then. And the organic phase was washed with brine, and dried over Na$_2$SO$_4$. The precipitate was purified by silicagel column chromatography, and fractions eluting with MeOH/EtOAc were concentrated under reduced pressure to obtain compound 105 (115 mg, 75%) as a white oil.

$^1$H-NMR (CDCl$_3$) δ: 1.56-2.33 (4H, m), 3.66 (2H, m), 3.90 (2H, m), 4.19 (1H, s), 4.66 (2H, m), 5.20 (1H, d, J=9.9 Hz), 5.37 (1H, d, J=9.9 Hz), 7.00 (2H, t, J=8.7 Hz), 7.33 (5H, m), 7.61 (2H, m), 8.39 (1H, m), 10.50 (1H, s).

7) A mixture of compound 105 (111 mg, 0.241 mmol) and palladium-carbon (10%, 22 mg) in THF (8 ml) and MeOH (2 ml) was stirred under hydrogen atmosphere for 3 h. After celite filteration the solvent was removed under reduced pressure to give the example X-1 (57 mg, 64%) as a white solid.

Melting point: 274° C.

1H-NMR (DMSO-d$_6$) δ: 1.56-2.25 (4H, m), 3.48-3.65 (2H, m), 4.01 (2H, m), 4.51 (2H, d, J=5.7 Hz), 4.71 (1H, d, J=9.9 Hz), 7.14 (2H, t, J=9.0 Hz), 7.33 (2H, dd, J=5.7, 8.7 Hz), 8.41 (1H, s), 10.44 (1H, t, J=6.0 Hz), 12.18 (1H, s).

The following compounds were synthesized using the similar method.

Example X-2

(R)-6-Hydroxy-5,7-dioxo-2,3,5,7,11,11a-hexahydro-1H-pyrido[1,2-a]pyrrolo[1,2-d]pyrazine-8-carboxylic acid 2,4-difluoro-benzylamide Melting point: 300° C.

1H-NMR (DMSO-d$_6$) δ: 1.03-2.20 (4H, m), 3.39-3.66 (2H, m), 4.02 (2H, m), 4.54 (2H, d, J=6.0 Hz), 4.71 (1H, d, J=9.9 Hz), 7.06 (1H, m), 7.23 (1H, m), 7.38 (1H, m), 8.41 (1H, s), 10.43 (1H, t, J=6.0 Hz), 12.19 (1H, s).

Example X-3

(R)-6-Hydroxy-5,7-dioxo-2,3,5,7,11,11a-hexahydro-1H-pyrido[1,2-a]pyrrolo[1,2-d]pyrazine-8-carboxylic acid 3-chloro-2-ffluoro-benzylamide Melting point: 304° C.

1H-NMR (DMSO-d$_6$) δ: 3.44-3.66 (2H, m), 4.01 (2H, m), 4.61 (2H, d, J=5.4 Hz), 4.70 (1H, d, J=9.0 Hz), 7.20 (1H, m), 7.31 (1H, m), 7.49 (1H, m), 8.41 (1H, s), 10.49 (1H, t, J=5.7 Hz), 12.20 (1H, s).

Example X-4

1-Hydroxy-2,9-dioxo-2,5,6,7,8,9,10,10a-octahydro-4a,8a-diaza-anthracene-3-carboxylic acid 4-fluoro-benzylamide Melting point: 269° C.
1H-NMR (DMSO-$d_6$) δ: 1.33-1.79 (6H, m), 2.51 (1H, m), 3.88 (1H, m), 4.12 (1H, dd, J=9.3, 14.1 Hz), 4.38 (1H, d, J=12.9 Hz), 4.53 (3H, m), 7.16 (2H, t, J=9.0 Hz), 7.34 (2H, dd, J=5.7, 8.7 Hz), 8.39 (1H, s), 10.44 (1H, t, J=6.3 Hz), 12.84 (1H, s).

According to the same manner as that of Example C-21, the following Example compounds Y-1 to Y-18 were synthesized.

Example Y-1

(3S,9aS)-5-Hydroxy-3-methyl-6,10-dioxo-3,4,6,9,9a,10-hexahydro-2H-1-oxa-4a,8a-diaza-anthracene-7-carboxylic acid 2,4-difluoro-benzylamide

Example Y-9

(3R,9aR)-5-Hydroxy-3-methyl-6,10-dioxo-3,4,6,9,9a,10-hexahydro-2H-1-oxa-4a,8a-diaza-anthracene-7-carboxylic acid 2,4-difluoro-benzylamide 1H-NMR (CDCl$_3$) δ: 0.90 (3H, d, J=6.9 Hz), 2.00-2.10 (1H, m), 2.70 (1H, dd, J=11.6, 13.4 Hz), 3.41 (1H, dd, J=11.2, 12.9 Hz), 4.05-4.45 (2H, m), 4.30-4.38 (1H, dd, J=4.0, 14.1 Hz), 4.63 (2H, d, J=5.9 Hz), 4.65-4.75 (1H, m), 4.98 (1H, t, J=3.7 Hz), 6.80-6.84 (2H, m), 7.32-7.40 (1H, m), 8.31 (1H, s), 10.38 (1H, brs), 12.37 (1H, s).

Example Y-2

(4S,9aR)-5-Hydroxy-4-methyl-6,10-dioxo-3,4,6,9,9a,10-hexahydro-2H-1-oxa-4a,8a-diaza-anthracene-7-carboxylic acid 2,4-difluoro-benzylamide

Example Y-3

(4R,9aS)-5-Hydroxy-4-methyl-6,10-dioxo-3,4,6,9,9a,10-hexahydro-2H-1-oxa-4a,8a-diaza-anthracene-7-carboxylic acid 2,4-difluoro-benzylamide 1H-NMR (CDCl$_3$) δ: 1.42 (3H, d, J=7.0 Hz), 1.56 (1H, dd, J=2.0, 14.0 Hz), 2.19-2.30 (1H, m), 4.02 (1H, d, J=2.2 Hz), 4.05 (1H, t, J=2.3 Hz), 4.12 (1H, dd, J=6.0, 13.6 Hz), 4.27 (1H, dd, J=4.2, 13.4 Hz), 4.64 (2H, d, J=5.9 Hz), 4.95-5.05 (1H, m), 5.26 (2H, d, J=4 μl, 5.8 Hz), 6.75-6.85 (2H, m), 7.30-7.40 (1H, m), 8.30 (1H, s), 10.38 (1H, brs), 12.45 (1H, s).

Example Y-4

(2R,9aR)-5-Hydroxy-2-methoxymethyl-6,10-dioxo-3,4,6,9,9a,10-hexahydro-2H-1-oxa-4a,8a-diazaanthracene-7-carboxylic acid 2,4-difluoro-benzylamide

Example Y-8

(2S,9aS)-5-Hydroxy-2-methoxymethyl-6,10-dioxo-3,4,6,9,9a,10-hexahydro-2H-1-oxa-4a,8a-diaza-anthracene-7-carboxylic acid 2,4-difluoro-benzylamide 1H-NMR (CDCl$_3$) δ: 1.60-1.80 (2H, m), 3.09-3.21 (1H, m), 3.37 (3H, s), 3.35-3.50 (2H, m), 4.00-4.11 (1H, m), 4.24 (1H, d, J=13.1 Hz), 4.36 (1H, d, J=10.1 Hz), 4.64 (1H, d, J=5.9 Hz), 4.70-4.80 (1H, m), 5.12 (1H, s), 6.75-6.85 (2H, m), 7.30-7.40 (1H, m), 8.30 (1H, s), 10.38 (1H, brs), 12.33 (1H, brs).

Example Y-5

(5aR,6aS,10aR)-1-Hydroxy-2,12-dioxo-2,5,5a,7,8,9,10,10a,11,12-decahydro-6aH-6-oxa-4a,11a-diaza-naphthacene-3-carboxylic acid 2,4-difluoro-benzylamide [racemate]

1H-NMR (DMSO-$d_6$) δ: 1.00-1.85 (9H, m), 2.90 (1H, t, J=4.2 Hz), 4.36 (1H, dd, J=4.2, 12.9 Hz), 4.44-4.57 (4H, m), 5.32 (1H, t, J=3.9 Hz), 7.03-7.09 (1H, m), 7.20-7.27 (1H, m), 7.35-7.43 (1H, m), 8.49 (1H, s), 10.34 (1H, brs).

Example Y-6

(2S,9aR)-2-Ethyl-5-hydroxy-6,10-dioxo-3,4,6,9,9a,10-hexahydro-2H-1-oxa-4a,8a-diaza-anthracene-7-carboxylic acid 2,4-difluoro-benzylamide

Example Y-7

(2R,9aS)-2-Ethyl-5-hydroxy-6,10-dioxo-3,4,6,9,9a,10-hexahydro-2H-1-oxa-4a,8a-diaza-anthracene-7-carboxylic acid 2,4-difluoro-benzylamide 1H-NMR (DMSO-$d_6$) δ: 0.87 (3H, d, J=5.4 Hz), 1.40-1.51 (3H, m), 1.75 (1H, d, J=10.8 Hz), 3.22 (1H, t, J=10.2 Hz), 3.73-3.78 (1H, m), 4.41-4.57 (4H, m), 5.29 (1H, s), 7.03-7.07 (1H, m), 7.21-7.26 (1H, m), 7.37-7.42 (1H, m), 8.50 (1H, s), 10.34 (1H, brs), 12.48 (1H, s).

Example Y-10

(2S,9aS)-5-Hydroxy-6,10-dioxo-2-phenyl-3,4,6,9,9a,10-hexahydro-2H-1-oxa-4a,8a-diaza-anthracene-7-carboxylic acid 2,4-difluoro-benzylamide 1H-NMR (CDCl$_3$) δ: 1.70-1.82 (1H, m), 1.98 (1H, d, J=9.6 Hz), 3.49 (1H, t, J=9.6 Hz), 4.54-4.68 (5H, m), 4.98 (1H, d, J=8.7 Hz), 5.51 (1H, s), 7.04-7.08 (1H, m), 7.21-7.42 (7H, m), 8.50 (1H, s), 10.38 (1H, s), 12.45 (1H, s).

Example Y-11

(2S,9aS)-5-Hydroxy-2-isopropyl-6,10-dioxo-3,4,6,9,9a,10-hexahydro-2H-1-oxa-4a,8a-diaza-anthracene-7-carboxylic acid 2,4-difluoro-benzylamide

Example Y-12

(2R,9aR)-5-Hydroxy-2-isopropyl-6,10-dioxo-3,4,6,9,9a,10-hexahydro-2H-1-oxa-4a,8a-diaza-anthracene-7-carboxylic acid 2,4-difluoro-benzylamide 1H-NMR (DMSO-$d_6$) δ: 0.86 (6H, dd, J=4.8, 13.5 Hz), 1.41-1.49 (1H, m), 1.57-1.69 (1H, m), 1.72-1.78 (1H, m), 3.20 (1H, t, J=8.4 Hz), 3.52-3.59 (1H, m), 4.41-4.46 (5H, m), 5.29 (1H, s), 7.01-7.08 (1H, m), 7.21-7.26 (1H, m), 7.37-7.43 (1H, m), 8.50 (1H, s), 10.35 (1H, brs), 12.48 (1H, s).

Example Y-13

(3S,9aS)-5-Hydroxy-3-methyl-6,10-dioxo-3,4,6,9,9a,10-hexahydro-2H-1-oxa-4a,8a-diaza-anthracene-7-carboxylic acid 4-fluoro-benzylamide Example Y-14

(3R,9aR)-5-Hydroxy-3-methyl-6,10-dioxo-3,4,6,9,9a,10-hexahydro-2H-1-oxa-4a,8a-diaza-anthracene-7-carboxylic acid 4-fluoro-benzylamide 1H-NMR (DMSO-$d_6$) δ: 0.81 (3H, d, J=6.6 Hz), 1.84-1.93 (1H, m), 2.86 (1H, t, J=12.5 Hz), 3.48 (1H, t, J=11.1 Hz), 3.97-4.03 (1H, m), 4.41-4.60 (3H, m), 4.52 (2H, d, J=5.9 Hz), 5.20 (1H, t, J=3.8 Hz), 7.12-7.20 (2H, m), 7.32-7.38 (2H, m), 8.52 (1H, s), 10.36 (1H, t, J=5.9 Hz), 12.45 (1H, s).

Example Y-15

(2R,9aS)-5-Hydroxy-2-methyl-6,10-dioxo-3,4,6,9,9a,10-hexahydro-2H-1-oxa-4a,8a-diaza-anthracene-7-carboxylic acid 2,4-difluoro-benzylamide Example Y-16

(2S,9aR)-5-Hydroxy-2-methyl-6,10-dioxo-3,4,6,9,9a,10-hexahydro-2H-1-oxa-4a,8a-diaza-anthracene-7-carboxylic acid 2,4-difluoro-benzylamide 1H-NMR (DMSO-$d_6$) δ: 1.14 (3H, d, J=6.0 Hz), 1.38 (1H, m), 1.75 (1H, d, J=13.8 Hz), 3.18-3.29 (1H, m), 3.95-4.06 (1H, m), 4.42-4.58 (3H, m), 4.54 (2H, d, J=5.7 Hz), 5.30 (1H, t, J=3.9 Hz), 7.03-7.10 (1H, m), 7.20-7.29 (1H, m), 7.35-7.44 (1H, m), 8.50 (1H, s), 10.35 (1H, t, J=5.7 Hz), 12.48 (1H, s).

Example Y-17

(2S,9aR)-5-Hydroxy-2-methyl-6,10-dioxo-3,4,6,9,9a,10-hexahydro-2H-1-oxa-4a,8a-diaza-anthracene-7-carboxylic acid 4-fluoro-benzylamide Example Y-18

(2R,9aS)-5-Hydroxy-2-methyl-6,10-dioxo-3,4,6,9,9a,10-hexahydro-2H-1-oxa-4a,8a-diaza-anthracene-7-carboxylic acid 4-fluoro-benzylamide 1H-NMR (DMSO-$d_6$) δ: 1.15 (3H, d, J=6.0 Hz), 1.35-1.50 (1H, m), 1.75 (1H, d, J=12.9 Hz), 3.23 (1H, td, J=13.0, 2.8 Hz), 3.96-4.03 (1H, m), 4.41-4.59 (3H, m), 4.52 (2H, d, J=6.0 Hz), 5.30 (1H, t, J=3.9 Hz), 7.12-7.19 (2H, m), 7.32-7.38 (2H, m), 8.52 (1H, s), 10.36 (1H, t, J=6.0 Hz), 12.48 (1H, s).

Corresponding amino-alcohol derivatives used in syntheses of Y-1 to Y-18 were prepared as optically pure version using methods similar to those described in the following reports.

3-Amino-2-methyl-propan-1-ol, and 4-Amino-butan-2-ol were prepared according to the method of Russell A. Barrow (J. Am. Chem. Soc. 1995, 117, 2479-2490).

3-Amino-butan-1-ol were prepared according to the method of P. Besse (Tetrahedron Asymmetry 10 (1999) 2213-2224).

1-Amino-pentan-3-ol, 1-Amino-4-methyl-pentan-3-ol, 4-Amino-1-methoxy-butan-2-ol, and 3-Amino-1-phenyl-propan-1-ol were prepared according to the method described in the following literatures, U.S. Pat. Appl. Publ., 2004133029, 8 Jul. 2004, PCT Int. Appl., 2002012173, 14 Feb. 2002.

All examples below consist of >95% ee and >6:1 diastereomeric purity unless indicated otherwise. The compounds shown in table ZZ consist of mixtures of diastereomers at the depicted stereocenter in ratios of 1:1 to >10:1. Stereocenters that were formed during the process' below have been assigned using NMR techniques well know in the art (1D and 2D method) and/or using vibrational circular dichroism techniques. Stereochemical assignment determinations were performed on representative examples and closely related compounds were assigned by analogy in some cases. The schemes below are meant to be genera) guidance to how examples were synthesized. It will be possible that one skilled in the art may rearrange the order of steps or change substituents to apply the method described below and in the examples to construct compounds of the general formula. Additional methods known to those skilled in the art or commonly present in the literature may also be applied to perform similar transformations and arriving at the same compounds of the general formula or amino alcohol and diamine precursors.

[Chemical formula 68]

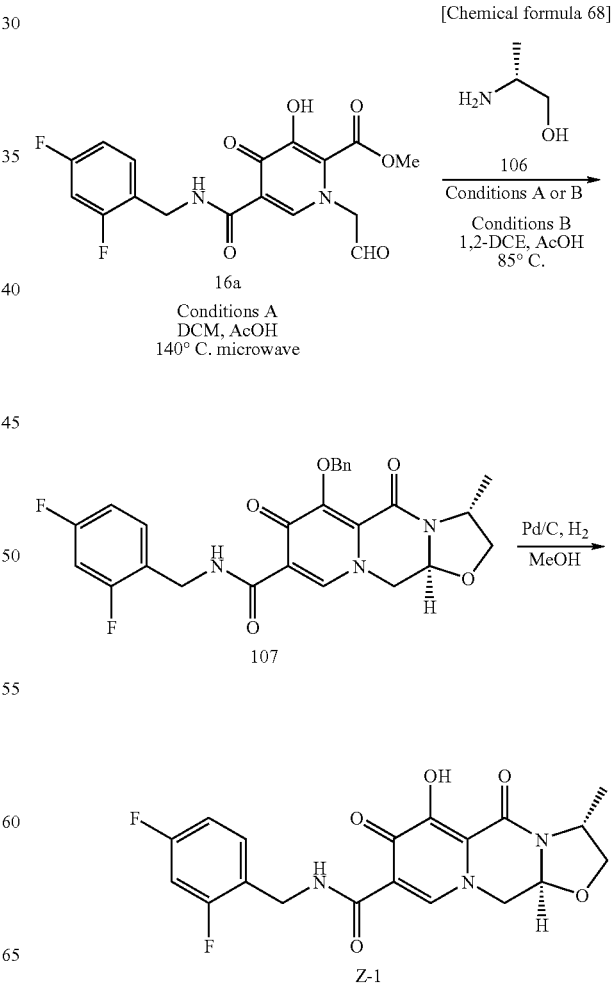

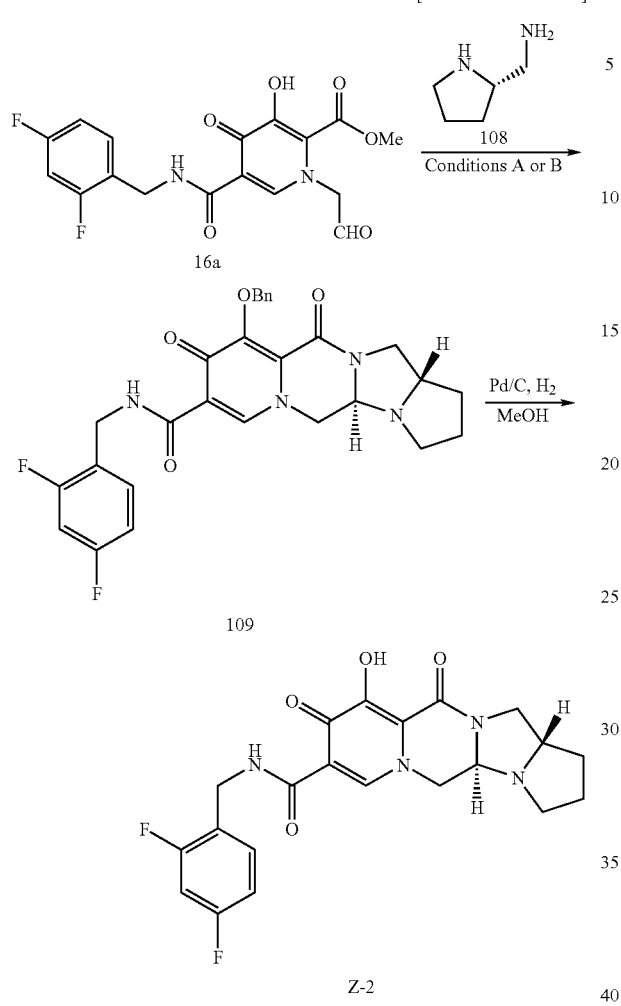
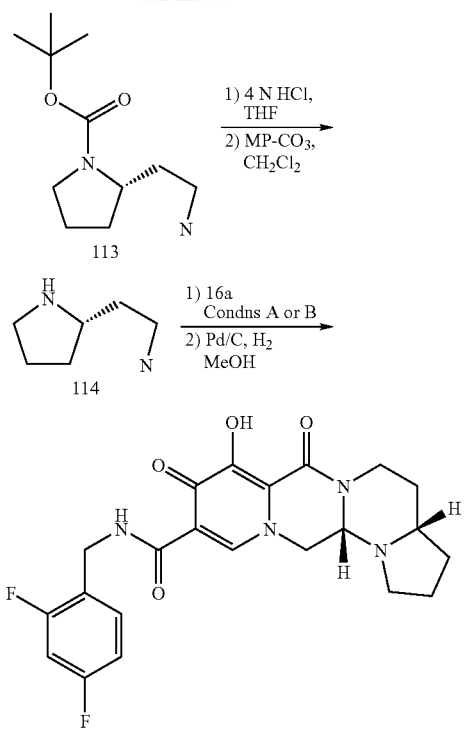
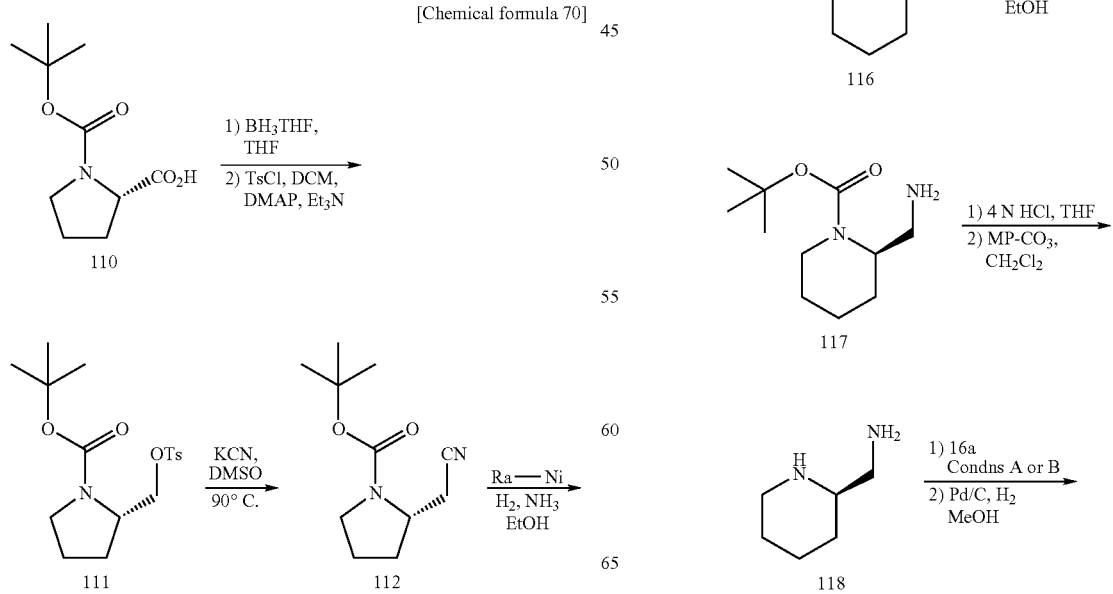

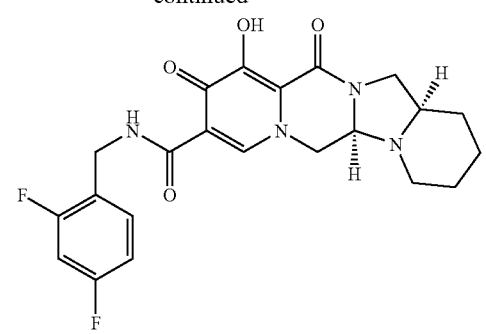
Z-18
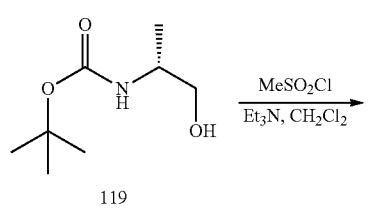
119
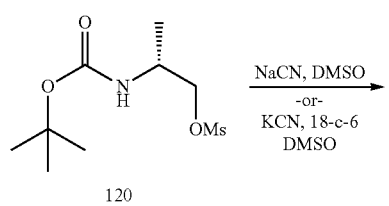
120
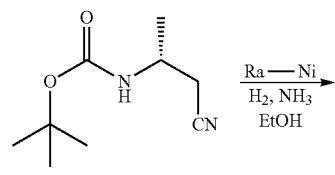
121
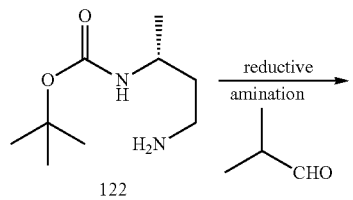
122
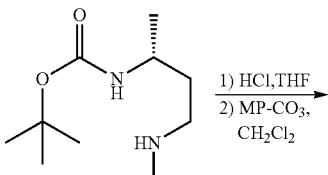
123
[Chemical formula 72]
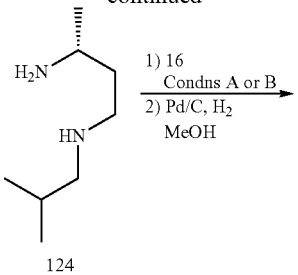
124
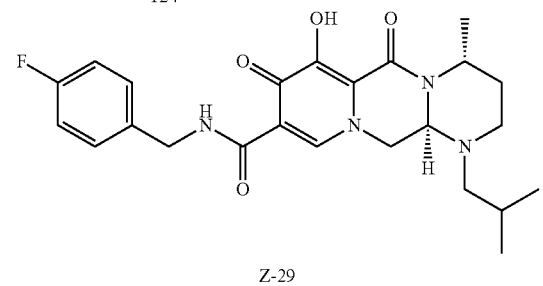
Z-29
[Chemical formula 73]
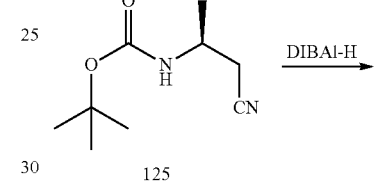
125
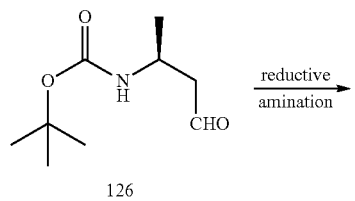
126
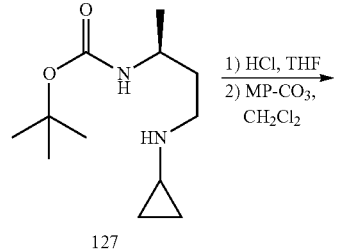
127
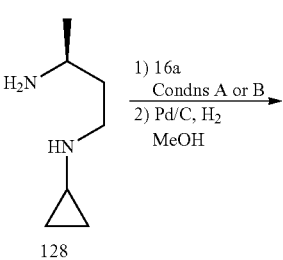
128

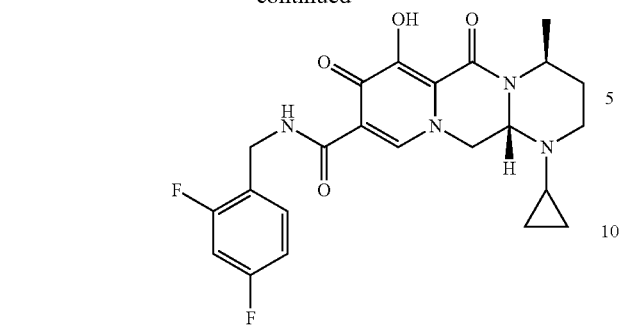
Z-47
[Chemical formula 74]
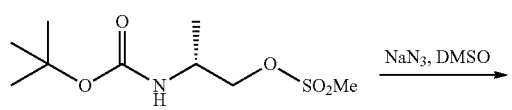
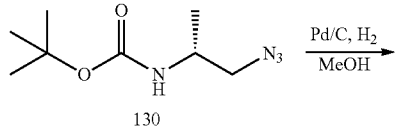
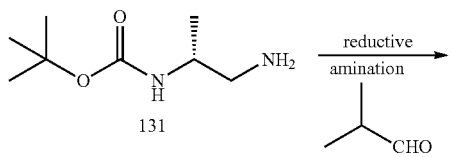
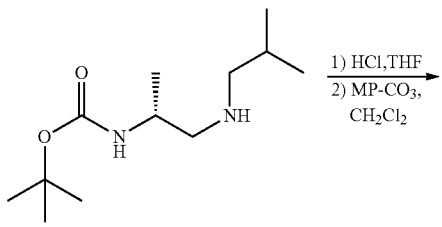
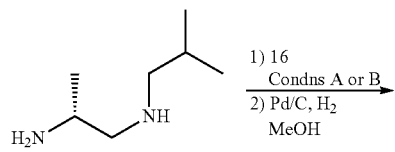
ZZ-16
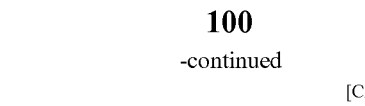
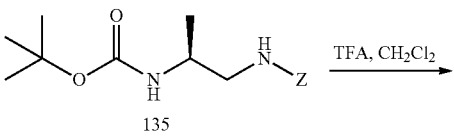
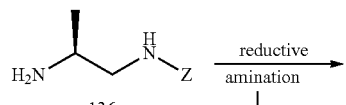
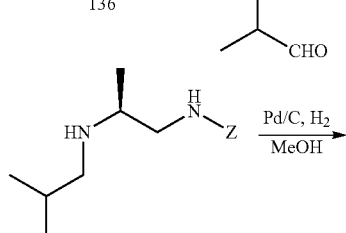
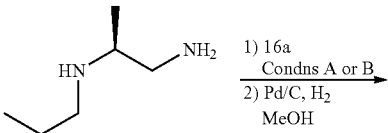
ZZ-17
[Chemical formula 75]
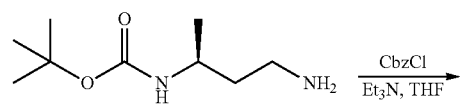
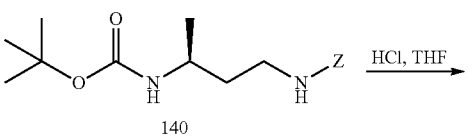
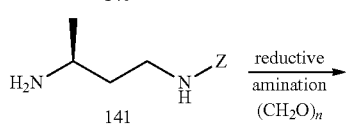

101
-continued
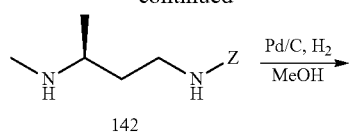
142
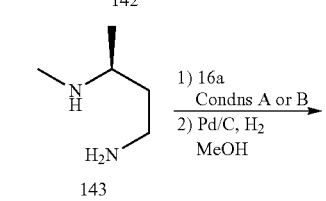
143
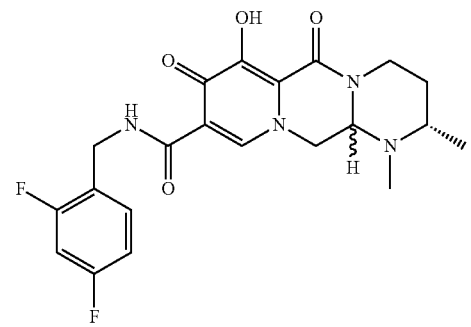
144
[Chemical formula 76]
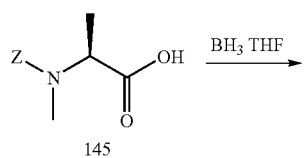
145
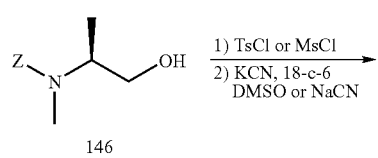
146
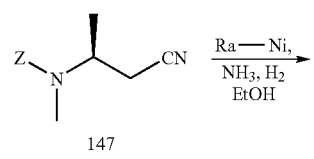
147
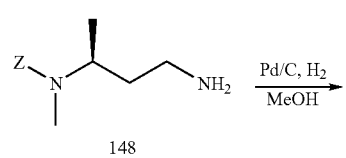
148
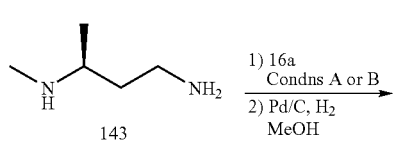
143
102
-continued
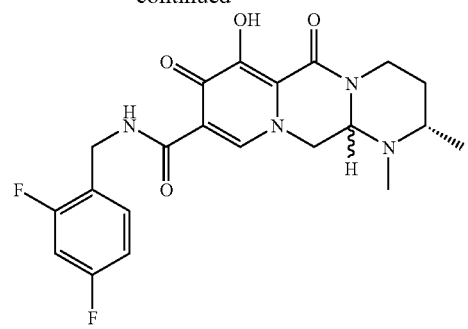
ZZ-5
[Chemical formula 77]
149
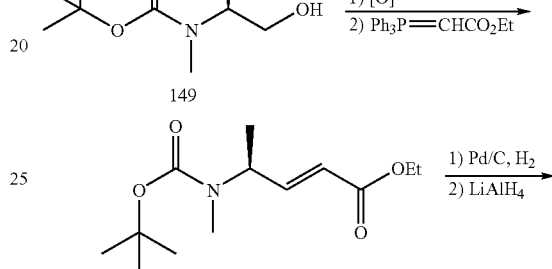
150
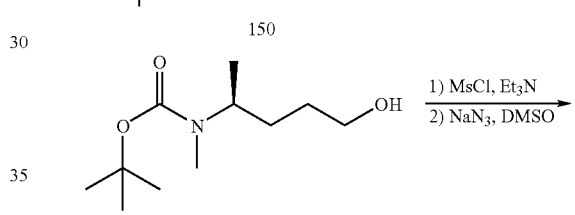
151
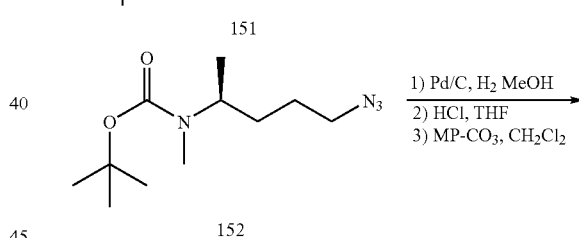
152
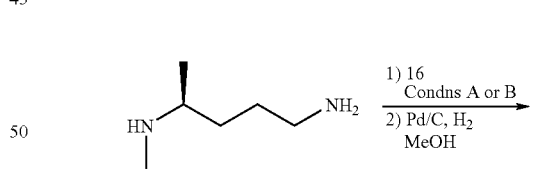
153
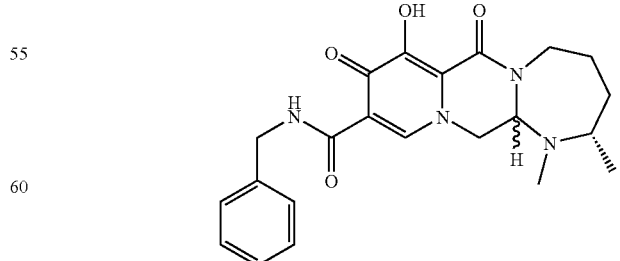
ZZ-4

[Chemical formula 78]
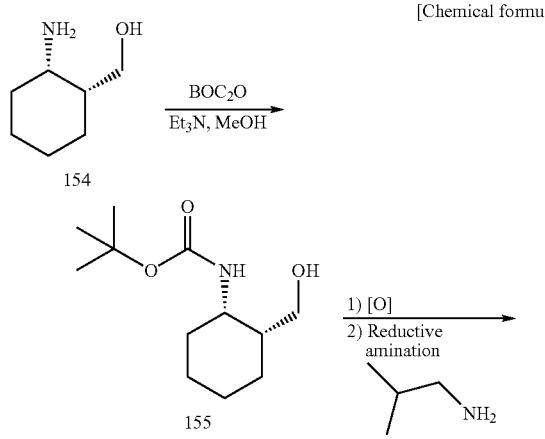
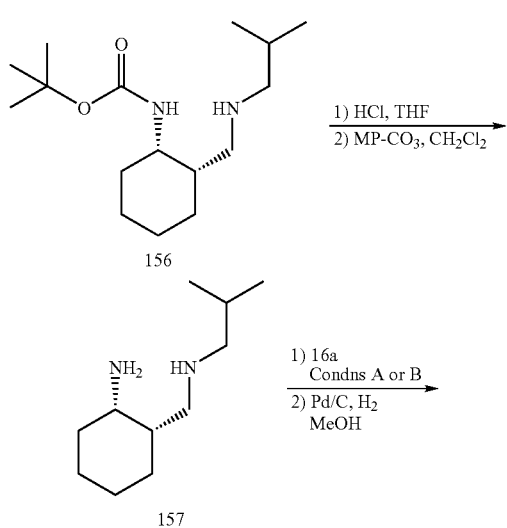
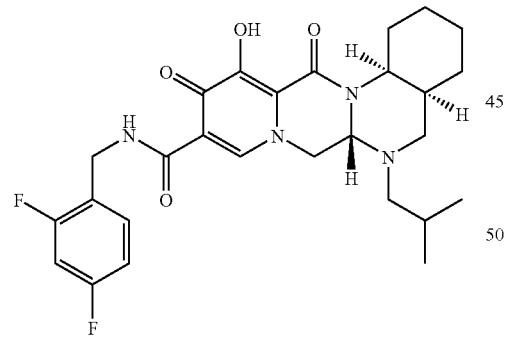
[Chemical formula 79]
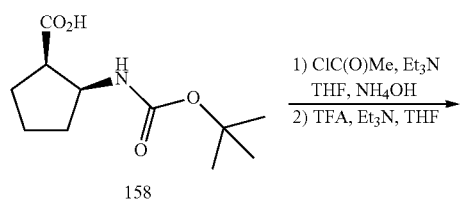
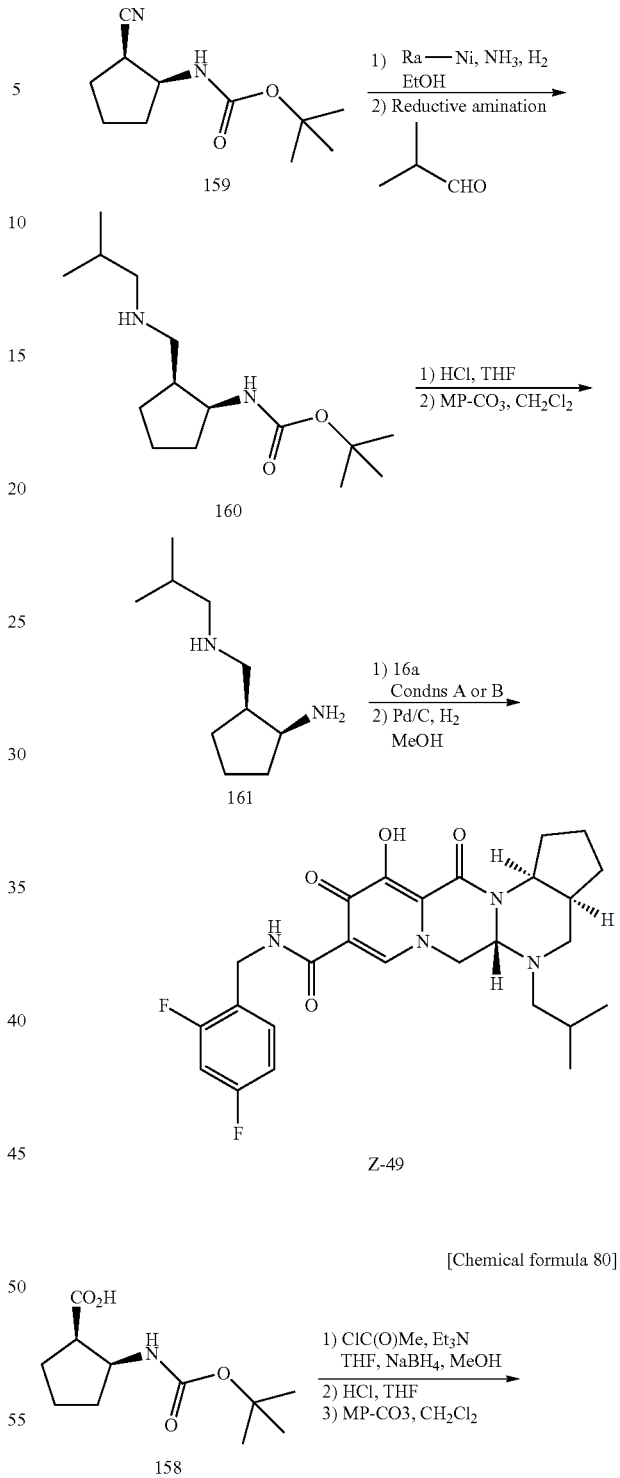
[Chemical formula 80]
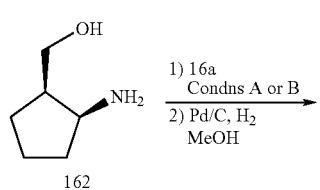

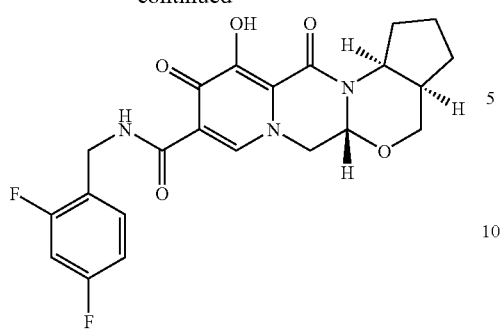
Z-52
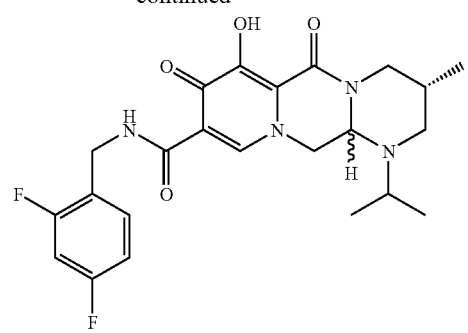
ZZ-9
[Chemical formula 81]
[Chemical formula 82]
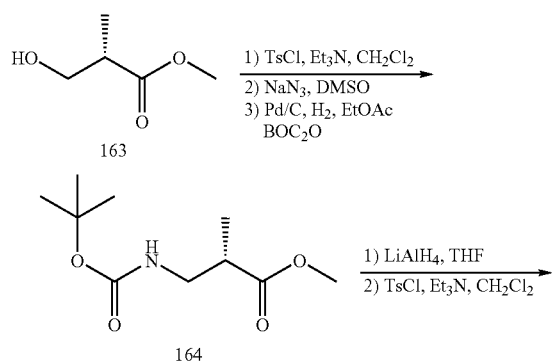
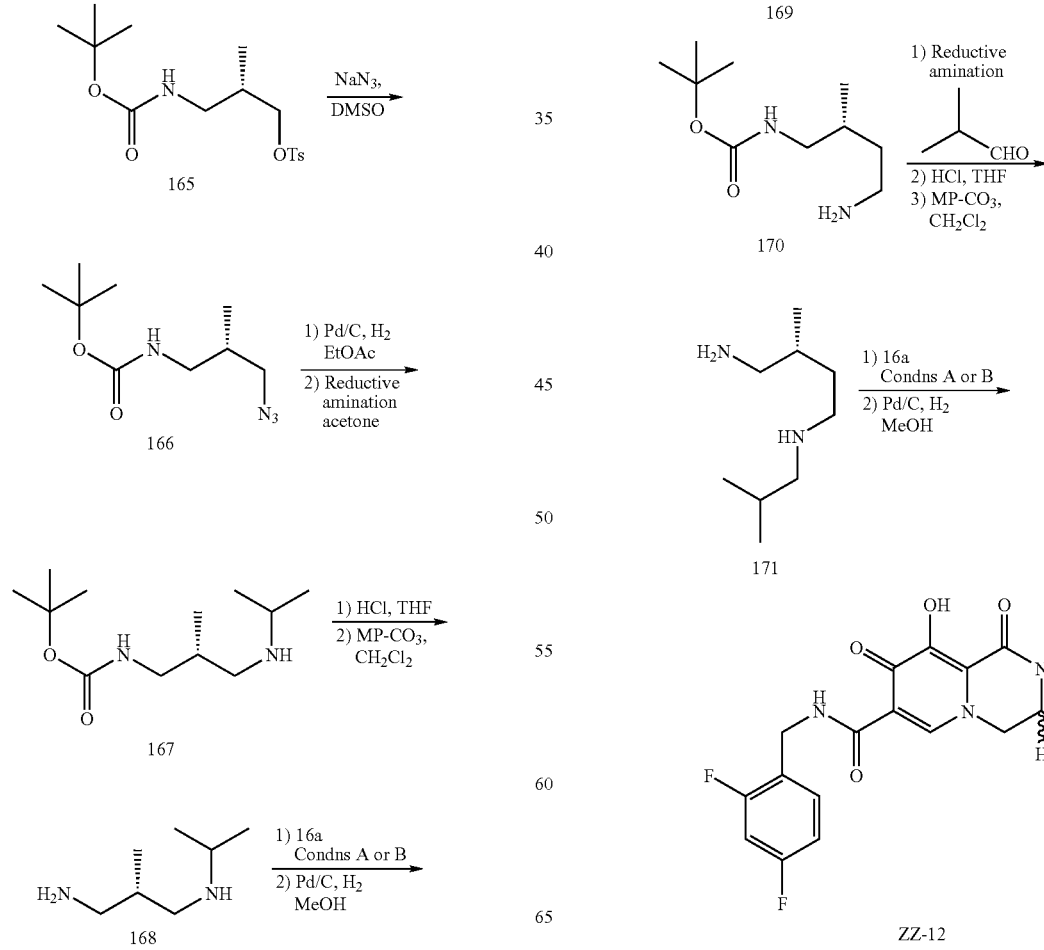

-continued

[Chemical formula 83]

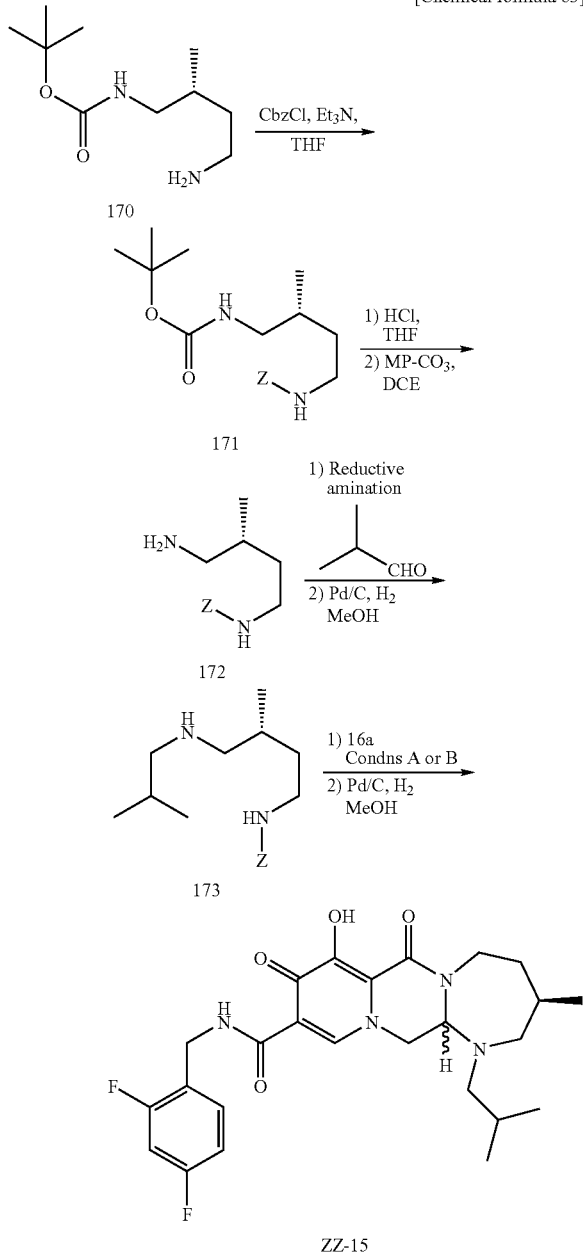

a)
(3R,11aS)—N-[(2,4-Difluorophenyl)methyl]-3-methyl-5,7-dioxo-6-[(phenylmethyl)oxy]-2,3,5,7,11,11a-hexahydro[1,3]oxazolo[3,2-a]pyrido[1,2-d]pyrazine-8-carboxamide. To a solution of 16a (409 mg, 0.87 mmol) in dichloroethane (20 mL) was added (2R)-2-amino-1-propanol (0.14 mL, 1.74 mmol) and 10 drops of glacial acetic acid. The resultant solution was heated at reflux for 2 h. Upon cooling, Celite was added to the mixture and the solvents removed in vacuo and the material was purified via silica gel chromatography (2% $CH_3OH/CH_2Cl_2$ gradient elution) to give (3R,11aS)—N-[(2,4-difluorophenyl)methyl]-3-methyl-5,7-dioxo-6-[(phenylmethyl)oxy]-2,3,5,7,11,11a-hexahydro[1,3]oxazolo[3,2-a]pyrido[1,2-d]pyrazine-8-carboxamide (396 mg, 92%) as a glass. $^1$H NMR ($CDCl_3$) δ 10.38 (m, 1H), 8.42 (s, 1H), 7.54-7.53 (m, 2H), 7.37-7.24 (m, 4H), 6.83-6.76 (m, 2H), 5.40 (d, J=10.0 Hz, 1H), 5.22 (d, J=10.0 Hz, 1H), 5.16 (dd, J=9.6, 6.0 Hz, 1H), 4.62 (m, 2H), 4.41 (m, 1H), 4.33-4.30 (m, 2H), 3.84 (dd, J=12.0, 10.0 Hz, 1H), 3.63 (dd, J=8.4, 7.2 Hz, 1H), 1.37 (d, J=6.0 Hz, 3H); ES$^+$ MS: 496 (M+1).

b)
(3R,11aS)—N-[(2,4-Difluorophenyl)methyl]-6-hydroxy-3-methyl-5,7-dioxo-2,3,5,7,11,11a-hexahydro[1,3]oxazolo[3,2-a]pyrido[1,2-d]pyrazine-8-carboxamide sodium salt. To a solution of (3R,11aS)—N-[(2,4-difluorophenyl)methyl]-3-methyl-5,7-dioxo-6-[(phenylmethyl)oxy]-2,3,5,7,11,11a-hexahydro[1,3]oxazolo[3,2-a]pyrido[1,2-d]pyrazine-8-carboxamide (396 mg, 0.80 mmol) in methanol (30 mL) was added 10% Pd/C (25 mg). Hydrogen was bubbled through the reaction mixture via a balloon for 2 h. The resultant mixture was filtered through Celite with methanol and dichloromethane. The filtrate was concentrated in vacuo to give (3R,11aS)—N-[(2,4-difluorophenyl)methyl]-6-hydroxy-3-methyl-5,7-dioxo-2,3,5,7,11,11a-hexahydro[1,3]oxazolo[3,2-a]pyrido[1,2-d]pyrazine-8-carboxamide as a pink tinted white solid (278 mg, 86%). $^1$H NMR ($CDCl_3$) δ 11.47 (m, 1H), 10.29 (m, 1H), 8.32 (s, 1H), 7.36 (m, 1H), 6.82 (m, 2H), 5.31 (dd, J=9.6, 3.6 Hz, 1H), 4.65 (m, 2H), 4.47-4.38 (m, 3H), 3.93 (dd, J=12.0, 10.0 Hz, 1H), 3.75 (m, 1H), 1.49 (d, J=5.6 Hz, 3H); ES$^+$ MS: 406 (M+1). The above material (278 mg, 0.66 mmol) was taken up in ethanol (10 mL) and treated with 1 N sodium hydroxide (aq) (0.66 ml, 0.66 mmol). The resulting suspension was stirred at room temperature for 30 min. Ether was added and the liquids were collected to provide the sodium salt of the title compound as a white powder (291 mg, 99%). $^1$H NMR (DMSO-$d_6$) δ 10.68 (m, 1H), 7.90 (s, 1H), 7.35 (m, 1H), 7.20 (m, 1H), 7.01 (m, 1H), 5.20 (m, 1H), 4.58 (m, 1H), 4.49 (m, 2H), 4.22 (m, 2H), 3.74 (dd, J=11.2, 10.4 Hz, 1H), 3.58 (m, 1H), 1.25 (d, J=4.4 Hz, 3H).

Example Z-1

(3R,11aS)—N-[(2,4-Difluorophenyl)methyl]-6-hydroxy-3-methyl-5,7-dioxo-2,3,5,7,11,11a-hexahydro[1,3]oxazolo[3,2-a]pyrido[1,2-d]pyrazine-8-carboxamide sodium salt

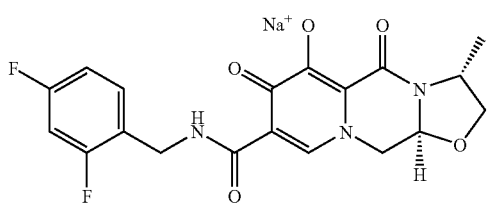

Example Z-2

(4aR,13aS)—N-[(2,4-Difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide

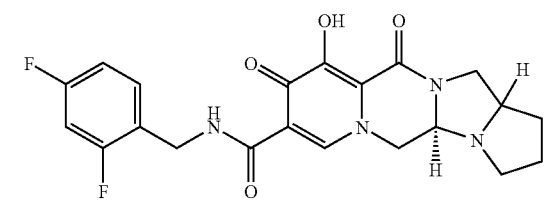

a)
(4aR,13aS)—N-[(2,4-Difluorophenyl)methyl]-9,11-dioxo-10-[(phenylmethyl)oxy]-2,3,4a,5,9,11,13,13a-octahydro-1H-pyrido[1,2-a]pyrrolo[1',2':3,4]imidazo[1,2-d]pyrazine-8-carboxamide. A solution of 16a (24 mg, 0.05 mmol), [(2S)-2-pyrrolidinylmethyl]amine (0.1 mL) and 2 drops of glacial acetic acid were heated under microwave conditions at 140° C. for 10 min. Upon cooling, Celite was added to the mixture and the solvents removed in vacuo and the material was purified via silica gel chromatography (2% $CH_3OH$/$CH_2Cl_2$ gradient elution) to give (4aR,13aS)—N-[(2,4-difluorophenyl)methyl]-9,11-dioxo-10-[(phenylmethyl)oxy]-2,3,4a,5,9,11,13,13a-octahydro-1H-pyrido[1',2':3,4]imidazo[1,2-d]pyrazine-8-carboxamide (19 mg, 71%) as a white solid. $^1$H NMR ($CDCl_3$) δ 10.41 (m, 1H), 8.38 (s, 1H), 7.56 (m, 2H), 7.38-7.24 (m, 4H), 6.80 (m, 2H), 5.38 (d, J=9.6 Hz, 1H), 5.10 (d, J=10.0 Hz, 1H), 4.62 (m, 2H), 4.40 (m, 1H), 4.25 (dd, J=12.0, 6.8 Hz, 1H), 4.10 (d, J=12.8 Hz, 1H), 3.83 (m, 1H), 3.71 (m, 1H), 3.14-3.04 (m, 2H), 2.78 (m, 1H), 2.11-1.58 (m, 4H); $ES^+$ MS: 521 (M+1).

b)
(4aR,13aS)—N-[(2,4-Difluorophenyl)methyl]-10-hydroxy-[9,11]-dioxo-2,3,4a,5,9,11,13,13a-octahydro-1H-pyrido[1,2-a]pyrrolo[1',2':3,4]imidazo[1,2-d]pyrazine-8-carboxamide. To a solution of (4aS,13aR)—N-[(2,4-difluorophenyl)methyl]-9,11-dioxo-10-[(phenylmethyl)oxy]-2,3,4a5,9,11,13,13a-octahydro-1H-pyrido[1,2-a]pyrrolo[1',2':3,4]imidazo[1,2-d]pyrazine-8-carboxamide (19 mg, 0.04 mmol) in methanol (8 mL) was added 10% Pd/C (10 mg). Hydrogen was bubbled through the reaction mixture via a balloon for 2 h. The resultant mixture was filtered through Celite with methanol and dichloromethane. The filtrate was concentrated in-vacuo to give the title compound (6 mg, 38%) as a white solid. $^1$H NMR ($CDCl_3$) δ 11.73 (m, 1H), 10.36 (m, 1H), 8.31 (s, 1H), 7.33 (m, 1H), 6.78 (m, 2H), 4.62 (m, 2H), 4.50 (m, 1H), 4.27-4.19 (m, 2H), 3.87-3.77 (m, 2H), 3.16-3.08 (m, 2H), 2.83 (m, 1H), 2.11-1.65 (m, 4H): $ES^+$ MS: 431 (M+1).

Example Z-3

(3aS,13aS)—N-[(2,4-Difluorophenyl)methyl]-8-hydroxy-7,9-dioxo-1,2,3,3a,4,5,7,9,13,13a-decahydropyrido[1',2':3,4]pyrazino[1,2-a]pyrrolo[1,2-c]pyrimidine-10-carboxamide

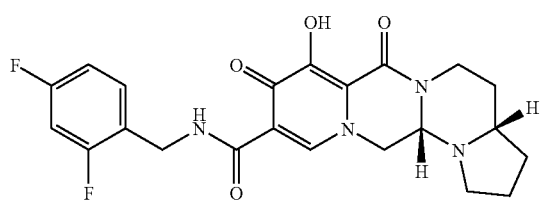

a) N-BOC-(2S)-2-(Hydroxymethyl)-1-pyrrolidine. To a solution of N-BOC-L-proline (4.17 g, 19.4 mmol) in THF (40 mL) at 0° C. was added $BH_3$-THF (21.4 mL, 1 M in THF, 21.4 mmol) dropwise. The bath was removed and the resultant solution stirred at room temperature for 2 h. Methanol was added to quench the mixture and the solvents were removed in vacuo. The residue was taken up in ethyl acetate and washed with sodium bicarbonate and brine. The aqueous layers were extracted twice with ethyl acetate. The combined organics were dried over $Na_2SO_4$, filtered and concentrated to give N-BOC-(2S)-2-(hydroxymethyl)-1-pyrrolidine (3.82 g, 98%) as a clear oil. This material was used without further purification. $^1$H NMR ($CDCl_3$) δ 3.94 (m, 1H), 3.62 (dd, J=11.2, 3.2 Hz, 1H), 3.56 (dd, J=10.8, 7.2 Hz, 1H), 3.44 (m, 1H), 3.29 (m, 1H), 2.62 (br, 1H), 1.98 (m, 1H), 1.85-1.72 (m, 2H), 1.58 (m, 1H).

b) N-BOC-(2S)-2-({[(4-Methylphenyl)sulfonyl]oxy}methyl)-1-pyrrolidine. To a cold (0° C.) solution of N-BOC-(2S)-2-(hydroxymethyl)-1-pyrrolidine (350 mg, 1.74 mmol) in dichloromethane (20 mL) was added triethylamine (0.29 mL, 2.08 mmol), and toluenesulfonyl chloride (398 mg, 2.08 mmol). N,N-dimethylaminopyridine (70 mg) was added and the resultant solution was allowed to warm to rt as the bath warmed and stirred for 4 h. Water was added and the layers separated. The aqueous layer was washed with sodium bicarbonate and then with brine. The combined organics were dried over $Na_2SO_4$, filtered and concentrated followed by flash chromatography purification to give N-BOC-(2S)-2-({[(4-methylphenyl)sulfonyl]oxy}methyl)-1-pyrrolidine (460 mg, 75%) as a clear oil. $^1$H NMR exists as rotamers ($CDCl_3$) δ 7.77 (d, 2H), 7.33 (m, 2H), 4.08 (m, 1H), 3.97-3.88 (m, 1H), 3.35-3.25 (m, 2H), 2.43 (s, 3H), 1.95-1.79 (m, 4H), 1.40 and 1.35 (s, 9H rotomeric BOC t-butyl).

c) N-BOC-(2S)-2-Cyano-1-pyrrolidine. A mixture of —N-BOC-(2S)-2-({[(4-methylphenyl)sulfonyl]oxy}methyl)-1-pyrrolidine (460 mg, 1.29 mmol) and KCN (256 mg, 3.88 mmol) were heated at 90° C. in DMSO (10 mL) for 6.5 h. The mixture was cooled to room temperature and EtOAc and water were added. The organics were washed with water twice and then with brine. The aqueous layers were extracted with EtOAc and the combined organics dried over $Na_2SO_4$, filtered and concentrated followed by flash chromatography purification to give N-BOC-(2S)-2-cyano-1-pyrrolidine (179 mg, 66%) as an oil. $^1$H NMR exists as rotamers ($CDCl_3$) δ 3.99 (m, 1H), 3.43-3.37 (m, 2H), 2.83-2.51 (m, 2H), 2.17-1.83 (m, 4H), 1.46 and 1.44 (s, 9H rotomeric BOC t-butyl).

d) N-BOC-(2S)-2-(2-Aminoethyl)-1-pyrrolidine. A solution of N-BOC-(2S)-2-cyano-1-pyrrolidine (179 mg, 0.85 mmol) in ethanol saturated with anhydrous ammonia was treated with Raney-Ni (1 mL of 50% aq. Suspension) and 50 psi of $H_2$ overnight. The mixture was filtered through Celite and the filtrate was concentrated in vacuo. The residue was purified by flash chromatography (10% $CH_3OH$/$CH_2Cl_2$ with 1% $NH_4OH$ gradient elution) through a short plug of silica gel to give —N-BOC-(2S)-2-(2-aminoethyl)-1-pyrrolidine (90 mg, 50%) as a clear oil. $^1$H NMR exists as rotamers ($CDCl_3$) δ 3.88-3.77 (m, 1H), 3.33-3.24 (m, 2H), 2.66 (m, 2H), 1.89-1.54 (m, 6H), 1.40 (s, 9H).

e) {2-[(2S)-2-Pyrrolidinyl]ethyl}amine. A solution of —N-BOC-(2S)-2-(2-aminoethyl)-1-pyrrolidine (90 mg, 0.42 mmol) in THF (6 mL) was treated with 4 N HCl (aq) (2 mL) and stirred at room temperature for 3 h. The mixture was concentrated in vacuo to give the title compound as its HCl salt. A portion of this material (40 mg) was dissolved in methanol and treated with solid supported carbonate resin (MP-Carbonate, Argonaut Technologies) to freebase the amines. After 30 minutes, the solution was filtered through a fritted tube and the solvents removed carefully in vacuo to give {2-[(2S)-2-pyrrolidinyl]ethyl}amine (30 mg) as its free base. $^1$H NMR ($CDCl_3$) δ 3.06 (m, 1H), 2.94 (m, 1H), 2.83 (m, 1H), 2.79-2.69 (m, 2H), 1.90-1.56 (m, 6H), f)
(3aS,13aS)—N-[(2,4-Difluorophenyl)methyl]-7,9-dioxo-8-[(phenylmethyl)oxy]-1,2,3,3a,4,5,7,9,13,13a-decahydropyrido[1',2':4,5]pyrazino[1,2-a]pyrrolo[1,2-c]pyrimidine-10-carboxamide. A solution of 16a (30 mg, 0.06 mmol), {2-[(2S)-2-pyrrolidinyl]ethyl}amine (30 mg, 0.26 mmol) and 2 drops of glacial acetic acid were heated under microwave conditions at 140° C. for 10 min. Upon cooling, Celite was added to the mixture and the solvents removed in vacuo and the material was purified via silica gel chromatography (2% CH$_3$OH/CH$_2$Cl$_2$ gradient elution) to give (3aS,13aS)—N-[(2,4-Difluorophenyl)methyl]-7,9-dioxo-8-[(phenylmethyl)oxy]-1,2,3,3a,4,5,7,9,13,13a-decahydropyrido[1',2':4,5]pyrazino[1,2-a]pyrrolo[1,2-c]pyrimidine-10-carboxamide. (25 mg, 74%) as a film. $^1$H NMR (CDCl$_3$) δ 10.44 (m, 1H), 8.32 (s, 1H), 7.59 (m, 2H), 7.38-7.24 (m, 4H), 6.80 (m, 2H), 5.28-5.22 (m, 2H), 4.67 (dd, J=13.6, 2.8 Hz, 1H), 4.62 (m, 2H), 4.26 (m, 1H), 4.11-4.03 (m, 2H), 2.91 (m, 1H), 2.81 (m, 1H), 2.37 (m, 1H), 2.24 (m, 1H), 1.92 (m, 1H), 1.82-1.76 (m, 3H), 1.52-1.38 (m, 2H); ES$^+$ MS: 535 (M+1).

g)
(3aS,13aS)—N-[(2,4-Difluorophenyl)methyl]-8-hydroxy-719-dioxo-1,2,3,3a,4,5,7,9,13,13a-decahydropyrido[1',2':4,5]pyrazino[1,2-a]pyrrolo[1,2-c]pyridine-10-carboxamide. To a solution of (3aS,13aS)—N-[(2,4-difluorophenyl)methyl]-7,9-dioxo-8-[(phenylmethyl)oxy]-1,2,3,3a,4,5,7,9,13,13a-decahydropyrido[1',2':4,5]pyrazino[1,2-a]pyrrolo[1,2-c]pyrimidine-10-carboxamide (25 mg, 0.05 mmol) in methanol (8 mL) was added 10% Pd/C (10 mg). Hydrogen was bubbled through the reaction mixture via a balloon for 18 h. The resultant mixture was filtered through Celite with methanol and dichloromethane. The filtrate was concentrated in vacuo to give the title compound (14 mg, 67%) as a white solid. $^1$H NMR (CDCl$_3$) δ 12.53 (br, 1H), 10.44 (s, 1H), 8.29 (s, 1H), 7.34 (m, 1H), 6.78 (m, 2H), 4.71-4.58 (m, 3H), 4.29-4.14 (m, 3H), 2.99 (m, 1H), 2.88 (m, 1H), 2:44 (m, 1H), 2.30 (m, 1H), 1.97-1.38 (m, 6H); ES$^+$ MS: 445 (M+1).

Example Z-4

(4aS,13aR)—N-[(2,4-Difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide sodium salt

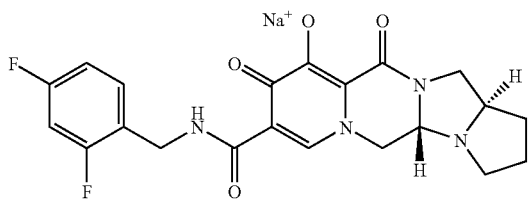

a) [(2R)-2-Pyrrolidinylmethyl]amine. To a solution of N-BOC-(2R)-2-(aminomethyl)-1-pyrrolidine (1.37 g, 6.85 mmol) in THF (20 mL) was added 4 N HCl (aq) (8 mL). The resultant solution was stirred at room temperature overnight. The solvents were removed in vacuo and the residue was treated with MP-carbonate resin in methanol and dichloromethane. After 1 h, the resin was removed via filtration through a fritted tube and the volatiles were removed carefully in vacuo to produce the free based amine (760 mg crude >100%) as a oil. This material was used without further purification. $^1$H NMR (CDCl$_3$) δ 3.13 (m, 1H), 2.92 (m, 1H), 2.82-2.62 (m, 5H), 1.88-1.30 (m, 4H).

b)
(4aS,13aR)—N-[(2,4-Difluorophenyl)methyl]-9,11-dioxo-10-[(phenylmethyl)oxy]-2,3,4a,5,9,11,13,13a-octahydro-1H-pyrido[1,2-a]pyrrolo[1',2':3,4]imidazo[1,2-d]pyrazine-8-carboxamide. In a similar manner as described in example Z-2 from 16a (435 mg, 0.93 mmol) and [(2R)-2-pyrrolidinylmethyl]amine (200 mg, 2.0 mmol) in 1,2-dichloroethane (20 mL) and 15 drops of glacial acetic acid was obtained (4aS,13aR)—N-[(2,4-difluorophenyl)methyl]-9,11-dioxo-10-[(phenylmethyl)oxy]-2,3,4a,5,9,11,13,13a-octahydro-1H-pyrido[1,2-a]pyrrolo[1',2':3,4]imidazo[1,2-d]pyrazine-8-carboxamide (321 mg, 67%) as a white solid. $^1$H NMR (CDCl$_3$) δ 10.41 (m, 1H), 8.35 (s, 1H), 7.56 (m, 2H), 7.55-7.24 (m, 4H), 6.80 (m, 2H), 5.35 (d, J=10.0 Hz, 1H), 5.13 (d, J=10.0 Hz, 1H), 4.60 (m, 2H), 4.38 (dd, J=10.4, 3.2 Hz, 1H), 4.21 (dd, J=12.0, 6.8 Hz, 1H), 4.04 (dd, J=12.4, 2.8 Hz, 1H), 3.77 (apparent t, J=11.6 Hz, 1H), 3.68 (m, 1H), 3.11-3.00 (m, 2H), 2.75 (m, 1H), 2.08-1.84 (m, 3H), 1.65 (m, 1H); ES$^+$ MS: 521 (M+1).

c)
(4aS,13aR)—N-[(2,4-Difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide. In a similar manner as described in example Z-2 from (4aS,13aR)—N-[(2,4-difluorophenyl)methyl]-9,11-dioxo-10-[(phenylmethyl)oxy]-2,3,4a,5,9,11,13,13a-octahydro-1H-pyrido[1,2-a]pyrrolo[1',2':3,4]imidazo[1,2-d]pyrazine-8-carboxamide (518 mg, 0.99 mmol) and 10% Pd/C (35 mg) in methanol (40 mL) was obtained (4aS,13aR)—N-[(2,4-Difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide (430 mg, 99%) as a white solid. $^1$H NMR (CDCl$_3$) δ 11.73 (m, 1H), 10.36 (m, 1H), 8.32 (s, 1H), 7.35 (m, 1H), 6.79 (m, 2H), 4.64 (m, 2H), 4.54 (dd, J=10.8, 4.0 Hz, 1H), 4.28-4.19 (m, 2H), 3.90-3.79 (m, 2H), 3.18-3.10 (m, 2H), 2.84 (m, 1H), 2.14-1.92 (m, 3H), 1.72 (m, 1H), d)
(4aS,13aR)—N-[(2,4-Difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide sodium salt. In a similar manner as described in example Z-1 from (4aS,13aR)—N-[(2,4-Difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide (430 mg, 1.0 mmol) and sodium hydroxide (1.0 mL, 1.0 M aq, 1.0 mmol) in 20 mL of ethanol was formed the corresponding sodium salt (425 mg, 94%) as a white solid. $^1$H NMR (D$_2$O) δ 7.85 (s, 1H), 7.23 (m, 1H), 6.82 (m, 2H), 4.51-4.46 (m, 3H), 4.28 (m, 1H), 3.95 (m, 1H), 3.84 (m, 1H), 3.62 (m, 1H), 3.16 (m, 1H), 2.89 (m, 1H), 2.84 (m, 1H), 1.90 (m, 2H), 1.73 (m, 1H), 1.60 (m, 1H). ES$^+$ MS: 431 (M+1).

Example Z-5

(4aS,13aR)—N-[(4-Fluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide

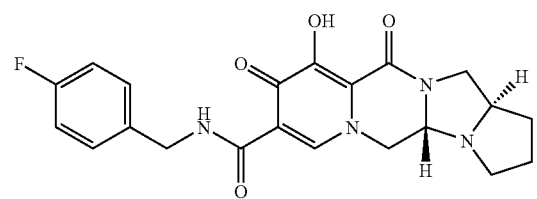

The title compound was made in two steps using a similar process to that described in example Z-2. 16 (60 mg, 0.13 mmol) and [(2R)-2-pyrrolidinylmethyl]amine (100 mg, 1.0 mmol) were reacted in dichloromethane (2 mL) with acetic acid to give (4aS,13aR)—N-[(4-fluorophenyl)methyl]-9,11-dioxo-10-[(phenylmethyl)oxy]-2,3,4a,5,9,11,13,13a-octahydro-1H-pyrido[1,2-a]pyrrolo[1',2':3,4]imidazo[1,2-a]pyrazine-8-carboxamide (60 mg, 91%). This material was hydrogenated in a second step as described in example Z-2 to give (4aS,13aR)—N-[(4-fluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-a]pyrazine-8-carboxamide (21 mg, 42%) as a white solid. $^1$H NMR (CDCl$_3$) δ 11.72 (m, 1H), 1.37 (m, 1H), 8.33 (s, 1H), 7.29 (m, 2H), 6.97 (m, 2H), 4.57 (m, 2H), 4.52 (m, 1H), 4.24-4.19 (m, 2H), 3.87-3.76 (m, 2H), 3.14-3.07 (m, 2H), 2.82 (m, 1H), 2.11-1.89 (m, 3H), 1.68 (m, 1H); ES$^+$ MS: 413 (M+1).

Example 2-6

(3S,11aR)—N-[(2,4-Difluorophenyl)methyl]-6-hydroxy-5,7-dioxo-3-(phenylmethyl)-2,3,5,7,11,11a-hexahydro[1,3]oxazolo[3,2-a]pyrido[1,2-d]pyrazine-8-carboxamide

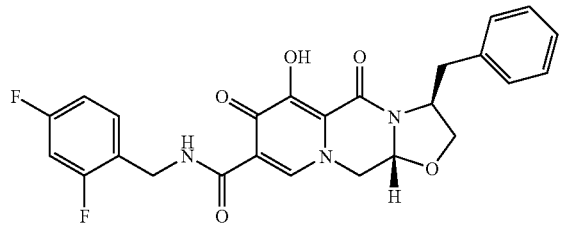

The title compound was made in two steps using a similar process to that described in example Z-2. 16a (37 mg, 0.08 mmol) and (2S)-2-amino-3-phenyl-1-propanol (35 mg, 0.24 mmol) were reacted in dichloromethane (2 mL) with acetic acid to give (3S,11aR)—N-[(2,4-difluorophenyl)methyl]-5,7-dioxo-3-(phenylmethyl)-6-[(phenylmethyl)oxy]-2,3,5,7,11,11a-hexahydro[1,3]oxazolo[3,2-a]pyrido[1,2-d]pyrazine-8-carboxamide (41 mg, 91%). This material was hydrogenated in a second step as described in example Z-2 to give (3S,11aR)—N-[(2,4-Difluorophenyl)methyl]-6-hydroxy-5,7-dioxo-3-(phenylmethyl)-2,3,5,7,11,11a-hexahydro[1,3]oxazolo[3,2-a]pyrido[1,2-d]pyrazine-8-carboxamide. (25 mg, 75%) as a white solid. $^1$H NMR (CDCl$_3$) δ 11.47 (br, 1H), 10.28 (m, 1H), 8.35 (m, 1H), 7.37-7.26 (m, 4H), 7.18 (m, 2H), 6.79 (m, 2H), 5.03 (m, 1H), 4.64-4.61 (m, 3H), 4.40 (m, 1H), 4.23 (apparent t, J=7.2 Hz, 1H), 3.96 (dd, J=8.8, 6.4 Hz, 1H), 3.88 (apparent t, J=11.2 Hz, 1H), 3.37 (dd, J=13.6, 3.2 Hz, 1H), 2.99 (dd, J=13.2-8.8 Hz, 1H); ES$^+$ MS: 482 (M+1).

Example Z-7

(3aS,13aS)—N-[(4-Fluorophenyl)methyl]-8-hydroxy-7,9-dioxo-1,2,3,3a,4,5,7,9,13,13a-decahydropyrido[1',2':3,4]pyrazino[1,2-a]pyrrolo[1,2-c]pyrimidine-10-carboxamide

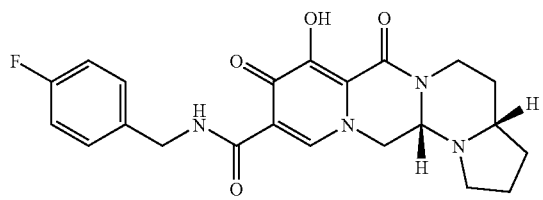

The title compound was made in two steps using a similar process to that described in example Z-2. 16 (84 mg, 0.13 mmol) and {2-[(2S)-2-Pyrrolidinyl]ethyl}amine (150 mg, 1.3 mmol) were reacted in dichloromethane (2 mL) with acetic acid to give (3aS,13aS)—N-[(4-fluorophenyl)methyl]-7,9-dioxo-8-[(phenylmethyl)oxy]-1,2,3,3a,4,5,7,9,13,13a-decahydropyrido[1',2':4,5]pyrazino[1,2-a]pyrrolo[1,2-c]pyrimidine-10-carboxamide (86 mg, 90%). This material was hydrogenated in a second step as described in example Z-2 to give (3aS,13aS)—N-[(4-Fluorophenyl)methyl]-8-hydroxy-7,9-dioxo-1,2,3,3a,4,5,7,9,13,13a-decahydropyrido[1',2':3,4]pyrazino[1,2-a]pyrrolo[1,2-c]pyrimidine-10-carboxamide. (63 mg, 88%) as a white solid. $^1$H NMR (CDCl$_3$/CD$_3$OD) δ 10.45 (m, 1H), 8.23 (s, 1H), 7.35 (m, 2H), 6.94 (t, J=8.8 Hz, 2H), 4.63 (m, 1H), 4.58-4.48 (m, 2H), 4.33 (dd, J=13.6, 3.6 Hz, 1H), 4.21 (m, 1H), 4.11 (m, 1H), 2.98 (m, 1H), 2.85 (td, J=13.2, 3.2 Hz, 1H), 2.41 (m, 1H), 2.29 (m, 1H), 1.92 (m, 1H), 1.83-1.75 (m, 3H), 1.54-1.35 (m, 2H); ES$^+$ MS: 427 (M+1).

Example Z-8

(3S,11aR)—N-[(2,4-Difluorophenyl)methyl]-6-hydroxy-3-[(1S)-1-methylpropyl]-5,7-dioxo-2,3,5,7,11,11a-hexahydro[1,3]oxazolo[3,2-a]pyrido[1,2-d]pyrazine-8-carboxamide sodium salt

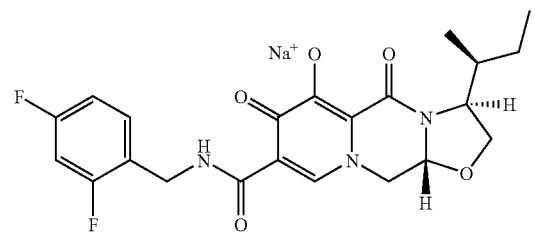

The title compound was made in two steps using a similar process to that described in example Z-1. 16a (417 mg, 0.89 mmol) and L-isoleucinol (259 mg, 2.21 mmol) were reacted in 1,2-dichloroethane (40 mL) with acetic acid to give (3S,11aR)—N-[(2,4-difluorophenyl)methyl]-3-[(1S)-1-methylpropyl]-5,7-dioxo-6-[(phenyl methyl)oxy]-2,3,5,7,11,11a-hexahydro[1,3]oxazolo[3,2-a]pyrido[1,2-d]pyrazine-8-carboxamide (426 mg, 90%). This material was hydrogenated in a second step as described in example Z-1 to give (3S,11aR)—N-[(2,4-Difluorophenyl)methyl]-6-hydroxy-3-[(1S)-1-methylpropyl]-5,7-dioxo-2,3,5,7,11,11a-hexahydro[1,3]oxazolo[3,2-a]pyrido[1,2-d]pyrazine-8-carboxamide (376 mg, 99%) as a coarse white solid. $^1$H NMR (CDCl$_3$) δ 11.43 (br, 1H), 10.27 (br, 1H), 8.32 (s, 1H), 7.33 (m, 1H), 6.79 (m, 2H), 5.26 (dd, J=9.6, 4.0 Hz, 1H), 4.62 (m, 2H), 4.42-4.35 (m, 2H), 4.19 (dd, J=8.8, 7.2 Hz, 1H), 4.01 (dd, J=8.8, 5.6 Hz, 1H), 3.86 (dd, J=12.0, 10.0 Hz, 1H), 2.27 (m, 1H), 1.40 (m, 1H), 1.15 (m, 1H), 0.97 (t, J=7.2 hz, 3H), 0.91 (d, J=6.8 Hz, 3H); ES$^+$ MS: 448 (M+1). This material (360 mg, 0.81 mmol) was treated with sodium hydroxide (0.81 mL, 1.0 M, 0.81 mmol) in ethanol (15 mL) as described in example Z-1 to provide its corresponding sodium salt (384 mg, 99%) as a white solid. $^1$H NMR (DMSO-d$_6$) δ 10.82 (m, 1H), 7.80 (m, 1H), 7.33 (m, 1H), 7.18 (m, 1H), 7.00 (m, 1H), 5.14 (m, 1H), 4.47 (d, J=5.6 Hz, 2H), 4.31 (m, 1H), 4.18 (m, 1H), 3.96 (m, 1H), 3.84 (m, 1H), 3.71 (m, 1H), 3.40 (m, 1H), 1.88 (m, 1H), 1.36 (m, 1H), 1.04 (m, 1H), 0.85 (t, J=7.2 Hz, 3H), 0.80 (d, J=6.8 Hz, 3H); ES$^+$ MS: 448 (M+1).

Example Z-9

(3S,11aR)—N-[(2,4-Difluorophenyl)methyl]-6-hydroxy-3-methyl-5,7-dioxo-2,3,5,7,11,11a-hexahydro[1,3]oxazolo[3,2-a]pyrido[1,2-d]pyrazine-8-carboxamide sodium salt

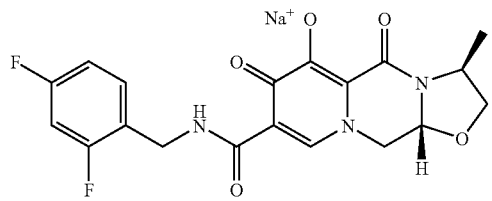

The title compound was made in two steps using a similar process to that described in example Z-1. 16a (510 mg, 1.08 mmol) and (2S)-2-amino-1-propanol (0.17 mL, 2.17 mmol) were reacted in 1,2-dichloroethane (20 mL) with acetic acid to give (3S,11aR)—N-[(2,4-difluorophenyl)methyl]-3-methyl-5,7-dioxo-6-[(phenylmethyl)oxy]-2,3,5,7,11,11a-hexahydro[1,3]oxazolo[3,2-a]pyrido[1,2-d]pyrazine-8-carboxamide (500 mg, 93%). This material was hydrogenated in a second step as described in example Z-1 to give (3S,11aR)—N-[(2,4-Difluorophenyl)methyl]-6-hydroxy-3-methyl-5,7-dioxo-2,3,5,7,11,11a-hexahydro[1,3]oxazolo[3,2-a]pyrido[1,2-d]pyrazine-8-carboxamide (386 mg, 94%) as a tinted white solid. $^1$H NMR (CDCl$_3$) δ 11.46 (m, 1H), 10.28 (m, 1H), 8.32 (s, 1H), 7.35 (m, 1H), 6.80 (m, 2H), 5.30 (dd, J=10.0, 4.0 Hz, 1H), 4.63 (m, 2H), 4.48-4.37 (m, 3H), 3.91 (dd, J=12.0, 10.0 Hz, 1H), 3.73 (m, 1H), 1.48 (d, J=6.0 Hz, 3H); ES$^+$ MS: 406 (M+1). This material (385 mg, 0.95 mmol) was treated with sodium hydroxide (0.95 mL, 1.0 M, 0.95 mmol) in ethanol (15 mL) as described in example Z-1 to provide its corresponding sodium salt (381 mg, 94%) as a white solid. $^1$H NMR (DMSO-d$_6$) δ 10.66 (m, 1H), 7.93 (s, 1H), 7.33 (m, 1H), 7.20 (m, 1H), 7.01 (m, 1H), 5.19 (m, 1H), 4.59 (m, 1H), 4.48 (m, 2H), 4.22 (m, 2H), 3.75 (m, 1 H), 3.57 (m, 1H), 1.24 (d, J=5.6 Hz, 3H).

Example Z-10

(3S,11aR)—N-[(4-Fluorophenyl)methyl]-6-hydroxy-3-methyl-5,7-dioxo-2,3,5,7,11,11a-hexahydro[1,3]oxazolo[3,2-a]pyrido[1,2-d]pyrazine-8-carboxamide

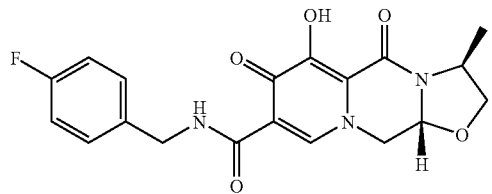

The title compound was made in two steps using a similar process to that described in example Z-2. 16 (100 mg, 0.22 mmol) and (2S)-2-amino-1-propanol (0.10 mL, 1.28 mmol) were reacted in dichloromethane (2 mL) with acetic acid to give (3S,11aR)—N-[(4-fluorophenyl)methyl]-3-methyl-5,7-dioxo-6-[(phenylmethyl)oxy]-2,3,5,7,11,11a-hexahydro[1,3]oxazolo[3,2-a]pyrido[1,2-d]pyrazine-8-carboxamide (100 mg, 95%). This material was hydrogenated in a second step as described in example Z-2 to give (3S,11aR)—N-[(4-Fluorophenyl)methyl]-6-hydroxy-3-methyl-5,7-dioxo-2,3,5,7,11,11a-hexahydro[1,3]oxazolo[3,2-a]pyrido[1,2-d]pyrazine-8-carboxamide (80 mg, 99%) as a white solid. $^1$H NMR (CDCl$_3$) δ 11.43 (br, 1H), 10.28 (br, 1H), 8.35 (s, 1H), 7.28 (m, 2H), 6.97 (m, 2H), 5.29 (m, 1H), 4.55/4.38 (m, 5H), 3.89 (apparent t, J=10.8 Hz, 1H), 3.70 (m, 1H), 1.45 (d, J=5.6 Hz, 3H); ES$^-$ MS: 386 (M−1).

Example Z-11

(3S,11aR)—N-[(2,4-Difluorophenyl)methyl]-3-(1,1-dimethylethyl)-6-hydroxy-5,7-dioxo-2,3,5,7,11,11a-hexahydro[1,3]oxazolo[3,2-a]pyrido[1,2-d]pyrazine-8-carboxamide

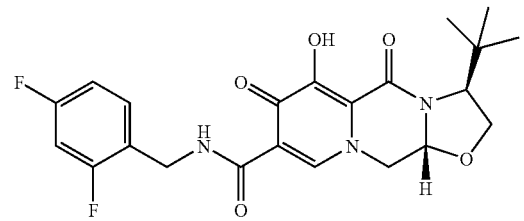

The title compound was made in two steps using a similar process to that described in example Z-2. 16a (41 mg, 0.09 mmol) and freebased L-tert-leucinol (59 mg, 0.50 mmol) were reacted in dichloromethane (2 mL) with acetic acid to give (3S,11aR)—N-[(2,4-difluorophenyl)methyl]-3-(1,1-dimethylethyl)-5,7-dioxo-6-[(phenylmethyl)oxy]-2,3,5,7,11,11a-hexahydro[1,3]oxazolo[3,2-a]pyrido[1,2-d]pyrazine-8-carboxamide (40 mg, 86%). This material was hydrogenated in a second step as described in example Z-2 to give (3S,11aR)—N-[(2,4-Difluorophenyl)methyl]-3-(1,1-dimethylethyl)-6-hydroxy-5,7-dioxo-2,3,5,7,11,11a-hexahydro[1,3]oxazolo[3,2-a]pyrido[1,2-d]pyrazine-8-carboxamide (33 mg, 99%) as a tinted white solid. $^1$H NMR (CDCl$_3$) δ 10.29 (s, 1H), 8.37 (s, 1H), 7.34 (m, 1H), 6.79 (m, 2H), 5.43 (m, 1H), 4.62 (m, 2H), 4.36 (m, 2H), 4.21 (m, 1H), 3.99 (, 1H), 3.81 (m, 1H), 1.03 (s, 9H); ES$^+$ MS: 448 (M+1).

Example Z-12

(3S,11aR)-3-(1,1-Dimethylethyl)-N-[(4-fluorophenyl)methyl]-6-hydroxy-5,7-dioxo-2,3,5,7,11,11a-hexahydro[1,3]oxazolo[3,2-a]pyrido[1,2-d]pyrazine-8-carboxamide

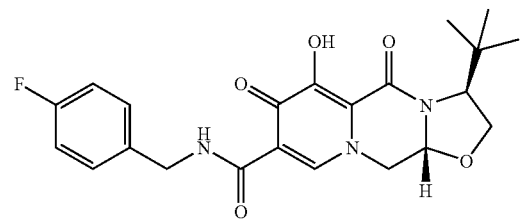

The title compound was made in two steps using a similar process to that described in example Z-2. 16 (41 mg, 0.09 mmol) and freebased L-tert-leucinol (59 mg, 0.50 mmol)

were reacted in dichloromethane (2 mL) with acetic acid to give (3S,11aR)-3-(1,1-dimethylethyl)-N-[(4-fluorophenyl)methyl]-5,7-dioxo-6-[(phenylmethyl)oxy]-2,3,5,7,11,11a-hexahydro[1,3]oxazolo[3,2-a]pyrido[1,2-d]pyrazine-8-carboxamide (40 mg, 85%). This material was hydrogenated in a second step as described in example Z-2 to give (3S,11aR)-3-(1,1-Dimethylethyl)-N-[(4-fluorophenyl)methyl]-6-hydroxy-5,7-dioxo-2,3,5,7,11,11a-hexahydro[1,3]oxazolo[3,2-a]pyrido[1,2-d]pyrazine-8-carboxamide (32 mg, 97%) as a tinted white solid. $^1$H NMR (CDCl$_3$) δ 11.15 (br, 1H), 10.32 (s, 1H), 8.38 (s, 1H), 7.29 (m, 2H), 6.98 (m, 2H), 5.43 (m, 1H), 4.58 (m, 2H), 4.36 (m, 2H), 4.21 (m, 1H), 3.99 (m, 1H), 3.79 (m, 1H), 1.02 (s, 9H); ES$^+$ MS: 430 (M+1).

Example Z-13

(3S,11aR)—N-[(2,4-Difluorophenyl)methyl]-6-hydroxy-5,7-dioxo-3-phenyl-2,3,5,7,11,11a-hexahydro[1,3]oxazolo[3,2-a]pyrido[1,2-d]pyrazine-8-carboxamide

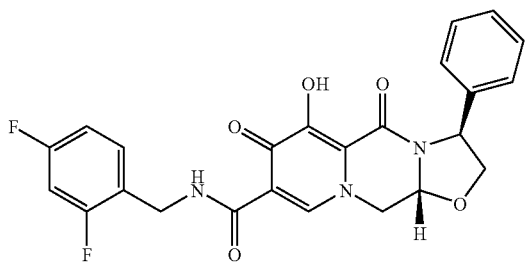

The title compound was made in two steps using a similar process to that described in example Z-2. 16a (33 mg, 0.07 mmol) and L-phenylglycinol (19 mg, 0.14 mmol) were reacted in dichloromethane (2 mL) with acetic acid to give (3S,11aR)—N-[(4-fluorophenyl)methyl]-5,7-dioxo-3-phenyl-6-[(phenylmethyl)oxy]-2,3,5,7,11,11a-hexahydro[1,3]oxazolo[3,2-a]pyrido[1,2-d]pyrazine-8-carboxamide (37 mg, 95%). This material was hydrogenated in a second step as described in example Z-2 to give (3S,11aR)—N-[(2,4-Difluorophenyl)methyl]-6-hydroxy-5,7-dioxo-3-phenyl-2,3,5,7,11,11a-hexahydro[1,3]oxazolo[3,2-a]pyrido[1,2-d]pyrazine-8-carboxamide (33 mg, 99%) as a tinted white solid. $^1$H NMR (CDCl$_3$) δ 11.23 (br, 1H), 10.27 (s, 1H), 8.39 (s, 1H), 7.43-7.32 (m, 6H), 6.80 (m, 2H), 5.58 (d, J=6.8 Hz, 1H), 5.37 (apparent t, J=6.8 Hz, 1H), 4.67-4.62 (m, 3H), 4.54 (d, J=10.4 Hz, 1H), 4.11 (m, 1H), 4.01 (m, 1H); ES$^+$ MS: 468 (M+1).

Example Z-14

(3S,11aR)—N-[(2,4-Difluorophenyl)methyl]-6-hydroxy-3-(hydroxymethyl)-5,7-dioxo-2,3,5,7,11,11a-hexahydro[1,3]oxazolo[3,2-a]pyrido[1,2-d]pyrazine-8-carboxamide

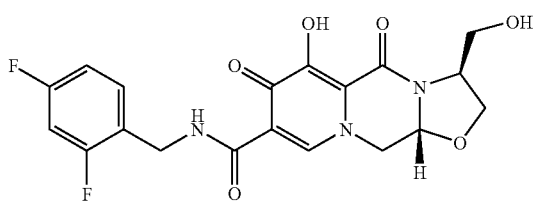

The title compound was made in two steps using a similar process to that described in example Z-2. 16a (50 mg, 0.10 mmol) and (2R)-2-amino-3-[(phenylmethyl)oxy]-1-propanol (0.1 mL) were reacted in dichloromethane (2 mL) with acetic acid to give (3S,11aR)—N-[2,4-difluorophenyl)methyl]-5,7-dioxo-6-[(phenylmethyl)oxy]-3-{[(phenyl methyl)oxy]methyl}-2,3,5,7,11,11a-hexahydro[1,3]oxazolo[3,2-a]pyrido[1,2-d]pyrazine-8-carboxamide (61 mg, 99%). This material was hydrogenated in a second step as described in example Z-2 to give (3S,11aR)—N-[(2,4-Difluorophenyl)methyl]-6-hydroxy-3-(hydroxymethyl)-5,7-dioxo-2,3,5,7,11,11a-hexahydro[1,3]oxazolo[3,2-a]pyrido[1,2-d]pyrazine-8-carboxamide (37 mg, 87%) as a tinted white solid. $^1$H NMR (CDCl$_3$/CD$_3$OD) δ 8.23 (s, 1H), 7.32 (m, 1H), 6.79 (m, 2H), 5.31 (d, J=7.6 Hz, 1H), 4.56 (s, 2H), 4.42-4.36 (m, 3H), 4.17-4.11 (m, 2H), 3.85 (m, 1H), 3.62 (d, J=11.2 Hz, 1H).

Example Z-15

(2S,3R)—N-[(2,4-Difluorophenyl)methyl]-6-hydroxy-3-methyl-5,7-dioxo-2-phenyl-2,3,5,7,11,11a-hexahydro[1,3]oxazolo[3,2-a]pyrido[1,2-d]pyrazine-8-carboxamide

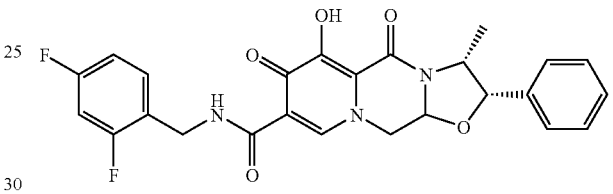

The title compound was made in two steps using a similar process to that described in example Z-2. 16a (25 mg, 0.05 mmol) and (1S,2R)-(+)-norephedrine (0.1 mL) were reacted in dichloromethane (2 mL) with acetic acid to give (2S,3R)—N-[(2,4-difluorophenyl)methyl]-3-methyl-5,7-dioxo-2-phenyl-6-[(phenylmethyl)oxy]-2,3,5,7,11,11a-hexahydro[1,3]oxazolo[3,2-a]pyrido[1,2-d]pyrazine-8-carboxamide (30 mg, 99%). This material was hydrogenated in a second step as described in example Z-2 to give (2S,3R)—N-[(2,4-difluorophenyl)methyl]-6-hydroxy-3-methyl-5,7-dioxo-2-phenyl-2,3,5,7,11,11a-hexahydro[1,3]oxazolo[3,2-a]pyrido[1,2-d]pyrazine-8-carboxamide (25 mg, 91%) as a white solid. This material is a single diastereomer (>6:1 diastereomeric ratio but unconfirmed relative stereochemistry at the aminal center). $^1$H NMR (CDCl$_3$/CD$_3$OD) δ 10.28 (m, 1H), 8.38 (s, 1H), 7.10-7.30 (m, 6H), 6.78 (m, 2H), 5.70 (d, J=7.6 Hz, 1H), 5.36 (d, J=5.2 Hz, 1H), 4.82 (m, 1H), 4.61 (m, 2H), 4.47 (d, J=10.4 Hz, 1H), 4.00 (apparent t, J=10.4 Hz, 1H), 0.94 (d, J=6.4 Hz, 3H); ES$^+$ MS: 482 (M+1).

Example Z-16

(3R,11aS)—N-[(2,4-Difluorophenyl)methyl]-6-hydroxy-5,7-dioxo-3-(phenylmethyl)-2,3,5,7,11,11a-hexahydro[1,3]oxazolo[3,2-a]pyrido[1,2-d]pyrazine-8-carboxamide

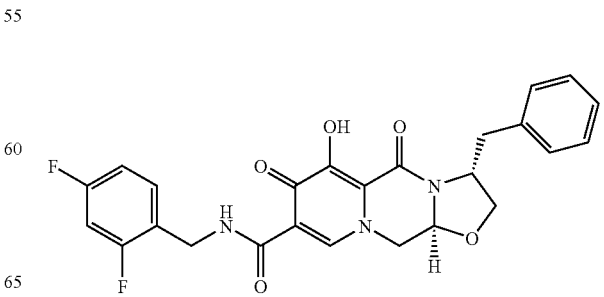

The title compound was made in two steps using a similar process to that described in example Z-2. 16a (34 mg, 0.07 mmol) and (2R)-2-amino-3-phenyl-1-propanol (D-phenylalaninol) (50 mg, 0.33 mmol) were reacted in dichloromethane (2 mL) with acetic acid to give (3R,11aS)—N-[(2,4-difluorophenyl)methyl]-5,7-dioxo-3-(phenylmethyl)-6-[(phenylmethyl)oxy]-2,3,5,7,11,11a-hexahydro[1,3]oxazolo[3,2-a]pyrido[1,2-d]pyrazine-8-carboxamide (29 mg, 70%). This material was hydrogenated in a second step as described in example Z-2 to give (3R,11aS)—N-[(2,4-Difluorophenyl)methyl]-6-hydroxy-5,7-dioxo-3-(phenylmethyl)-2,3,5,7,11,11a-hexahydro[1,3]oxazolo[3,2-a]pyrido[1,2-d]pyrazine-8-carboxamide (24 mg, 98%) as a white solid. $^1$H NMR (CDCl$_3$) δ 11.46 (br, 1H), 10.27 (m, 1H), 8.33 (m, 1H), 7.32-7.16 (m, 6H), 6.78 (m, 2H), 5.02 (m, 1H), 4.61 (m, 3H), 4.39 (m, 1H), 4.22 (m, 1H), 3.95 (m, 1H), 3.87 (m, 1H), 3.36 (m, 1H), 2.97 (dd, J=13.2 8.8 Hz, 1H); ES$^+$ MS: 482 (M+1).

Example Z-17

(3R,11aS)—N-[(2,4-Difluorophenyl)methyl]-6-hydroxy-3-(2-methylpropyl)-5,7-dioxo-2,3,5,7,11,11a-hexahydro[1,3]oxazolo[3,2-a]pyrido[1,2-d]pyrazine-8-carboxamide

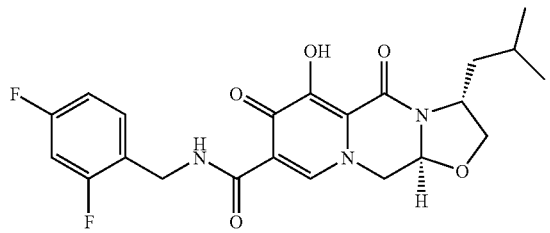

The title compound was made in two steps using a similar process to that described in example Z-2. 16a (32 mg, 0.07 mmol) and (2R)-2-amino-4-methyl-1-pentanol (0.1 mL) were reacted in dichloromethane (2 mL) with acetic acid to give (3R,11aS)—N-[(2,4-difluorophenyl)methyl]-3-(2-methylpropyl)-5,7-dioxo-6-[(phenylmethyl)oxy]-2,3,5,7,11,11a-hexahydro[1,3]oxazolo[3,2-a]pyrido[1,2-d]pyrazine-8-carboxamide (43 mg, 99%). This material was hydrogenated in a second step as described in example Z-2 to give (3R,11aS)—N-[(2,4-Difluorophenyl)methyl]-6-hydroxy-3-(2-methylpropyl)-5,7-dioxo-2,3,5,7,11,11a-hexahydro[1,3]oxazolo[3,2-a]pyrido[1,2-d]pyrazine-8-carboxamide (32 mg, 90%) as a white solid. $^1$H NMR (CDCl$_3$) δ 11.47 (br, 1H), 10.29 (m, 1H), 8.35 (s, 1H), 7.39 (m, 1H), 6.80 (m, 2H), 5.31 (m, 1H), 4.62 (m, 2H), 4.44 (m, 2H), 4.37 (m, 1H), 3.88 (m, 1H), 3.84 (dd, J=8.0, 5.6 Hz, 1H), 2.04 (m, 1H), L$^{62}$ (m, 1H), 1.41 (m, 1H), 1.00 (d, J=5.6 Hz, 3H), 0.99 (d, J=6.0 Hz, 3H); ES$^+$ MS: 448 (M+1).

Example Z-18

(5aR,14aR)—N-[(2,4-Difluorophenyl)methyl]-11-hydroxy-10,12-dioxo-1,2,3,4,5a,6,10,12,14,14a-decahydropyrido[1,2-a]pyrido[1',2':3,4]imidazo[1,2-d]pyrazine-9-carboxamide

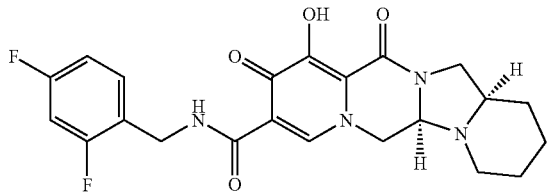

a) 1,1-Dimethylethyl (2R)-2-(aminocarbonyl)-1-piperidinecarboxylate. To a cold (0° C.) solution of (2R)-1-{[(1,1-dimethylethyl)oxy]carbonyl}-2-piperidinecarboxylic acid (1.0 g, 4.36 mmol) in THF (20 mL) was added triethylamine (0.60 mL, 4.36 mmol) followed by slow addition of methyl chloroformate (0.34 mL, 4.36 mmol). After a few minutes a suspension had formed. To this mixture was added concentrated NH$_4$OH (1.5 mL) and the solution was allowed to warm to rt as the bath warmed and stirred for a total of 4 h. The mixture was concentrated in vacuo and the residue was taken up in EtOAc. The organic layer was washed with citric acid, sodium bicarbonate and then brine, dried over Na$_2$SO$_4$. Filtration and concentration gave 1,1-dimethylethyl (2R)-2-(aminocarbonyl)-1-piperidinecarboxylate (1.0 g, 99%). $^1$H NMR (CDCl$_3$) δ 6.03 (br, 1H), 5.45 (br, 1H), 4.77 (br, 1H), 4.06 (br, 1H), 2.82 (m, 1H), 2.29 (m, 1H), 1.67-1.43 (m, 13H).

b) 1,1-Dimethylethyl (2R)-2-cyano-1-piperidinecarboxylate. To a cold (0° C.) solution of 1,1-dimethylethyl (2R)-2-(aminocarbonyl)-1-piperidinecarboxylate (269 mg, 1.17 mmol) in THF (10 mL) was added triethylamine (0.33 mL, 2.34 mmol) and then trifluoroacetic anhydride (0.17 mL, 1.17 mmol). The mixture was stirred at 0° C. for 1 h and concentrated in vacuo. The residue was taken up in EtOAc and washed successively with sodium bicarbonate, 0.5 N HCl and brine. The organics were dried over Na$_2$SO$_4$, filtered and concentrated to give 1,1-dimethylethyl (2R)-2-cyano-1-piperidinecarboxylate (255 mg, 99%) as a crystalline solid upon standing. $^1$H NMR (CDCl$_3$) δ 5.23 (br, 1H), 4.05 (br, 1H), 2.93 (br, 1H), 1.93-1.39 (m, 6H), 1.46 (s, 9H).

c) 1,1-Dimethylethyl (2R)-2-(aminomethyl)-1-piperidinecarboxylate. An ammonia saturated ethanol solution of 1,1-dimethylethyl (2R)-2-cyano-1-piperidinecarboxylate (255 mg, 1.19 mmol) was reduced with Raney-Ni in a similar manner to that described in example Z-3 to give after filtration through a short plug of silica, 1,1-dimethylethyl (2R)-2-(aminomethyl)-1-piperidinecarboxylate (236 mg, 91%), as an oil. $^1$H NMR (CDCl$_3$/CD$_3$OD) δ 4.15 (br, 1H), 3.97 (m, 1 h), 2.96 (m, 1H), 2.75-2.69 (m, 2H), 2.23-2.08 (m, 3H), 1.59-1.55 (m, 3H), 1.43 (s, 9H).

d) [(2R)-2-Piperidinylmethyl]amine bis HCl salt. A solution of 1,1-dimethylethyl (2R)-2-(aminomethyl)-1-piperidinecarboxylate (236 mg, 1.08 mmol) in THF (10 mL) was treated with 4 N HCl (3 mL) as described in example Z-3 to give the bis HCl salt of [(2R)-2-Piperidinylmethyl]amine. $^1$H NMR (DMSO-d$_6$) δ 9.67 (br, 1H), 9.48 (br, 1H), 8.48 (br, 2H), 3.70 (br, 2H), 3.20 (m, 1H), 3.04 (m, 1H), 2.86 (m, 1H), 1.89-1.41 (m, 6H), e)

(5aR,14aR)—N-[(2,4-Difluorophenyl)methyl]-11-hydroxy-10,12-dioxo-1,2,3,4,5a,6,10,12,14,14a-decahydropyrido[1,2-a]pyrido[1',2':3,4]imidazo[1,2-d]pyrazine-9-carboxamide. The title compound was made in two steps using a similar process to that described in example Z-2. 16a (50 mg, 0.11 mmol) and [(2R)-2-Piperidinylmethyl]amine (150 mg, 1.31 mmol) (free based using carbonate resin as described in example Z-3) were reacted in dichloromethane (2 mL) with acetic acid to give (5aR,14aR)—N-[(2,4-difluorophenyl)methyl]-10,12-dioxo-11-[(phenylmethyl)oxy]-1,2,3,4,5a,6,10,12,14,14a-decahydropyrido[1,2-a]pyrido[1',2':3,4]imidazo[1,2-d]pyrazine-9-carboxamide (50 mg, 88%). This material was hydrogenated in a second step as described in example Z-2 to give (5aR,14aR)—N-[(2,4-difluorophenyl)methyl]-11-hydroxy-10,12-dioxo-1,2,3,4,5a,6,10,12,14,14a-decahydropyrido[1,2-a]pyrido[1',2':3,4]imidazo[1,2-d]pyrazine-9-carboxamide (11 mg, 44%) as a white solid. $^1$H NMR (CD$_3$OD/CDCl$_3$) δ 10.46 (m, 1H), 8.32 (s, 1H), 7.31 (m, 1H), 6.80 (m, 2H), 4.64-4.52 (m, 3H), 4.14 (dd, J=10.4, 2.8 Hz, 1H), 3.91-3.82 (m, 2H), 3.19 (apparent t, J=10.8 Hz, 1H), 3.08 (d, J=10.4 Hz, 1H), 2.50 (m, 1H), 2.27 (m, 1H), 1.99-1.30 m, 6H); ES$^+$ MS: 445 (M+1).

Example Z-19

(2S,3S)—N-[(2,4-Difluorophenyl)methyl]-6-hydroxy-3-[(methyloxy)methyl]-5,7-dioxo-2-phenyl-2,3,5,7,11,11a-hexahydro[1,3]oxazolo[3,2-a]pyrido[1,2-d]pyrazine-8-carboxamide

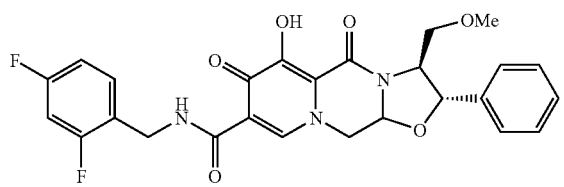

The title compound was made in two steps using a similar process to that described in example Z-2. 16a (36 mg, 0.07 mmol) and (2R)-2-amino-4-methyl-1-pentanol (0.1 mL) were reacted in dichloromethane (2 mL) with acetic acid to give (2S,3S)—N-[(2,4-difluorophenyl)methyl]-3-[(methyloxy)methyl]-5,7-dioxo-2-phenyl-6-[(phenylmethyl)oxy]-2,3,5,7,11,11a-hexahydro[1,3]oxazolo[3,2-a]pyrido[1,2-d]pyrazine-8-carboxamide. This material was hydrogenated in a second step as described in example Z-2 to give (2S,3S)—N-[(2,4-Difluorophenyl)methyl]-6-hydroxy-3-[(methyloxy)methyl]-5,7-dioxo-2-phenyl-2,3,5,7,11,11a-hexahydro[1,3]oxazolo[3,2-a]pyrido[1,2-d]pyrazine-8-carboxamide (25 mg, 64% for 2 steps) as a white solid. This material is a single diastereomer (>6:1 diastereomeric ratio but unconfirmed relative stereochemistry at the aminal center). $^1$H NMR (CDCl$_3$) δ 11.48 (br, 1H), 10.30 (m, 1H), 8.39 (s, 1H), 7.39-7.24 (m, 6H), 6.78 (m, 2H), 5.46 (dd, J=10.0, 3.6 Hz, 1H), 5.33 (d, J=7.2 Hz, 1H), 4.63 (m, 2H), 4.54 (dd, J=12.4, 4.0 Hz, 1H), 4.19 (m, 1H), 4.12 (dd, J=10.4, 3.2 Hz, 1H), 4.06 (m, 1H), 3.55 (dd, J=10.4, 1.6 Hz, 1H), 3.40 (s, 3H); ES$^+$ MS: 512 (M+1).

Example Z-20

(3S,11aR)-3-(Cyclohexylmethyl)-N-[(2,4-difluorophenyl)methyl]-6-hydroxy-5,7-dioxo-2,3,5,7,11,11a-hexahydro[1,3]oxazolo[3,2-a]pyrido[1,2-d]pyrazine-8-carboxamide

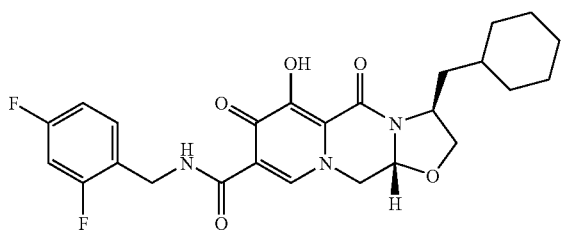

The title compound was made in two steps using a similar process to that described in example Z-2. 16a (36 mg, 0.08 mmol) and (2S)-2-amino-3-cyclohexyl-1-propanol (30 mg, 0.19 mmol) were reacted in dichloromethane (2 mL) with acetic acid to give (3S,11aR)-3-(cyclohexylmethyl)-N-[(2,4-difluorophenyl)methyl]-5,7-dioxo-6-[(phenylmethyl)oxy]-2,3,5,7,11,11a-hexahydro[1,3]oxazolo[3,2-a]pyrido[1,2-d]pyrazine-8-carboxamide (27 mg, 61%). This material was hydrogenated in a second step as described in example Z-2 to give (3S,11aR)-3-(cyclohexylmethyl)-N-[(2,4-difluorophenyl)methyl]-6-hydroxy-5,7-dioxo-2,3,5,7,11,11a-hexahydro[1,3]oxazolo[3,2-a]pyrido[1,2-d]pyrazine-8-carboxamide (25 mg, 99%) as a white solid. $^1$H NMR (CDCl$_3$) δ 11.48 (br, 1H), 10.28 (s, 1H), 8.33 (s, 1H), 7.33 (m, 1H), 6.78 (m, 2H), 5.29 (m, 1H), 4.61 (m, 2H), 4.47-4.33 (m, 3H), 3.87-3.81 (m, 2H), 2.05 (m, 1H), 1.75-1.64 (m, 6H), 1.39 (m, 1H), 1.25-1.14 (m, 3H), 1.02-0.97 (m, 2H); ES$^+$ MS: 488 (M+1).

Example Z-21

(3S,11aR)—N-[(2,4-Difluorophenyl)methyl]-6-hydroxy-3-(1-methylethyl)-5,7-dioxo-2,3,5,7,11,11a-hexahydro[1,3]oxazolo[3,2-a]pyrido[1,2-d]pyrazine-8-carboxamide

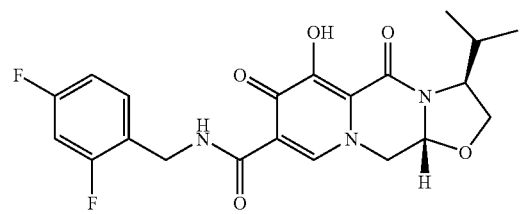

The title compound was made in two steps using a similar process to that described in example Z-1. 16a (42 mg, 0.09 mmol) and (2S)-2-amino-3-methyl-1-butanol (0.1 mL) were reacted in 1,2-dichloroethane (8 mL) with acetic acid to give (3R,11aS)—N-[(2,4-difluorophenyl)methyl]-3-(1-methylethyl)-5,7-dioxo-6-[(phenylmethyl)oxy]-2,3,5,7,11,11a-hexahydro[1,3]oxazolo[3,2-a]pyrido[1,2-d]pyrazine-8-carboxamide (40 mg, 86%). This material was hydrogenated in a second step as described in example Z-1 to give (3S,11aR)—N-[(2,4-difluorophenyl)methyl]-6-hydroxy-3-(1-methylethyl)-5,7-dioxo-2,3,5,7,11,11a-hexahydro[1,3]oxazolo[3,2-a]pyrido[1,2-d]pyrazine-8-carboxamide (34 mg, 99%) as a white solid. $^1$H NMR (CDCl$_3$) δ 10.29 (br, 1H), 8.36 (s, 1H), 7.33 (m, 1H), 6.79 (m, 2H), 5.29 (d, J=6.4 Hz, 1H), 4.61 (m, 2H), 4.44 (d, J=9.6 Hz, 1H), 4.34 (m, 1H), 4.17 (m, 1H), 4.02 (dd, J=8.4, 5.2 Hz, 1H), 3.86 (m, 1H), 2.37 (m, 1H), 0.97 (m, 6H); ES$^+$ MS: 434 (M+1).

Example Z-22

(5aR,14aS)—N-[(2,4-Difluorophenyl)methyl]-12-hydroxy-11,13-dioxo-5a,6a,7,11,13,14a-hexahydro-5H-indeno[1',2':3,4][1,3]oxazolo[3,2-a]pyrido[1,2-d]pyrazine-10-carboxamide

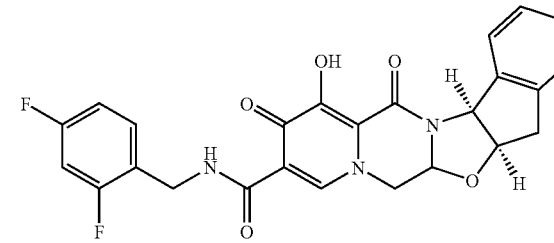

The title compound was made in two steps using a similar process to that described in example Z-1. 16a (42 mg, 0.09 mmol) and (1S,2R)-1-amino-2,3-dihydro-1H-inden-2-ol (100 mg, 0.67 mmol) were reacted in 1,2-dichloroethane (5 mL) with acetic acid to give (5aR,14aS)—N-[(2,4-difluorophenyl)methyl]-11,13-dioxo-12-[(phenylmethyl)oxy]-5a,6a,7,11,13,14a-hexahydro-5H-indeno[1',2':4,5][1,3]oxazolo[3,2-a]pyrido[1,2-d]pyrazine-10-carboxamide (55 mg, 99%). This material was hydrogenated in a second step as described in example Z-1 to give (5aR,14aR)—N-[(2,4-difluorophenyl)methyl]-12-hydroxy-11,13-dioxo-5a,6a,7,11,13,14a-hexahydro-5H-indeno[1',2':3,4][1,3]oxazolo[3,2-a]pyrido[1,2-d]pyrazine-10-carboxamide (45 mg, 97%) as a white solid. $^1$H NMR (CDCl$_3$) δ 10.28 (m, 1H), 8.33 (s, 1H), 7.69 (d, J=7.2 Hz, 1H), 7.34-7.19 (m, 4H), 6.78 (m, 2H), 5.96 (d, J=6.0 Hz, 1H), 5.32 (m, 1H), 5.22 (m, 1H), 4.60 (m, 2H), 4.45 (d, J=9.2 Hz, 1H), 3.96 (apparent t, J=10.8 Hz, 1H), 3.40 (dd, J=18.0, 6.8 Hz, 1H), 3.24 (d, J=17.6 Hz, 1H); ES$^+$ MS: 480 (M+1).

Example Z-23 & Z-24

(2S,3R,11aS)—N-[(2,4-Difluorophenyl)methyl]-6-hydroxy-5,7-dioxo-2,3-diphenyl-2,3,5,7,11,11a-hexahydro[1,3]oxazolo[3,2-a]pyrido[1,2-d]pyrazine-8-carboxamide &

(2S,3R,11aR)—N-[(2,4-difluorophenyl)methyl]-6-hydroxy-5,7-dioxo-2,3-diphenyl-2,3,5,7,11,11a-hexahydro[1,3]oxazolo[3,2-a]pyrido[1,2-d]pyrazine-8-carboxamide

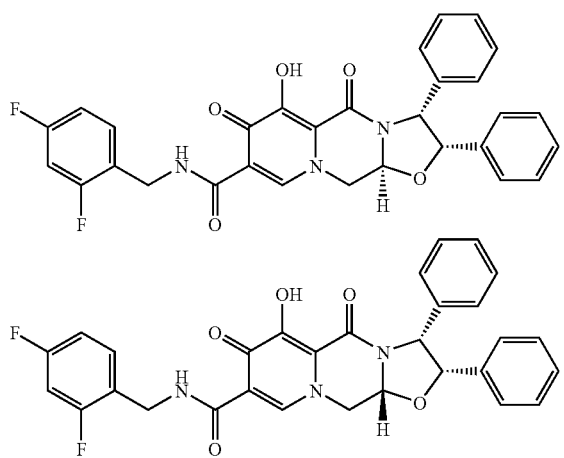

The title compounds were made in two steps using a similar process to that described in example Z-1. 16a (40 mg, 0.09 mmol) and (1S,2R)-amino-1,2-diphenylethanol (50 mg, 0.23 mmol) were reacted in 1,2-dichloroethane (5 mL) with acetic acid to give (2S,3R,11aS)—N-[(2,4-difluorophenyl)methyl]-5,7-dioxo-2,3-diphenyl-6-[(phenylmethyl) oxy]-2,3,5,7,11,11a-hexahydro[1,3]oxazolo[3,2-a]pyrido[1,2-d]pyrazine-8-carboxamide (34 mg, 63%) and (2S,3R,11aR)—N-[(2,4-difluorophenyl)methyl]-5,7-dioxo-2,3-diphenyl-6-[(phenylmethyl)oxy]-2,3,5,7,11,11a-hexahydro[1,3]oxazolo[3,2-a]pyrido[1,2-d]pyrazine-8-carboxamide (13 mg, 24%). These materials were hydrogenated in a second step as described in example Z-1 to give (2S,3R,11aS)—N-[(2,4-Difluorophenyl)methyl]-6-hydroxy-5,7-dioxo-2,3-diphenyl-2,3,5,7,11,11a-hexahydro[1,3]oxazolo[3,2-a]pyrido[1,2-d]pyrazine-8-carboxamide (example Z-23, 29 mg, 99%) as a white solid and (2S,3R,11aR)—N-[(2,4-difluorophenyl)methyl]-6-hydroxy-5,7-dioxo-2,3-diphenyl-2,3,5,7,11,11a-hexahydro[1,3]oxazolo[3,2-a]pyrido[1,2-d]pyrazine-8-carboxamide (example Z-24, 10 mg, 89%) as a white solid respectively. For example Z-23: $^1$H NMR (DMSO-d$_6$) δ 10.29 (t, J=5.6 Hz, 1H), 8.65 (s, 1H), 7.38 (m, 1H), 7.22 (m, 1H), 7.11-6.95 (m, 11H), 6.16 (dd, J=10.4, 3.6 Hz, 1H), 5.71 (m, 2H), 4.90 (m, 1H), 4.54 (m, 2H), 4.38 (t, J=11.2 Hz, 1H); ES$^+$ MS: 544 (M+1). For example Z-24: $^1$H NMR (CDCl$_3$) δ 11.64 (br, 1H), 10.30 (s, 1H), 8.45 (s, 1H), 7.34 (m, 1H), 7.01-6.90 (m, 10H), 6.80 (m, 2H), 5.56 (m, 2H), 5.42 (d, J=6.4 Hz, 1H), 4.73 (m, 1H), 4.63 (m, 2H), 4.49 (m, 1H); ES$^+$ MS: 544 (M+1).

Example Z-25

(3R,11aS)—N-[(2,4-Difluorophenyl)methyl]-6-hydroxy-3-(1-methylethyl)-5,7-dioxo-2,3,5,7,11,11a-hexahydro[1,3]oxazolo[3,2-a]pyrido[1,2-d]pyrazine-8-carboxamide

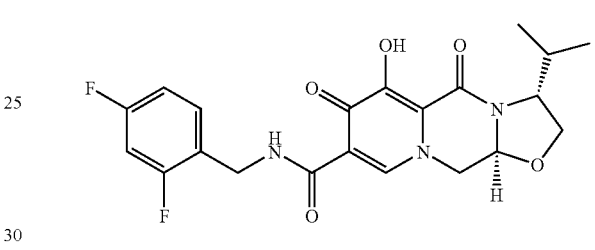

The title compound was made in two steps using a similar process to that described in example Z-1. 16a (40 mg, 0.09 mmol) and (2R)-2-amino-3-methyl-1-butanol (0.1 mL) were reacted in 1,2-dichloroethane (8 mL) with acetic acid to give (3R,11aS)—N-[(2,4-difluorophenyl)methyl]-3-(1-methylethyl)-5,7-dioxo-6-[(phenylmethyl)oxy]-2,3,5,7,11,11a-hexahydro[1,3]oxazolo[3,2-a]pyrido[1,2-d]pyrazine-8-carboxamide (41 mg, 92%). This material was hydrogenated in a second step as described in example Z-1 to give (3R,11aS)—N-[(2,4-Difluorophenyl)methyl]-6-hydroxy-3-(1-methylethyl)-5,7-dioxo-2,3,5,7,11,11a-hexahydro[1,3]oxazolo[3,2-a]pyrido[1,2-d]pyrazine-8-carboxamide (32 mg, 94%) as a white solid. $^1$H NMR (CDCl$_3$) δ 11.42 (br, 1H), 10.27 (br, 1H), 8.34 (s, 1H), 7.31 (m, 1H), 6.78 (m, 2H), 5.28 (d, J=6.0 Hz, 1H), 4.60 (m, 2H), 4.42 (m, 1H), 4.33 (m, 1H), 4.16 (m, 1H), 4.01 (dd, J=8.8, 5.2 Hz, 1H), 3.85 (m, 1H), 2.37 (m, 1H), 0.97 (d, J=6.8 Hz, 3H), 0.95 (d, J=6.4 Hz, 3H); ES$^+$ MS: 434 (M+1).

Example Z-26

(3S,11aR)—N-[(2,4-Difluorophenyl)methyl]-6-hydroxy-3-[2-(methylthio)ethyl]-5,7-dioxo-2,3,5,7,11,11a-hexahydro[1,3]oxazolo[3,2-a]pyrido[1,2-d]pyrazine-8-carboxamide

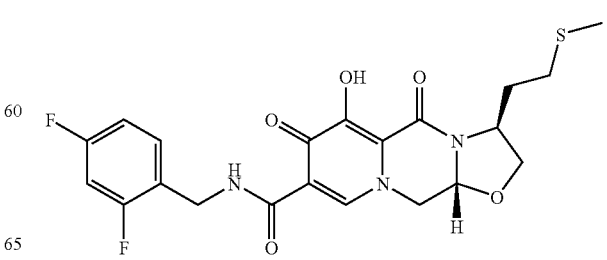

The title compound was made in two steps using a similar process to that described in example Z-1. 16a (43 mg, 0.09 mmol) and (2S)-2-amino-4-(methylthio)-1-butanol (0.1 mL) were reacted in 1,2-dichloroethane (5 mL) with acetic acid to give (3S,11aR)—N-[(2,4-difluorophenyl)methyl]-3-[2-(methylthio)ethyl]-5,7-dioxo-6-[(phenyl methyl)oxy]-2,3,5,7,11,11a-hexahydro[1,3]oxazolo[3,2-a]pyrido[1,2-d]pyrazine-8-carboxamide (41 mg, 81%). This material (20 mg, 0.04 mmol) was treated with trifluoroacetic acid (1 mL) in dichloromethane (3 mL) at 0° C. to rt over 6 h. The mixture was concentrated in vacuo and subjected to reverse phase preparative HPLC purification to provide (3S,11aR)—N-[(2,4-Difluorophenyl)methyl]-6-hydroxy-3-[2-(methylthio)ethyl]-5,7-dioxo-2,3,5,7,11,11a-hexahydro[1,3]oxazolo[3,2-a]pyrido[1,2-d]pyrazine-8-carboxamide (12 mg, 72%) as a white solid. $^1$H NMR (CDCl$_3$) δ 11.35 (br, 1H), 10.25 (s, 1H), 8.34 (s, 1H), 7.33 (m, 1H), 6.79 (m, 2H), 5.32 (m, 1H), 4.62-4.53 (m, 3H), 4.43-4.39 (m, 2H), 3.91-3.87 (m, 2H), 2.63-2.53 (m, 2H), 2.39 (m, 1H), 2.12 (s, 3H), 1.89 (m, 1H); ES$^+$ MS: 466 (M+1).

Example Z-27

(3S,11aR)—N-[(2,4-Difluorophenyl)methyl]-6-hydroxy-3-[2-(methylsulfonyl)ethyl]-5,7-dioxo-2,3,5,7,11,11a-hexahydro[1,3]oxazolo[3,2-a]pyrido[1,2-d]pyrazine-8-carboxamide

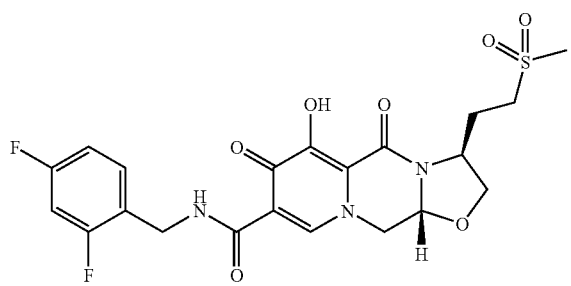

To a solution of (3S,11aR)—N-[(2,4-difluorophenyl)methyl]-3-[2-(methylthio)ethyl]-5,7-dioxo-6-[(phenyl methyl)oxy]2,3,5,7,11,11a-hexahydro[1,3]oxazolo[3,2-a]pyrido[1,2-d]pyrazine-8-carboxamide (20 mg, 0.04 mmol) in dichloromethane (5 mL) at 0° C. was added m-CPBA (20 mg, 70%, 0.082 mmol). The resultant solution was allowed to warm as the bath warmed and stirred a total of 3 h. The reaction was quenched by the addition of Na$_2$S$_2$O$_3$ (aq) and sodium bicarbonate. The layers were separated and the organic layer washed with brine. The aqueous layer was extracted with dichloromethane and the combined organics dried over Na$_2$SO$_4$. Filtration and concentration provided (3S,11aR)—N-[(2,4-difluorophenyl)methyl]-3-[2-(methylsulfonyl)ethyl]-5,7-dioxo-6-[(phenylmethyl)oxy]-2,3,5,7,11,11a-hexahydro[1,3]oxazolo[3,2-a]pyrido[1,2-d]pyrazine-8-carboxamide (26 mg, 99%) as a white solid. This material was hydrogenated in a second step as described in example Z-1 to give (3S,11aR)—N-[(2,4-Difluorophenyl)methyl]-6-hydroxy-3-[2-(methylsulfonyl)ethyl]-5,7-dioxo-2,3,5,7,11,11a-hexahydro[1,3]oxazolo[3,2-a]pyrido[1,2-d]pyrazine-8-carboxamide (22 mg, 99%) as a white solid. $^1$H NMR (CDCl$_3$) δ 11.00 (br, 1H), 10.16 (s, 1H), 8.33 (s, 1H), 7.36 (m, 1H), 6.81 (m, 2H), 5.42 (m, 1H), 4.62 (m, 3H), 4.41 (m, 2H), 3.93 (m, 2H), 3.31 (m, 2H), 2.98 (s, 3H), 2.40 (m, 1H), 2.28 (m, 1H); ES$^+$ MS: 498 (M+1).

Example Z-28

(3S,11aR)—N-[(2,4-Difluorophenyl)methyl]-6-hydroxy-3-(1H-indol-3-ylmethyl)-5,7-dioxo-2,3,5,7,11,11a-hexahydro[1,3]oxazolo[3,2-a]pyrido[1,2-d]pyrazine-8-carboxamide

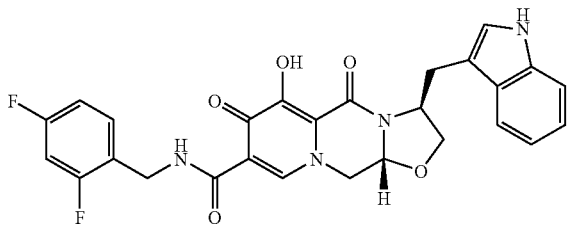

The title compound was made in two steps using a similar process to that described in example Z-1. 16a (43 mg, 0.09 mmol) and (2S)-2-amino-3-(1H-indol-3-yl)-1-propanol (100 mg, 0.52 mmol) were reacted in 1,2-dichloroethane (5 mL) with acetic acid to give (3S,11aR)—N-[(2,4-difluorophenyl)methyl]-3-(1H-indol-3-ylmethyl)-5,7-dioxo-6-[(phenyl methyl)oxy]-2,3,5,7,11,11a-hexahydro[1,3]oxazolo[3,2-a]pyrido[1,2-d]pyrazine-8-carboxamide (36 mg, 64%). This material was hydrogenated in a second step as described in example Z-1 to give (3S,11aR)—N-[(2,4-Difluorophenyl)methyl]-6-hydroxy-3-(1H-indol-3-ylmethyl)-5,7-dioxo-2,3,5,7,11,11a-hexahydro[1,3]oxazolo[3,2-a]pyrido[1,2-d]pyrazine-8-carboxamide (29 mg, 95%) as a white solid. $^1$H NMR (CDCl$_3$/CD$_3$OD) δ 10.34 (m, 1H), 8.98 (br, 1H), 8.24 (s, 1H), 7.58 (d, J=8.0 Hz, 1H), 7.32 (m, 2H), 7.15-7.01 (m, 3H), 6.78 (m, 2H), 4.94 (d, J=68 Hz, 1H), 4.71 (d, J=5.6 Hz, 1H), 4.59 (m, 2H), 4.35 (d, J=10.4 Hz, 1H), 4.22 (m, 1H), 3.99 (m, 1H), 3.81 (m, 1H), 3.40 (dd, J=13.6, 11.6 Hz, 1H), 3.18 (dd, J=14.0, 8.4 Hz, 1H); ES$^+$ MS: 521 (M+1).

Example Z-29

(4R,12aR)—N-[(4-fluorophenyl)methyl]-7-hydroxy-4-methyl-1-(2-methylpropyl)-6,8-dioxo-1,2,3,4,6,8,12,12a-octahydropyrido[1',2':3,4]pyrazino[1,2-a]pyrimidine-9-carboxamide

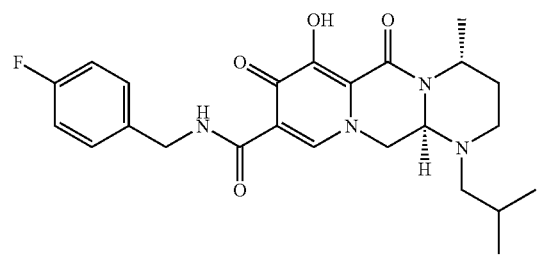

a) (2R)-2-({[(1,1-Dimethylethyl)oxy]carbonyl}amino)propyl methanesulfonate. To a stirred solution of 1,1-dimethylethyl[(1R)-2-hydroxy-1-methylethyl]carbamate (5.00 g, 28.5 mmol) and triethylamine (5.92 mL, 42.9 mmol) in CH$_2$Cl$_2$ (30 mL) cooled to 0° C. and under a nitrogen atmosphere was added dropwise a solution of methanesulfonyl chloride (2.43 mL, 31.5 mmol) in CH$_2$Cl$_2$ (25 mL). Stirring was continued for 20 minutes at 0° C., after which time the reaction was judged complete by TLC analysis (1:1 hexanes/ EtOAc). The solution was poured into water and the layers were separated. The organic phase was washed with 0.1 N HCl and then with 5% NaHCO$_3$, dried over Na$_2$SO$_4$, filtered and concentrated to give (2R)-2-({[(1,1-dimethylethyl)oxy] carbonyl}amino)propyl methanesulfonate (7.08 g, 98%) as a white solid. $^1$H NMR (400 MHz, CDCl$_3$) δ 1.23 (d, J=6.8 Hz, 3H), 1.44 (s, 9H), 3.03 (s, 3H), 3.97 (m, 1H), 4.15 (dd, J=4.2, 9.8 Hz, 1H), 4.21 (m, 1H), 4.61 (br s, 1H).

b) 1,1-Dimethylethyl[(1R)-2-cyano-1-methylethyl]carbamate. To a stirred solution of (2R)-2-({[(1,1-dimethylethyl) oxy]carbonyl}amino)propyl methanesulfonate (7.08 g, 27.9 mmol) in DMSO (50 mL) was added NaCN (3.78 g, 84.0 mmol). The solution was stirred at 70° C. for 2 hours, over which time the formation of a precipitate was observed. After cooling at room temperature, water was added and the mixture was extracted with Et$_2$O. The ethereal layers were washed with a brine solution, dried over Na$_2$SO$_4$, filtered and concentrated to give 1,1-dimethylethyl [(1R)-2-cyano-1-methylethyl]carbamate (3.81 g, 73%) as a pale yellow solid. $^1$H NMR (400 MHz, CDCl$_3$) δ 1.30 (d, J=6.8 Hz, 3H), 1.42 (s, 9H), 2.51 (dd, J=3.8, 16.6 Hz, 1H), 2.73 (m, 1H), 3.93 (m, 1H), 4.63 (br s, 1H).

c) 1,1-Dimethylethyl[(1R)-3-amino-1-methylpropyl]carbamate. A solution of 1,1-dimethylethyl[(1R)-2-cyano-1-methylethyl]carbamate (1.30 g, 7.1 mmol) in ethanol saturated with anhydrous ammonia was treated with Raney-Ni (1.5 mL of 50% aq. Suspension) and 55 psi of H$_2$ overnight. The mixture was filtered through Celite and the filtrate was concentrated in vacuo. The residue was purified by flash chromatography (80:19:1 CH$_2$Cl$_2$/MeOH/NH$_4$OH (37%) gradient elution) through a short plug of silica gel to give 1,1-dimethylethyl [(1R)-3-amino-1-methylpropyl]carbamate (1.37 g, 100%) as a clear oil that solidified. $^1$H NMR (400 MHz, CDCl$_3$) δ 1.14 (d, J=6.8 Hz, 3H), 1.43-1.62 (m, 13H), 2.76 (m, 2H), 3.77 (m, 1H), 4.57 (m, 1H).

d) 1,1-Dimethylethyl {(1R)-1-methyl-3-[(2-methylpropyl) amino]propyl}carbamate. 1,1-dimethylethyl[(1R)-3-amino-1 methylpropyl]carbamate (0.320 g, 1.70 mmol), isobutyraldehyde (150 µL, 1.62 mmol), and sodium triacetoxyborohydride (0.512 g, 2.42 mmol) were stirred in anhydrous dichloroethane (10 mL) at ambient temperature overnight. The reaction was quenched by the addition of saturated NaHCO$_3$ and then extracted with dichloromethane. The combined extracts were washed with water, dried over Na$_2$SO$_4$, filtered and concentrated. The residue was purified by flash chromatography (80:19:1 CH$_2$Cl$_2$/MeOH/NH$_4$OH (37%) gradient elution) through a short plug of silica gel to afford 1,1-dimethylethyl {(1R)-1-methyl-3-[(2-methylpropyl) amino]propyl}carbamate (0.158 g, 40%) as a clear oil. $^1$H NMR (400 MHz, CDCl$_3$) δ 0.90 (d, J=6.4 Hz, 6H), 1.13 (d, J=6.4 Hz, 3H), 1.42-1.51 (m, 11H), 1.67-1.75 (m, 2H), 2.33-2.42 (m, 2H), 2.58-2.72 (m, 2H), 3.72 (m, 1H), 5.20 (m, 1H).

e) [(3R)-3-Aminobutyl](2-methylpropyl)amine. An ice cold solution of 1,1-dimethylethyl {(1R)-1-methyl-3-[(2-methylpropyl)amino]propyl}carbamate (0.158 g, 0.65 mmol) in THF (8 mL) was treated with 4 N HCl (aq) (2 mL) and then stirred at room temperature for 2 h. The mixture was concentrated in vacuo to give [(3R)-3-aminobutyl](2-methylpropyl) amine dihydrochloride. The HCl salt, was then dissolved in dichloromethane and a minimal amount of methanol and treated with solid supported carbonate resin (MP-Carbonate, Argonaut Technologies). After 30 minutes, the solution was filtered through a fritted tube and the solvents removed carefully in vacuo to give [(3R)-3-aminobutyl](2-methylpropyl) amine (65 mg). $^1$H NMR (400 MHz, CDCl$_3$) δ 0.88 (d, J=6.0 Hz, 6H), 1.06 (d, J=5.6 Hz, 3H), 1.23-1.53 (m, 5H), 1.71-1.74 (m, 1H), 2.39 (m, 2H), 2.65 (m, 2H), 2.97 (m, 1H), f)

(4R,12aR)—N-[(4-Fluorophenyl)methyl]-7-hydroxy-4-methyl-1-(2-methylpropyl)-6,8-dioxo-1,2,3,4,6,8,12,12a-octahydropyrido[1',2':4,5]pyrazino[1,2-a]pyrimidine-9-carboxamide. The title compound was made in two steps using a similar process to that described in example Z-2. 16 (40 mg, 0.09 mmol) and [(3R)-3-aminobutyl](2-methylpropyl)amine (65 mg, 0.45 mmol) were reacted in dichloromethane (2 mL) with acetic acid to give (4R,12aR)—N-[(4-fluorophenyl)methyl]-4-methyl-1-(2-methylpropyl)-6,8-dioxo-7-[(phenylmethyl)oxy]-1,2,3,4,6,8,12,12a-octahydropyrido[1',2':4,5] pyrazino[1,2-a]pyrimidine-9-carboxamide (29 mg, 60%). This material was hydrogenated in a second step as described in example Z-2 to give (4R,12aR)—N-[(4-fluorophenyl)methyl]-7-hydroxy-4-methyl-1-(2-methylpropyl)-6,8-dioxo-1, 2,3,4,6,8,12,12a-octahydropyrido[1',2':4,5]pyrazino[1,2-a] pyrimidine-9-carboxamide (18 mg, 75%) as a tan solid. $^1$H NMR (400 MHz, CDCl$_3$) δ 0.77 (d, J=6.4 Hz, 3H), 0.84 (d, J=6.4 Hz, 3H), 1.32 (d, J=7.2 Hz), 1.45-1.49 (m, 1H), 1.57-1.67 (m, 1H), 2.03-2.12 (m, 2H), 2.21-2.27 (m, 1H), 2.73-2.79 (m, 1H), 2.87-2.92 (m, 1H), 4.16-4.24 (m, 2H), 4.45 (s, 1H), 4.54-4.64 (m, 2H), 4.96-4.99 (m, 1H), 6.96-7.00 (m, 2H), 7.29-7.32 (m, 2H), 8.27 (s, 1H), 10.46 (s, 1H), 12.55 (s, 1H); ES$^+$ MS: 456 (M+1).

Example Z-30

(4R,12aR)—N-[(4-Fluorophenyl)methyl]-7-hydroxy-4-methyl-1-(1-methylethyl)-6,8-dioxo-1,2,3,4, 6,8,12,12a-octahydropyrido[1',2':4,5]pyrazino[1,2-a] pyrimidine-9-carboxamide

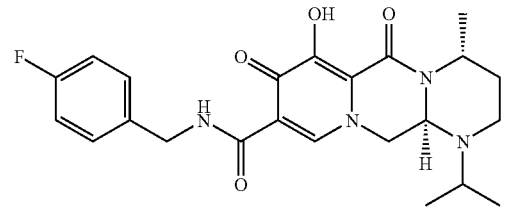

a) [(3R)-3-Aminobutyl](1-methylethyl)amine. The free diamine was prepared in a similar manner as described in example Z-29. $^1$H NMR (400 MHz, CDCl$_3$) δ 1.04 (d, J=6.4 Hz, 6H), 1.06 (d, J=6.4 Hz, 3H), 1.41-1.58 (m, 5H), 2.62-2.66 (m, 2H), 2.74-2.80 (m, 1H), 2.92-3.00 (m, 1H).

b)

(4R,12aR)—N-[(4-Fluorophenyl)methyl]-7-hydroxy-4-methyl-1-(1-methylethyl)-6,8-dioxo-1,2,3,4,6,8,12,12a-octahydropyrido[1',2':4,5]pyrazino[1,2-a]pyrimidine-9-carboxamide. The title compound was made in two steps using a similar process to that described in example Z-2. 16 (40 mg, 0.088 mmol) and [(3R)-3-aminobutyl](1-methylethyl)amine (78 mg, 0.60 mmol) were reacted in dichloromethane (2 mL) with acetic acid to give (4R,12aR)—N-[(4-fluorophenyl)methyl]-4-methyl-1-(1-methylethyl)-6,8-dioxo-7-[(phenyl methyl)oxy]-1,2,3,4,6,8,12,12a-octahydropyrido[1',2':4,5] pyrazino[1,2-a]pyrimidine-9-carboxamide (26 mg, 56%). This material was hydrogenated in a second step as described in example Z-2 to give (4R,12aR)—N-[(4-fluorophenyl)methyl]-7-hydroxy-4-methyl-1-(1-methylethyl)-6,8-dioxo-1,2, 3,4,6,8,12,12a-octahydropyrido[1',2':4,5]pyrazino[1,2-a]pyrimidine-9-carboxamide (21 mg, 90%) as an off-white solid. $^1$H NMR (400 MHz, CDCl$_3$) δ 1.01 (d, J=5.6 Hz, 3H), 1.06 (d, J=6.0 Hz, 3H), 1.31 (d, J=6.8 Hz, 3H), 1.57 (m, 1H), 1.98 (m, 1H), 2.70-2.82 (m, 2H), 3.15 (m, 1H), 4.15-4.19 (m, 1H), 4.30 (m, 1H), 4.48 (s, 1H), 4.54-4.59 (m, 2H), 4.97 (m, 1H), 6.98 (m, 2H), 7.29-7.32 (m, 2H), 8.27 (s, 1H), 10.49 (s, 1H), 12.52 (s, 1H).

Example Z-31

(4S,12aS)—N-[(2,4-Difluorophenyl)methyl]-7-hydroxy-4-methyl-1-(2-methylpropyl)-6,8-dioxo-1,2,3,4,6,8,12,12a-octahydropyrido[1',2':4,5]pyrazino[1,2-a]pyrimidine-9-carboxamide

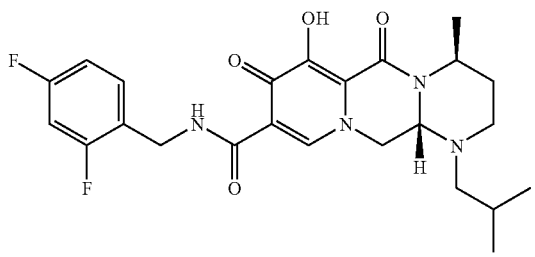

a) 1,1-Dimethylethyl[(1S)-2-cyano-1-methylethyl]carbamate. The nitrile was prepared in two steps using a modified procedure as described in example Z-29. To a stirred solution of (2S)-2-({[(1,1-dimethylethyl)oxy]carbonyl}amino)propyl methanesulfonate (8.40 g, 33.2 mmol) in DMSO (50 mL) and KCN (6.51 g, 100.0 mmol) cooled to 0° C. was added 18-crown-6 (9.05 g, 34.3 mmol). The solution was allowed to warm to room temperature and then heated to 70° C. for 1 hour. After cooling at room temperature, water was added and the mixture was extracted with Et$_2$O. The ethereal layers were washed with a brine solution, dried over Na$_2$SO$_4$, filtered and concentrated to give 1,1-dimethylethyl [(1S)-2-cyano-1-methylethyl]carbamate (5.37 g, 88%) as a pale yellow solid. $^1$H NMR (400 MHz, CDCl$_3$) δ 1.32 (d, J=6.8 Hz, 3H), 1.44 (s, 9H), 2.52 (dd, J=4.0, 16.4 Hz, 1H), 2.74 (m, 1H), 3.95 (m, 1H), 4.65 (br s, 1H).

b) [(3S)-3-Aminobutyl](2-methylpropyl)amine dihydrochloride was prepared in a similar manner as described in example Z-29. $^1$H NMR (400 MHz, CDCl$_3$/CD$_3$OD) δ 0.99 (m, 6H), 1.34 (m, 3H), 2.13-2.27 (m, 3H), 2.76 (m, 2H), 3.07 (m, 2H), 3.47 (m, 1H), 8.22 (m, 1H), 8:83 (m, <1H).

c) (4S,12aS)—N-[(2,4-Difluorophenyl)methyl]-7-hydroxy-4-methyl-1-(2-methylpropyl)-6,8-dioxo-1,2,3,4,6,8,12,12a-octahydropyrido[1',2':4,5]pyrazino[1,2-a]pyrimidine-9-carboxamide. The title compound was made in two steps using a similar process to that described in example Z-2. 16a (80 mg, 0.17 mmol) and free based [(3S)-3-aminobutyl](2-methylpropyl)amine (107 mg, 0.74 mmol) were reacted in dichloromethane (2 mL) with acetic acid to give (4S,12aS)—N-[(2,4-difluorophenyl)methyl]-4-methyl-1-(2-methylpropyl)-6,8-dioxo-7-[(phenylmethyl)oxy]-1,2,3,4,6,8,12,12a-octahydropyrido[1',2':4,5]pyrazino[1,2-a]pyrimidine-9-carboxamide (76 mg, 76%) as a film. This material was hydrogenated in a second step as described in example Z-2 to give (4S,12aS)—N-[(2,4-difluorophenyl)methyl]-7-hydroxy-4-methyl-1-(2-methylpropyl)-6,8-dioxo-1,2,3,4,6,8,12,12a-octahydropyrido[1',2':4,5]pyrazino[1,2-a]pyrimidine-9-carboxamide (39 mg, 80%) as an off-white solid. $^1$H NMR (400 MHz, CDCl$_3$) δ 0.76 (d, J=6.4 Hz, 3H), 0.84 (d, J=6.4 Hz, 3H), 1.32 (d, J=7.2 Hz, 3H), 1.45-1.50 (m, 1H), 1.60-1.69 (m, 1H), 2.03-2.12 (m, 2H), 2.21-2.27 (m, 1H), 2.73-2.79 (m, 1H), 2.87-2.93 (m, 1H), 4.16-4.25 (m, 2H), 4.45 (s, 1H), 4.57-4.68 (m, 2H), 4.96-5.01 (m, 1H), 6.75-6.82 (m, 2H), 7.32-7.38 (m, 1H), 8.26 (s, 1H), 10.45 (s, 1H), 12.56 (s, 1H); ES$^+$ MS: 475 (M+1).

Example Z-32

(4S,12aS)-1-(Cyclopropylmethyl)-N-[(2,4-difluorophenyl)methyl]-7-hydroxy-4-methyl-6,8-dioxo-1,2,3,4,6,8,12,12a-octahydropyrido[1',2':4,5]pyrazino[1,2-a]pyrimidine-9-carboxamide.

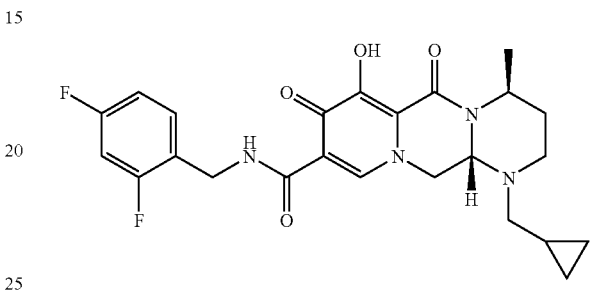

a) 1,1-Dimethylethyl {(1S)-3-[(cyclopropylmethyl)amino]-1-methylpropyl}carbamate. The protected diamine was prepared using a modified procedure as described in example Z-29. 1,1-dimethylethyl[(1S)-3-amino-1-methylpropyl]carbamate (0.293 g, 1.56 mmol), cyclopropane carboxaldehyde (96 μL, 1.30 mmol), and sodium triacetoxyborohydride (0.439 g, 2.07 mmol were stirred in a 1:1 mixture of anhydrous dichloroethane and tetrahydrofuran (10 mL) at ambient temperature overnight. The reaction was quenched by the addition of saturated NaHCO$_3$ and then extracted with EtOAc. The combined extracts were washed with saturated NaHCO$_3$, then a solution of brine, dried over Na$_2$SO$_4$, filtered and concentrated. The residue was purified by flash chromatography (80:1.9:1 CH$_2$Cl$_2$/MeOH/NH$_4$OH (37%) gradient elution) through a short plug of silica gel to afford 1,1-dimethylethyl {(1S)-3-[(cyclopropylmethyl)amino]-1-methylpropyl}carbamate (76 mg, 26%) as a clear oil. $^1$H NMR (400 MHz, CDCl$_3$) δ 0.09-0.13 (m, 2H), 0.44-0.49 (m, 2H), 0.92-0.95 (m, 1H), 1.14 (d, J=6.4 Hz, 3H), 1.43-1.70 (m, 12H), 2.38-2.50 (m, 2H), 2.62-2.73 (m, 2H), 3.74 (m, 1H), 4.88 (m, 1H).

b) [(3S)-3-Aminobutyl](cyclopropylmethyl)amine dihydrochloride was prepared in a similar manner as described in example Z-29. $^1$H NMR (400 MHz, CDCl$_3$/CD$_3$OD) δ 0.40 (m, 2H), 0.64 (m, 2H), 1.15 (m, 1H), 1.34 (m, 3H), 2.12-2.25 (m, 2H), 2.82 (m, 2H), 3.08 (m, 2H), 3.47 (m, 1H), 8.25 (br, <1H), 9.04 (br, <1H), c) (4S,12aS)-1-(Cyclopropylmethyl)-N-[(2,4-difluorophenyl)methyl]-7-hydroxy-4-methyl-6,8-dioxo-1,2,3,4,6,8,12,12a-octahydropyrido[1',2':4,5]pyrazino[1,2-a]pyrimidine-9-carboxamide. The title compound was made in two steps using a similar process to that described in example Z-2. 16a (50 mg, 0.106 mmol) and free based [(3S)-3-aminobutyl](cyclopropylmethyl)amine (44 mg, 0.31 mmol) were reacted in dichloromethane (2 mL) with acetic acid to give (4S,12aS)-1-(cyclopropylmethyl)-N-[(2,4-difluorophenyl)methyl]-4-methyl-6,8-dioxo-7-[(phenylmethyl)oxy]-1,2,3,4,6,8,12,12a-octahydropyrido[1',2':4,5]pyrazino[1,2-a]pyrimidine-9-carboxamide (50 mg, 83%) as a film. This material was hydrogenated in a second step as described in example Z-2 to give (4S,12aS)-1-(cyclopropylmethyl)-N-[(2,4-difluorophenyl)methyl]-7-hydroxy-4-methyl-6,8-dioxo-1,2,3,4,6,8,12,12a-octahydropyrido[1',2':4,5]pyrazino[1,2-a]pyrimidine-9-carboxamide (23 mg, 56%) as an off-white solid. $^1$H NMR (400 MHz, CDCl$_3$) δ 0.11 (m, 2H), 0.56-0.59 (m, 2H), 0.77 (m, 1H), 1.34 (d, J=7.2 Hz, 3H), 1.46-1.50 (m, 1H), 2.04-2.13 (m, 1H), 2.30-2.34 (m, 1H), 2.46-2.51 (m, 1H), 2.90-2.96 (m, 1H), 3.16-3.19 (m, 1H). 4.21-4.30 (m, 2H), 4.51 (s, 1H), 4.58-4.67 (m, 2H), 5.00-5.05 (m, 1H), 6.75-6.82 (m, 2H), 7.31-7.37 (m, 1H), 8.28 (s, 1H), 10.46 (s, 1H), 12.55 (br, 1H); ES$^+$ MS: 473 (M+1).

Example Z-33

(4S,12aS)—N-[(2,4-Difluorophenyl)methyl]-1-(2-furanylmethyl)-7-hydroxy-4-methyl-6,8-dioxo-1,2,3,4,6,8,12,12a-octahydropyrido[1',2':4,5]pyrazino[1,2-a]pyrimidine-9-carboxamide

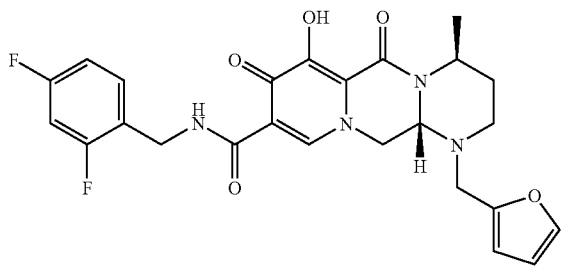

a) [(3S)-3-Aminobutyl](2-furanylmethyl)amine dihydrochloride was prepared in a similar manner as described in example Z-32. $^1$H NMR (400 MHz, CDCl$_3$/CD$_3$OD) δ 1.27 (d, J=6.4 Hz, 3H), 1.96-2.05 (m, 1H), 2.14-2.19 (m, 1H), 3.00-3.04 (m, 2H), 3.38-3.39 (m, 1H), 4.11-4.18 (m, 2H), 6.34 (m, 1H), 6.59 (m, 1H), 7.40 (m, 1H), 8.18 (br, <1H), 9.41 (br, <1H).

b)

(4S,12aS)—N-[(2,4-Difluorophenyl)methyl]-1-(2-furanylmethyl)-7-hydroxy-4-methyl-6,8-dioxo-1,2,3,4,6,8,12,12a-octahydropyrido[1',2':4,5]pyrazino[1,2-a]pyrimidine-9-carboxamide. The title compound was made in two steps using a similar process to that described in example Z-2. 16a (36 mg, 0.076 mmol) and free based [(3S)-3-aminobutyl](2-furanylmethyl)amine (70 mg, 0.42 mmol) were reacted in dichloromethane (2 mL) with acetic acid to give (4S,12aS)—N-[(2,4-difluorophenyl)methyl]-1-(2-furanylmethyl)-4-methyl-6,8-dioxo-7-[(phenylmethyl)oxy]-1,2,3,4,6,8,12,12a-octahydropyrido[1',2':4,5]pyrazino[1,2-a]pyrimidine-9-carboxamide (32 mg, 70%) as a film. This material was hydrogenated in a second step as described in example Z-2 to give (4S,12aS)—N-[(2,4-difluorophenyl)methyl]-1-(2-furanylmethyl)-7-hydroxy-4-methyl-6,8-dioxo-1,2,3,4,6,8,12,12a-octahydropyrido[1',2':4,5]pyrazino[1,2-a]pyrimidine-9-carboxamide (20 mg, 76%), as an off-white solid. $^1$H NMR (400 MHz, CDCl$_3$) δ 1.24 (d, J=6.8 Hz, 3H), 1.45-1.49 (m, 1H), 2.04-2.13 (m, 1H), 2.77-2.82 (m, 1H), 2.94-3.01 (m, 1H), 3.65 (d, J=15.6 Hz, 1H), 3.89 (d, J=16.0 Hz, 1H), 4.27-4.31 (m, 1H), 4.39-4.41 (m, 1H), 4.49-4.53 (m, 1H), 4.58-4.66 (m, 1H), 4.98-5.03 (m, 1H), 6.24 (m, 1H), 6.36 (m, 1H), 6.75-6.82 (m, 2H), 7.31-7.39 (m, 1H), 7.40 (m, 1H), 8.26 (s, 1H), 10.47 (m, 1H), 12.50 (br, 1H); ES$^+$ MS: 499 (M+1).

Example Z-34

(4S,12aS)—N-[(2,4-Difluorophenyl)methyl]-7-hydroxy-4-methyl-6,8-dioxo-1-(1,3-thiazol-2-ylmethyl)-1,2,3,4,6,8,12,12a-octahydropyrido[1',2':4,5]pyrazino[1,2-a]pyrimidine-9-carboxamide

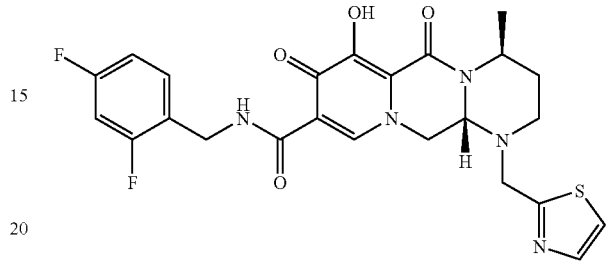

a) [(3S)-3-Aminobutyl](1,3-thiazol-2-ylmethyl)amine dihydrochloride was prepared in a similar manner as described in example Z-32. $^1$H NMR (400 MHz, CDCl$_3$/CD$_3$-OD) δ 1.28 (d, J=6.4 Hz, 3H), 2.05 (m, 1H), 2.17 (m, 1H), 3.20 (m, 2H), 3.39 (m, 1H), 4.51-4.58 (m, 2H), 7.52 (d, 1H), 7.82 (d, 1H).
b)
(4S,12aS)—N-[(2,4-Difluorophenyl)methyl]-7-hydroxy-4-methyl-6,8-dioxo-1-(1,3-thiazol-2-ylmethyl)-1,2,3,4,6,8,12,12a-octahydropyrido[1',2':4,5]pyrazino[1,2-a]pyrimidine-9-carboxamide. The title compound was made in two steps using a similar process to that described in example Z-2. 16a (35 mg, 0.074 mmol) and free based [(3S)-3-aminobutyl](1,3-thiazol-2-ylmethyl)amine were reacted in dichloromethane (2 mL) with acetic acid to give (4S,12aS)—N-[(2,4-difluorophenyl)methyl]-4-methyl-6,8-dioxo-7-[(phenylmethyl)oxy]-1-(1,3-thiazol-2-ylmethyl)-1,2,3,4,6,8,12,12a-octahydropyrido[1',2':4,5]pyrazino[1,2-a]pyrimidine-9-carboxamide (36 mg, 80%) as a film. This material was debenzylated in a second step to in a manner similar to Z-26 to give (4S,12aS)—N-[(2,4-difluorophenyl)methyl]-7-hydroxy-4-methyl-6,8-dioxo-1-(1,3-thiazol-2-ylmethyl)-1,2,3,4,6,8,12,12a-octahydropyrido[1',2':4,5]pyrazino[1,2-a]pyrimidine-9-carboxamide (18 mg, 60%) as an off-white solid. $^1$H NMR (400 MHz, CDCl$_3$) δ 1.30 (d, J=7.2 Hz, 3H), 1.49-1.53 (m, 1H), 2.12-2.18 (m, 1H), 2.93-2.96 (m, 1H), 3.07-3.13 (m, 1H), 3.99-4.03 (m, 1H), 4.13-4.17 (m, 1H), 4.24-4.27 (m, 1H), 4.57-4.61 (m, 3H), 5.03-5.06 (m, 1H), 6.75-6.82 (m, 2H), 7.26 (m, 1H), 7.31-7.37 (m, 2H), 7.76 (m, 1H), 7.94 (m, 1H), 10.40 (m, 1H), 12.48 (m, 1H); ES$^+$ MS: 516 (M+1).

Example Z-35 racemic-(4aR,6aR,14aS)—N-[(2,4-Difluorophenyl)methyl]-12-hydroxy-11,13-dioxo-1,3,4,4a,5,6a,7,11,13,14a-decahydro-2H-pyrido[1',2':4,5]pyrazino[1,2-a][3,1]benzoxazine-10-carboxamide

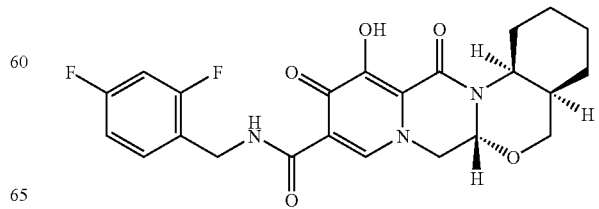

a)

racemic-(4aR,6aR,14aS)—N-[(2,4-Difluorophenyl)methyl]-11,13-dioxo-12-[(phenylmethyl)oxy]-1,3,4,4a,5,6a,7,11,13,14a-decahydro-2H-pyrido[1',2':4,5]pyrazino[1,2-a][3,1]benzoxazine-10-carboxamide. racemic-cis-2-Hydroxymethyl-1-cyclohexylamine hydrochloride (24 mg, 0.186 mmol) was dissolved in a dichloromethane solution containing a small amount of methanol (to dissolve) and excess MP-Carbonate (Argonaut Technologies) was added, the mixture was stirred for 30 minutes, and the MP-Carbonate was removed by filtration. The free amine solution was transferred to a microwave vessel containing 16a (29 mg, 0.0617 mmol). One drop of glacial acetic acid was added and the solution was heated for 10 minutes at 140° C. The resultant solution was absorbed on celite and the material was purified by silica gel chromatography (0-12% methanol/dichloromethane gradient elution) to yield the desired product as a white solid (18 mg, 53%). $^1$H NMR (CDCl$_3$) δ 10.40 (m, 1H), 8.35 (s, 1H), 7.60 (m, 2H), 7.34-7.26 (m, 4H), 6.80 (m, 2H), 5.35-5.23 (m, 2H), 5.13 (m, 1H), 4.77 (m, 1H), 4.70 (m, 2H), 4.22 (dd, J=13.2, 3.2 Hz, 1H), 4.07 (dd, J=13.2, 6.4, 1H), 3.96 (m, 1H), 3.76 (dd, J=11.2, 4.4, 1H), 2.22 (m, 1H), 1.84 (m, 1H), 1.74-1.40 (m, 6H), 1.17 (m, 1H); ES$^+$ MS: 550 (M+1).

b)

racemic-(4aR,6aR,14aS)—N-[(2,4-Difluorophenyl)methyl]-12-hydroxy-11,13-dioxo-1,3,4,4a,5,6a,7,11,13,14a-decahydro-2H-pyrido[1',2':4,5]pyrazino[1,2-a][3,1]benzoxazine-10-carboxamide.

racemic-(4aR,6aR,14aS)—N-[(2,4-Difluorophenyl)methyl]-11,13-dioxo-12-[(phenylmethyl)oxy]-1,3,4,4a,5,6a,7,11,13,14a-decahydro-2H-pyrido[1',2':4,5]pyrazino[1,2-a][3,1]benzoxazine-10-carboxamide (13 mg, 0.0236 mmol) was dissolved in tetrahydrofuran and 10 w.t. % Pd/C (13 mg) was added. Hydrogen was passed through the solution several times and the mixture was stirred at 1 atm hydrogen for 18 hours until the reaction was determined complete by TLC (5% methanol/dichloromethane). The mixture was filtered through Celtite, eluting with methanol/chloroform and the filtrate was concentrated under reduced pressure and purified by HPLC to yield the title compound (7.3 mg, 73%) $^1$H NMR (CDCl$_3$) δ 12.45 (m, 1H), 10.38 (s, 1H), 8.30 (s, 1H), 7.32 (m, 1H), 6.83-6.76 (m, 2H), 5.23 (m, 1H), 4.75 (m, 1H), 4.63 (m, 2H), 4.26 (m, 1H), 4.12-4.01 (m, 2H), 3.83 (m, 1H), 2.30 (m, 1H), 1.91 (m, 1H), 1.80 (m, 1H), 1.67-1.40 (m, 5H), 1.20 (m, 1H); ES$^+$ MS: 460 (M+1).

Example Z-36 racemic (4aR,6aR,14aS)—N-[(4-Fluorophenyl)methyl]-12-hydroxy-11,13-dioxo-1,3,4,4a,5,6a,7,11,13,14a-decahydro-2H-pyrido[1',2':4,5]pyrazino[1,2-a][3,1]benzoxazine-10-carboxamide

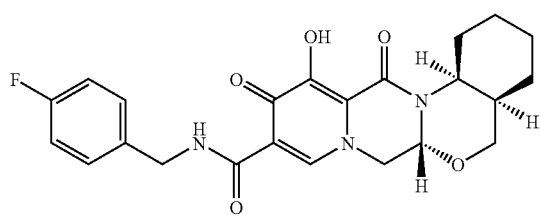

a)

racemic-(4aR,6aR,14aS)—N-[(4-Fluorophenyl)methyl]-11,13-dioxo-12-[(phenyl methyl)oxy]-1,3,4,4a,5,6a,7,11,13,14a-decahydro-2H-pyrido[1',2':4,5]pyrazino[1,2-a][3,1]benzoxazine-10-carboxamide. In a manner similar to that described in example Z-35, from racemic-cis-2-Hydroxymethyl-1-cyclohexylamine hydrochloride (50 mg, 0.303 mmol) and 16 (45 mg, 0.0995 mmol) was prepared racemic-(4aR,6aR,14aS)—N-[(4-fluorophenyl)methyl]-11,13-dioxo-12-[(phenylmethyl)oxy]-1,3,4,4a,5,6a,7,11,13,14a-decahydro-2H-pyrido[1',2':4,5]pyrazino[1,2-a][3,1]benzoxazine-10-carboxamide (48 mg, 91%) as a white solid. $^1$H NMR (CDCl$_3$) δ 10.42 (m, 1H), 8.37 (s, 1H), 7.59 (m, 2H), 7.38-7.24 (m, 5H), 6.98 (m, 2H), 5.26-5.18 (m, 2H), 5.07 (m, 1H), 4.74 (m, 1H), 4.62-4.51 (m, 2H), 4.20 (dd, J=13.6, 4 Hz, 1H), 4.04 (m, 1H), 3.91 (m, 1H), 3.71 (dd, J=11.3, 4.8 Hz, 1H), 2.18 (m, 1H), 1.82 (m, 1H), 1.73-1.63 (m, 2H), 1.62-1.56 (m, 2H), 1.48 (, 1H), 1.38 (m, 1H), 1.14 (m, 1H); ES$^+$ MS: 532 (M+1), b)

racemic-(4aR,6aR,14aS)—N-[(4-Fluorophenyl)methyl]-12-hydroxy-11,13-dioxo-1,3,4,4a,5,6a,7,11,13,14a-decahydro-2H-pyrido[1',2':4,5]pyrazino[1,2-a][3,1]benzoxazine-10-carboxamide. In a manner similar to that described in example Z-37, from racemic-(4aR,6aR,14aS)—N-[(4-fluorophenyl)methyl]-11,13-dioxo-12-[(phenylmethyl)oxy]-1,3,4,4a,5,6a,7,11,13,14a-decahydro-2H-pyrido[1',2':4,5]pyrazino[1,2-a][3,1]benzoxazine-10-carboxamide (37 mg, 0.0696 mmol) and 10 w.t. % Pd/C (3 mg) was prepared the title compound (18 mg, 58%) as a white solid after purification by HPLC. $^1$H NMR (CDCl$_3$) δ 12.47 (s, 1H), 10.39 (m, 1H), 8.32 (s, 1H), 7.30 (m, 2H), 6.98 (m, 2H), 5.22 (m, 1H), 4.74 (m, 1H), 4.58 (m, 2H), 4.28 (dd, J=13.2, 4 Hz, 1H), 4.12-3.98 (m, 2H), 3.81 (dd, J=11.6, 4.8 Hz, 1H), 2.29 (m, 1H), 1.91-1.19 (m, 8H); ES$^+$ MS: 442 (M+1).

Example Z-37 racemic-(3S,4aR,6aR,14aS)—N-[(2,4-Difluorophenyl)methyl]-12-hydroxy-11,13-dioxo-3-phenyl-1,3,4,4a,5,6a,7,11,13,14a-decahydro-2/H-pyrido[1',2':4,5]pyrazino[1,2-a][3,1]benzoxazine-10-carboxamide

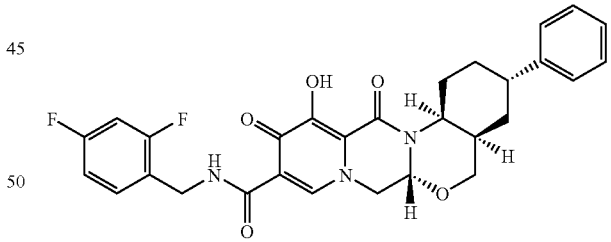

a)

racemic-(3S,4aR,6aR,14aS)—N-[(2,4-Difluorophenyl)methyl]-11,13-dioxo-3-phenyl-12-[(phenylmethyl)oxy]-1,3,4,4a,5,6a,7,11,13,14a-decahydro-2/H-pyrido[1',2':4,5]pyrazino[1,2-a][3,1]benzoxazine-10-carboxamide. In a manner similar to that described in example Z-35, from racemic-[(1R,2S,5S)-2-amino-5-phenylcyclohexyl]methanol hydrochloride (32 mg, 0.160 mmol) and 16a (30 mg, 0.064 mmol) was prepared racemic-(3S,4aR,6aR,14aS)—N-[(2,4-difluorophenyl)methyl]-11,13-dioxo-3-phenyl-12-[(phenylmethyl)oxy]-1,3,4,4a,5,6a,7,11,13,14a-decahydro-2H-pyrido[1',2':4,5]pyrazino[1,2-a][3,1]benzoxazine-10-carboxamide (35 mg, 88%) as a white solid. $^1$H NMR (CDCl$_3$) δ 10.41 (m, 1H), 8.38 (s, 1H), 7.66 (m, 2H), 7.40-

7.26 (m, 6H), 6.81 (m, 3H), 5.32-5.25 (m, 2H), 5.17 (m, 1H), 4.89 (m, 1H), 4.66-4.62 (m, 2H), 4.26 (dd, J=13.6, 4 Hz, 1H), 4.13-4.04 (m, 2H), 3.85 (dd, J=11.2, 4.4 Hz, 1H), 2.56 (m, 1H), 2.37 (m, 1H), 2.03-1.64 (m, 6H); ES+ MS: 626 (M+1).

b) racemic-(3S,4aR,6aR,14aS)—N-[(2,4-Difluorophenyl)methyl]-12-hydroxy-11,13-dioxo-3-phenyl-1,3,4,4a,5,6a,7,11,13,14a-decahydro-2H-pyrido[1',2':4,5]pyrazino[1,2-a][3,1]benzoxazine-10-carboxamide.

racemic-(3S,4aR,6aR,14aS)—N-[(2,4-Difluorophenyl)methyl]-11,13-dioxo-3-phenyl-12-[(phenylmethyl)oxy]-1,3,4,4a,5,6a,7,11,13,14a-decahydro-2H-pyrido[1',2':4,5]pyrazino[1,2-a][3,1]benzoxazine-10-carboxamide (27 mg, 0.0432 mmol) was suspended in methanol, 1.0 w.t. % Pd/C (3 mg) was added and hydrogen was bubbled through the system several times until the reaction was determined complete by TLC (5% methanol/dichloromethane). The suspension was filtered through Celite eluting with methanol/chloroform and the filtrate was concentrated under reduced pressure and purified by HPLC to give the title compound (13 mg, 57%) as a white solid. ¹H NMR (CDCl₃) δ 12.40 (br s, 1H), 10.37 (m, 1H), 8.32 (s, 1H), 7.37-7.28 (m, 3H), 7.24-7.15 (m, 4H), 6.79 (m, 2H), 5.78 (br s, 1H), 4.85 (m, 1H), 4.62 (m, 2H), 4.29 (m, 1H), 4.16-4.09 (m, 2H), 3.92 (dd, J=11.6, 4.8 Hz, 1H), 2.58 (m, 1H), 2.46 (m, 1H), 2.07-1.64 (m, 7H); ES+ MS: 536 (M+1).

Example Z-38

Sodium racemic-(4aS,6aS,14aS)-10-({[(2,4-difluorophenyl)methyl]amino}carbonyl)-6-(2-methylpropyl)-11,13-dioxo-1,2,3,4,4a,5,6,6a,7,11,13,14a-dodecahydropyrido[1',2':4,5]pyrazino[1,2-a]quinazolin-12-olate a) racemic-1,1-Dimethylethyl[(1S,2R)-2-(hydroxymethyl)cyclohexyl]carbamate. racemic-[(1R,2S,5S)-2-Amino-5-phenylcyclohexyl]methanol hydrochloride (800 mg, 4.82 mmol) was dissolved in MeOH (40 mL) and bis(1,1-dimethylethyl)dicarbonate (1.16 g, 5.30 mmol) and triethylamine (4 mL, 28.92 mmol) were added and the mixture was stirred 18 hours at ambient temperature. The solvents were removed under reduced pressure, ethyl acetate and aqueous saturated sodium bicarbonate were added and the product was extracted with ethyl acetate. The combined organics were dried over sodium sulfate and the solvents were removed under reduced pressure. Purification by silica gel chromatography (9:1 hexanes:ethyl acetate to ethyl acetate gradient elution) gave 1,1-dimethylethyl racemic-[(1S,2R)-2-(hydroxymethyl)cyclohexyl]carbamate (934 mg, 85%) as a white solid. ¹H NMR (CDCl₃) δ 4.87 (m, 1H), 4.03-3.95 (m, 2H), 3.26 (m, 1H), 3.15 (m, 1H), 1.73-1.48 (m, 5H), 1.38 (s, 9H), 1.27-1.15 (m, 3H), 0.887 (m, 1H).

b) racemic-1,1-Dimethylethyl[(1S,2R)-2-Formylcyclohexyl]carbamate. To a solution of dimethylsulfoxide (0.2 mL, 2.88 mmol) in dichloromethane (3 mL) at −78° C. was added oxalyl chloride (0.72 mL, 1.44 mmol) dropwise. The mixture was stirred 10 minutes and racemic-1,1-dimethylethyl [(1S,2R)-2-(hydroxymethyl)cyclohexyl]carbamate (220 mg, 0.961 mmol) in dichlormethane was added dropwise and stirred 10 minutes. Triethylamine (0.53 mL, 3.84 mmol) was added slowly and the reaction was stirred at −78° C. for one hour and allowed to warm to ambient temperature. Water was added and product was extracted with dichloromethane. The combined organics were washed with brine and dried over sodium sulfate. Removal of solvents under reduced pressure afforded racemic-1,1-dimethylethyl[(1S,2R)-2-formylcyclohexyl]carbamate (223 mg, quantitative) as a yellow oil. ¹H NMR (CDCl₃) δ 9.61 (s, 1H), 5.19 (m, 1H), 3.88 (m, 1H), 2.61 (m, 1H), 1.85 (m, 1H), 1.63-1.49 (m, 4H), 1.37-1.16 (m, 12H).

c) racemic-1,1-dimethylethyl ((1S,2S)-2-{[(2-Methylpropyl)amino]methyl}cyclohexyl)carbamate. racemic-1,1-Dimethylethyl [(1S,2R)-2-formylcyclohexyl]carbamate (223 mg, 0.982 mmol) was dissolved in dichloroethane and 2-methylpropyl)amine (0.15 mL, 1.47 mmol) and sodium triacetoxyborohydride (290 mg, 1.37 mmol) were added and the reaction was stirred at ambient temperature for 18 hours. Aqueous sodium bicarbonate was added and the product was extracted with dichloromethane. The combined extracts were dried over sodium sulfate and the solvents were removed under reduced pressure. Purification by silica gel chromatography (dichloromethane to 1% ammonium hydroxide 19% methanol 80% dichloromethane gradient elution) afforded racemic-1,1-dimethylethyl ((1S,2S)-2-{[(2-methylpropyl)amino]methyl}cyclohexyl)carbamate (112 mg, 40%) as a clear colorless oil. ¹H NMR (CDCl₃) δ 6.06 (br s, 1H), 3.76 (br s, 1H), 2.63 (m, 1H), 2.43-2.37 (m, 2H), 2.25 (m, 1H), 1.81 (m, 1H), 1.71-1.59 (m, 3H), 1.44-1.32 (m, 14H), 1.27-1.19 (m, 2H), 0.866 (m, 6H).

d) racemic-(1S,2S)-2-{[(2-Methylpropyl)amino]methyl}cyclohexanamine hydrochloride.

In a manner similar to that describe in example Z-3, step e, from racemic-1,1-dimethylethyl ((1S,2S)-2-{[(2-methylpropyl)amino]methyl}cyclohexyl)carbamate (112 mg, 0.394 mmol) was prepared (1S,2S)-2-{[(2-methylpropyl)amino]methyl}cyclohexanamine hydrochloride (130 mg, >100%) as a white solid. ¹H NMR (methanol-d₄/CDCl₃) δ 8.68-8.28 (m, 1H), 3.62 (br s, 1H), 3.26 (m, 1H), 2.83-2.78 (m, 3H), 2.54 (br s, 1H), 2.12 (m, 1H), 1.82-1.66 (m, 3H), 1.53-1.39 (m, 5H), 0.96 (m, 6H), 0.766 (m, 1H).

e) racemic-(4aS,6aS,14aS)—N-[(2,4-Difluorophenyl)methyl]-6-(2-methylpropyl)-11,13-dioxo-12-[(phenylmethyl)oxy]-1,2,3,4,4a,5,6,6a,7,11,13,14a-dodecahydropyrido[1',2':4,5]pyrazino[1,2-a]quinazoline-10-carboxamide. In a manner similar to that described in Z-35, from racemic-(1S,2S)-2-{[(2-methylpropyl)amino]methyl}cyclohexanamine hydrochloride (130 mg, 0.508 mmol) and 16a (55 mg, 0.117 mmol) was prepared racemic-(4aS,6aS,14aS)—N-[(2,4-difluorophenyl)methyl]-6-(2-methylpropyl)-11,13-dioxo-12-[(phenylmethyl)oxy]-1,2,3,4,4a,5,6,6a,7,11,13,14a-dodecahydropyrido[1',2':4,5]pyrazino[1,2-a]quinazoline-10-carboxamide (44 mg, 62%) with a 12:1 d.r. ¹H NMR (CDCl₃) δ 10.46 (m, 1H), 8.33 (s, 1H), 7.59 (m, 2H), 7.37-7.24 (m, 4H), 6.79 (m, 2H), 5.30-5.23 (m, 2H), 4.75-4.56 (m, 3H), 4.23-4.09 (m, 3H), 2.69-2.66 (m, 2H), 2.21-1.98 (m, 3H), 1.80 (m, 1H), 1.71-1.33 (m, 6H), 1.26-1.19 (m, 2H), 0.810 (m, 3H), 0.720 (m, 3H); ES⁺ MS: 605 (M+1).

f)

racemic-(4aS,6aS,14aS)—N-[(2,4-Difluorophenyl)methyl]-12-hydroxy-6-(2-methylpropyl)-11,13-dioxo-1,2,3,4,4a,5,6,6a,7,11,13,14a-dodecahydropyrido[1',2':4,5]pyrazino[1,2-a]quinazoline-10-carboxamide. In a manner similar to that described in example Z-37, from racemic-(4aS,6aS,14aS)—N-[(2,4-difluorophenyl)methyl]-6-(2-methylpropyl)-11,13-dioxo-12-[(phenylmethyl)oxy]-1,2,3,4,4a,5,6,6a,7,11,13,14a-dodecahydropyrido[1',2':4,5]pyrazino[1,2-a]quinazoline-10-carboxamide (39 mg, 0.064 mmol) and 10 w.t. % Pd/C (7 mg) was prepared racemic-(4aS,6aS,14aS)—N-[(2,4-difluorophenyl)methyl]-12-hydroxy-6-(2-methylpropyl)-11,13-dioxo-1,2,3,4,4a,5,6,6a,7,11,13,14a-dodecahydropyrido[1',2':4,5]pyrazino[1,2-a]quinazoline-10-carboxamide (36 mg, >100%) as a tan solid. ¹H NMR (CDCl₃) δ 12.60 (br s, 1H), 10.43 (br s, 1H), 8.25 (s, 1H), 7.35 (m, 1H), 6.78 (m, 2H), 4.77 (m, 1H), 4.63 (m, 2H), 4.49 (br s, 1H), 4.30-4.13 (m, 2H), 3.63-3.40 (m, 2H), 2.88-2.71 (m, 2H), 2.32-2.21 (m, 2H), 2.05 (m, 1H), 1.88-1.11 (m, 7H), 0.830 (m, 3H), 0.760 (m, 3H); AP⁺ MS: 515 (M+1).

g) Sodium racemic-(4aS,6aS,14aS)-10-({[2,4-Difluorophenyl)methyl]amino}carbonyl)-6-(2-methylpropyl)-11,13-dioxo-1,2,3,4,4a,5,6,6a,7,11,13,14a-dodecahydropyrido[1',2':4,5]pyrazino[1,2-a]quinazolin-12-olate. In a manner similar to that described in example Z-1, from racemic-(4aS,6aS,14aS)—N-[(2,4-difluorophenyl)methyl]-12-hydroxy-6-(2-methylpropyl)-11,13-dioxo-1,2,3,4,4a,5,6,6a,7,11,13,14a-dodecahydropyrido[1',2':4,5]pyrazino[1,2-a]quinazoline-10-carboxamide (37 mg, 0.071 mmol) and 1 N sodium hydroxide (0.07 mL) the title compound was prepared as a yellow solid (26 mg, 68%). ¹H NMR (DMSO-d₆) δ 10.73 (m, 1H), 7.94 (s, 1H), 7.32 (m, 1H), 7.19 (m, 1H), 7.00 (m, 1H), 4.59-4.41 (m, 3H), 4.28 (m, 2H), 4.14 (br s, 1H), 2.63-2.60 (m, 2H), 1.98-1.61 (m, 5H), 1.48-1.36 (m, 4H), 0.997 (m, 3H), 0.760 (m, 3H), 0.660 (m, 2H); AP⁺ MS: 515 (M+1 of free acid).

Example Z-39

(6aR,7aS,11aS)—N-[(2,4-Difluorophenyl)methyl]-1-hydroxy-2,13-dioxo-2,6a,7,7a,8,9,10,11,11a,13-decahydro-6H-pyrido[1',2':4,5]pyrazino[1,2-a]benzimidazole-3-carboxamide & Example Z-40

(6aS,7aS,11aS)—N-[(2,4-Difluorophenyl)methyl]-1-hydroxy-2,13-dioxo-2,6a,7,7a,8,9,10,11,11a,13-decahydro-6H-pyrido[1',2':4,5]pyrazino[1,2-a]benzimidazole-3-carboxamide

-continued

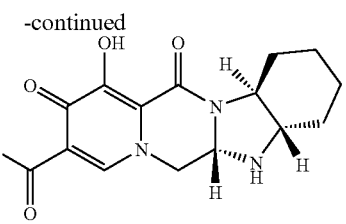

a)

(6aR,7aS,11aS)—N-[(2,4-Difluorophenyl)methyl]-2,13-dioxo-1-[(phenylmethyl)oxy]-2,6a,7,7a,8,9,10,11,11a13-decahydro-6H-pyrido[1',2':4,5]pyrazino[1,2-a]benzimidazole-3-carboxamide and (6aS,7aS,11aS)—N-[(2,4-difluorophenyl)methyl]-2,13-dioxo-1-[(phenylmethyl)oxy]-2,6a,7,7a,8,9,10,11,11a13-decahydro-6H-pyrido[1',2':4,5]pyrazino[1,2-a]benzimidazole-3-carboxamide. In a manner similar to that described in example Z-2, from [(1S,2S)-2-aminocyclohexyl]amine (122 mg, 1.07 mmol) and 16a (200 mg, 0.426 mmol) was prepared (6aR,7aS,11aS)—N-[(2,4-difluorophenyl)methyl]-2,13-dioxo-1-[(phenylmethyl)oxy]-2,6a,7,7a,8,9,10,11,11a13-decahydro-6H-pyrido[1',2':4,5]pyrazino[1,2-a]benzimidazole-3-carboxamide (58 mg) and (6aR,7aS,11aS)—N-[(2,4-difluorophenyl)methyl]-2,13-dioxo-1-[(phenylmethyl)oxy]-2,6a,7,7a,8,9,10,11,11a13-decahydro-6H-pyrido[1',2':4,5]pyrazino[1,2-a]benzimidazole-3-carboxamide (10.6 mg) after separation of the diastereomers using silica gel chromatography (0-12% methanol/dichloromethane). (6aR,7aS,11aS)—N-[(2,4-difluorophenyl)methyl]-2,13-dioxo-1-[(phenylmethyl)oxy]-2,6a,7,7a,8,9,10,11,11a,13-decahydro-6H-pyrido[1',2':4,5]pyrazino[1,2-a]benzimidazole-3-carboxamide (major): ¹H NMR (CDCl₃) δ 10.40 (m, 1H), 8.33 (s, 1H), 7.57 (m, 2H), 7.40-7.25 (m, 4H), 6.81 (m, 2H), 5.32 (d, J=10 Hz, 1H), 5.13 (d, J=10 Hz, 1H), 4.64-4.58 (m, 3H), 4.21 (dd, J=12.4, 3.2 Hz, 1H), 3.79 (m, 1H), 3.04 (m, 1H), 2.73 (m, 1H), 2.53 (m, 1H), 2.01-1.79 (m, 4H), 1.36-1.24 (m, 4H); ES⁺ MS: 535 (M+1). (6aS,7aS,11aS)—N-[(2,4-difluorophenyl)methyl]-2,13-dioxo-1-[(phenylmethyl)oxy]-2,6a,7,7a,8,9,10,11,11a13-decahydro-6H-pyrido[1',2':4,5]pyrazino[1,2-a]benzimidazole-3-carboxamide (minor diastereomer): ¹H NMR (CDCl₃) δ 10.33 (m, 1H), 8.28 (s, 1H), 7.61 (m, 2H), 7.39-7.28 (m, 3H), 6.79 (m, 2H), 5.29 (d, J=9.6 Hz, 1H), 5.05 (d, J=9.6 Hz, 1H), 4.84 (m, 1H), 4.60 (m, 2H), 3.90-3.84 (m, 2H), 3.07 (m, 1H), 2.75 (m, 1H), 2.49 (m, 1H), 2.07 (m, 1H), 1.90-1.51 (m, 4H), 1.33-1.19 (m, 4H); MS data matches that of its diastereomer.

b) (For example Z-39). (6aR,7aS,11aS)—N-[(2,4-Difluorophenyl)methyl]-1-hydroxy-2,13-dioxo-2,6a,7,7a,8,9,10,11,11a,13-decahydro-6H-1-pyrido[1',2':4,5]pyrazino[1,2-a]benzimidazole-3-carboxamide. In a manner similar to that described in example Z-37, from the minor diastereomer prepared in step a (6aS,7aS,11aS)—N-[(2,4-difluorophenyl)methyl]-2,13-dioxo-1-[(phenylmethyl)oxy]-2,6a,7,7a,8,9,10,11,11a,13-decahydro-6H-pyrido[1',2':4,5]pyrazino[1,2-a]benzimidazole-3-carboxamide (7 mg, 0.0131 mmol) and 10 w.t. % Pd/C (catalytic amount) was prepared (6aR,7aS,11aS)—N-[(2,4-difluorophenyl)methyl]-1-hydroxy-2,13-dioxo-2,6a,7,7a,8,9,10,11,11a,13-decahydro-6H-pyrido[1',2':4,5]pyrazino[1,2-a]benzimidazole-3-carboxamide (2.8 mg, 48%) after purification by HPLC. ¹H NMR (CDCl₃) δ 12.15 (br s, 1H), 10.42 (br s, 1H), 8.31 (s, 1H), 7.36 (m, 1H), 6.80 (m, 1H), 5.01 (m, 1H), 4.63 (m, 2H), 4.16 (m, 1H), 3.96 (m, 1H), 3.06-2.93 (m, 2H), 2.61 (m, 1H), 2.18 (m, 1H), 1.93 (m, 1H), 1.60-1.13 (m, 4H), 0.893-0.840 (m, 2H); ES⁺ MS: 445 (M+1).

c) (For example Z-40). (6aS,7aS,11aS)—N-[(2,4-Difluorophenyl)methyl]-1-hydroxy-2,13-dioxo-2,6a,7,7a,8,9,10,11,11a,13-decahydro-6H-pyrido[1',2':4,5]pyrazino[1,2-a]benzimidazole-3-carboxamide. In a manner similar to that described in example Z-37, from the major diastereomer (30 mg, 0.0561 mmol) prepared in step a and 10 w.t. % Pd/C (catalytic amount), (6aS,7aS,11aS)—N-[(2,4-Difluorophenyl)methyl]-1-hydroxy-2,13-dioxo-2,6a,7,7a,8,9,10,11,11a,13-decahydro-6H-pyrido[1',2':4,5]pyrazino[1,2-a]benzimidazole-3-carboxamide was prepared as a white solid (15 mg, 60%) after purification by HPLC. $^1$H NMR (methanol-$d_4$/CDCl$_3$) δ 10.41 (m, 1H), 8.25 (s, 1H), 7.30 (m, 1H), 6.77 (m, 2H), 4.77 (m, 1H), 4.57 (m, 2H), 4.45 (m, 1H), 3.91 (m, 1H), 3.12 (m, 1H), 2.67 (m, 1H), 2.12 (m, 1H), 1.87-1.84 (m, 2H), 1.47-1.33 (m, 4H); ES$^+$ MS: 445 (M+1).

Example Z-41

(5aS,14aS)—N-[(2,4-Difluorophenyl)methyl]-11-hydroxy-10,12-dioxo-1,2,3,4,5a,6,10,12,14,14a-decahydropyrido[1,2-a]pyrido[1',2':3,4]imidazo[1,2-d]pyrazine-9-carboxamide

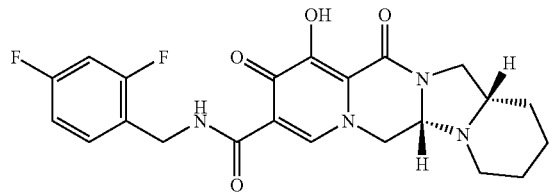

a)
(5aS,14aS)—N-[(2,4-Difluorophenyl)methyl]-10,12-dioxo-11-[(phenylmethyl)oxy]-1,2,3,4,5a,6,10,12,14,14a-decahydropyrido[1,2-a]pyrido[1',2':3,4]imidazo[1,2-d]pyrazine-9-carboxamide. In a manner similar to that described in example Z-18, from 16a (50 mg, 0.108 mmol) and [(2S)-2-piperidinylmethyl]amine hydrochloride (50 mg, 0.269 mmol, made in a similar manner as described in example Z-18) was prepared (5aS,14aS)—N-[(2,4-difluorophenyl)methyl]-10,12-dioxo-11-[(phenylmethyl)oxy]-1,2,3,4,5a,6,10,12,14,14a-decahydropyrido[1,2-a]pyrido[1',2':3,4]imidazo[1,2-d]pyrazine-9-carboxamide (40 mg, 78%). $^1$H NMR (CDCl$_3$) δ 10.43 (m, 1H), 8.38 (s, 1H), 7.59 (m, 2H), 7.59-7.25 (m, 4H), 6.81 (m, 2H), 5.38 (d, J=10 Hz, 1H), 5.19 (d, J=10 Hz, 1H), 4.65-4.62 (m, 2H), 4.20 (dd, J=12, 2.8 Hz, 1H), 4.00 (dd, J=12.4, 2.8 Hz, 1H), 3.85 (m, 1H), 3.74 (m, 1H), 3.27 (m, 1H), 2.99 (m, 1H), 2.43 (m, 1H), 2.24 (m, 1H), 1.94-1.87 (m, 2H), 1.77-1.58 (m, 2H), 1.39-1.24 (m, 2H); ES$^+$ MS: 535 (M+1).
b)
(5aS,14aS)—N-[(2,4-Difluorophenyl)methyl]-11-hydroxy-10,12-dioxo-1,2,3,4,5a,6,10,12,14,14a-decahydropyrido[1,2-a]pyrido[1',2':3,4]imidazo[1,2-d]pyrazine-9-carboxamide. In a manner similar to that described in example Z-37, from (5aS,14aS)—N-[(2,4-difluorophenyl)methyl]-10,12-dioxo-11-[(phenylmethyl)oxy]-3-1,2,3,4,5a,6,10,12,14,14a-decahydropyrido[1,2-a]pyrido[1',2':3,4]imidazo[1,2-d]pyrazine-9-carboxamide (18 mg, 0.0337 mmol) and 10 w.t. % Pd/C (catalytic amount) was prepared the title compound as a white solid (13 mg, 87%) after purification by HPLC. $^1$H NMR (CDCl$_3$) δ 11.71 (br s, 1H), 10.36 (br s, 1H), 8.31 (s, 1H), 7.34 (m, 1H), 6.78 (m, 2H), 4.64-4.57 (m, 2H), 4.28 (m, 1H), 4.12 (m, 1H), 3.92-3.89 (m, 2H), 3.22 (m, 1H), 3.04 (m, 1H), 2.49 (m, 1H), 2.28 (m, 1H), 1.97-1.89 (m, 2H), 1.78 (m, 1H), 1.66-1.60 (m, 2H), 1.43-1.36 (m, 2H); ES$^+$ MS: 445 (M+1).

Example Z-42

(4aR,14aR)—N-[(2,4-Difluorophenyl)methyl]-9-hydroxy-8,10-dioxo-2,3,4,4a,5,6,8,10,14,14a-decahydro-1H-pyrido[1,2-c]pyrido[1',2':4,5]pyrazino[1,2-a]pyrimidine-11-carboxamide

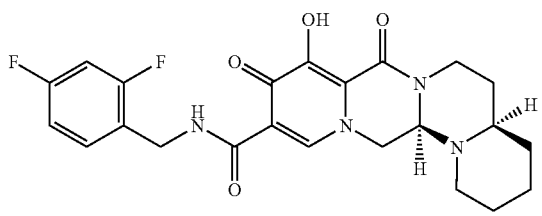

a) Phenylmethyl (2R)-2-(hydroxymethyl)-1-piperidinecarboxylate. In a manner similar to that described in example Z-3a, from (2R)-1-{[(phenylmethyl)oxy]carbonyl}-2-piperidinecarboxylic acid (4.93 g, 18.75 mmol) was prepared phenylmethyl (2R)-2-(hydroxymethyl)-1-piperidinecarboxylate (2.24 g, 48%) as an oil that solidified upon standing to a white solid. $^1$H NMR (CDCl$_3$) δ 7.36-7.26 (m, 5H), 5.18-5.10 (m, 2H), 4.37 (m, 1H), 4.03 (m, 1H), 3.84 (, m, 1H), 3.63 (m, 1H), 2.96 (br s, 1H), 1.71-1.42 (m, 6H).
b) Phenylmethyl (2R)-2-(cyanomethyl)-1-piperidinecarboxylate. In a manner similar to that described in example Z-3b, from phenylmethyl (2R)-2-(hydroxymethyl)-1-piperidinecarboxylate (1.09 g, 4.38 mmol) was prepared phenylmethyl (2R)-2-({[(4-methylphenyl)sulfonyl]oxy}methyl)-1-piperidinecarboxylate (1.05 g, 59% impure with uncharacterized byproduct) as a clear colorless oil after purification using silica gel chromatography (10-100% ethyl acetate-hexanes). It is necessary to use this material in the next step as soon as possible or yields deteriorate dramatically. In a manner similar to that described in example Z-3c, from phenylmethyl (2R)-2-({[(4-methylphenyl)sulfonyl]oxy}methyl)-1-piperidinecarboxylate (1.05 g, 2.61 mmol) and sodium cyanide (383 mg, 7.82 mmol) was prepared phenylmethyl (2R)-2-(cyanomethyl)-1-piperidinecarboxylate (171 mg, 25%) as a yellow oil. $^1$H NMR (CDCl$_3$) δ 7.35-7.29 (m, 5H), 5.13 (s, 2H), 4.65 (m, 1H), 4.10 (m, 1H), 2.96 (m, 1H), 2.60 (m, 2H), 1.82-1.67 (m, 4H), 1.54-1.39 (m, 2H).
d) Phenylmethyl (2R)-2-(2-aminoethyl)-1-piperidinecarboxylate. In a manner similar to that described in example Z-3d, from phenylmethyl (2R)-2-(cyanomethyl)-1-piperidinecarboxylate (171 mg, 0.663 mmol) was prepared phenylmethyl (2R)-2-(2-aminoethyl)-1-piperidinecarboxylate (119 mg, 68%) as a clear colorless residue. $^1$H NMR (CDCl$_3$) δ 7.32-7.25 (m, 5H), 5.08 (m, 2H), 4.39 (br s, 1H), 4.01 (br s, 1H), 2.78 (m, 1H), 2.60-2.56 (m, 2H), 1.95-1.86 (m, 3H), 1.63-1.35 (m, 6H).
e) {2-[(2R)-2-Piperidinyl]ethyl}amine. Phenylmethyl (2R)-2-(2-aminoethyl)-1-piperidinecarboxylate (119 mg, 0.454 mmol) was dissolved in methanol and 10 w.t. % Pd/C (120 mg) was added. Hydrogen was bubbled through the solution for 15 minutes and the reaction was stirred under 1 atm hydrogen for 18 hours until determined complete by TLC (1% ammonium hydroxide 19% methanol 80% dichloromethane). The suspension was filtered through Celite eluting with methanol and the filtrate was carefully concentrated under reduce pressure to yield a clear colorless liquid (58 mg, quantitative). $^1$H NMR (CDCl$_3$) δ 2.99 (m, 1H), 2.71-2.66 (m, 2H), 2.57-2.48 (m, 2H), 1.72 (m, 1H), 1.61-1.52 (m, 2H), 1.48-1.42 (m, 2H), 1.35-1.25 (m, 2H), 1.05 (m, 1H), f)

(4aR,14aR)—N-[(2,4-Difluorophenyl)methyl]-8,10-dioxo-9-[(phenylmethyl)oxy]-2,3,4,4a,5,6,8,10,14,14a-decahydro-1H-pyrido[1,2-c]pyrido[1',2':4,5]pyrazino[1,2-a]pyrimidine-11-carboxamide. In a manner similar to that described in example Z-35, from 16a (50 mg, 0.106 mmol) and {2-[(2R)-2-piperidinyl]ethyl}amine (58 mg, 0.454 mmol) was prepared (4aR,4aR)—N-[(2,4-difluorophenyl)methyl]-8,10-dioxo-9-[(phenylmethyl)oxy]-2,3,4,4a,5,6,8,10,14,14-a-decahydro-1H-pyrido[1,2-c]pyrido[1',2':4,5]pyrazino[1,2-a]pyrimidine-11-carboxamide (47 mg, 81%). $^1$H NMR (CDCl$_3$) δ 10.50 (br s, 1H), 8.33 (s, 1H), 7.60 (s, 2H), 7.38-7.24 (m, 4H), 6.80 (m, 2H), 5.29-5.22 (m, 2H), 4.66-4.56 (m, 3H), 4.30 (m, 1H), 4.19 (m, 1H), 3.78 (br s, 1H), 2.86-2.80 (m, 2H), 2.18 (br s, 1H), 1.94 (m, 1H), 1.68-1.36 (m, 6H), 1.23 (br s, 2H); ES$^+$ MS: 549 (M+1).

g)

(4aR,14aR)—N-[(2,4-Difluorophenyl)methyl]-9-hydroxy-8,10-dioxo-2,3,4,4a,5,6,8,10,14,14a-decahydro-1H-pyrido[1,2-c]pyrido[1',2':4,5]pyrazino[1,2-a]pyrimidine-11-carboxamide. In a manner similar to that described in example Z-37, from (4aR,14aR)—N-[(2,4-difluorophenyl)methyl]-8,10-dioxo-9-[(phenylmethyl)oxy]-2,3,4,4a,5,6,8,10,14,14a-decahydro-1H-pyrido[1,2-c]pyrido[1',2':4,5]pyrazino[1,2-a]pyrimidine-11-carboxamide (47 mg, 0.0857 mmol) and a catalytic amount of 10 w.t. % Pd/C was prepared the title compound as a white solid (19 mg, 54%) after purification by HPLC. $^1$H NMR (CDCl$_3$) δ 10.49 (m, 1H), 8.29 (s, 1H), 7.34 (m, 1H), 6.79 (m, 2H), 4.67-4.56 (m, 3H), 4.41 (m, 1H), 4.20 (m, 1H), 3.93 (s, 1H), 2.94-2.87 (m, 2H), 2.28 (br s, 1H), 2.01 (m, 1H), 1.68-1.54 (m, 4H), 1.44 (m, 1H), 1.29-1.23 (m, 3H), 0.850 (m, 1H); ES$^+$ MS: 459 (M+1).

Example Z-43

(4R,12aR)—N-[(2,4-Difluorophenyl)methyl]-7-hydroxy-4-methyl-1-(3-methylbutyl)-6,8-dioxo-1,2,3,4,6,8,12,12a-octahydropyrido[1',2':4,5]pyrazino[1,2-a]pyrimidine-9-carboxamide

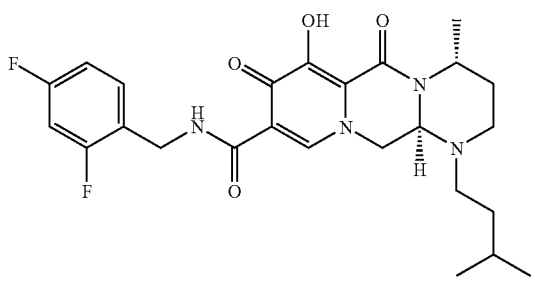

a) [(3R)-3-Aminobutyl](3-methylbutyl)amine dihydrochloride was prepared in a similar manner as described in example Z-32. $^1$H NMR (400 MHz, CDCl$_3$/CD$_3$OD) δ 0.87 (d, J=5.2 Hz, 6H), 1.32 (m, 3H), 1.61 (m, 3H), 2.10-2.20 (m, 2H), 2.90-3.04 (m, 4H), 3.45 (m, 1H), 8.23 (br, <1H), 8.96 (br, <1H).

b)

(4R,12aR)—N-[(2,4-Difluorophenyl)methyl]-7-hydroxy-4-methyl-1-(3-methylbutyl)-6,8-dioxo-1,2,3,4,6,8,12,12a-octahydropyrido[1',2':4,5]pyrazino[1,2-a]pyrimidine-9-carboxamide. The title compound was made in two steps using a similar process to that described in example Z-2. 16a (40 mg, 0.085 mmol) and free [(3R)-3-aminobutyl](3-methylbutyl)amine (46 mg, 0.35 mmol) were reacted in dichloromethane (2 mL) with acetic acid to give (4R,12aR)—N-[(2,4-difluorophenyl)methyl]-4-methyl-1-(3-methylbutyl)-6,8-dioxo-7-[(phenylmethyl)oxy]-1,2,3,4,6,8,12,12a-octahydropyrido[1',2':4,5]pyrazino[1,2-a]pyrimidine-9-carboxamide (44 mg, 90%) as a film. This material was hydrogenated in a second step as described in example Z-2 to give (4R,12aR)—N-[(2,4-difluorophenyl)methyl]-7-hydroxy-4-methyl-1-(3-methylbutyl)-6,8-dioxo-1,2,3,4,6,8,12,12a-octahydropyrido[1',2':4,5]pyrazino[1,2-a]pyrimidine-9-carboxamide (11 mg, 30%) as an off-white solid. $^1$H NMR (400 MHz, CDCl$_3$) δ 0.84 (d, J=6.8 Hz, 3H), 0.86 (d, J=6.8 Hz, 3H), 1.24-1.36 (m, 5H), 1.47-1.53 (m, 2H), 2.02-2.11 (m, 1H), 2.36-2.43 (m, 1H), 2.54-2.61 (m, 1H), 2.77-2.92 (m, 2H), 4.16-4.26 (m, 2H), 4.44 (m, 1H), 4.62-4.64 (m, 2H), 4.95-5.02 (m, 1H), 6.75-6.81 (m, 2H), 7.31-7.37 (m, 1H), 8.27 (s, 1H), 10.43 (m, 1H), 12.54 (s, 1H); ES$^+$ MS: 489 (M+1).

Example Z-44

(4S,12aS)—N-[(2,4-Difluorophenyl)methyl]-7-hydroxy-4-methyl-1-(1-methylethyl)-6,8-dioxo-1,2,3,4,6,8,12,12a-octahydropyrido[1',2':4,5]pyrazino[1,2-a]pyrimidine-9-carboxamide

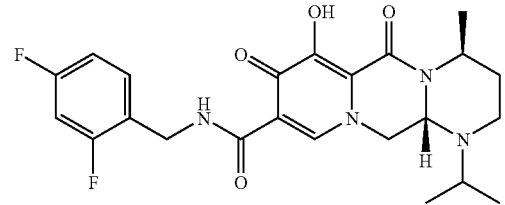

a) [(3S)-3-Aminobutyl](1-methylethyl)amine dihydrochloride was prepared in a similar manner as described in example Z-29. $^1$H NMR (400 MHz, CDCl$_3$/CD$_3$OD) δ 1.20-1.25 (m, 9H), 1.93-2.02 (m, 2H), 2.92 (m, 2H), 3.20-3.29 (m, 2H), 8.04 (br, <1H), 8.64 (br, <1H), b)

(4S,12aS)—N-[(2,4-Difluorophenyl)methyl]-7-hydroxy-4-methyl-1-(1-methylethyl)-6,8-dioxo-1,2,3,4,6,8,12,12a-octahydropyrido[1',2':4,5]pyrazino[1,2-a]pyrimidine-9-carboxamide. The title compound was made in two steps using a similar process to that described in example Z-2. 16a (60 mg, 0.13 mmol) and free based [(3S)-3-aminobutyl](1-methylethyl)amine (55 mg, 0.42 mmol) were reacted in dichloromethane (2 mL) with acetic acid to give (4S,12aS)—N-[(2,4-difluorophenyl)methyl]-4-methyl-1-(1-methylethyl)-6,8-dioxo-7-[(phenylmethyl)oxy]-1,2,3,4,6,8,12,12a-octahydropyrido[1',2':4,5]pyrazino[1,2-a]pyrimidine-9-carboxamide (40 mg, 57%) as a film. This material was hydrogenated in a second step as described in example Z-2 to give (4S,12aS)—N-[(2,4-difluorophenyl)methyl]-7-hydroxy-4-methyl-1-(1-methylethyl)-6,8-dioxo-1,2,3,4,6,8,12,12a-octahydropyrido[1',2':4,5]pyrazino[1,2-a]pyrimidine-9-carboxamide (17 mg, 50%) as an off-white solid. $^1$H NMR (400 MHz, CDCl₃) δ 1.02 (d, J=6.4 Hz, 3H), 1.07 (d, J=6.4 Hz, 3H), 1.33 (d, J=7.2 Hz, 3H), 1.55-1.58 (m, 1H), 1.94-2.03 (m, 1H), 2.70-2.77 (m, 1H), 2.81-2.86 (m, 1H), 3.11-3.18 (m, 1H), 4.17 (dd, J=3.0, 13.8 Hz, 1H), 4.32 (dd, J=3.2, 14.0 Hz, 1H), 4.48 (m, 1H), 4.59-4.69 (m, 2H), 4.97-5.00 (m, 1H), 6.77-6.83 (m, 2H), 7.33-7.39 (m, 1H), 8.28 (s, 1H), 10.50 (m, 1H), 12.55 (s, 1H); ES⁺ MS: 461 (M+1).

Example Z-45

(4S,12aS)—N-[(2,4-Difluorophenyl) methyl]-7-hydroxy-4-methyl-1-(3-methylethyl)-6,8-dioxo-1,2,3,4,6,8,12,12a-octahydropyrido[1',2':4,5]pyrazino[1,2-a]pyrimidine-9-carboxamide

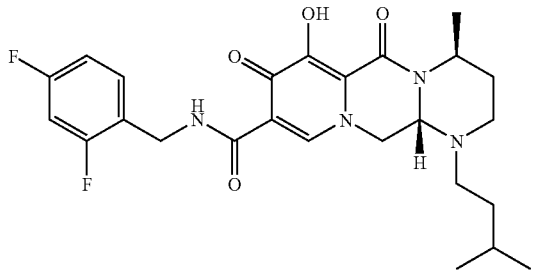

a) [(3S)-3-Aminobutyl](3-methylbutyl)amine dihydrochloride was prepared in a similar manner as described in example Z-32. ¹H NMR (400 MHz, CDCl₃/CD₃OD) δ 0.86 (d, J=5.6 Hz, 6H), 1.27 (d, J=6.0 Hz, 3H), 1.58 (m, 3H), 2.03-2.14 (m, 2H), 2.87-2.99 (m, 4H), 3.38 (m, 1H), 8.15 (br, <1H), 8.87 (br, <1H), b)

(4S,12aS)—N-[(2,4-Difluorophenyl)methyl]-7-hydroxy-4-methyl-1-(3-methylbutyl)-6,8-dioxo-1,2,3,4,6,8,12,12a-octahydropyrido[1',2':4,5]pyrazino[1,2-a]pyrimidine-9-carboxamide. The title compound was made in two steps using a similar process to that described in example Z-2. 16a (0.100 g, 0.21 mmol) and free based [(3S)-3-aminobutyl](3-methylbutyl)amine (0.104 g, 0.66 mmol) were reacted in dichloromethane (2 mL) with acetic acid to give (4S,12aS)—N-[(2,4-difluorophenyl)methyl]-4-methyl-1-(3-methylbutyl)-6,8-dioxo-7-[(phenylmethyl)oxy]-1,2,3,4,6,8,12,12a-octahydropyrido[1',2':4,5]pyrazino[1,2-a]pyrimidine-9-carboxamide (88 mg, 72%) as a film. This material was hydrogenated in a second step as described in example Z-2 to give (4S,12aS)—N-[(2,4-difluorophenyl)methyl]-7-hydroxy-4-methyl-1-(3-methylbutyl)-6,8-dioxo-1,2,3,4,6,8,12,12a-octahydropyrido[1',2':4,5]pyrazino[1,2-a]pyrimidine-9-carboxamide (55 mg, 74%). ¹H NMR (400 MHz, CDCl₃) δ 0.84 (d, J=6.4 Hz, 3H), 0.85 (d, J=6.4 Hz, 3H), 1.24-1.37 (m, 5H), 1.45-1.53 (m, 2H), 2.02-2.11 (m, 1H), 2.37-2.44 (m, 1H), 2.56-2.63 (m, 1H), 2.80-2.92 (m, 2H), 4.22-4.29 (m, 2H), 4.45 (s, 1H), 4.62-4.63 (m, 2H), 4.97-5.00 (m, 1H), 6.75-6.82 (m, 2H), 7.31-7.37 (m, 1H), 8.37 (s, 1H), 10.48 (m, 1H), 12.53 (br, 1H); ES⁺ MS: 489 (M+1).

Example Z-46

(4S,12aS)—N-[(2,4-Difluorophenyl)methyl]-7-hydroxy-4-methyl-6,8-dioxo-1-(3-pyridinylmethyl)-1,2,3,4,6,8,12,12a-octahydropyrido[1',2':4,5]pyrazino[1,2-a]pyrimidine-9-carboxamide

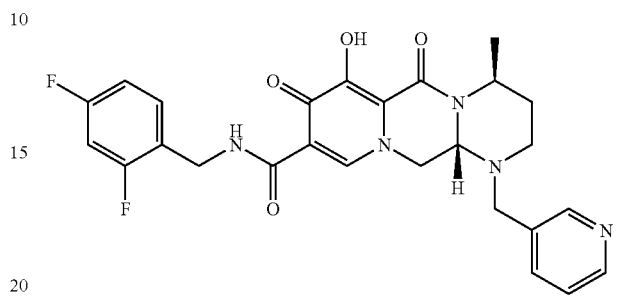

a) 1,1-Dimethylethyl {(1S)-1-methyl-3-[(3-pyridinylmethyl)amino]propyl}carbamate. The protected diamine was prepared using a modified procedure as described in example Z-32. A solution of 1,1-dimethylethyl [(1S)-3-amino-1-methylpropyl]carbamate (0.296 g, 1.6 mmol) and 3-pyridinecarboxaldehyde (120 μL, 1.3 mmol) in a 1:1 mixture of anhydrous dichloroethane and tetrahydrofuran (10 mL) was treated with acetic acid (374 μL, 6.6 mmol) and stirred for 30 minutes. Sodium triacetoxyborohydride (0.444 g, 2.1 mmol) was added and the solution was stirred for 2 hours. The resultant was subjected to a workup and purification procedure as described in example Z-32 to give 1,1-dimethylethyl {(1S)-1-methyl-3-[(3-pyridinylmethyl)amino] propyl}carbamate (0.245 g, 66%) as a clear oil. ¹H NMR (400 MHz, CDCl₃) δ 1.12 (d, J=6.4 Hz, 3H), 1.42 (s, 9H), 1.46-1.54 (m, 1H), 1.68 (m, 1H), 2.61-2.75 (m, 2H), 3.73-3.80 (m, 3H), 4.86 (m, 1H), 7.22-7.24 (m, 1H), 7.68 (d, J=8.0 Hz, 1H), 8.48 (m, 1H), 8.53 (m, 1H).

b) [(3S)-3-Aminobutyl](3-pyridinylmethyl)amine dihydrochloride was prepared in a similar manner as described in example Z-29.

c)

(4S,12aS)—N-[(2,4-Difluorophenyl)methyl]-7-hydroxy-4-methyl-6,8-dioxo-1-(3-pyridinylmethyl)-1,2,3,4,6,8,12,12a-octahydropyrido[1',2':4,5]pyrazino[1,2-a]pyrimidine-9-carboxamide. The title compound was made in two steps using a similar process to that described in example Z-2. 16a (60 mg, 0.13 mmol) and free based [(3S)-3-aminobutyl](3-pyridinylmethyl)amine (83 mg, 0.47 mmol) were reacted in dichloromethane (2 mL) with acetic acid to give (4S,12aS)—N-[(2,4-difluorophenyl)methyl]-4-methyl-6,8-dioxo-7-[(phenylmethyl)oxy]-1-(3-pyridinylmethyl)-1,2,3,4,6,8,12,12a-octahydropyrido[1',2':4,5]pyrazino[1,2-a]pyrimidine-9-carboxamide (72 mg, 95%) as a film. This material was hydrogenated in a second step as described in example Z-2 to give (4S,12aS)—N-[(2,4-difluorophenyl)methyl]-7-hydroxy-4-methyl-6,8-dioxo-1-(3-pyridinyl methyl)-1,2,3,4,6,8,12,12a-octahydropyrido[1',2':4,5]pyrazino[1,2-a]pyrimidine-9-carboxamide (34 mg, 56%) as an off-white solid. ¹H NMR (400 MHz, CDCl₃) δ 1.37 (d, J=6.8 Hz, 3H), 1.43-1.47 (m, 1H), 2.12 (m, 1H), 2.60-2.92 (m, 2H), 3.53 (d, J=14.0 Hz, 1H), 3.82 (d, J=14.4 Hz, 1H), 4.23-4.31 (m, 2H), 4.55-4.64 (m, 3H), 5.06-5.11 (m, 1H), 6.75-6.82 (m, 2H), 7.20-7.23 (m, 1H), 7.31-7.36 (m, 1H), 7.50 (m, 1H), 7.92 (s, 1H), 8.48 (s, 1H), 10.39 (m, 1H), 12.5 (br, 1H); ES⁺ MS: 510 (M+1).

Example Z-47

(4S,12aS)-1-Cyclopropyl-N-[(2,4-difluorophenyl)methyl]-7-hydroxy-4-methyl-6,8-dioxo-1,2,3,4,6,8,12,12a-octahydropyrido[1',2':4,5]pyrazino[1,2-a]pyrimidine-9-carboxamide

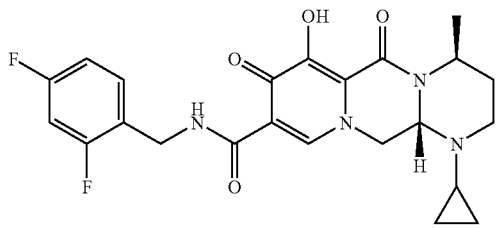

a) 1,1-Dimethylethyl[(1S)-1-methyl-3-oxopropyl]carbamate. To a stirred solution of 1,1-dimethylethyl[(1S)-2-cyano-1-methylethyl]carbamate (0.656 g, 3.56 mmol) in anhydrous ether cooled to −40° C. was added dropwise a 1.0 M solution of diisobutylaluminum hydride in hexanes (14.2 mL, 14.2 mmol) over 20 minutes. Stirring was continued at this temperature for an additional 20 minutes. The yellow solution was quenched with Rochelle's salt and the resultant stirred at room temperature for 1 hour. The solids were filtered off through celite and rinsed with EtOAc. The organics were washed with brine, concentrated, and flash chromatographed (10-100% EtOAc/hexanes) to give 1,1-dimethylethyl [(1S)-1-methyl-3-oxopropyl]carbamate (0.193 g, 30%) as a clear oil. ¹H NMR (400 MHz, CDCl₃) δ 1.22 (d, J=6.8 Hz, 3H), 1.41 (s, 9H), 2.53-2.65 (m, 2H), 4.08-4.13 (m, 1H), 4.63 (m, 1H), 9.74-9.75 (m, 1H).
b) 1,1-Dimethylethyl[(1S)-3-(cyclopropylamino)-1-methylpropyl]carbamate. The protected diamine was prepared using a modified procedure as described in example Z-32. A solution of 1,1-dimethylethyl[(1S)-1-methyl-3-oxopropyl]carbamate (0.178 g, 0.95 mmol) and cyclopropylamine (197 µL, 2.85 mmol) in anhydrous dichloroethane (10 mL) was treated with acetic acid (272 µL, 4.8 mmol) and stirred for 30 minutes. Sodium triacetoxyborohydride (0.444 g, 2.1 mmol) was added and the solution was stirred for 20 hours. The resultant was subjected to a workup and purification procedure as described in example Z-32 to give 1,1-dimethylethyl [(1S)-3-(cyclopropylamino)-1-methylpropyl]carbamate (0.136 g, 63%) as a clear oil. ¹H NMR (400 MHz, CDCl₃) δ 0.32-0.42 (m, 4H), 1.12 (d, J=6.8 Hz, 3H), 1.39-1.51 (m, 10H), 1.58-1.92 (m, 2H), 2.05-2.10 (m, 1H), 2.67-2.80 (m, 2H), 3.71 (m, 1H), 4.78 (m, 1H).
c) [(3S)-3-Aminobutyl]cyclopropylamine dihydrochloride was prepared in a similar manner as described in example Z-29. ¹H NMR (400 MHz, CDCl₃/CD₃OD) δ 0.70-0.75 (m, 2H), 0.90-0.94 (m, 2H), 1.18 (d, J=6.8 Hz, 3H), 1.84-1.94 (m, 1H), 1.97-2.05 (m, 1H), 2.49-2.54 (m, 1H), 2.99-3.04 (m, 2H), 3.23-3.28 (m, 1H),
d)
(4S,12aS)-1-Cyclopropyl-N-[(2,4-difluorophenyl)methyl]-7-hydroxy-4-methyl-6,8-dioxo-1,2,3,4,6,8,12,12a-octahydropyrido[1',2':4,5]pyrazino[1,2-a]pyrimidine-9-carboxamide. The title compound was made in two steps using a similar process to that described in example Z-2. 16a (80 mg, 0.17 mmol) and free based [(3S)-3-aminobutyl]cyclopropylamine (75 mg, 0.59 mmol) were reacted in dichloromethane (2 mL) with acetic acid to give (4S,12S)-cyclopropyl-N-[(2,4-difluorophenyl)methyl]-4-methyl-6,8-dioxo-7-[(phenylmethyl)oxy]-1,2,3,4,6,8,12,12a-octahydropyrido[1',2':4,5]pyrazino[1,2-a]pyrimidine-9-carboxamide (74 mg, 80%) as a film. This material was hydrogenated in a second step as described in example Z-2 to give (4S,12aS)-1-cyclopropyl-N-[(2,4-difluorophenyl)methyl]-7-hydroxy-4-methyl-6,8-dioxo-1,2,3,4,6,8,12,12a-octahydropyrido[1',2':4,5]pyrazino[1,2-a]pyrimidine-9-carboxamide (32 mg, 52%) as an off-white solid. ¹H NMR (400 MHz, CDCl₃) δ 0.37-0.54 (m, 3H), 0.64-0.70 (m, 1H), 1.35 (d, J=7.2 Hz, 3H), 1.45-1.49 (m, 1H), 1.76-1.80 (m, 1H), 2.03-2.12 (m, 1H), 2.86-2.93 (m, 1H), 2.99-3.04 (m, 1H), 4.30 (dd, J=4.0, 13.6 Hz, 1H), 4.49-4.67 (m, 4H), 5.00-5.07 (m, 1H), 6.75-6.82 (m, 2H), 7.32-7.36 (m, 1H), 8.28 (s, 1H), 10.49 (m, 1H), 12.53 (s, 1H); ES⁺ MS: 459 (M+1).

Example Z-48

(4S,12aS)—N-[(2,4-Difluorophenyl)methyl]-7-hydroxy-4-methyl-1-[2-(methyloxy)ethyl]-6,8-dioxo-1,2,3,4,6,8,12,12a-octahydropyrido[1',2':4,5]pyrazino[1,2-a]pyrimidine-9-carboxamide

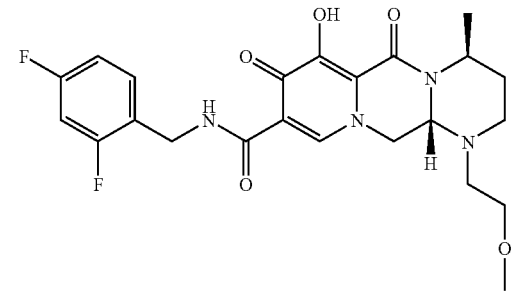

a) [(3S)-3-Aminobutyl][2-(methyloxy)ethyl]amine dihydrochloride. The protected diamine, 1,1-dimethylethyl ((1S)-1-methyl-3-{[2-(methyloxy)ethyl]amino}propyl)carbamate was prepared in a similar manner as described in example Z-47. Subsequently, [(3S)-3-aminobutyl][2-(methyloxy)ethyl]amine dihydrochloride was prepared in a similar manner as described in example Z-29. ¹H NMR (400 MHz, CDCl₃/CD₃OD) δ 1.21 (d, J=5.6 Hz, 3H), 1.93 (m, 1H), 2.04 (m, 1H), 2.98-3.05 (m, 4H), 3.22 (m, 2H), 3.26-3.31 (m, 4H), 8.06 (br, <1H), 8.81 (br, <1H),
b)
(4S,12aS)—N-[(2,4-Difluorophenyl)methyl]-7-hydroxy-4-methyl-1-[2-(methyloxy)ethyl]-6,8-dioxo-1,2,3,4,6,8,12,12a-octahydropyrido[1',2':4,5]pyrazino[1,2-a]pyrimidine-9-carboxamide. The title compound was made in two steps using a similar process to that described in example Z-2. 16a (60 mg, 0.13 mmol) and free based [(3S)-3-aminobutyl][2-(methyloxy)ethyl]amine (53 mg, 0.37 mmol) were reacted in dichloromethane (2 mL) with acetic acid to give (4S,12aS)—N-[(2,4-difluorophenyl)methyl]-4-methyl-1-[2-(methyloxy)ethyl]-6,8-dioxo-7-[(phenylmethyl)oxy]-1,2,3,4,6,8,12,12a-octahydropyrido[1',2':4,5]pyrazino[1,2-a]pyrimidine-9-carboxamide (47 mg, 63%) as a film. This material was hydrogenated in a second step as described in example Z-2 to give (4S,12aS)—N-[2,4-difluorophenyl)methyl]-7-hydroxy-4-methyl-1-[2-(methyloxy)ethyl]-6,8-dioxo-1,2,3,4,6,8,12,12a-octahydropyrido[1',2':4,5]pyrazino[1,2-a]pyrimidine-9- carboxamide (38 mg, 97%) as an off-white solid. $^1$H NMR (400 MHz, CDCl$_3$) δ 1.34 (d, J=7.2 Hz, 3H), 1.49 (m, 1H), 2.03-2.12 (m, 1H), 2.67-2.70 (m, 1H), 2.81-2.92 (m, 2H), 3.06-3.15 (m, 1H), 3.30-3.37 (m, 4H), 3.58-3.63 (m, 1H), 4.20 (dd, J=3.4, 14.2 Hz, 1H), 4.50-4.59 (m, 1H), 4.62-4.65 (m, 3H), 5.00-5.03 (m, 1H), 6.75-6.81 (m, 2H), 7.31-7.37 (m, 1H), 8.27 (s, 1H), 10.46 (s, 1H), 12.54 (s, 1H); ES$^+$ MS: 477 (M+1).

Example Z-49 racemic-(3aS,5aS,13aS)—N-[(2,4-Difluorophenyl)methyl]-11-hydroxy-5-(2-methylpropyl)-10,12-dioxo-2,3,3a,4,5,6a,6,10,12,13a-decahydro-1H-cyclopenta[e]pyrido[1',2':4,5]pyrazino[1,2-a]pyrimidine-9-carboxamide

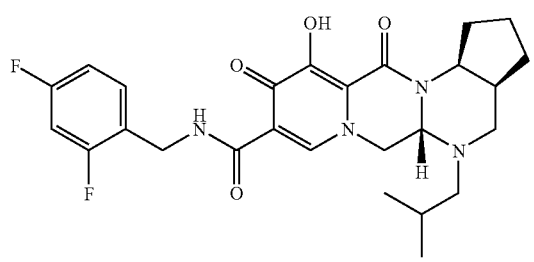

a) racemic-(1S,2S)-2-{[(2-Methylpropyl)amino]methyl}cyclopentanamine hydrochloride.

In a manner similar to example Z-18a-c, from racemic-(1R,2S)-2-({[(1,1-dimethylethyl)oxy]carbonyl}amino)cyclopentanecarboxylic acid (255 mg, 1.11 mmol) was prepared racemic-1,1-dimethylethyl [(1S,2S)-2-(aminomethyl)cyclopentyl]carbamate (153 mg, 64% over 3 steps) as a white green residue. Reductive amination with isobutyraldehyde followed by deprotection as described in Z-38 steps c and d respectively, gave racemic-(1S,2S)-2-{[(2-methylpropyl)amino]methyl}cyclopentanamine hydrochloride (105 mg, 39% over 5 steps from amino acid). $^1$H NMR (methanol-d$_4$/CDCl$_3$) 8.90 (br s, <1H), 8.64 (br s, <1H), 8.28 (m, 1H), 3.97 (br s, 1H), 3.37 (m, 1H), 2.83-2.69 (m, 3H), 2.18-1.69 (m, 7H), 0.996 (m, 6H).

b)
racemic-(3aS,5aS,13aS)—N-[(2,4-Difluorophenyl)methyl]-11-hydroxy-5-(2-methylpropyl)-10,12-dioxo-2,3,3a,4,5,5a,6,10,12,13a-decahydro-1H-cyclopenta[e]pyrido[1',2':4,5]pyrazino[1,2-a]pyrimidine-9-carboxamide. In a manner similar to that described in example Z-35, from racemic-(1S,2S)-2-{[(2-methylpropyl)amino]methyl}cyclopentanamine hydrochloride 105 mg, 0.434 mmol) and 16a (56 mg, 0.119 mmol) was prepared racemic-(3aS,5aS,13aS)—N-[(2,4-difluorophenyl)methyl]-5-(2-methylpropyl)-10,12-dioxo-11-[(phenylmethyl)oxy]-2,3,3a,4,5,5a,6,10,12,13a-decahydro-1H-cyclopenta[e]pyrido[1',2':4,5]pyrazino[1,2-a]pyrimidine-9-carboxamide (52 mg, 74%). This material was deprotected in a second step similar to the procedure described in example Z-37. Thus, from racemic-(3aS,5aS, 13aS)—N-[(2,4-difluorophenyl)methyl]-5-(2-methylpropyl)-10,12-dioxo-11-[(phenylmethyl)oxy]-2,3,3a,4,5,5a,6,10,12,13a-decahydro-1H-cyclopenta[e]pyrido[1',2':4,5]pyrazino[1,2-a]pyrimidine-9-carboxamide (48 mg, 0.081 mmol) and 10% Pd/C (catalytic amount), the title compound was prepared as a white solid after purification by HPLC (30 mg, 75%). $^1$H NMR (CDCl$_3$) 12.59 (s, 1H), 10.42 (s, 1H), 828 (s, 1H), 7.34 (m, 1H), 6.79 (m, 2H), 4.83 (s, 1H), 4.63-4.58 (m, 3H), 4.29 (m, 1H), 4.14 (m, 1H), 2.91 (m, 1H), 2.46-2.32 (m, 3H), 2.15-2.09 (m, 2H), 1.85-1.61 (m, 5H), 1.39 (m, 1H), 0.88 (m, 6H); ES$^+$ MS: 501 (M+1).

Example Z-50

(3R,11aS)—N-[(2,4-Difluorophenyl)methyl]-3-ethyl-6-hydroxy-5,7-dioxo-2,3,5,7,11,11a-hexahydro[1,3]oxazolo[3,2-a]pyrido[1,2-d]pyrazine-8-carboxamide

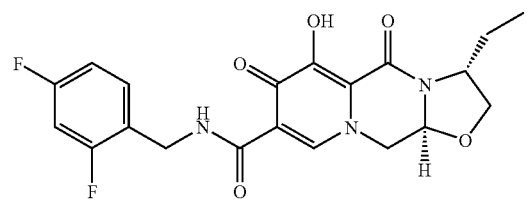

The title compound was made in two steps using a similar process to that described in example Z-2. 16a (40 mg, 0.09 mmol) and (2R)-2-amino-1-butanol (0.02 mL, 0.21 mmol) were reacted in dichloromethane (2 mL) with acetic acid to give (3R,11aS)—N-[(2,4-difluorophenyl)methyl]-3-ethyl-5,7-dioxo-6-[(phenylmethyl)oxy]-2,3,5,7,11,11a-hexahydro[1,3]oxazolo[3,2-a]pyrido[1,2-d]pyrazine-8-carboxamide (40 mg, 93%). This material was hydrogenated in a second step as described in example Z-2 to give (3R,11aS)—N-[(2,4-Difluorophenyl)methyl]-3-ethyl-6-hydroxy-5,7-dioxo-2,3,5,7,11,11a-hexahydro[1,3]oxazolo[3,2-a]pyrido[1,2-d]pyrazine-8-carboxamide (30 mg, 91%) as a white solid. $^1$H NMR (CDCl$_3$) δ 11.49 (br, 1H), 10.28 (m, 1H), 8.35 (s, 1H), 7.34 (m, 1H), 6.79 (m, 2H), 5.30 (m, 1H), 4.62 (m, 2H), 4.45-4.32 (m, 3H), 3.93-3.86 (m, 2H), 2.11 (m, 1H), 1.65 (m, 1H), 0.98 (t, J=7.6 Hz, 3H); ES$^+$ MS: 420 (M+1).

Example Z-51 racemic-(4aS,6aS,14aS)—N-[(2,4-Difluorophenyl)methyl]-12-hydroxy-6-[2-(4-morpholinyl)ethyl]-11,13-dioxo-1,2,3,4,4a,5,6,6a,7,11,13,14a-dodecahydropyrido[1',2':4,5]pyrazino[1,2-a]quinazoline-10-carboxamide

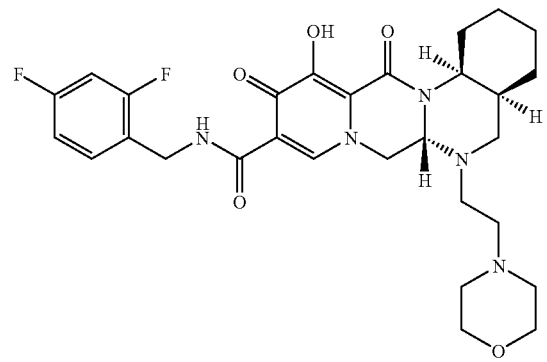

a) racemic-1,1-Dimethylethyl[(1S,2R)-2-formylcyclohexyl]carbamate. An alternative procedure from the one given in example Z-38b follows: To a solution of Dess-Martin Periodane (564 mg, 1.33 mmol) in dichloromethane was added racemic-1,1-dimethylethyl[(1S,2R)-2-(hydroxymethyl)cyclohexyl]carbamate (305 mg, 1.33 mmol, see example Z-38a)

dropwise as a solution in dichloromethane. The reaction was stirred 1 hour at ambient temperature until judged complete by TLC (1:1 hexanes:ethyl acetate KMnO$_4$ stain). The reaction was quenched with aqueous sodium bicarbonate and sodium thiosulfate solutions, extracted with dichloromethane, and the combined organics were dried over sodium sulfate. Silica gel chromatography (0-50% ethyl acetate/hexanes gradient elution) gave racemic-1,1-dimethylethyl[(1S,2R)-2-formylcyclohexyl]carbamate (280, 93%). See example Z-38b for NMR data.

b) racemic-{[(1S,2S)-2-Aminocyclohexyl]methyl}[(2-(4-morpholinyl)ethyl]amine hydrochloride. In a manner similar to that described in example Z-38c-d from racemic-1,1-dimethylethyl[(1S,2R)-2-formylcyclohexyl]carbamate (78 mg, 0.344 mmol, prepared using the procedure from example Z-38b) and [2-(4-morpholinyl)ethyl]amine (67 mg, 0.515 mmol) was prepared racemic-{[(1S,2S)-2-aminocyclohexyl]methyl}[2-(4-morpholinyl)ethyl]amine hydrochloride (95 mg, 78% over 2 steps) as a white solid. $^1$H NMR (methanol-d$_4$/CDCl$_3$) 8.18 (br s, 1H), 3.84-3.493 (m, 11H), 3.19-3.119 (m, 5H), 2.42 (m, 1H), 2.11 (br s, 2H), 1.87-1.17 (m, 10H).

c) racemic-4aS,6aS,14aS)—N-[(2,4-Difluorophenyl)methyl]-12-hydroxy-6-[2-(4-morpholinyl)ethyl]-11,13-dioxo-1,2,3,4,4a5,6,6a,7,11,13,14a-dodecahydropyrido[1',2':4,5]pyrazino[1,2-a]quinazoline-10-carboxamide. In a manner similar to that described in example Z-35, from racemic-{[(1S,2S)-2-aminocyclohexyl]methyl}[2-(4-morpholinyl)ethyl]amine hydrochloride (95 mg, 0.272 mmol) and 16a (45 mg, 0.0957 mmol) was prepared racemic-(4aS,6aS,14aS)—N-[(2,4-difluorophenyl)methyl]-6-[2-(4-morpholinyl)ethyl]-11,13-dioxo-12-[(phenylmethyl)oxy]-1,2,3,4,4a,5,6,6a,7,11,13,14a-dodecahydropyrido[1',2':4,5]pyrazino[1,2-a]quinazoline-10-carboxamide (27 mg, 43%). This material was deprotected in a second step similar to the procedure described in example Z-37. From racemic-(4aS,6aS,14aS)—N-[(2,4-difluorophenyl)methyl]-6-[2-(4-morpholinyl)ethyl]-11,13-dioxo-12-[(phenylmethyl)oxy]-1,2,3,4,4a,5,6,6a,7,11,13,14a-dodecahydropyrido[1',2':4,5]pyrazino[1,2-a]quinazolino-10-carboxamide (27 mg, 0.0408 mmol) and 10% Pd/C (1 mg) the title compound was prepared as a white solid after purification by HPLC. $^1$H NMR (CDCl$_3$) 12.30 (br s, <1H), 10.41 (br s, 1H), 8.29 (s, 1H), 7.34 (m, 2H), 6.78 (m, 2H), 4.76 (m, 1H), 4.62-4.54 (m, 3H), 4.29 (m, 2H), 3.65 (m, 4H), 3.01 (m, 1H), 2.76 (m, 2H), 2.58-2.42 (m, 7H), 2.21 (m, 1H), 1.89-1.23 (m, 8H); ES$^+$ MS: 572 (M+1).

Example Z-52 racemic-(3aR,5aR,13aS)—N-[(2,4-Difluorophenyl)methyl]-11-hydroxy-10,12-dioxo-1,2,3,3a,4,5a,6,10,12,13a-decahydrocyclopenta[d]pyrido[1',2':4,5]pyrazino[2,1-b][1,3]oxazine-9-carboxamide

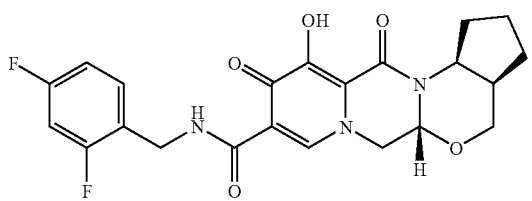

a) racemic-1,1-Dimethylethyl[(1S,2R)-2-(hydroxymethyl)cyclopentyl]carbamate. racemic-(1R,2S)-2-({[1,1-Dimethylethyl)oxy]carbonyl}amino)cyclopentanecarboxylic acid (22 mg, 0.096 mmol) was dissolved in tetrahydrofuran and placed in an ice-water bath. Triethylamine was added, followed by the slow addition of methyl chloroformate. The reaction was stirred ten minutes in the ice-bath and sodium borohydride was added. Methanol was then added slowly and stirring was continued for two hours while the ice-bath expired. 1 M Potassium hydrogen sulfate was added, the reaction was partially concentrated, and product was extracted with dichloromethane. The combined organics were washed with sodium bicarbonate, brine, and dried over sodium sulfate. Removal of solvents under reduced pressure afforded racemic-1,1-dimethylethyl[(1S,2R)-2-(hydroxymethyl)cyclopentyl]carbamate (25 mg, >100%). $^1$H NMR (CDCl$_3$) 4.50 (br s, 1H), 4.06 (m, 1H), 3.54 (m, 1H), 3.37 (m, 1H), 2.09 (m, 1H), 1.96 (m, 1H), 1.64 (m, 3H), 1.52 (m, 1H), 1.43 (s, 9H), 1.11 (m, 2H).

b) racemic-[(1R,2S)-2-Aminocyclopentyl]methanol hydrochloride. In a manner similar to that described in example, from racemic-1,1-dimethylethyl [(1S,2R)-2-(hydroxymethyl)cyclopentyl]carbamate and 4 N HCl was prepared racemic-[(1R,2S)-2-aminocyclopentyl]methanol hydrochloride (20 mg, quantitative). $^1$H NMR (methanol-d4-CDCl$_3$) 7.76 (br s, <1H), 3.73 (m, 1H), 3.61-3.28 (m, 3H), 2.27 (br s, 1H), 2.01 (m, 2.01 (m, 1H), 1.74-1.70 (m, 2H), 1.56-1.42 (m, 2H), 1.16 (br s, 1H), 1.05 (br s, 1H).

c) racemic-(3aR,13aS)—N-[(2,4-Difluorophenyl)methyl]-11-hydroxy-10,12-dioxo-1,2,3,3a,4,5a,6,10,12,13a-decahydrocyclopenta[d]pyrido[1',':4,5]pyrazino[2,1-b][1,3]oxazine-9-carboxamide. In a manner similar to that described in example Z-35, from racemic-[(1R,2S)-2-aminocyclopentyl]methanol hydrochloride (20 mg, 0.132 mmol) and 16a (24 mg, 0.051 mmol) was prepared racemic-(3aR,13aS)—N-[(2,4-difluorophenyl)methyl]-10,12-dioxo-11-[(phenylmethyl)oxy]-1,2,3,3a,4,5a,6,10,12,13a-decahydrocyclopenta[d]pyrido[1',2':4,5]pyrazino[2,1-b][1,3]oxazine-9-carboxamide (7 mg, 26%) as a white solid. This material was deprotected in a second step similar to the procedure described in example Z-37. Thus, from racemic-(3aR,13aS)—N-[(2,4-difluorophenyl)methyl]-10,12-dioxo-11-[(phenylmethyl)oxy]-1,2,3,3a,4,5a,6,10,12,13a-decahydrocyclopenta[d]pyrido[1',':4,5]pyrazino[2,1-b][1,3]oxazine-9-carboxamide (7 mg, 0.012 mmol) and 10% Pd/C (1 mg), was obtained racemic-(3aR,13aS)—N-[(2,4-difluorophenyl)methyl]-11-hydroxy-10,12-dioxo-1,2,3,3a,4,5a,6,10,12,13a-decahydrocyclopenta[d]pyrido[1',':4,5]pyrazino[2,1-b][1,3]oxazine-9-carboxamide (4 mg, 72%) white solid. $^1$H NMR (CDCl$_3$) 12.20 (br s, 1H), 10.37 (br s, 1H), 8.31 (s, 1H), 7.35 (m, 1H), 6.80 (m, 2H), 5.16 (m, 1H), 4.77 (m, 1H), 4.64 (m, 2H), 4.28 (m, 1H), 4.09 (m, 1H), 3.97 (m, 1H), 3.45 (m, 1H), 2.49-2.20 (m, 2H), 1.89-1.58 (m, 4H), 0.936-0.840 (m, 1H); ES$^+$ MS: 446 (M+1).

Example Z-53 racemic-(4aS,6aS,14aS)—N-[(2,4-Difluorophenyl)methyl]-12-hydroxy-6-methyl-11,13-dioxo-1,2,3,4,4a,5,6,6a,7,11,13,14a-dodecahydropyrido[1',2':4,5]pyrazino[1,2-a]quinazoline-10-carboxamide

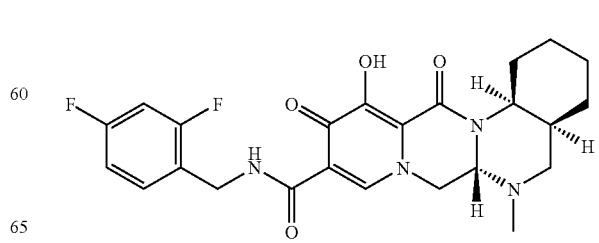

a) racemic-{[(1S,2S)-2-Aminocyclohexyl]methyl}methylamine hydrochloride. In a manner similar to that described in example Z-38c-d from racemic-1,1-dimethylethyl[(1S,2R)-2-formylcyclohexyl]-carbamate (0.410 mmol) and methyl amine (0.5 mL of a 2 M tetrahydrofuran solution) was prepared racemic-{[(1S,2S)-2-aminocyclohexyl]methyl}methylamine hydrochloride in two steps as a white solid (46 mg, 53% 2 steps). $^1$H NMR (methanol-d$_4$/CDCl$_3$) 9.05 (br s<1H), 8.72 (br s, <1H), 8.24 (br s, 1H), 3.34 (m, 1H), 3.29 (m, 1H), 2.85 (br s, 1H), 2.66 (br s, 4H), 2.38 (br s, 1H), 2.07-1.83 (m, 2H), 1.67-1.14 (m, 6H), b)
racemic-(4aS,6aS,14aS)—N-[(2,4-Difluorophenyl)methyl]-12-hydroxy-6-methyl-11,13-dioxo-1,2,3,4,4a,5,6,6a,7,11,13,14a-dodecahydropyrido[1',2':4,5]pyrazino[1,2-a]quinazoline-10-carboxamide. In a manner similar to that described in example Z-35, from racemic-{[(1S,2S)-2-aminocyclohexyl]methyl}methylamine hydrochloride (46 mg, 0.215 mmol) and 16a (35 mg, 0.0744 mmol) was prepared racemic-(4aS,6aS,14aS)—N-[(2,4-difluorophenyl)methyl]-6-methyl-11,13-dioxo-12-[(phenylmethyl)oxy]-1,2,3,4,4a,5,6,6a,7,11,13,14a-dodecahydropyrido[1',2':4,5]pyrazino[1,2-a]quinazoline-10-carboxamide (17 mg, 41%) as a white solid. This material was deprotected in a second step similar to the procedure described in example Z-37. Thus, from racemic-(4aS,6aS,14aS)—N-[(2,4-difluorophenyl)methyl]-6-methyl-11,13-dioxo-12-[(phenylmethyl)oxy]-1,2,3,4,4a,5,6,6a,7,11,13,14a-dodecahydropyrido[1',2':4,5]pyrazino[1,2-a]quinazoline-10-carboxamide (17 mg, 0.0302 mmol) and 10% Pd/C (1 mg) was prepared the title compound as a white solid (9 mg, 64%). $^1$H NMR (CDCl$_3$) 10.44 (m, 1H), 8.29 (s, 1H), 7.34 (m, 1H), 6.79 (m, 2H), 4.78 (m, 1H), 4.62 (br s, 2H), 4.29 (br s, 2H), 3.41 (s, 1H), 2.92 (m, 1H), 2.66 (m, 1H), 2.35-2.25 (m, 4H), 1.90-1.74 (m, 2H), 1.67-1.24 (m, 6H); ES$^+$ MS: 473 (M+1).

Example Z-54 racemic-(4aS,6aS,14aS)—N-[(2,4-Difluorophenyl)methyl]-12-hydroxy-6-[2-(methyloxy)ethyl]-11,13-dioxo-1,2,3,4,4a,5,6,6a,7,11,13,14a-dodecahydropyrido[1',2':4,5]pyrazino[1,2-a]quinazoline-10-carboxamide

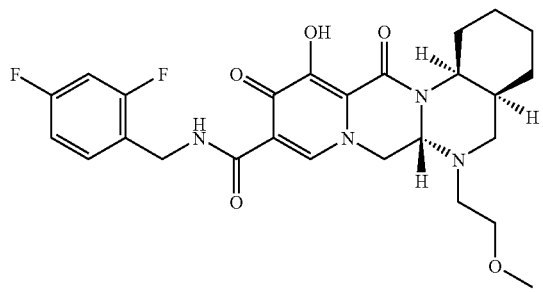

a) racemic-{[(1S,2S)-2-Aminocyclohexyl]methyl}[2-(methyloxy)ethyl]amine hydrochloride.

In a manner similar to that described in example Z-38c-d from racemic-1,1-dimethylethyl [(1S,2R)-2-formylcyclohexyl]carbamate (93 mg, 0.410 mmol) and [2-(methyloxy)ethyl]amine (0.05 mL, 0.615 mmol) was prepared in two steps racemic-{[(1S,2S)-2-aminocyclohexyl]methyl}[2-(methyloxy)ethyl]amine hydrochloride (63 mg, 60% 2 steps) as a white solid. $^1$H NMR (methanol-d$_4$/CDCl$_3$) 9.02 (br s, <1H), 8.78 (br s, <1, H), 8.29 (br s, 1H), 3.69 (br s, 2H), 3.46 (s, 3H), 3.36-3.18 (m, 4H), 2.97 (br s, 1H), 2.46 (br s, 1H), 1.86-1.40 (m, 8H).

b)
racemic-4aS,6aS,14aS)—N-[(2,4-Difluorophenyl)methyl]-12-hydroxy-6-[2-(methyloxy)ethyl]-11,13-dioxo-1,2,3,4,4a,5,6,6a,7,11,13,14a-dodecahydropyrido[1',2':4,5]pyrazino[1,2-a]quinazoline-10-carboxamide. In a manner similar to that described in example Z-35, from racemic-{[(1S,2S)-2-aminocyclohexyl]methyl}[2-(methyloxy)ethyl]amine hydrochloride (63 mg. 0.244 mmol) and 16a (40 mg, 0.0851 mmol) was prepared racemic-(4aS,6aS,14aS)—N-[(2,4-difluorophenyl)methyl]-6-[2-(methyloxy)ethyl]-11,13-dioxo-12-[(phenylmethyl)oxy]-1,2,3,4,4a,5,6,6a,7,11,13,14a-dodecahydropyrido[1',2':4,5]pyrazino[1,2-a]quinazoline-10-carboxamide (44 mg, 81%) as a white solid. This material was deprotected in a second step similar to the procedure described in example Z-37. Thus, from racemic (4aS,6aS,14aS)—N-[(2,4-difluorophenyl)methyl]-6-[2-(methyloxy)ethyl]-11,13-dioxo-12-[(phenylmethyl)oxy]-1,2,3,4,4a5,6,6a,7,11,13,14a-dodecahydropyrido[1',2':4,5]pyrazino[1,2-a]quinazoline-10-carboxamide (44 mg, 0.0726 mmol) and 10% Pd/C (1 mg) the title compound was prepared as a white solid (37 mg, quantitative). $^1$H NMR (CDCl$_3$) 12.60 (br s, 1H), 10.47 (m, 1H), 8.28 (s, 1H), 7.34 (m, 1H), 6.79 (m, 2H), 4.81 (m, 1H), 4.64 (m 3H), 4.51 (m, 1H), 4.26 (m, 1H), 3.63 (m, 1H), 3.31 (s, 3H), 3.19 (m, 1H), 2.86 (m, 1H), 2.67 (2m, 2H), 2.21 (m, 1H), 1.91-1.78 (m, 2H), 1.67-1.52 (m, 4H), 1.46-1.24 (m, 3H); ES$^+$ MS: 517 (M+1).

Example Z-55 racemic-(4aS,6aS,14aS)-6-[2-(Acetylamino)ethyl]-N-[(2,4-difluorophenyl)methyl]-12-hydroxy-11,13-dioxo-1,2,3,4,4a,5,6,6a,7,11,13,14a-dodecahydropyrido[1',2':4,5]pyrazino[1,2-a]quinazoline-10-carboxamide

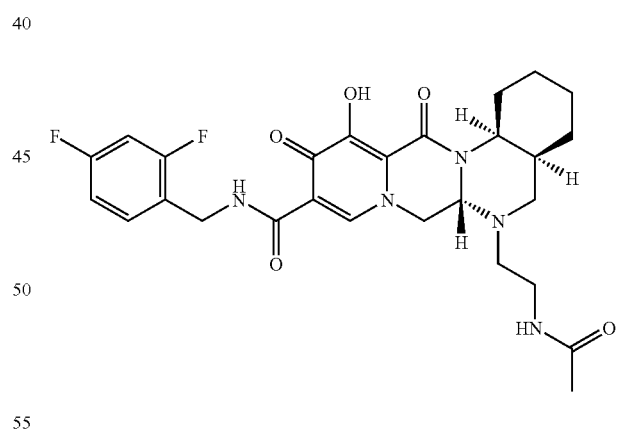

a) racemic-N-[2-({[(1S,2S)-2-Aminocyclohexyl]methyl}amino)ethyl]acetamide hydrochloride. In a manner similar to that described in example Z-38c-d from racemic-1,1-dimethylethyl[(1S,2R)-2-formylcyclohexyl]carbamate (93 mg, 0.41 mmol) and N-(2-aminoethyl)acetamide (63 mg, 0.615 mmol), racemic-N-[2-({[(1S,2S)-2-aminocyclohexyl]methyl}amino)ethyl]acetamide hydrochloride was prepared in two steps as a white solid (82 mg), 71% 2 steps). $^1$H NMR (methanol-d$_4$/CDCl$_3$) 8.86 (br s, 1H), 8.29 (br s, 1H), 3.62-3.51 (m, 3H), 3.40-3.28 (m, 4H), 3.22-2.93 (m, 3H), 2.47 (m, 1H), 2.08-2.06 (m, 4H), 1.83-1.75 (m, 2H), 1.56-1.44 (m, 3H), 1.23 (m, 1H).

b)

racemic-4aS,6aS,14aS)-6-[2-(Acetylamino)ethyl]-N-[(2,4-difluorophenyl)methyl]-12-hydroxy-11,13-dioxo-1,2,3,4,4a,5,6,6a,7,11,13,14a-dodecahydropyrido[1',2':4,5]pyrazino[1,2-a]quinazoline-10-carboxamide. In a manner similar to that described in example Z-35, from racemic-N-[2-({[(1S,2S)-2-aminocyclohexyl]methyl}amino)ethyl]acetamide hydrochloride (82 mg, 0.349 mmol) and 16a (50 mg, 0.106 mmol) was prepared the title compound (24 mg, 36%). This material was deprotected in a second step similar to the procedure described in example Z-37. Thus, from racemic (4aS,6aS,14aS)-6-[2-(acetylamino)ethyl]-N-[(2,4-difluorophenyl)methyl]11,13-dioxo-12-[(phenylmethyl)oxy]-1,2,3,4,4a,5,6,6a,7,11,13,14a-dodecahydropyrido[1',2':4,5]pyrazino[1,2-a]quinazoline-10-carboxamide (24 mg, 0.0379 mmol) and 10% Pd/C (1 mg) was prepared the title compound as a white solid after purification by HPLC. ¹H NMR (CDCl₃) 12.59 (s, 1H), 10.44 (s, 1H), 8.35 (s, 1H), 7.32 (m, 1H), 6.79 (m, 2H), 5.86 (s, 1H), 4.78 (m, 1H), 4.61-4.50 (m, 3H), 4.30 (m, 1H), 3.35 (m, 1H), 3.18 (m, 1H), 2.96 (m, 1H), 2.76 (m, 2H), 2.48 (m, 1H), 2.19 (m, 1H), 1.89-1.23 (m, 12H): ES⁺ MS: 544 (M+1).

Example Z-56

(3S,11aR)—N-[(2,4-Difluorophenyl)methyl]-3-ethyl-6-hydroxy-5,7-dioxo-2,3,5,7,11,11a-hexahydro[1,3]oxazolo[3,2-a]pyrido[1,2-d]pyrazine-8-carboxamide

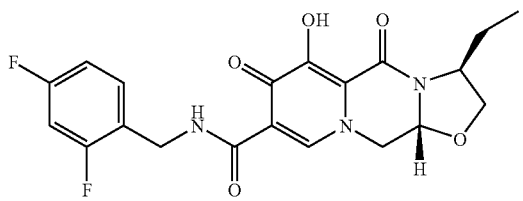

The title compound was made in two steps using a similar process to that described in example Z-2. 16a (40 mg, 0.09 mmol) and (2S)-2-amino-1-butanol (0.1 mL) were reacted in dichloromethane (2 mL) with acetic acid to give (3S,11aR)—N-[(2,4-difluorophenyl)methyl]-3-ethyl-5,7-dioxo-6-[(phenylmethyl)oxy]-2,3,5,7,11,11a-hexahydro[1,3]oxazolo[3,2-a]pyrido[1,2-d]pyrazine-8-carboxamide (39 mg, 90%). This material was hydrogenated in a second step as described in example Z-2 to give (3S,11aR)—N-[(2,4-difluorophenyl)methyl]-3-ethyl-6-hydroxy-5,7-dioxo-2,3,5,7,11,11a-hexahydro[1,3]oxazolo[3,2-a]pyrido[1,2-d]pyrazine-8-carboxamide (37 mg, 99%) as a tinted white solid. ¹H NMR (CDCl₃) δ 11.47 (br, 1H), 10.26 (m, 1H), 8.35 (s, 1H), 7.32 (m, 1H), 6.77 (m, 2), 5.29 (m, 1H), 4.60 (m, 2H), 4.47-4.32 (m, 3H), 3.93-3.85 (m, 2H), 2.08 (m, 1H), 1.68 (m, 1H), 0.95 (t, J=7.6 Hz, 3H); ES⁺ MS: 420 (M+1).

Example Z-57

(3S,11aR)-3-Butyl-N-[(2,4-difluorophenyl)methyl]-6-hydroxy-5,7-dioxo-2,3,5,7,11,11a-hexahydro[1,3]oxazolo[3,2-a]pyrido[1,2-d]pyrazine-8-carboxamide

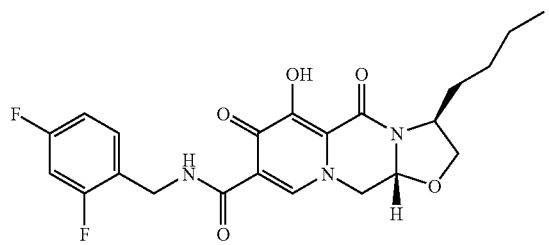

The title compound was made in two steps using a similar process to that described in example Z-2. 16a (40 mg, 0.09 mmol) and (2S)-2-amino-1-hexanol (100 mg) were reacted in dichloromethane (2 mL) with acetic acid to give (3S,11aR)-3-butyl-N-[(2,4-difluorophenyl)methyl]-5,7-dioxo-6-[(phenylmethyl)oxy]-3-2,3,5,7,11,11a-hexahydro[1,3]oxazolo[3,2-a]pyrido[1,2-d]pyrazine-8-carboxamide (43 mg, 94%). This material was hydrogenated in a second step as described in example Z-2 to give (3S,11aR)-3-butyl-N-[(2,4-difluorophenyl)methyl]-6-hydroxy-5,7-dioxo-2,3,5,7,11,11a-hexahydro[1,3]oxazolo[3,2-a]pyrido[1,2-d]pyrazine-8-carboxamide (33 mg, 92%) as a tinted white solid. ¹H NMR (CDCl₃) δ 11.48 (br, 1H), 10.27 (br, 1H), 8.36 (br, 1H), 7.31 (m, 1H), 6.77 (m, 2), 5.28 (m, 1H), 4.59-4.36 (m, 5H), 3.83 (m, 2H), 2.08 (m, 1H), 1.58 (m, 1H), 1.39-1.23 (m, 4H), 0.90 (t, J=6.8 Hz, 3H); ES⁺ MS: 448 (M+1).

Example Z-58

(3S,11aR)—N-[(2,4-Difluorophenyl)methyl]-6-hydroxy-3-[(4-hydroxyphenyl)methyl]-5,7-dioxo-2,3,5,7,11,11a-hexahydro[1,3]oxazolo[3,2-a]pyrido[1,2-d]pyrazine-8-carboxamide

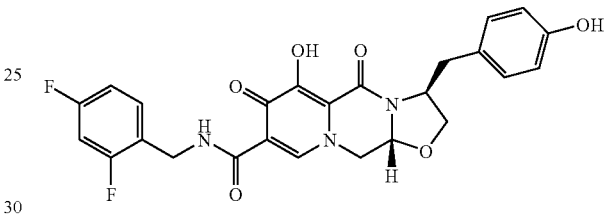

The title compound was made in two steps using a similar process to that described in example Z-2. 16a (40 mg, 0.09 mmol) and 4-[(2S)-2-amino-3-hydroxypropyl]phenol (43 mg, 0.21 mmol) were reacted in dichloromethane (2 mL) with acetic acid to give (3S,11aR)—N-[(2,4-difluorophenyl)methyl]-3-[(4-hydroxyphenyl)methyl]-5,7-dioxo-6-[(phenylmethyl)oxy]-2,3,5,7,11,11a-hexahydro[1,3]oxazolo[3,2-a]pyrido[1,2-d]pyrazine-8-carboxamide (10 mg, 20%). This material was hydrogenated in a second step as described in example Z-2 and purified via preparative HPLC to give (3S,11aR)—N-[(2,4-difluorophenyl)methyl]-6-hydroxy-3-[(4-hydroxyphenyl)methyl]-5,7-dioxo-2,3,5,7,11,11a-hexahydro[1,3]oxazolo[3,2-a]pyrido[1,2-d]pyrazine-8-carboxamide (7 mg, 63%) as a white solid. ¹H NMR (CD₃OD) δ 10.43 (m, 1H), 8.34 (s, 1H), 7.33 (m, 1H), 7.00 (d, J=8.4 Hz, 2H), 6.82 (m, 2H), 6.71 (d, J=8.4 Hz, 2H), 5.05 (m, 1H), 4.67-4.57 (m, 4H), 4.21 (dd, J=8.8, 7.2 Hz, 1H), 3.94 (dd, J=8.8, 6.4 Hz, 1H), 3.21 (dd, J=13.2, 3.2 Hz, 1H), 2.90 (dd, J=13.6, 8.8 Hz, 1H); ES⁺ MS: 498 (M+1).

Example Z-59

(4S,12aS)-1-Cyclobutyl-N-[(2,4-difluorophenyl)methyl]-7-hydroxy-4-methyl-6,8-dioxo-1,2,3,4,6,8,12,12a-octahydropyrido[1',2':4,5]pyrazino[1,2-a]pyrimidine-9-carboxamide

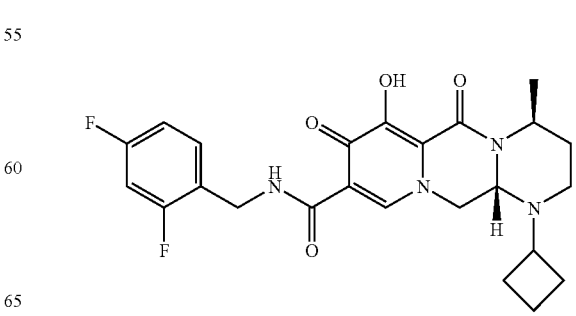

a) [(3S)-3-Aminobutyl]cyclobutylamine dihydrochloride was prepared in a similar manner as described in example Z-47. ¹H NMR (400 MHz, CDCl₃/CD₃OD) δ 1.23 (d, J=6.4 Hz, 3H), 1.69-2.26 (m, 8H), 2.83 (m, 2H), 3.31-3.33 (m, 1H), 3.55 (m, 1H), 8.08 (br, <1H), 9.07 (br. <1H), b) (4S,12aS)-1-Cyclobutyl-N-[2,4-difluorophenyl)methyl]-7-hydroxy-4-methyl-6,8-dioxo-1,2,3,4,6,8,12,12a-octahydropyrido[1',2':4,5]pyrazino[1,2-s]pyrimidine-9-carboxamide. The title compound was made in two steps using a similar process to that described in example Z-2. 16a (80 mg, 0.17 mmol) and free based [(3S)-3-aminobutyl]cyclobutylamine (96 mg, 0.68 mmol) were reacted in dichloromethane (2 mL) with acetic acid to give (4S,12aS)-1-cyclobutyl-N-[(2,4-difluorophenyl)methyl]-4-methyl-6,8-dioxo-7-[(phenylmethyl)oxy]-1,2,3,4,6,8,12,12a-octahydropyrido[1',2':4,5]pyrazino[1,2-a]pyrimidine-9-carboxamide (68 mg, 70%) as a film. This material was hydrogenated in a second step as described in example Z-2 to give (4S,12aS)-1-cyclobutyl-N-[(2,4-difluorophenyl)methyl]-7-hydroxy-4-methyl-6,8-dioxo-1,2,3,4,6,8,12,12a-octahydropyrido[1,2-a]pyrimidine-9-carboxamide (57 mg, 100%) as an off-white solid. ¹H NMR (400 MHz, CDCl₃) δ 1.31 (d, J=6.8 Hz, 3H), 1.46-1.70 (m, 4H), 1.91-2.12 (m, 4H), 2.52 (m, 1H), 2.90-2.93 (m, 1H), 3.06 (m, 1H), 4.16-4.29 (m, 3H), 4.57-4.66 (m, 2H), 4.99-5.05 (m, 1H), 6.75-6.82 (m, 2H), 7.32-7.38 (m, 1H), 8.20 (s, 1H), 10.44 (s, 1H), 12.51 (s, 1H); ES⁺ MS: 473 (M+1).

Example Z-60

(4S,12aS)—N-[(2,4-Difluorophenyl)methyl]-7-hydroxy-4-methyl-6,8-dioxo-1-(tetrahydro-2H-thiopyran-4-yl)-1,2,3,4,6,8,12,12a-octahydropyrido[1',2':4,5]pyrazino[1,2-a]pyrimidine-9-carboxamide

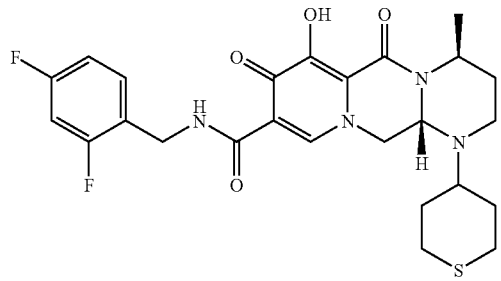

a) [(3S)-3-Aminobutyl]tetrahydro-2H-thiopyran-4-ylamine dihydrochloride was prepared in a similar manner as described in example Z-47. ¹H NMR (400 MHz, CDCl₃/CD₃OD) δ 1.21 (d, J=6.4 Hz, 3H), 1.65-1.75 (m, 2H), 1.90-2.10 (m, 2H), 2.35 (m, 2H), 2.56-2.61 (m, 4H), 2.92-2.98 (m, 3H), 3.27-3.31 (m, 1H), 8.05 (br, <1H), 8.90 (br, <1H).

b) (4S,12aS)—N-[(2,4-difluorophenyl)methyl]-7-hydroxy-4-methyl-6,8-dioxo-1-(tetrahydro-2H-thiopyran-4-yl)-1,2,3,4,6,8,12,12a-octahydropyrido[1',2':4,5]pyrazino[1,2-a]pyrimidine-9-carboxamide. The title compound was made in two steps using a similar process to that described in example Z-2. 16a (80 mg, 0.17 mmol) and free based [(3S)-3-aminobutyl]tetrahydro-2H-thiopyran-4-ylamine (108 mg, 0.58 mmol) were reacted in dichloromethane (2 mL) with acetic acid to give (4S,12aS)—N-[(2,4-difluorophenyl)methyl]-4-methyl-6,8-dioxo-7-[(phenylmethyl)oxy]-1-(tetrahydro-2H-thiopyran-4-yl)-1,2,3,4,6,8,12,12a-octahydropyrido[1',2':4,5]pyrazino[1,2-a]pyrimidine-9-carboxamide (56 mg, 54%) as a film. This material was debenzylated in a second step to in a manner similar to Z-26 to give (4S,12aS)—N-[(2,4-difluorophenyl)methyl]-7-hydroxy-4-methyl-6,8-dioxo-1-(tetrahydro-2H-thiopyran-4-yl)-1,2,3,4,6,8,12,12a-octahydropyrido[1',2':4,5]pyrazino[1,2-a]pyrimidine-9-carboxamide (56 mg, >100%) as an off-white solid. ¹H NMR (400 MHz, CDCl₃) δ 1.30 (d, J=6.8 Hz, 3H), 1.54-1.58 (m, 1H), 1.72-1.82 (m, 3H), 1.97-2.11 (m, 2H), 2.60-2.76 (5H), 2.86 (m, 2H), 4.17-4.30 (m, 2H), 4.62-4.66 (m, 3H), 4.92-4.96 (m, 1H), 6.75-6.82 (m, 2H), 7.32-7.38 (m, 1H), 8.31 (s, 1H), 10.46 (s, 1H), 12.48 (s, 1H); ES⁺ MS: 519 (M+1).

Example Z-61

(4S,12aS)—N-[(2,4-Difluorophenyl)methyl]-7-hydroxy-1,4-bis(2-methylpropyl)-6,8-dioxo-1,2,3,4,6,8,12,12a-octahydropyrido[1',2':4,5]pyrazino[1,2-a]pyrimidine-9-carboxamide

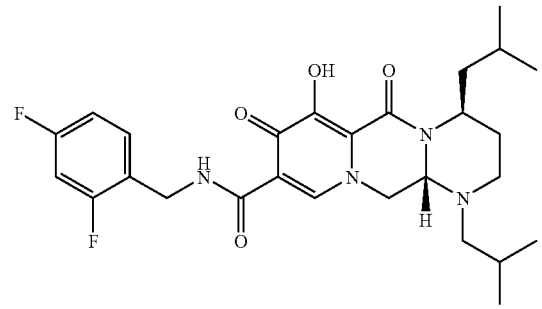

a) [(3S)-3-Amino-5-methylhexyl](2-methylpropyl)amine dihydrochloride was prepared in a similar manner as described in example Z-32. ¹H NMR (400 MHz, CDCl₃/CD₃OD) δ 0.87 (d, J=6.4 Hz, 6H), 0.97 (d, J=6.8 Hz, 6H), 1.34-1.41 (m, 1H), 1.45-1.52 (m, 1H), 1.58-1.66 (m, 1H), 2.01-2.13 (m, 2H), 2.72-2.73 (m, 2H), 3.03-3.06 (m, 2H), 3.29 (m, 2H), 8.07 (br, <1H), 8.71 (br, <1H).

b) (4S,12aS)—N-[(2,4-Difluorophenyl)methyl]-7-hydroxy-1,4-bis(2-methylpropyl)-6,8-dioxo-1,2,3,4,6,8,12,12a-octahydropyrido[1',2':4,5]pyrazino[1,2-a]pyrimidine-9-carboxamide. The title compound was made in two steps using a similar process to that described in example Z-2. 16a (80 mg, 0.17 mmol) and free based [(3S)-3-amino-5-methylhexyl](2-methylpropyl)amine (117 mg, 0.63 mmol) were reacted in dichloromethane (2 mL) with acetic acid to give (4S,12aS)—N-[(2,4-difluorophenyl)methyl]-1,4-bis(2-methylpropyl)-6,8-dioxo-7-[(phenylmethyl)oxy]-1,2,3,4,6,8,12,12a-octahydropyrido[1',2':4,5]pyrazino[1,2-a]pyrimidine-9-carboxamide (68 mg, 66%) as a film. This material was hydrogenated in a second step as described in example Z-2 to give (4S,12aS)—N-[(2,4-difluorophenyl)methyl]-7-hydroxy-1,4-bis(2-methylpropyl)-6,8-dioxo-1,2,3,4,6,8,12,12a-octahydropyrido[1',2':4,5]pyrazino[1,2-a]pyrimidine-9-carboxamide (56 mg, 97%) as an off-white solid. ¹H NMR (400 MHz, CDCl₃) δ 0.74 (d, J=6.4 Hz, 3H), 0.84 (d, J=6.4 Hz, 3H), 0.97-1.00 (m, 6H), 1.37-1.83 (m, 5H), 2.03-2.12 (m, 2H), 2.21-2.28 (m, 1H), 2.77 (m, 1H), 2.90-2.93 (m, 1H), 4.19-4.40 (m, 3H), 4.59-4.70 (m, 2H), 4.96-4.97 (m, 1H), 6.77-6.83 (m, 2H), 7.33-7.39 (m, 1H), 8.28 (s, 1H), 10.47 (s, 1H), 12.59 (br, 1H); ES+ MS: 517 (M+1).

Example Z-62 racemic-4aS,6aS,14aS)—N-[(2,4-Difluorophenyl)methyl]-12-hydroxy-6-(2-hydroxyethyl)-11,13-dioxo-1,2,3,4,4a,5,6,6a,7,11,13,14a-dodecahydropyrido[1',2':4,5]pyrazino[1,2-a]quinazoline-10-carboxamide

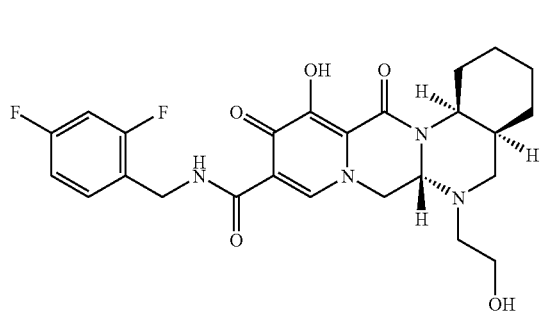

a) racemic-2-({[(1S,2S)-2-Aminocyclohexyl]methyl}amino)ethanol hydrochloride. In a manner similar to that described in example Z-55a, from racemic-1,1-dimethylethyl [(1S,2R)-2-formylcyclohexyl]carbamate (112 mg, 0.497 mmol) and 2-aminoethanol (0.04 mL 0.746 mmol) was prepared racemic-2-({[(1S,2S)-2-aminocyclohexyl]methyl}amino)ethanol bis-hydrochloride in two steps (102 mg, 84% over 2 steps). $^1$H NMR (methanol-$d_4$/CDCl$_3$) 8.81-8.40 (m, <2H), 8.16 (br s, 1H), 4.02-3.93 (m, 2H), 3.80 (br s, 2H), 3.53 (m, 1H), 3.36-2.93 (m, 6H), 2.41 (br s, 1H), 2.05 (m, 1H), 1.75-1.41 (m, 4H).

b) racemic-(4aS,6aS,14aS)—N-[(2,4-Difluorophenyl)methyl]-12-hydroxy-6-(2-hydroxyethyl)-11,13-dioxo-1,2,3,4,4a,5,6,6a,7,11,13,14a-dodecahydropyrido[1',2':4,5]pyrazino[1,2-a]quinazoline-10-carboxamide. In a manner similar to that described in example Z-35, from 16a (45 mg, 0.0957 mmol) and racemic-2-({[(1S,2S)-2-aminocyclohexyl]methyl}amino)ethanol hydrochloride (102 mg, 0.418 mmol) was prepared racemic-(4aS,6aS,14aS)—N-[(2,4-difluorophenyl)methyl]-6-(2-hydroxyethyl)-11,13-dioxo-12-[(phenylmethyl)oxy]-1,2,3,4,4a,5,6,6a,7,11,13,14a-dodecahydropyrido[1',2':4,5]pyrazino[1,2-a]quinazoline-10-carboxamide (7 mg, 12%) as a white solid after silica gel chromatography (1-12% methanol/dichloromethane gradient elution). This material was deprotected in a second step similar to the procedure described in example Z-37. Thus, from racemic-(4aS,6aS,14aS)—N-[(2,4-difluorophenyl)methyl]-6-(2-hydroxyethyl)-11,13-dioxo-12-[(phenylmethyl)oxy]-1,2,3,4,4a,5,6,6a,7,11,13,14a-dodecahydropyrido[1',2':4,5]pyrazino[1,2-a]quinazoline-10-carboxamide (7 mg, 0.0118 mmol) the title compound was prepared after purification by HPLC (3 mg, 50%). $^1$H NMR (CDCl$_3$) 12.57 (br s, 1H), 10.45 (m, 1H), 8.29 (s, 1H), 7.34 (m, 1H), 6.78 (m, 2H), 4.80 (m, 1H), 4.71 (s, 1H), 4.62 (m, 2H), 4.44 (m, 1H), 4.33 (m, 1H), 3.75 (m, 1H), 3.62-3.20 (m, 3H), 3.13 (m, 1H), 2.74-2.71 (m, 2H), 2.24 (m, 1H), 1.90-137 (m, 12H), 1.27-1.23 (m, 3H) 1.12 (m, 1H); ES+ MS: 503 (M+1).

Example Z-63 racemic-(4aS,6aS,14aS)-6-Cyclopropyl-N-[(2,4-difluorophenyl)methyl]-12-hydroxy-11,13-dioxo-1,2,3,4,4a,5,6,6a,7,11,13,14a-dodecahydropyrido[1',2':4,5]pyrazino[1,2-a]quinazoline-10-carboxamide

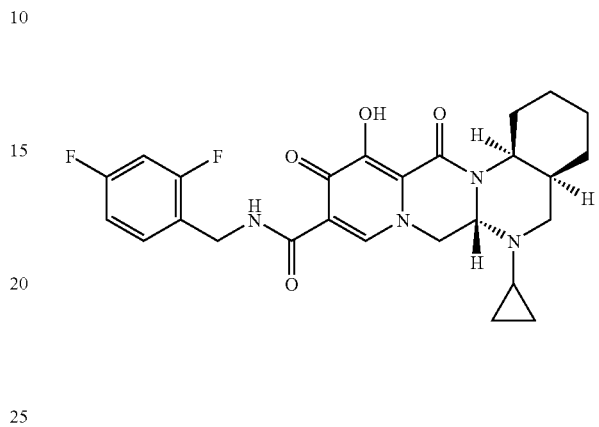

a) racemic-(1S,2S)-2-[(Cyclopropylamino)methyl]cyclohexanamine hydrochloride. In a manner similar to that described in example Z-55a, from racemic-1,1-dimethylethyl [(1S,2R)-2-formylcyclohexyl]carbamate (112 mg, 0.497 mmol) and cyclopropylamine (0.05 mL, 0.746 mmol) was prepared racemic-(1S,2S)-2-[(cyclopropylamino)methyl]cyclohexanamine bis hydrochloride salt in two steps (102 mg, 86% over 2 steps). This material was used without further purification. $^1$H NMR (methanol-$d_4$/CDCl$_3$) 8.31 (br s, 1H), 3.75 (br s, 1H), 3.54 (m, 1H), 2.96 (m, 1H), 2.71 (m, 1H), 2.27 (m, 1H), 1.94 (m, 1H), 1.76-1.15 (m, 8H), 0.88-0.78 (m, 3H).

b) racemic-(4aS,6aS,14aS)-6-Cyclopropyl-N-[(2,4-difluorophenyl)methyl]-12-hydroxy-11,13-dioxo-1,2,3,4,4a,5,6,6a,7,11,13,14a-dodecahydropyrido[1',2':4,5]pyrazino[1,2-a]quinazoline-10-carboxamide. In a manner similar to that described in example Z-35, from 16a (45 mg, 0.0957 mmol) and racemic-(1S,2S)-2-[(cyclopropylamino)methyl]cyclohexanamine hydrochloride (102 mg, 0.425 mmol) was prepared racemic-(4aS,6aS,14aS)-6-cyclopropyl-N-[(2,4-difluorophenyl)methyl]-11,13-dioxo-12-[(phenylmethyl)oxy]-1,2,3,4,4a,5,6,6a,7,11,13,14a-dodecahydropyrido[1',2':4,5]pyrazino[1,2-a]quinazoline-10-carboxamide as a white solid after silica gel chromatography (1-12% methanol/dichloromethane gradient elution). This material was deprotected in a second step similar to the procedure described in example Z-37. Thus, from racemic-(4aS,6aS,14aS)-6-cyclopropyl-N-[(2,4-difluorophenyl)methyl]-11,13-dioxo-12-[(phenylmethyl)oxy]-1,2,3,4,4a,5,6,6a,7,11,13,14a-dodecahydropyrido[1',2':4,5]pyrazino[1,2-a]quinazoline-10-carboxamide (56 mg, 0.0949 mmol) the title compound was prepared as a white solid (41 mg, 81%). $^1$H NMR (CDCl$_3$) 12.10 (br s, <1H), 10.45 (m, 1H), 8.27 (s, 1H), 7.33 (m, 1H), 6.88 (m, 2H), 4.77 (m, 1H), 4.61-4.49 (m, 4H), 4.33 (m, 1H), 2.94 (m, 1H), 2.79 (m, 1H), 2.17 (m, 1H), 1.86-0.86 (m, 10H), 0.658 (m, 1H), 0.499-0.32 (m, 2H); ES+ MS: 499 (M+1).

Example Z-64 racemic-(4aS,6aS,14aS)—N-[(2,4-Difluorophenyl)methyl]-12-hydroxy-11,13-dioxo-6-[2-(1-pyrrolidinyl)ethyl]-1,2,3,4,4a,5,6,6a,7,11,13,14a-dodecahydropyrido[1',2':4,5]pyrazino[1,2-a]quinazoline-10-carboxamide formic acid salt

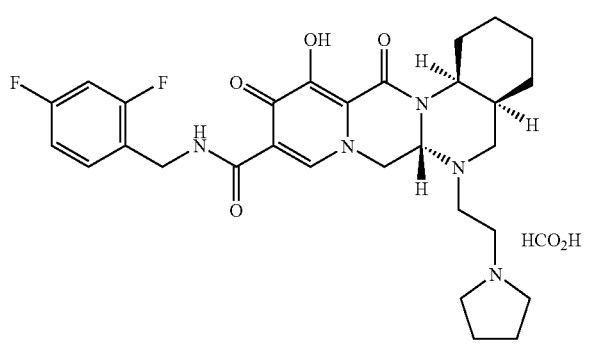

a) racemic-(1S,2S)-2-({[(2-(1-Pyrrolidinyl)ethyl]amino}methyl)cyclohexanamine hydrochloride. In a manner similar to that described in example Z-55a, from racemic-1,1-dimethylethyl[(1S,2R)-2-formylcyclohexyl]carbamate (112 mg, 0.497 mmol) and 2-(1-pyrrolidinyl)ethanamine (0.09 mL, 0.746 mmol) was prepared racemic-(1S,2S)-2-({[2-(1-pyrrolidinyl)ethyl]amino}methyl)cyclohexanamine (88 mg, 60% 2 steps) as the bis hydrochloride salt in two steps as a white solid. $^1$H NMR (methanol-$d_4$/CDCl$_3$) 9.68 (br s, <1H), 9.24 (br s, <1H), 8.25 (br s, 1H), 3.75-3.04 (m, 11H), 2.37 (br s, 1H), 2.06-1.20 (m, 12H).

b)

racemic-(4aS,6aS,14aS)—N-[(2,4-Difluorophenyl)methyl]-12-hydroxy-11,13-dioxo-6-[2-(1-pyrrolidinyl)ethyl]-1,2,3,4,4a,5,6,6a,7,13,14a-dodecahydropyrido[1',2':4,5]pyrazino[1,2-a]quinazoline-10-carboxamide formic acid salt.

In a manner similar to that described in example Z-35, from 16a (30 mg, 0.0638 mmol) and racemic-(1S,2S)-2-({[2-(1-pyrrolidinyl)ethyl]amino}methyl)cyclohexanamine hydrochloride (88 mg, 0.296 mmol) was prepared racemic-(4aS,6aS,14aS)—N-[(2,4-difluorophenyl)methyl]-11,13-dioxo-12-[(phenylmethyl)oxy]-6-[2-(1-pyrrolidinyl)ethyl]-1,2,3,4,4a,5,6,6a,7,11,13,14a-dodecahydropyrido[1',2':4,5]pyrazino[1,2-a]quinazoline-10-carboxamide as a white solid (31 mg, 76%) after silica gel chromatography (1-12% methanol/dichloromethane gradient elution). This material was deprotected in a second step similar to the procedure described in example Z-37. Thus, from racemic-(4aS,6aS,14aS)—N-[(2,4-difluorophenyl)methyl]-11,13-dioxo-12-[(phenylmethyl)oxy]-6-[2-pyrrolidinyl)ethyl]-1,2,3,4,4a5,6,6a,7,11,13,14a-dodecahydropyrido[1',2':4,5]pyrazino[1,2-a]quinazoline-10-carboxamide (31 mg, 0.048 mmol) the title compound was prepared as a yellow solid after purification by HPLC (1.8 mg, 66%). $^1$H NMR (CDCl$_3$) 10.39 (br s, 1H), 8.56 (br s, 1H), 8.39 (br s, 1H), 7.34 (m, 1H), 6.78 (m, 2H), 4.76-4.40 (m, 6H), 3.26-2.89 (m, 7H), 2.73 (m, 1H), 2.15 (m, 1H), 2.02-1.18 (m, 14H); ES$^+$ MS: 556 (M+1).

Example Z-65

(4aS,14aS)—N-[(2,4-Difluorophenyl)methyl]-9-hydroxy-8,10-dioxo-2,3,4,4a,5,6,8,10,14,14a-decahydro-1H-pyrido[1,2-c]pyrido[1',2':4,5]pyrazino[1,2-a]pyrimidine-11-carboxamide

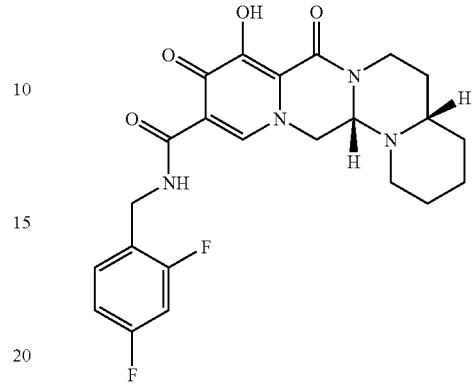

a) {2-[(2S)-2-Piperidinyl]ethyl}amine. This compound was prepared in a similar manner as its enantiomer described in example Z-42a.

b)

(4S,12aS)—N-[(2,4-Difluorophenyl)methyl]-9-hydroxy-8,10-dioxo-2,3,4,4a,5,6,8,10,14,14a-decahydro, 1H-pyrido[1,2-c]pyrido[1',2':4,5]pyrazino[1,2-a]pyrimidine-11-carboxamide. In a manner similar to that described in example Z-35, from {2-[(2S)-2-piperidinyl]ethyl}amine (28 mg, 0.218 mmol) and 16a (30 mg, 0.0638 mmol) was prepared (4aS,14aS)—N-[(2,4-difluorophenyl)methyl]-8,10-dioxo-9-[(phenylmethyl)oxy]-2,3,4,4a,5,6,8,10,14,14a-decahydro-1H-pyrido[1,2-c]pyrido[1',2':4,5]pyrazino[1,2-a]pyrimidine-11-carboxamide (29 mg, 82%). This material was deprotected in a second step similar to that described in example Z-37 to give the title compound as a white solid (26 mg, quantitative). $^1$H NMR (CDCl$_3$) δ 12.44 (br s, 1H), 10.48 (s, 1H), 8.26 (s, 1H), 7.35 (m, 1H), 6.80 (m, 2H), 4.68-4.57 (m, 2H), 4.38 (m, 1H), 4.20 (m, 1H), 3.93 (s, 1H), 3.63-3.39 (m, 2H), 2.91 (m, 2H), 2.29 (br s, 1H), 2.02 (m, 1H), 1.69-1.45 (m, 4H), 1.30-1.24 (m, 2H), 1.12 (br s, 1H); ES$^+$ MS: 459 (M+1).

Example Z-66

(4S,12aS)—N-[(4-Fluorophenyl)methyl]-7-hydroxy-4-methyl-1-[(2-methyloxy)ethyl]-6,8-dioxo-1,2,3,4,6,8,12,12a-octahydropyrido[1',2':4,5]pyrazino[1,2-a]pyrimidine-9-carboxamide

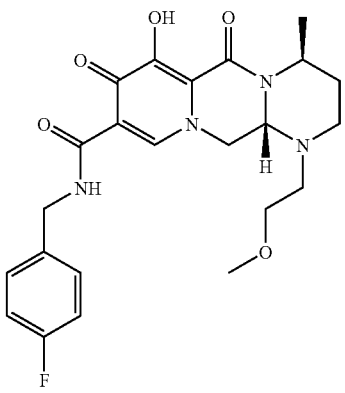

a) [(3S)-3-Aminobutyl][2-(methyloxy)ethyl]amine bis hydrochloride. In a manner similar to that described in example Z-47, from 1,1-dimethylethyl [(1S)-1-methyl-3-oxopropyl]carbamate (76 mg, 0.406 mmol) and 2-(methyloxy)ethyl]amine (0.05 mL, 0.609 mmol) was prepared [(3S)-3-aminobutyl][2-(methyloxy)ethyl]amine as the bis hydrochloride salt in two steps (19 mg, quantitative). $^1$H NMR (methanol-d$_4$/CDCl$_3$) δ 9.02 (<1H), 8.24 (<1H), 3.68 (br s, 2H), 3.49 (br s, 1H), 3.34 (br s, 4H), 3.15 (br s, 4H), 2.26-2.11 (m, 2H), 1.35 (brs, 3H), b)
(4S,12aS)—N-[(4-Fluorophenyl)methyl]-7-hydroxy-4-methyl-1-[2-(methyloxy)ethyl]-6,8-dioxo-1,2,3,4,6,8,12,12a-octahydropyrido[1',2':4,5]pyrazino[1,2-a]pyrimidine-9-carboxamide. In a manner similar to that described in example Z-35, from 16 (15 mg, 0.034 mmol) and [(3S)-3-Aminobutyl][2-(methyloxy)ethyl]amine bis hydrochloride (19 mg, 0.087 mmol), (4S,12aS)—N-[(4-fluorophenyl)methyl]-4-methyl-1-[2-(methyloxy)ethyl]-6,8-dioxo-7-[(phenylmethyl)oxy]-1,2,3,4,6,8,12,12a-octahydropyrido[1',2':4,5]pyrazino[1,2-a]pyrimidine-9-carboxamide was prepared as a white solid after silica gel chromatography (1-12% methanol/dichloromethane). This material was deprotected in a second step similar to that described in example Z-37 to give the title compound as a yellow solid (9 mg, 60%, 2 steps). $^1$H NMR (CDCl$_3$) δ 12.56 (s, 1H), 10.51 (m, 1H), 8.29 (s, 1H), 7.32 (m, 2H), 6.98 (m, 2H), 5.03 (m, 1H), 4.65-4.59 (m, 2H), 4.53 (m, 1H), 4.21 (m, 1H), 3.61-3.40 (m, 2H), 3.34-3.13 (m, 3H), 3.08 (m, 1H), 2.94-2.84 (m, 2H), 2.68 (m, 1H), 2.07 (m, 1H), 1.50 (m, 1H), 1.35 (d, J=7.2 Hz, 3H), 1.14 (m, 1H); ES$^+$ MS: 459 (M+1).

Example Z-67

(4S,12aS)-1-Cyclobutyl-N-[(4-fluorophenyl)methyl]-7-hydroxy-4-methyl-6,8-dioxo-1,2,3,4,6,8,12,12a-octahydropyrido[1',2':4,5]pyrazino[1,2-a]pyrimidine-9-carboxamide

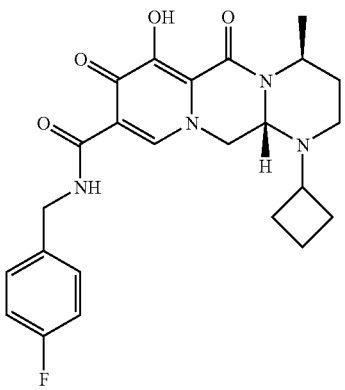

a) [(3S)-3-Aminobutyl]cyclobutylamine bis-hydrochloride. In a manner similar to that described in example Z-47, from 1,1-dimethylethyl [(1S)-1-methyl-3-oxopropyl]carbamate (76 mg, 0.406 mmol) and cyclobutylamine (0.05 mL, 0.609 mmol) was prepared [(3S)-3-Aminobutyl]cyclobutylamine bis-hydrochloride in two steps (23 mg, 27%). $^1$H NMR (methanol-d$_4$/CDCl$_3$) δ 8.86 (s, <1H), 7.97 (s, <1H), 3.46 (m, 1H), 3.21 (m, 1H), 2.74 (m, 2H), 2.14-2.08 (m, 4H), 1.94-1.62 (m, 5H), 1.13 (d, J=6 Hz, 1H).

b)
(4S,12aS)-1-Cyclobutyl-N-[(4-fluorophenyl)methyl]-7-hydroxy-4-methyl-6,8-dioxo-1,2,3,4,6,8,12,12a-octahydropyrido[1',2':4,5]pyrazino[1,2-a]pyrimidine-9-carboxamide. In a similar manner to that described in example Z-35a, from 16 (18 mg, 0.39 mmol) and [(3S)-3-Aminobutyl]cyclobutylamine bis-hydrochloride (23 mg, 0.107 mmol), (4S,12aS)-1-cyclobutyl-N-[(4-fluorophenyl)methyl]-4-methyl-6,8-dioxo-7-[(phenylmethyl)oxy]-1,2,3,4,6,8,12,12a-octahydropyrido[1',2':4,5]pyrazino[1,2-a]pyrimidine-9-carboxamide was prepared as a white solid. This material was deprotected in a second step similar to that described in example Z-37 to give the title compound as a white solid after purification by HPLC (4.5 mg, 25% 2 steps). $^1$H NMR (CDCl$_3$) δ 12.54 (s, 1H), 10.48 (s, 1H), 8.20 (s, 1H), 7.31 (m, 2H), 6.98 (m, 2H), 5.02 (m, 1H), 4.61-4.57 (m, 2H), 4.26-4.14 (m, 3H), 3.05 (m, 1H), 2.90 (m, 1H), 2.49 (m, 1H), 2.12 (m, 1H), 2.05-1.87 (m, 3H), 1.84-1.61 (m, 3H), 1.46 (m, 1H), 1.32 (m, 3H); ES$^+$ MS: 455 (M+1).

Example Z-68

(4S,12aS)—N-[(4-Fluorophenyl)methyl]-7-hydroxy-4-methyl)-1-(2-methylpropyl)-6,8-dioxo-1,2,3,4,6,8,12,12a-octahydropyrido[1',2':4,5]pyrazino[1,2-a]pyrimidine-9-carboxamide

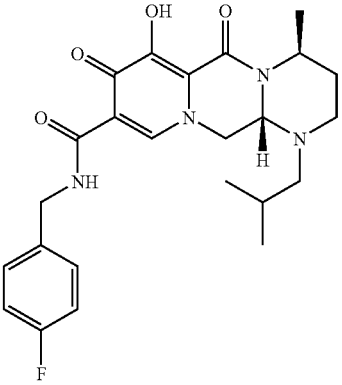

a) [(3S)-3-Aminobutyl](2-methylpropyl)amine bis-hydrochloride. In a manner similar to that described in example Z-47, this compound was prepared from 1,1-dimethylethyl [(1S)-1-methyl-3-oxopropyl]carbamate (76 mg, 0.406 mmol) and (2-methylpropyl)amine (0.06 mL, 0.609 mmol) in two steps as the bis-hydrochloride salt (22 mg, 25%). $^1$H NMR (methanol-d$_4$/CDCl$_3$) δ 3.25 (br s, 1H), 2.91 (br s, 2H), 2.64 (m, 2H), 2.02-1.93 (m, 3H), 1.17 (m, 3H), 0.88 (m, 6H).

b)
(4S,12aS)—N-[(4-Fluorophenyl)methyl]-7-hydroxy-4-methyl-1-(2-methylpropyl)-6,8-dioxo-1,2,3,4,6,8,12,12a-octahydropyrido[1',2':4,5]pyrazino[1,2-a]pyrimidine-9-carboxamide. In a similar manner to that described in example Z-35, from 16 (16 mg, 0.035 mmol) and [(3S)-3-Aminobutyl](2-methylpropyl)amine bis-hydrochloride (20 mg, 0.0925 mmol), (4S,12aS)—N-[(4-fluorophenyl)methyl]-4-methyl-1-(2-methylpropyl)-6,8-dioxo-7-[(phenylmethyl)oxy]-1,2,3,4,6,8,12,12a-octahydropyrido[1',2':4,5]pyrimidine-9-carboxamide was prepared as a white solid. This material was deprotected in a second step similar to that described in example Z-37 to give the title compound as a tan solid (1.3 mg, 68% 2 steps). $^1$H NMR (CDCl$_3$) δ 12.57 (s, 1H), 10.46 (s, 1H), 8.27 (s, 1H), 7.32 (m, 2H), 6.99 (m, 2H), 4.98 (m, 1H), 4.63-4.51 (m, 2H), 4.45 (m, 1H), 4.26-4.16 (m, 2H), 2.91 (m, 1H), 2.77 (m, 1H), 2.24 (m, 1H), 2.14-2.03 (m, 2H), 1.63 (m, 1H), 1.48 (m, 1H), 1.33 (m, 3H), 1.09 (m, 1H), 0.850 (m, 3H), 0.789 (m, 3H); ES$^+$ MS: 457 (M+1).

Example Z-69

(4S,12aS)—N-[(4-Fluorophenyl)methyl]-7-hydroxy-1,4-dimethyl-6,8-dioxo-1,2,3,4,6,8,12,12a-octahydropyrido[1',2':4,5]pyrazino[1,2a]pyrimidine-9-carboxamide

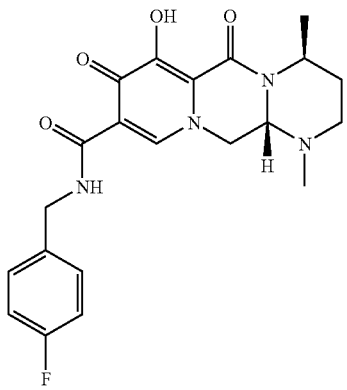

a) [(3S)-3-Aminobutyl]methylamine bis-hydrochloride. In a manner similar to that described in example Z-47, this compound was prepared from 1,1-dimethylethyl [(1S)-1-methyl-3-oxopropyl]carbamate (76 mg, 0.409 mmol) and excess methylamine (2 M in tetrahydrofuran) in two steps as the bis hydrochloride salt (17% 2 steps). $^1$H NMR (methanol-$d_4$/CDCl$_3$) δ 3.16 (m, 1H), 3.08 (s, 2H), 2.83 (m, 2H), 2.45 (s, 3H), 1.88 (m, 1H), 1.75 (m, 1H), 1.09 (m, 3H).

b)

(4S,12aS)—N-[(4-Fluorophenyl)methyl]-7-hydroxy-1,4-dimethyl-6,8-dioxo-1,2,3,4,6,8,12,12a-octahydropyrido[1',2':4,5]pyrazino[1,2-a]pyrimidine-9-carboxamide. In a similar manner to that described in example Z-35, from 16 (18 mg, 0.0398 mmol) and [(3S)-3-aminobutyl]methylamine bis-hydrochloride (19 mg, 0.109 mmol, (4S,12aS)—N-[(4-fluorophenyl)methyl]-1,4-dimethyl-6,8-dioxo-7-[(phenylmethyl)oxy]-1,2,3,4,6,8,12,12a-octahydropyrido[1',2':4,5]pyrazino[1,2-a]pyrimidine-9-carboxamide was prepared as a white solid. This material was deprotected in a second step similar to that described in example Z-37 to give the title compound as a tan solid (7 mg, 44% 2 steps). $^1$H NMR (CDCl$_3$) δ 12.53 (s, 1H), 10.47 (s, 1H), 8.29 (s, 1H), 7.32 (m, 2H), 6.99 (m, 2H), 5.04 (1H), 4.60 (m, 2H), 4.23 (s, 3H), 2.83-2.80 (m, 2H), 2.32 (s, 3H), 2.13 (m, 1H), 1.48 (m, 1H), 1.34 (m, 3H); ES$^+$ MS: 415 (M+1).

Example Z-70

(4S,12aS)—N-[(4-Fluorophenyl)methyl]-7-hydroxy-4-methyl-6,8-dioxo-1-(tetrahydro-2H-thiopyran-4-yl)-1,2,3,4,6,8,12,12a-octahydropyrido[1',2':4,5]pyrazino[1,2-a]pyrimidine-9-carboxamide

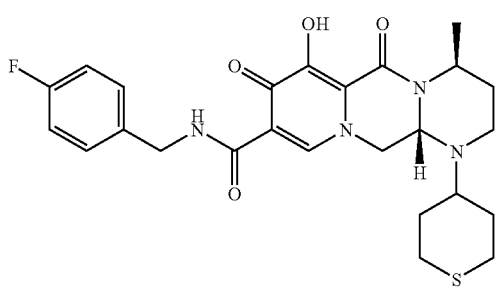

The title compound was made in two steps using a similar process to that described in example Z-2. 16 (25 mg, 0.055 mmol) and free based [(3S)-3-aminobutyl]tetrahydro-2H-thiopyran-4-ylamine (48 mg, 0.26 mmol) were reacted in dichloromethane (2 mL) with acetic acid to give (4S,12aS)—N-[(4-fluorophenyl)methyl]-4-methyl-6,8-dioxo-7-[(phenylmethyl)oxy]-1-(tetrahydro-2H-thiopyran-4-yl)-1,2,3,4,6,8,12,12a-octahydropyrido[1',2':4,5]pyrazino[1,2-a] pyrimidine-9-carboxamide (16 mg, 49%) as a film. This material was debenzylated in a second step in a manner similar to Z-26 to give (4S,12aS)—N-[(4-fluorophenyl)methyl]-7-hydroxy-4-methyl-6,8-dioxo-1-(tetrahydro-2H-thiopyran-4-yl)-1,2,3,4,6,8,12,12a-octahydropyrido[1',2':4,5]pyrazino[1,2-a]pyrimidine-9-carboxamide (8 mg, 59%) as an off-white solid. $^1$H NMR (400 MHz, CDCl3) δ 1.30 (d, J=7.2 Hz, 3H), 1.53-1.58 (m, 1H), 1.72-2.10 (m, 5H), 2.56-2.76 (m, 5H), 2.84-2.87 (m, 2H), 4.18 (dd, J=2.8, 14.0 Hz, 1H), 4.26 (dd, J=3.4, 14.2 Hz, 1H), 4.92-4.97 (m, 1H), 6.96-7.00 (m, 2H), 7.29-7.36 (m, 2H), 8.31 (s, 1H), 10.48 (m, 1H), 12.48 (br, 1H); ES$^+$ MS: 501 (M+1).

Example Z-71

(4S,12aS)—N-[(2,4-Difluorophenyl)methyl]-7-hydroxy-1,4-dimethyl-6,8-dioxo-1,2,3,4,6,8,12,12a-octahydropyrido[1',2':4,5]pyrazino[1,2-a]pyrimidine-9-carboxamide

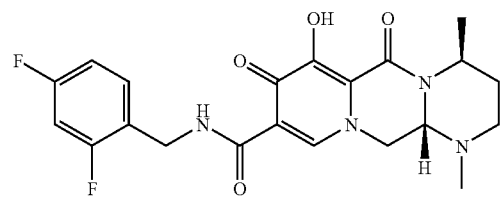

a) [(3S)-3-Aminobutyl]methylamine dihydrochloride was prepared in a similar manner as described in example Z-47. $^1$H NMR (400 MHz, CDCl$_3$) δ 1.18 (d, J=6.8 Hz, 3H), 1.82-1.91 (m, 1H), 1.94-2.03 (m, 1H), 2.53 (s, 3H), 2.89-2.93 (m, 2H), 3.22-3.30 (m, 1H), 8.02 (br, <1H), 8.81 (br, <1H).

b)

(4S,12aS)—N-[(2,4-Difluorophenyl)methyl]-7-hydroxy-1,4-dimethyl-6,8-dioxo-1,2,3,4,6,8,12,12a-octahydropyrido[1',2':4,5]pyrazino[1,2-a]pyrimidine-9-carboxamide. The title compound was made in two steps using a similar process to that described in example Z-2. 16a (40 mg, 0.085 mmol) and free based [(3S)-3-aminobutyl]methylamine (24 mg, 0.23 mmol) were reacted in dichloromethane (2 mL) with acetic acid to give (4S,12aS)—N-[(2,4-difluorophenyl)me thyl]-1,4-dimethyl-6,8-dioxo-7-[(phenylmethyl)oxy]-1,2,3,
4,6,8,12,12a-octahydropyrido[1',2':4,5]pyrazino[1,2-a]pyrimidine-9-carboxamide (39 mg, 89%) as a film. This material was hydrogenated in a second step as described in example Z-2 to give (4S,12aS)—N-[(2,4-difluorophenyl)methyl]-7-hydroxy-1,4-dimethyl-6,8-dioxo-1,2,3,4,6,8,12,12a-octahydropyrido[1',2':4,5]pyrazino[1,2-a]pyrimidine-9-carboxamide (32 mg, 97%) as an off-white solid. ¹H NMR (400 MHz, CDCl₃) δ 1.33 (d, J=6.4 Hz, 3H), 1.46-1.50 (m, 1H), 2.12-2.14 (m, 1H), 2.32 (s, 3H), 2.83 (m, 2H), 4.24 (m, 3H), 4.62 (m, 2H), 5.02 (m, 1H), 6.77-6.79 (m, 2H), 7.33 (m, 1H), 8.30 (s, 1H), 10.43 (s, 1H), 12.50 (br, 1H); ES⁺ MS: 433 (M+1).

Example Z-72

(4S,12aS)—N-[(4-Fluorophenyl)methyl]-7-hydroxy-4-methyl-1-(1-methylethyl)-6,8-dioxo-1,2,3,4,6,8,12,12a-octahydropyrido[1',2':4,5]pyrazino[1,2-a]pyrimidine-9-carboxamide

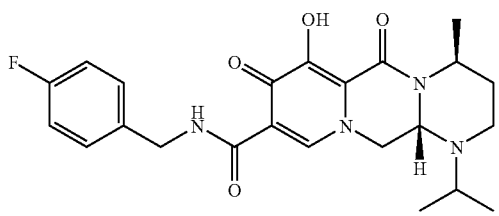

The title compound was made in two steps using a similar process to that described in example Z-2. 16 (27 mg, 0.060 mmol) and free based [(3S)-3-aminobutyl](1-methylethyl)amine (67 mg, 0.51 mmol) were reacted in dichloromethane (2 mL) with acetic acid to give (4S,12aS)—N-[(4-fluorophenyl)methyl]-4-methyl-1-(1-methylethyl)-6,8-dioxo-7-[(phenyl methyl)oxy]-1,2,3,4,6,8,12,12a-octahydropyrido[1',2':4,5]pyrazino[1,2-a]pyrimidine-9-carboxamide (18 mg, 56%) as a film. This material was hydrogenated in a second step as described in example Z-2 to give (4S,12aS)—N-[(4-fluorophenyl)methyl]-7-hydroxy-4-methyl-1-(1-methylethyl)-6,8-dioxo-1,2,3,4,6,8,12,12a-octahydropyrido[1',2':4,5]pyrazino[1,2-a]pyrimidine-9-carboxamide (15 mg, >100%) as an off-white solid. ¹H NMR (400 MHz, CDCl₃) δ 1.02 (d, J=6.4 Hz, 3H), 1.07 (d, J=6.4 Hz, 3H), 1.32 (d, J=6.8 Hz, 3H), 1.54-1.58 (m, 1H), 1.94-2.03 (m, 1H), 2.71-2.76 (m, 1H), 2.82-2.88 (m, 1H), 3.13-3.16 (m, 1H), 4.16-4.19 (m, 1H), 4.30-4.33 (m, 1H), 4.48 (m, 1H), 4.55-4.65 (m, 2H), 4.97-5.00 (m, 1H), 6.97-7.01 (m, 2H), 7.30-7.34 (m, 2H), 8.28 (s, 1H), 10.51 (m, 1H), 12.55 (s, 1H); ES⁺ MS: 443 (M+1).

Example Z-73

(4S,12aS)—N-[(4-Fluorophenyl)methyl]-7-hydroxy-1,4-bis(2-methylpropyl)-6,8-dioxo-1,2,3,4,6,8,12,12a-octahydropyrido[1',2':4,5]pyrazino[1,2-a]pyrimidine-9-carboxamide

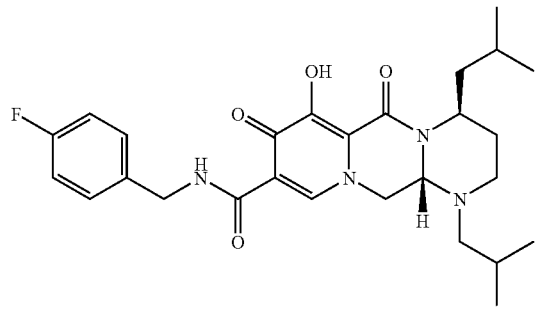

The title compound was made in two steps using a similar process to that described in example Z-2. 16 (25 mg, 0.055 mmol) and free based [(3S)-3-amino-5-methylhexyl](2-methylpropyl)amine (21 mg, 0.11 mmol) were reacted in dichloromethane (2 mL) with acetic acid to give (4S,12aS)—N-[(4-fluorophenyl)methyl]-1,4-bis(2-methylpropyl)-6,8-dioxo-7-[(phenylmethyl)oxy]-1,2,3,4,6,8,12,12a-octahydropyrido[1',2':4,5]pyrazino[1,2-a]pyrimidine-9-carboxamide (8 mg, 25%) as a film. This material was hydrogenated in a second step as described in example Z-2 to give (4S,12aS)—N-[(4-fluorophenyl)methyl]-7-hydroxy-1,4-bis(2-methylpropyl)-6,8-dioxo-1,2,3,4,6,8,12,12a-octahydropyrido[1',2':4,5]pyrazino[1,2-a]pyrimidine-9-carboxamide (5 mg, 78%) as an off-white solid. ¹H NMR (400 MHz, CDCl₃) δ 0.74 (d, J=6.4 Hz, 3H), 0.84 (d, J=6.4 Hz, 3H), 0.97-1.00 (m, 6H), 1.37-1.66 (m, 5H), 1.75-1.82 (m, 1H), 2.05-2.09 (m, 2H), 2.21-2.26 (m, 1H), 2.72-2.79 (m, 1H), 2.87-2.93 (m, 1H), 4.16-4.26 (m, 2H), 4.38 (m, 1H), 4.55-4.66 (m, 2H), 4.93-4.99 (m, 1H), 6.97-7.02 (m, 2H), 7.31-7.34 (m, 2H), 8.27 (s, 1H), 10.49 (m, 1H), 12.61 (s, 1H); ES⁺ MS: 499 (M+1).

Example ZZ-1 TO ZZ-24

Examples in table below were isolated as a mixture of diastereomers ranging from 1:1 to >10:1 ratios of stereoisomers at the center indicated as undefined. Characterization data reported herein consists of observed mass spectral signals for molecular ions (M+1) of the compounds using electrospray ionization methods in the positive mode using LC/MS techniques well known in the field. Reported retention times refer to observed UV peaks confirmed by NMR methods for the examples below using the following gradient on a phenomenex C18 reverse phase HPLC column (150 mm×4.6 mm 5 micron). Solvent A=water w/0.1% formic acid, solvent B=acetonitrile w/0.1% formic acid. Gradient=10% B for 1 min, gradient from 10% to 90% B from 1 to 9 min, ramping to 100% B at 9.01 min and holding at 100% B for 2 min. In several cases the diastereomers were not separable by the standard HPLC conditions reported above and thus reported as a single retention time.

TABLE A

| Example No. | Structure | Observed LC/MS or HPLC data |
|---|---|---|
| ZZ-1 | 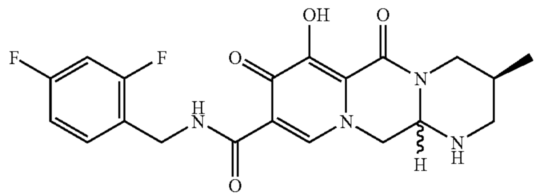 | ES+ MS: 419 (M + 1) |
| ZZ-2 | 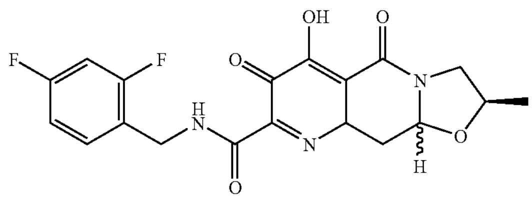 | ES+ MS: 406 (M + 1) |
| ZZ-3 | 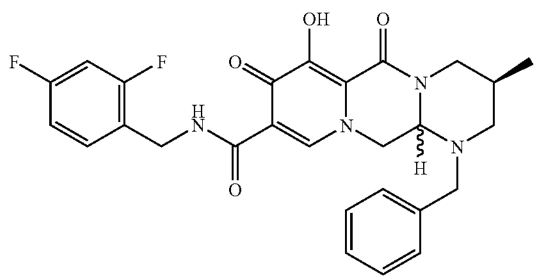 | ES+ MS: 509 (M + 1) |
| ZZ-4 | 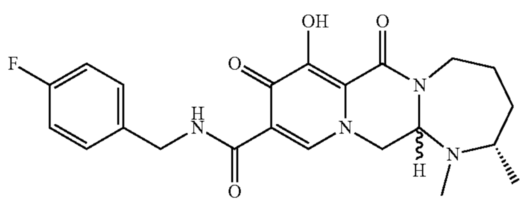 | ES+ MS: 429 (M + 1) |
| ZZ-5 | 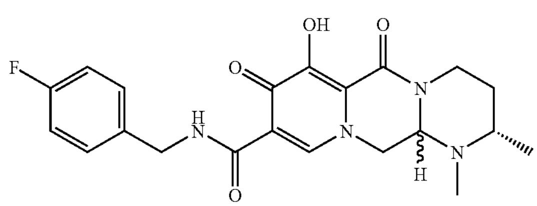 | ES+ MS: 415 (M + 1) |
| ZZ-6 | 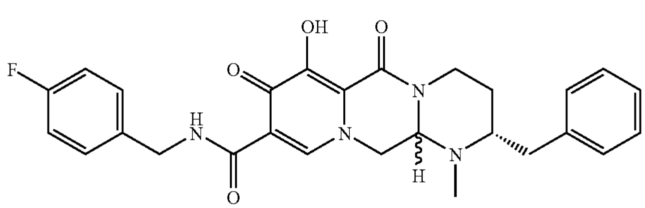 | ES+ MS: 491 (M + 1) |
| ZZ-7 | 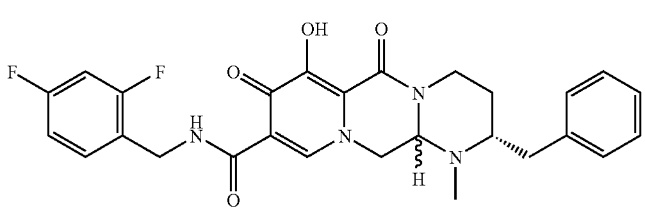 | ES+ MS: 509 (M + 1) |

TABLE A-continued

| Example No. | Structure | Observed LC/MS or HPLC data |
|---|---|---|
| ZZ-8 | 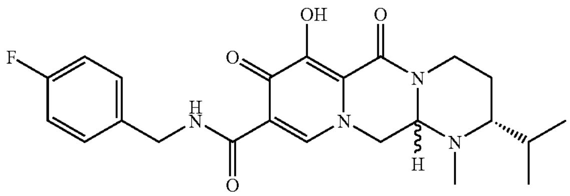 | ES⁺ MS: 443 (M + 1) |
| ZZ-9 | 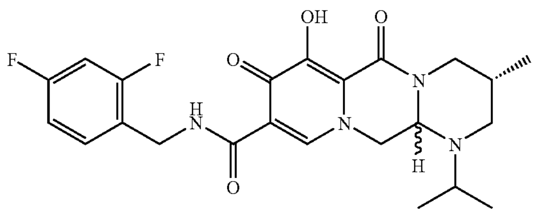 | ES⁺ MS: 461 (M + 1) |
| ZZ-10 | 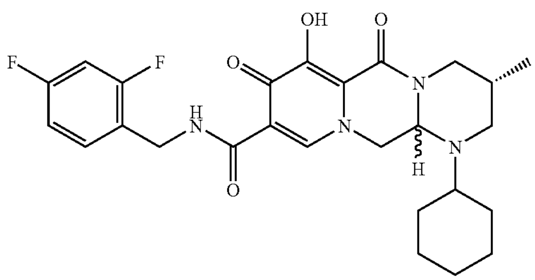 | ES⁺ MS: 501 (M + 1) |
| ZZ-11 | 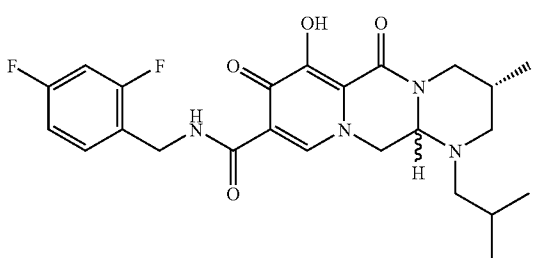 | ES⁺ MS: 475 (M + 1) |
| ZZ-12 | 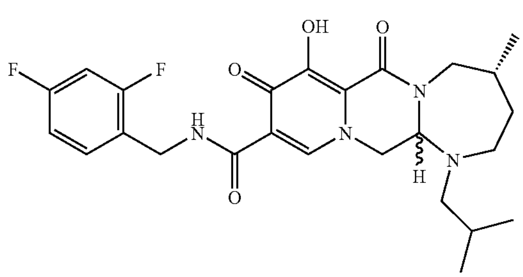 | ES⁺ MS: 489 (M + 1) |
| ZZ-13 | 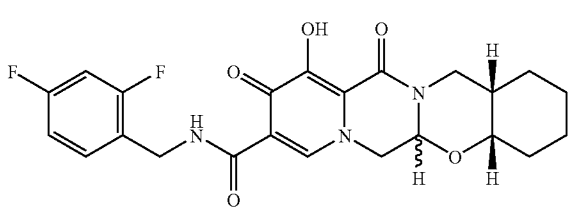 | ES⁺ MS: 460 (M + 1) |

TABLE A-continued

| Example No. | Structure | Observed LC/MS or HPLC data |
|---|---|---|
| ZZ-14 | 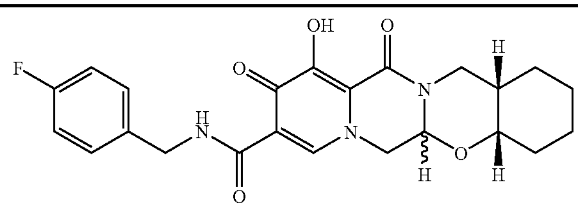 | ES+ MS: 442 (M + 1) |
| ZZ-15 | 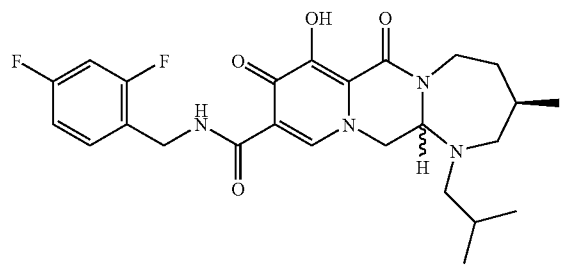 | ES+ MS: 489 (M + 1) |
| ZZ-16 | 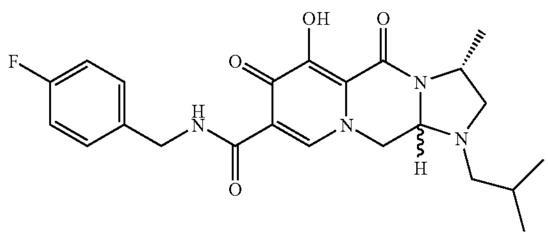 | 8.174 & 8.295 min. |
| ZZ-17 | 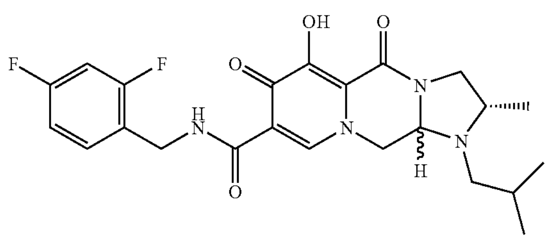 | ES+ MS: 461 (M + 1) |
| ZZ-18 | 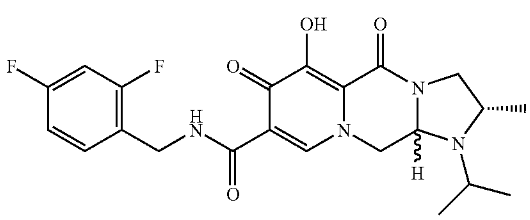 | ES+ MS: 447 (M + 1) |
| ZZ-19 | 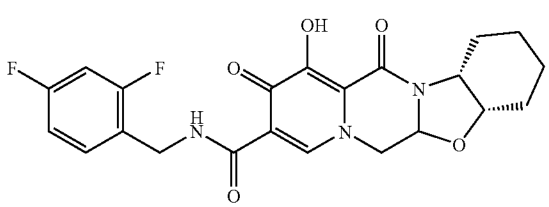 | ES+ MS: 446 (M + 1) |
| ZZ-20 | 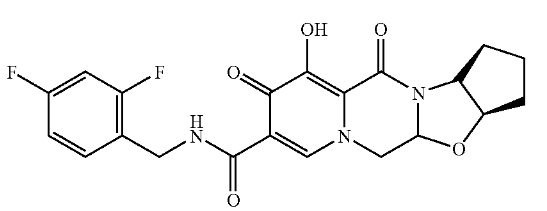 | ES+ MS: 432 (M + 1) |

TABLE A-continued

| Example No. | Structure | Observed LC/MS or HPLC data |
|---|---|---|
| ZZ-21 | 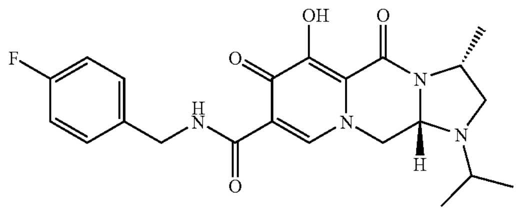 | 7.368 min |
| ZZ-22 | 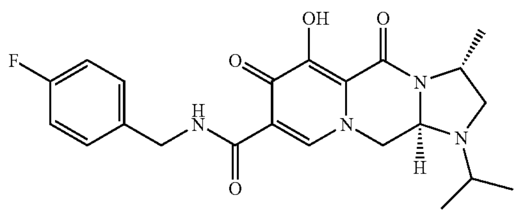 | 7.150 min |
| ZZ-23 | 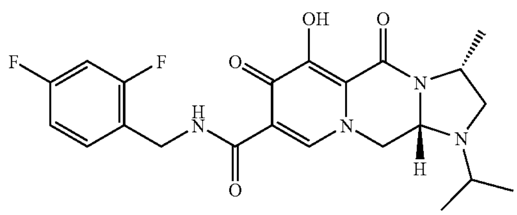 | ES+ MS: 447 (M + 1) |
| ZZ-24 | 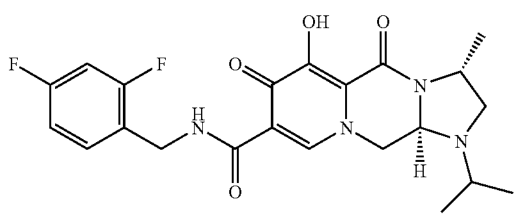 | ES+ MS: 447 (M + 1) |

The present invention further includes the following compounds.

TABLE B (I-7)

| No | (R)m | $R^a$ |
|---|---|---|
| 1 | 4-F | —CH$_3$ |
| 2 | 4-F | —CH(CH$_3$)$_2$ |
| 3 | 4-F | —CH$_2$CH$_2$OCH$_3$ |
| 4 | 2,4-F | —CH$_3$ |
| 5 | 2,4-F | —CH(CH$_3$)$_2$ |
| 6 | 2,4-F | —CH$_2$CH$_2$OCH$_3$ |
| 7 | 2-F, 3-Cl | —CH$_3$ |
| 8 | 2-F, 3-Cl | —CH(CH$_3$)$_2$ |
| 9 | 2-F, 3-Cl | —CH$_2$CH$_2$OCH$_3$ |

Experimental Example 1

The HIV integrase inhibitory activity was investigated based on the following assay method.

(1) Preparation of DNA Solution

By the same method as that described in Experimental Example 1 of WO 2004/024693, a substrate DNA solution (2 pmol/µl) and a target DNA solution (5 pmol/µl) were prepared. After each target DNA solution was once boiled, a temperature was slowly lowered to anneal complementary chains, which was used. Each sequence of a substrate DNA and a target DNA is as described in the same Experimental Example.

(2) Measurement of Inhibition Rate (IC$_{50}$ Value)

Streptavidin (manufactured by Vector Laboratories) was dissolved in a 0.1M carbonate buffer solution (composition: 90 mM Na$_2$CO$_3$, 10 mM NaHCO$_3$) to a concentration of 40 µg/ml. Each 50 µl of this solution was added to a well of an immunoplate (manufactured by NUNC), this is allowed to stand at 4° C. overnight to adsorb. Then, each well was washed with a phosphate buffer (composition: 13.7 mM NaCl, 0.27 mM KCl, 0.43 mM Na$_2$HPO$_4$, 0.14 mM KH$_2$PO$_4$) two times, and 300 µl of a phosphate buffer containing 1% skim milk to block it for 30 minutes. Further, each well was washed with a phosphate buffer two times, 50 µl of a substrate DNA solution (2 pmol/µl) was added to adsorb at room temperature for 30 minutes while shaking, and this was washed with a phosphate buffer two times and, then, distilled water once.

Then, to each well prepared as described above were added 12 μl of a buffer (composition: 150 mM MOPS (pH7.2), 75 mM MnCl$_2$, 50 mM 2-mercaptoethanol, 25% glycerol, 500 μg/ml bovine serum albumin-fraction V), and 51 μl of a reaction solution prepared from 39 μl of distilled water. Then, 9 μl of an integrase solution (30 μmol) was added, and the mixture was mixed well. To a well as a negative control (NC) was added 9 μl of a diluting solution (composition: 20 mM MOPS (pH7.2), 400 mM potassium glutamate, 1 mM EDTA, 0.1% NP-40, 20% glycerol, 1 mM DTT, 4 M urea), and this was mixed well using a plate mixer.

After the plate was incubated at 30° C. for 60 minutes, the reaction solution was discarded, followed by washing with 250 μl of a washing buffer (composition: 150 mM MOPS (pH7.2), 50 mM 2-mercaptoethanol, 25% glycerol, 500 μg/ml bovine serum albumin-fraction V) three times.

Then, to each well were added 12 μl of a buffer (composition: 150 mM MOPS (pH7.2), 75 mM MgCl$_2$, 50 mM 2-mercaptoethanol, 25% glycerol, 500 μg/ml bovine serum albumin-fraction V), and 53 μl of a reaction solution prepared from 41 μl of distilled water. Further, 6 μl of a solution of a test compound in DMSO was added to each well, and 6 μl of DMSO was added to a well as a positive control (PC), followed by mixing well using a plate mixer. After the plate was incubated at 30° C. for 30 minutes, 1 μl of a target DNA (5 pmol/μl) was added, and this was mixed well using a plate mixer.

After each plate was incubated at 30° C. for 10 minutes, the reaction solution was discarded, followed by washing with a phosphate buffer two times. Then, an anti-digoxigenin antibody labeled with alkaline phosphatase (sheep Fab fragment: manufactured by Boehringer) was diluted 2000-fold with an antibody diluting solution, 100 μl of the diluent was added to bind at 30° C. for 1 hour, and this was washed successively with a phosphate buffer containing 0.05% Tween20 two times, and a phosphate buffer once. Then, 150 μl of an alkaline phosphatase coloring buffer (composition: 10 mM paranitrophenyl phosphate (manufactured by Vector Laboratories), 5 mM MgCl$_2$, 100 mM NaCl, 100 mM Tris-HCl (pH 9.5)) was added to react at 30° C. for 2 hours, 50 μl of a 1N NaOH solution was added to stop the reaction, an absorbance (OD405 nm) of each well was measured, and an inhibition rate (IC$_{50}$) was obtained according to the following calculation equation.

Inhibition rate (%)=100[1−{(C abs.−NC abs.)/(PC abs.−NC abs.)}]

C abs.; absorbance of well of compound
NC abs.; absorbance of NC
PC abs.; absorbance of PC
Results are shown below.

TABLE 1

| Example No. | Integrase inhibitory activity (IC50, ng/ml) |
|---|---|
| C-2 | 3.3 |
| F-2 | 3.8 |
| H-2 | 3.2 |

The present compound showed the strong integrase inhibitory activity against HIV.

Experimental Example 2

A derivative of 293T cells expressing an attachment factor to improve adherence to plastic were used for the assay. A VSV-g pseudotyped HIV vector that expresses luciferase (herein referred to as PHIV) was produced by transfection of cells with the pGJ3-Luci vector plasmid (Jármy, G. et al., J. Medical Virology, 64:223-231, 2001) and pVSV-g (Clontech). Cells were mixed with the PHIV vector and then mixed with serially diluted compounds. After incubation at 37° C. and 5% CO$_2$ for two days, the plates were read by using Steady Glo luciferase assay reagent (Promega) as recommended by the manufacturer. To assess non-HIV specific inhibition, a similar assay was performed, except that cell/PHIV vector mixture was replaced by cells which had been previously transduced and constitutively expressed luciferase.

TABLE 2

| Example number | PHIV IC$_{50}$<br>* = <10 nM,<br>** = 10-100 nM,<br>*** >100 nM |
|---|---|
| Z-1 | * |
| Z-2 | * |
| Z-3 | * |
| Z-4 | * |
| Z-5 | * |
| Z-6 | * |
| Z-7 | * |
| Z-8 | ** |
| Z-9 | * |
| Z-10 | * |
| Z-11 | * |
| Z-12 | * |
| Z-13 | ** |
| Z-14 | ** |
| Z-15 | * |
| Z-16 | * |
| Z-17 | * |
| Z-18 | * |
| Z-19 | * |
| Z-20 | ** |
| Z-21 | * |
| Z-22 | * |
| Z-23 | * |
| Z-24 | * |
| Z-25 | * |
| Z-26 | * |
| Z-27 | *** |
| Z-28 | * |
| Z-29 | * |
| Z-30 | * |
| Z-31 | * |
| Z-32 | * |
| Z-33 | * |
| Z-34 | * |
| Z-35 | * |
| Z-36 | * |
| Z-37 | * |
| Z-38 | ** |
| Z-39 | * |
| Z-40 | * |
| Z-41 | * |
| Z-42 | * |
| Z-43 | * |
| Z-44 | * |
| Z-45 | * |
| Z-46 | * |
| Z-47 | * |
| Z-48 | * |
| Z-49 | * |
| Z-50 | * |
| Z-51 | * |
| Z-52 | * |
| Z-53 | * |
| Z-54 | * |
| Z-55 | ** |
| Z-59 | * |
| Z-60 | * |

Formulation Example

A term "active ingredient" means the present compound, a tautomer thereof, a pharmaceutically acceptable salt thereof, or a solvate thereof.

Formulation Example 1

A hard gelatin capsule is prepared using the following ingredients:

|  | dose (mg/capsule) |
|---|---|
| Active ingredient | 250 |
| Starch (dried) | 200 |
| Magnesium stearate | 10 |
| Total | 460 mg |

Formulation Example 2

A tablet is prepared using the following ingredients:

|  | dose (mg/tablet) |
|---|---|
| Active ingredient | 250 |
| Cellulose (microcrystalline) | 400 |
| Silicon dioxide (fumed) | 10 |
| Stearic acid | 5 |
| Total | 665 mg |

Ingredients are mixed, and compressed to obtain tablets, each weighing 665 mg.

I claim:

1. A compound of the formula:

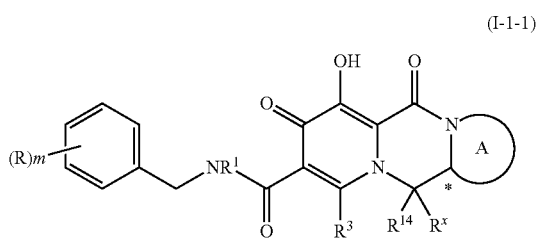

(I-1-1)

wherein,
ring A is

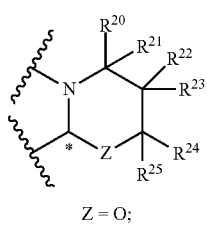

$Z = O$;

$R^{20}$, $R^{21}$, $R^{22}$, $R^{23}$, $R^{24}$ and $R^{25}$ are independently hydrogen, $C_1$-$C_8$alkyl, $C_6$-$C_{14}$aryl$C_1$-$C_8$alkyl, $C_6$-$C_{14}$aryl, or alkoxy;

the stereochemistry of an asymmetric carbon represented by * shows R- or S-configuration, or a mixture thereof;

$R^X$ is hydrogen;

$R^{14}$ is hydrogen or lower alkyl which is optionally substituted with 1 to 4 substituents selected from the group consisting of hydroxy, carboxy, halogen, halo lower alkyl, halo lower alkoxy, lower alkyl, lower alkenyl, lower alkynyl, cycloalkyl, cycloalkenyl, lower alkoxy, lower alkenyloxy, lower alkoxycarbonyl, nitro, nitroso, amino, alkylamino, acylamino, aralkylamino, aryl, aralkyl, cyano, isocyano, isocyanate, thiocyanate, isothiocyanate, mercapto, alkylthio, alkylsulfonyl, alkylsulfonylamino, carbamoyl, alkylcarbamoyl, sulfamoyl, acyl, formyloxy, haloformyl, oral, thioformyl, thiocarboxy, dithiocarboxy, thiocarbamoyl, sulfino, sulfo, sulfoamino, hydrazino, azido, ureido, guanidino, phthalimide, oxo, phosphoric acid, lower alkyl which is substituted with phosphoric acid and may be intervened with a heteroatom, aryl substituted with phosphoric acid, aralkyl substituted with phosphoric acid and hydroxy lower alkyl;

$R^3$ is hydrogen;

$R^1$ is hydrogen or lower alkyl;

R is halogen;

and m is 1, 2 or 3;

or a pharmaceutically acceptable salt thereof.

2. A compound according to claim 1, or a pharmaceutically acceptable salt thereof, wherein $R^X$ is hydrogen; $R^{14}$ is hydrogen; $R^3$ is hydrogen; m is 1, 2 or 3 and R is halogen.

3. A compound according to claim 1 wherein the pharmaceutically acceptable salt is a sodium salt.

4. A compound of formula (1-7):

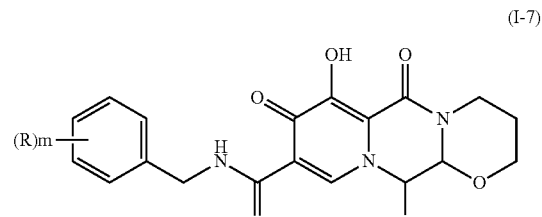

(I-7)

wherein:

$R^a$ is —$CH_3$, —$CH(CH_3)_2$, or —$CH_2CH_2OCH_3$, and (R)m and the phenyl ring to which it is attached is 4-fluorophenyl, 2,4-difluorophenyl or 3-chloro-2-fluorophenyl;

or a pharmaceutically acceptable salt thereof.

5. A compound selected from the group consisting of:

(3S,9aS)-5-Hydroxy-3-methyl-6,10-dioxo-3,4,6,9,9a,10-hexahydro-2H-1-oxa-4a,8a-diaza-anthracene-7-carboxylic acid 2,4-difluoro-benzylamide;

(3R,9aR)-5-Hydroxy-3-methyl-6,10-dioxo-3,4,6,9,9a,10-hexahydro-2H-1-oxa-4a,8a-diaza-anthracene-7-carboxylic acid 2,4-difluoro-benzylamide;

(4S,9aR)-5-Hydroxy-4-methyl-6,10-dioxo-3,4,6,9,9a,10-hexahydro-2H-1-oxa-4a,8a-diaza-anthracene-7-carboxylic acid 2,4-difluoro-benzylamide;

(2R,9aR)-5-Hydroxy-2-methoxymethyl-6,10-dioxo-3,4, 6,9,9a,10-hexahydro-2H-1-oxa-4a,8a-diaza-anthracene-7-carboxylic acid 2,4-difluoro-benzylamide;

(2S,9aS)-5-Hydroxy-2-methoxymethyl-6,10-dioxo-3,4,6, 9,9a,10-hexahydro-2H-1-oxa-4a,8a-diaza-anthracene-7-carboxylic acid 2,4-difluoro-benzylamide;

(2S,9aR)-2-Ethyl-5-hydroxy-6,10-dioxo-3,4,6,9,9a,10-hexahydro-2H-1-oxa-4a,8a-diaza-anthracene-7-carboxylic acid 2,4-difluoro-benzylamide;

(2R,9aS)-2-Ethyl-5-hydroxy-6,10-dioxo-3,4,6,9,9a,10-hexahydro-2H-1-oxa-4a,8a-diaza-anthracene-7-carboxylic acid 2,4-difluoro-benzylamide;

(2S,9aS)-5-Hydroxy-6,10-dioxo-2-phenyl-3,4,6,9,9a,10-hexahydro-2H-1-oxa-4a,8a-diaza-anthracene-7-carboxylic acid 2,4-difluoro-benzylamide;

(2S,9aS)-5-Hydroxy-2-isopropyl-6,10-dioxo-3,4,6,9,9a, 10-hexahydro-2H-1-oxa-4a,8a-diaza-anthracene-7-carboxylic acid 2,4-difluoro-benzylamide;

(2R,9aR)-5-Hydroxy-2-isopropyl-6,10-dioxo-3,4,6,9,9a, 10-hexahydro-2H-1-oxa-4a,8a-diaza-anthracene-7-carboxylic acid 2,4-difluoro-benzylamide;

(3S,9aS)-5-Hydroxy-3-methyl-6,10-dioxo-3,4,6,9,9a,10-hexahydro-2H-1-oxa-4a,8a-diaza-anthracene-7-carboxylic acid 4-fluoro-benzylamide;

(3R,9aR)-5-Hydroxy-3-methyl-6,10-dioxo-3,4,6,9,9a,10-hexahydro-2H-1-oxa-4a,8a-diaza-anthracene-7-carboxylic acid 4-fluoro-benzylamide;

(2R,9aS)-5-Hydroxy-2-methyl-6,10-dioxo-3,4,6,9,9a,10-hexahydro-2H-1-oxa-4a,8a-diaza-anthracene-7-carboxylic acid 2,4-difluoro-benzylamide;

(2S,9aR)-5-Hydroxy-2-methyl-6,10-dioxo-3,4,6,9,9a,10-hexahydro-2H-1-oxa-4a,8a-diaza-anthracene-7-carboxylic acid 2,4-difluoro-benzylamide;

(2S,9aR)-5-Hydroxy-2-methyl-6,10-dioxo-3,4,6,9,9a,10-hexahydro-2H-1-oxa-4a,8a-diaza-anthracene-7-carboxylic acid 4-fluoro-benzylamide;

(2R,9aS)-5-Hydroxy-2-methyl-6,10-dioxo-3,4,6,9,9a,10-hexahydro-2H-1-oxa-4a,8a-diaza-anthracene-7-carboxylic acid 4-fluoro-benzylamide;

5-Hydroxy-6,10-dioxo-3,4,6,9,9a,10-hexahydro-2H-1-oxa-4a,8a-diazaanthracene-7-carboxylic acid 4-fluorobenzylamide;

5-Hydroxy-3,3-dimethyl-6,10-dioxo-3,4,6,9,9a,10-hexahydro-2H-1-oxa-4a,8a-diaza-anthracene-7-carboxylic acid 4-fluoro-benzylamide;

5-Hydroxy-2-methyl-6,10-dioxo-3,4,6,9,9a,10-hexahydro-2H-1-oxa-4a,8a-dizazaanthracene-7-carboxylic acid 4-fluorobenzylamide;

5-Hydroxy-6,10-dioxo-3,4,6,9,9a,10-hexahydro-2H-1-oxa-4a,8a-diaza-anthracene-7-carboxylic acid 2,4-difluoro-benzylamide;

5-Hydroxy-6,10-dioxo-3,4,6,9,9a,10-hexahydro-2H-1-oxa-4a,8a-diaza-anthracene-7-carboxylic acid 3-chloro-2-fluoro-benzylamide;

enantiomers thereof; diastereomers thereof; mixtures of enantiomers thereof; mixtures of diastereomers thereof; mixtures of enantiomers and diastereomers thereof; and pharmaceutically acceptable salts thereof.

6. A compound selected from the group consisting of (4R, 9aS)-5-Hydroxy-4-methyl-6,10-dioxo-3,4,6,9,9a,10-hexahydro-2H-1-oxa-4a,8a-diaza-anthracene-7-carboxylic acid 2,4-difluoro-benzylamide; an enantiomer thereof; diastereomer thereof; mixtures of enantiomers thereof; mixtures of diastereomers thereof; mixtures of enantiomers and diastereomers thereof; or a pharmaceutically acceptable salt thereof.

7. A compound which is (4R,9aS)-5-hydroxy-4-methyl-6, 10-dioxo-3,4,6,9,9a,10-hexahydro-2H-1-oxa-4a,8a-diaza-anthracene-7-carboxylic acid 2,4-difluoro-benzylamide or a pharmaceutically acceptable salt thereof.

8. A compound which is (4R,9aS)-5-hydroxy-4-methyl-6, 10-dioxo-3,4,6,9,9a,10-hexahydro-2H-1-oxa-4a,8a-diaza-anthracene-7-carboxylic ac id 2,4-difluoro-benzylamide sodium salt.

9. A compound which is (4R,9aS)-5-hydroxy-4-methyl-6, 10-dioxo-3,4,6,9,9a,10-hexahydro-2H-1-oxa-4a,8a-diaza-anthracene-7-carboxylic acid 2,4-difluoro-benzylamide.

10. A pharmaceutical composition comprising (4R,9aS)-5-hydroxy-4-methyl-6,10-dioxo-3,4,6,9,9a,10-hexahydro-2H-1-oxa-4a,8a-diaza-anthracene-7-carboxylic acid 2,4-difluoro-benzylamide or a pharmaceutically acceptable salt thereof, together with a pharmaceutically acceptable carrier or diluent.

11. A pharmaceutical composition comprising a compound according to any one of claims 1, 5, 6, 7, 8, 9 or 4, or a pharmaceutically acceptable salt thereof, together with a pharmaceutically acceptable carrier or diluent.

\* \* \* \* \*

UNITED STATES PATENT AND TRADEMARK OFFICE
CERTIFICATE OF CORRECTION

PATENT NO. : 8,129,385 B2  
APPLICATION NO. : 11/919386  
DATED : March 6, 2012  
INVENTOR(S) : Brian Alvin Johns Page 1 of 1

It is certified that error appears in the above-identified patent and that said Letters Patent is hereby corrected as shown below:

On the Title Page, Item (54), and in the Specification, Column 1, in the title, please change "SUBSTITUTED 5-HYDROXY-3,4,6,9,9A,10-HEXANHYDRO-2H-1-OXA04A,8A-DIAZA-ANTHRACENE-6,10-DIONESS" to -- SUBSTITUTED 5-HYDROXY-3,4,6,9,9A,10-HEXAHYDRO-2H-1-OXA-4A,8A-DIAZA-ANTHRACENE-6,10-DIONES --.

In the Specification

Column 9, line 35, change "$R^5$" to -- R --.

Column 91, line 50, change "J=4 µl," to -- J=4.1 --.

Column 115, line 21, change "(25)" to -- (2S) --.

In the Claims

Claim 1, column 178, line 9, change "l" to -- 1 --;
line 12, change "alkynyl." to -- alkynyl, --;
line 15, change "aralkyl." to -- aralkyl, --;
line 18, change "formyloxy." to -- formyloxy, --;
line 19, change "oral" to -- oxal --.

Claim 8, column 180, line 28, change "ac id" to -- acid --.

Signed and Sealed this
Twelfth Day of May, 2015

Michelle K. Lee
*Director of the United States Patent and Trademark Office*